: US010519143B2

United States Patent
Lu et al.

(10) Patent No.: US 10,519,143 B2
(45) Date of Patent: Dec. 31, 2019

(54) SUBSTITUTED-INDOLE-COMPOUNDS AS ESTROGEN RECEPTOR DOWN-REGULATORS

(71) Applicants: LUOXIN PHARMACEUTICAL (SHANGHAI) CO., LTD, Shanghai (CN); SHANDONG LUOXIN PHARMACEUTICAL GROUP STOCK CO., LTD., Linyi (CN)

(72) Inventors: Jianyu Lu, Shanghai (CN); Charles Z. Ding, Shanghai (CN); Lihong Hu, Shanghai (CN); Huijun He, Shanghai (CN); Shuhui Chen, Shanghai (CN); Jiaqiang Dong, Shanghai (CN); Tie-Lin Wang, Shanghai (CN)

(73) Assignee: LUOXIN PHARMACEUTICAL (SHANGHAI) CO., LTD. (CN)

( * ) Notice: Subject to any disclaimer, the term of this patent is extended or adjusted under 35 U.S.C. 154(b) by 0 days.

(21) Appl. No.: 16/087,861

(22) PCT Filed: Mar. 24, 2017

(86) PCT No.: PCT/CN2017/078139
§ 371 (c)(1),
(2) Date: Sep. 24, 2018

(87) PCT Pub. No.: WO2017/162206
PCT Pub. Date: Sep. 28, 2017

(65) Prior Publication Data
US 2019/0106414 A1    Apr. 11, 2019

(30) Foreign Application Priority Data

Mar. 25, 2016  (CN) .......................... 2016 1 0180518
Sep. 29, 2016  (CN) .......................... 2016 1 0867918

(51) Int. Cl.
| | | |
|---|---|---|
| A61K 31/437 | (2006.01) | |
| C07D 409/06 | (2006.01) | |
| C07D 403/12 | (2006.01) | |
| A61K 31/404 | (2006.01) | |
| C07D 209/18 | (2006.01) | |
| C07D 401/06 | (2006.01) | |
| C07D 405/06 | (2006.01) | |
| A61P 35/00 | (2006.01) | |

(52) U.S. Cl.
CPC .......... *C07D 409/06* (2013.01); *A61K 31/404* (2013.01); *C07D 209/18* (2013.01); *C07D 401/06* (2013.01); *C07D 403/12* (2013.01); *C07D 405/06* (2013.01); *A61P 35/00* (2018.01)

(58) Field of Classification Search
CPC .. A61K 31/437; A61K 31/404; C07D 403/12; C07D 471/04
USPC .............................. 546/113, 277.4; 548/465
See application file for complete search history.

(56) References Cited

U.S. PATENT DOCUMENTS

| | | |
|---|---|---|
| 8,455,534 B2 | 6/2013 | Smith et al. |
| 2010/0317635 A1 | 12/2010 | Labrie |
| 2015/0105403 A1 | 4/2015 | Smith et al. |

FOREIGN PATENT DOCUMENTS

| | | |
|---|---|---|
| CN | 102458404 | 5/2012 |
| CN | 103189361 | 7/2013 |
| CN | 104220426 | 12/2014 |
| WO | 2011042474 | 4/2011 |
| WO | 2012037411 | 3/2012 |
| WO | 2015136016 | 9/2015 |
| WO | 2015136017 | 9/2015 |

OTHER PUBLICATIONS

Wolff et. al., "Burger's Medicinal Chemistry and Drug Discovery," 5th Ed. Part 1, pp. 975-977 (1995).*
Banker, et. al., (1996), Modern Pharmaceuticals, p. 596.*
International Search Report of PCT/CN2017/078139 dated Jun. 21, 2017.
Written Opinion of PCT/CN2017/078139 dated Jun. 21, 2017.
J.Med.Chem. 2015,58(12),4888-4904.

* cited by examiner

Primary Examiner — Jeffrey H Murray
(74) Attorney, Agent, or Firm — Dilworth IP, LLC

(57) ABSTRACT

Disclosed is a new indole compound, in particular, the compound as shown in formula (I), and a preparation method, pharmaceutical composition and use thereof as an estrogen receptor down-regulator in preparing drugs for treating estrogen receptor-positive breast cancer.

25 Claims, No Drawings

SUBSTITUTED-INDOLE-COMPOUNDS AS ESTROGEN RECEPTOR DOWN-REGULATORS

FIELD OF INVENTION

The present invention relates to a novel class of indole derivatives, particularly a compound represented by formula (I), a preparation method, a pharmaceutical composition and a use as estrogen receptor down-regulator in preparing a medicament for treating estrogen receptor-positive breast cancer.

PRIOR ARTS

According to WHO's statistics, breast cancer has become a cancer with second highest incidence rate in the world and a cancer with the highest incidence rate among women. After years of research, the role of the estrogen-estrogen receptor signaling pathway in the progression of breast cancer has been confirmed; and the estrogen receptor (ER) has become the most important biomarker for breast cancer. According to the expression of estrogen receptor, breast cancer can be classified into estrogen receptor-positive breast cancer and estrogen receptor-negative breast cancer, wherein estrogen receptor-positive breast cancer accounts for more than 70% among the total number of breast cancer patients.

Endocrine therapy (ET) which targets the estrogen-estrogen receptor signaling pathway in breast cancer cells, has been the first choice for the treatment of estrogen receptor-positive breast cancer because of its minimal risk and remarkable efficacy. Endocrine therapy mainly includes three therapies which are ovarian suppression therapy, aromatase inhibitor (AI), and selective estrogen receptor modulator (SERM). The use of ovarian suppression therapy is less than the other two therapies because of poor efficacy and low patient satisfaction. Early aromatase inhibitors (first generation, second generation) have low target selectivity and severe side effects. After years of research, the third generation of aromatase inhibitors which have greatly improved the target selectivity and solved the problem of earlier aromatase inhibitors has been widely used. Among them, letrozole has been used as a first-line drug for the treatment of estrogen receptor-positive breast cancer. The selective estrogen receptor modulator (SERM) which targets directly at the estrogen receptor to block the signaling pathway has a significant therapeutic efficiency and a long history of application. Among them, tamoxifen is the most representative selective estrogen receptor modulator. As a first-line drug recommended for priority of use, tamoxifen has exhibited significant clinical efficacy in the prevention and treatment of estrogen receptor-positive breast cancer.

Although the aromatase inhibitor letrozole and the selective estrogen receptor modulator tamoxifen have exhibited good efficacy in the treatment of estrogen receptor-positive breast cancer, the resistance in estrogen receptor-positive breast cancer to the aromatase inhibitor and the selective estrogen receptor modulator has been becoming more prominent along with their use. A large number of studies have shown that the drug resistance mechanism in breast cancer to the above two endocrine therapies is not exactly the same. As for the aromatase inhibitor, estrogen receptor can produce corresponding mutations. The mutated estrogen receptor itself maintains the agonistic conformation in the absence of estrogen, so continues to function as a receptor to promote breast cancer cell proliferation. The drug resistance mechanism in breast cancer to the selective estrogen receptor modulator tamoxifen is more complicated. Firstly, breast cancer cells can compensate the loss of function of the estrogen receptor estrogen receptor activation function-2 (AF-2) caused by tamoxifen by activating the function of estrogen receptor activation function-1 (AF-1). Meanwhile, breast cancer cells can adapt to the conformation of the estrogen receptor binding to tamoxifen by regulating the structure or concentration of the estrogen receptor coactivator to recover the function of estrogen receptor, thereby causing drug resistance.

Selective estrogen receptor down-regulator (SERD) has exhibited unique advantages in the treatment of breast cancer resistant to the two endocrine therapies. The mechanism is that selective estrogen receptor down regulation antagonizes the function of estrogen receptor, greatly accelerates the ubiquitination and degradation of the estrogen receptor in breast cancer cells (normal or mutant) and completely blocks the estrogen/estrogen receptor signaling pathway resulting in the inhibition of growth and proliferation of normal or drug-resistant breast cancer cells. Studies have shown that the selective estrogen receptor down-regulator can effectively inhibit the proliferation of endocrine-resistant breast cancer cells. Fulvestrant which is the only selective estrogen receptor down-regulator on the market has shown good result in the treatment of endocrine-resistant breast cancer, demonstrating the unique advantage of selective estrogen receptor down-regulator. However, fulvestrant itself has many defects. Firstly, because of poor PK properties, fulvestrant exhibits zero oral bioavailability, and fulvestrant has a higher blood clearance rate. For the above two reasons, this drug can only be administered by intramuscular injection. However, due to its strong lipophilic structure, fulvestrant administered by intramuscular injection also has serious problems in tissue distribution, its clinical manifestation is that only about 50% of the breast cancer patients treated with fulvestrant shows clinical response. Therefore, the selective estrogen receptor down-regulation with oral bioavailability is needed in medical treatment.

WO2012037411A2 has disclosed an oral selective estrogen receptor down-regulator ARN-810, a phase II clinical trial of which for the treatment of ER-positive breast cancer is under way. According to the report [*J. Med. Chem.* 2015, 58 (12), 4888-4904], the important pharmacophore of this molecule is the indazole structure on the left side of the molecule, and the nitrogen atom in the indazole structure acts as a hydrogen bond acceptor when binding to estrogen receptor.

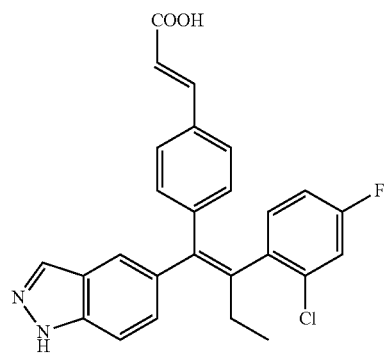

ARN-810

CONTENT OF THE PRESENT INVENTION

The present invention discloses a compound represented by formula (I), a pharmaceutically acceptable salt, a hydrate or a prodrug thereof,

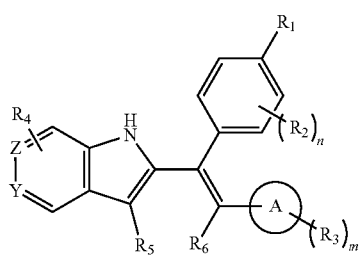

wherein,
$R_1$ is selected from

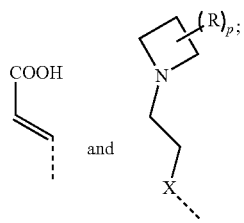

X is selected from a single bond, O and S;
Y and Z are each independently selected from N and CH;
ring A is selected from 5-10 membered aryl and 5-10 membered heteroaryl;
$R_2$ is selected from H, halogen, CN, $NO_2$, OH, COOH, $NH_2$, or the group consisting of $C_{1-6}$ alkyl, $C_{1-6}$ heteroalkyl, $C_{3-6}$ cycloalkyl and 3-6 membered heterocycloalkyl, each of which is optionally substituted with 1, 2, or 3 R;
$R_3$ is selected from H, halogen, CN, $NO_2$, OH, COOH, $NH_2$, or the group consisting of $C_{1-6}$ alkyl, $C_{1-6}$ heteroalkyl, $C_{3-6}$ cycloalkyl and 3-6 membered heterocycloalkyl, each of which is optionally substituted with 1, 2, or 3 R;
$R_4$ and $R_5$ are each independently selected from H, halogen, CN, $NO_2$, OH, COOH, $NH_2$, or the group consisting of $C_{1-6}$ alkyl, $C_{1-6}$ heteroalkyl, $C_{3-6}$ cycloalkyl and 3-6 membered heterocycloalkyl, each of which is optionally substituted with 1, 2, or 3 R;
$R_6$ is selected from the group consisting of $C_{1-6}$ alkyl, $C_{1-6}$ heteroalkyl, $C_{3-6}$ cycloalkyl and 3-6 membered heterocycloalkyl, each of which is optionally substituted with 1, 2, or 3 R;
R is selected from H, F, Cl, Br, I, OH, CN, $NH_2$, COOH, C(=O)$NH_2$, or the group consisting of $C_{1-8}$ alkyl, $C_{1-8}$ heteroalkyl, $C_{3-6}$ cycloalkyl, 3-6 membered heterocycloalkyl and $C_{3-6}$ cycloalkyl-$C_{1-3}$ alkyl-, each of which is optionally substituted with 1, 2, or 3 R';
n is selected from 0, 1, 2, 3 and 4;
m is selected from 0, 1, 2, 3 and 4;
P is selected from 0, 1, 2 and 3;
or, when m is 2, $R_3$ and $R_3$ are connected together to form a 5-6 membered ring;
R' is selected from the group consisting of F, Cl, Br, I, OH, CN, $NH_2$, COOH, Me, Et, $CF_3$, $CHF_2$, $CH_2F$, $NHCH_3$ and $N(CH_3)_2$;

"hetero" represents a heteroatom or a heteroatom group, which is selected from the group consisting of —C(=O)N(R)—, —N(R)—, —S(=O)$_2$N(R)—, —S(=O)N(R)—, —O—, —S—, =O, =S, —O—N=, —C(=O)O—, —C(=O)—, —C(=S)—, —S(=O)—, —S(=O)$_2$— and —N(R)C(=O)N(R)—;
in any of the above cases, the number of the heteroatom or the heteroatom group is independently selected from 1, 2 and 3.

The present invention discloses a compound represented by formula (I), a pharmaceutically acceptable salt, a hydrate or a prodrug thereof,

wherein,
$R_1$ is selected from

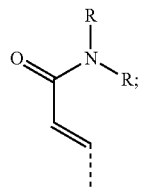

Y and Z are each independently selected from N and CH;
ring A is selected from 5-10 membered aryl and 5-10 membered heteroaryl;
$R_2$ is selected from H, halogen, CN, $NO_2$, OH, COOH, $NH_2$, or the group consisting of $C_{1-6}$ alkyl, $C_{1-6}$ heteroalkyl, $C_{3-6}$ cycloalkyl and 3-6 membered heterocycloalkyl, each of which is optionally substituted with 1, 2, or 3 R;
$R_3$ is selected from H, halogen, CN, $NO_2$, OH, COOH, $NH_2$, or the group consisting of $C_{1-6}$ alkyl, $C_{1-6}$ heteroalkyl, $C_{3-6}$ cycloalkyl and 3-6 membered heterocycloalkyl, each of which is optionally substituted with 1, 2, or 3 R;
$R_4$ and $R_5$ are each independently selected from H, halogen, CN, $NO_2$, OH, COOH, $NH_2$, or the group consisting of $C_{1-6}$ alkyl, $C_{1-6}$ heteroalkyl, $C_{3-6}$ cycloalkyl and 3-6 membered heterocycloalkyl, each of which is optionally substituted with 1, 2, or 3 R;
$R_6$ is selected from the group consisting of $C_{1-6}$ alkyl, $C_{1-6}$ heteroalkyl, $C_{3-6}$ cycloalkyl and 3-6 membered heterocycloalkyl, each of which is optionally substituted with 1, 2, or 3 R;
R is selected from H, F, Cl, Br, I, OH, CN, $NH_2$, COOH, C(=O)$NH_2$, or the group consisting of $C_{1-8}$ alkyl, $C_{1-8}$ heteroalkyl, $C_{3-6}$ cycloalkyl, 3-6 membered heterocycloalkyl and $C_{3-6}$ cycloalkyl-$C_{1-3}$ alkyl-, each of which is optionally substituted with 1, 2, or 3 R';
n is selected from 0, 1, 2, 3 and 4;
m is selected from 0, 1, 2, 3 and 4;
or, when m is 2, $R_3$ and $R_3$ are connected together to form a 5-6 membered ring;

R' is selected from the group consisting of F, Cl, Br, I, OH, CN, NH$_2$, COOH, Me, Et, CF$_3$, CHF$_2$, CH$_2$F, NHCH$_3$ and N(CH$_3$)$_2$;

"hetero" represents a heteroatom or a heteroatom group, which is selected from the group consisting of —C(=O)N(R)—, —N(R)—, —S(=O)$_2$N(R)—, —S(=O)N(R)—, —O—, —S—, =O, =S, —O—N=, —C(=O)O—, —C(=O)—, —C(=S)—, —S(=O)—, —S(=O)$_2$— and —N(R)C(=O)N(R)—;

in any of the above cases, the number of the heteroatom or the heteroatom group is independently selected from 1, 2 and 3.

In some embodiments of the present invention, R is selected from H, F, Cl, Br, I, OH, CN, NH$_2$, COOH, or the group consisting of C$_{1-5}$ alkyl, C$_{1-5}$ heteroalkyl, C$_{3-6}$ cycloalkyl-C$_{1-3}$ alkyl-, each of which is optionally substituted with 1, 2, or 3 R'.

In some embodiments of the present invention, R is selected from H, F, Cl, Br, I, OH, CN, NH$_2$, COOH, C(=O)NH$_2$, or the group consisting of CH$_3$, CH$_3$CH$_2$, S(=O)CH$_3$,

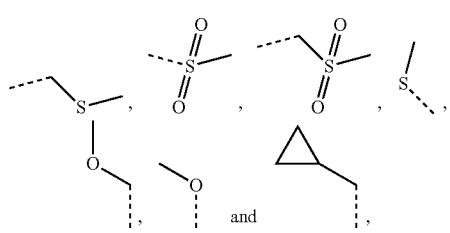

each of which is optionally substituted with 1, 2, or 3 R'.

In some embodiments of the present invention, R is selected from the group consisting of H, F, Cl, Br, I, OH, CN, NH$_2$, COOH, C(=O)NH$_2$, CH$_3$, CH$_2$Cl, CH$_2$F, CHF$_2$, CF$_3$, OCF$_3$, CH$_2$OH, Et, S(=O)CH$_3$,

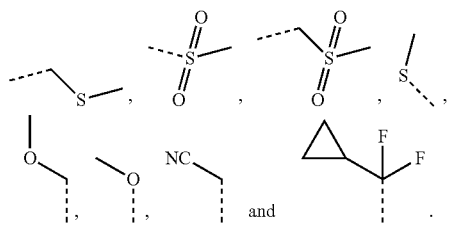

In some embodiments of the present invention, R is selected from H, F, Cl, Br, I, OH, CN, NH$_2$, COOH, or the group consisting of C$_{1-5}$ alkyl, C$_{1-5}$ heteroalkyl and C$_{3-6}$ cycloalkyl-C$_{1-3}$ alkyl-, each of which is optionally substituted with 1, 2, or 3 R'.

In some embodiments of the present invention, R is selected from H, F, Cl, Br, I, OH, CN, NH$_2$, COOH, C(=O)NH$_2$, or the group consisting of CH$_3$, CH$_3$CH$_2$, S(=O)CH$_3$,

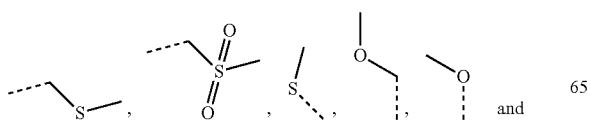

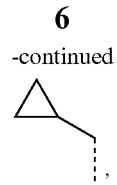

each of which is optionally substituted with 1, 2, or 3 R'.

In some embodiments of the present invention, R is selected from the group consisting of H, F, Cl, Br, I, OH, CN, NH$_2$, COOH, C(=O)NH$_2$, CH$_3$, CH$_2$Cl, CH$_2$F, CHF$_2$, CF$_3$, OCF$_3$, CH$_2$OH, Et, S(=O)CH$_3$,

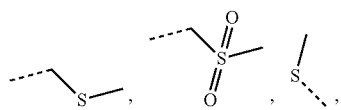

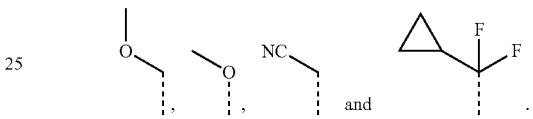

In some embodiments of the present invention, the moiety

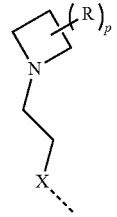

is selected from

In some embodiments of the present invention, the moiety

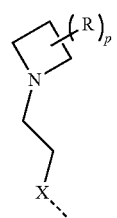

is selected from

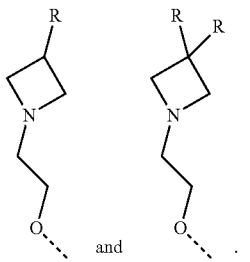
and

In some embodiments of the present invention, the moiety

is selected from the group consisting of

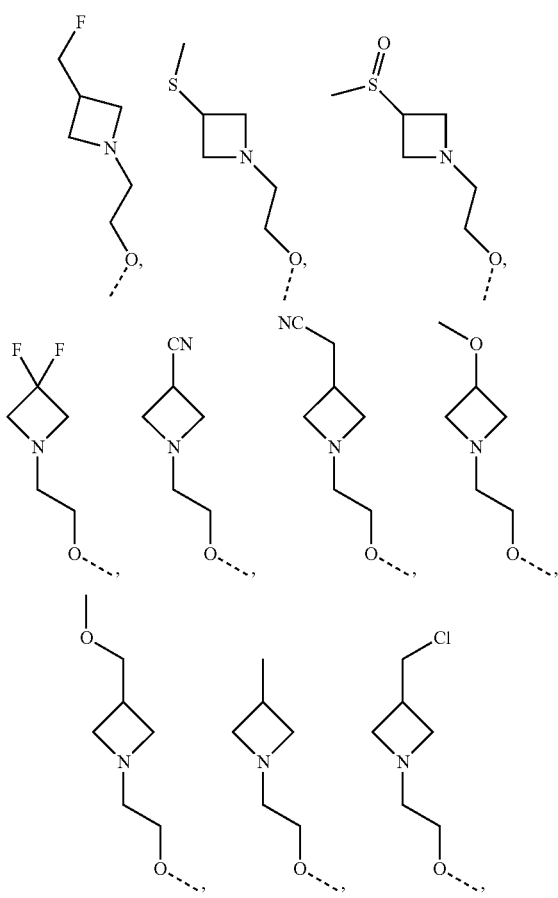

-continued

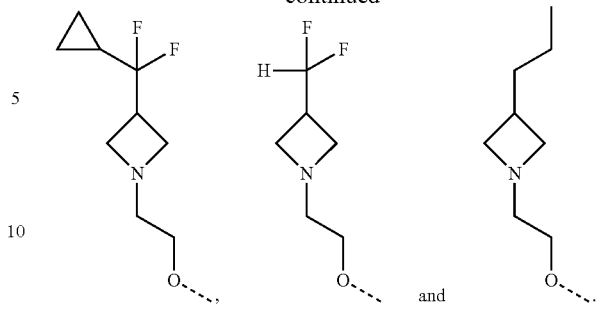
and

In some embodiments of the present invention, $R_2$ is selected from H, F, Cl, Br, I, CN, $NO_2$, OH, COOH, $NH_2$, or the group consisting of $C_{1-4}$ alkyl, $C_{1-4}$ alkoxy, $C_{1-4}$ alkylthio, $NH(C_{1-4}$ alkyl), N,N-di($C_{1-3}$ alkyl)amino and $C_{3-6}$ cycloalkyl, each of which is optionally substituted with 1, 2, or 3 R.

In some embodiments of the present invention, $R_3$ is selected from H, F, Cl, Br, I, CN, $NO_2$, OH, COOH, $NH_2$, or the group consisting of $C_{1-4}$ alkyl, $C_{1-4}$ alkoxy, $C_{1-4}$ alkylthio, $NH(C_{1-4}$ alkyl), N,N-di($C_{1-3}$ alkyl)amino, $C_{3-6}$ cycloalkyl, 3-6 membered heterocycloalkyl, 5-6 membered aryl and 5-6 membered heteroaryl, each of which is optionally substituted with 1, 2, or 3 R.

In some embodiments of the present invention, $R_3$ is selected from H, F, Cl, Br, I, CN, $NO_2$, OH, COOH, $NH_2$, or the group consisting of $CH_3$, $CH_3CH_2$, $CH_3O$, $CH_3CH_2O$ and

each of which is optionally substituted with 1, 2, or 3 R.

In some embodiments of the present invention, $R_3$ is selected from the group consisting of H, F, Cl, CN, $CH_3$, $CF_3$ and

In some embodiments of the present invention, $R_4$ and $R_5$ are each independently selected from H, F, Cl, Br, I, CN, $NO_2$, OH, COOH, $NH_2$, or the group consisting of $C_{1-4}$ alkyl, $C_{1-4}$ alkoxy, $C_{1-4}$ alkylthio, $NH(C_{1-4}$ alkyl), N,N-di($C_{1-3}$ alkyl)amino and $C_{3-6}$ cycloalkyl, each of which is optionally substituted with 1, 2, or 3 R.

In some embodiments of the present invention, $R_4$ and $R_5$ are each independently selected from the group consisting of H, F, Cl, Br, CN and $CH_3$.

In some embodiments of the present invention, ring A is selected from the group consisting of phenyl, pyridyl, pyrazinyl, imidazolyl, pyrazolyl, oxazolyl, isoxazolyl, thiazolyl, isothiazolyl, thienyl, benzofuranyl, benzothienyl, indolyl, benzimidazolyl, benzothiazolyl, purinyl, quinolinyl and isoquinolinyl.

In some embodiments of the present invention, the moiety

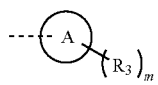

is selected from the group consisting of

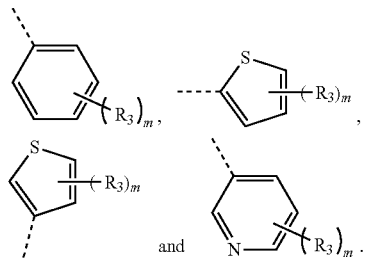

In some embodiments of the present invention, the moiety

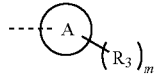

is selected from the group consisting of

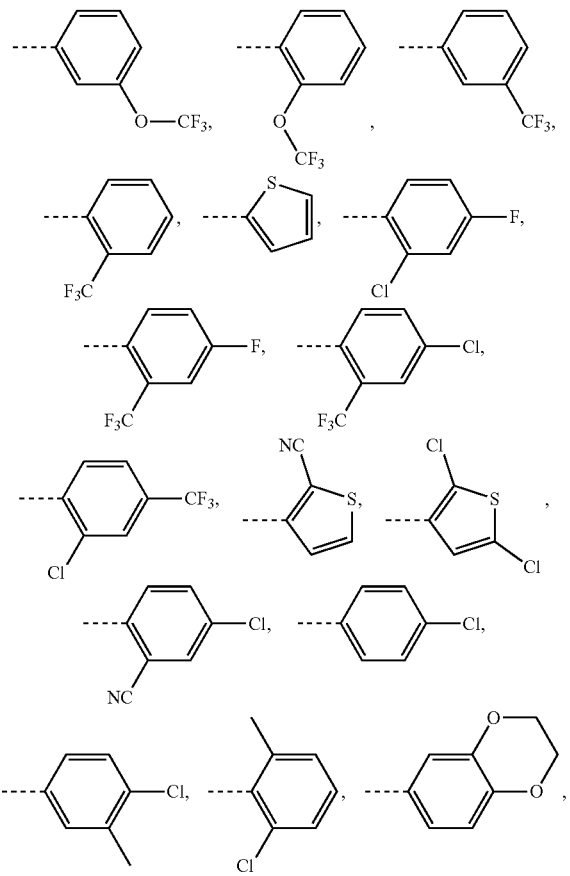

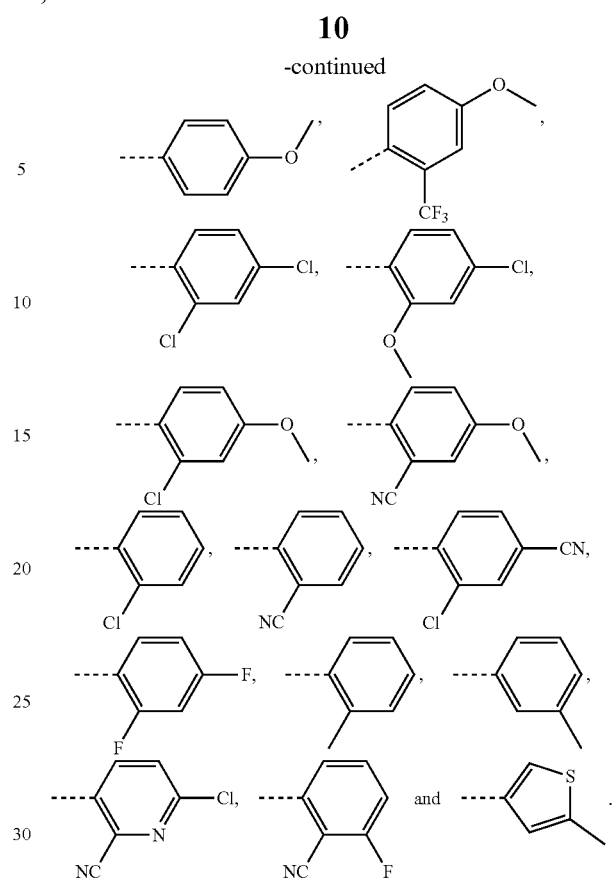

In some embodiments of the present invention, $R_6$ is selected from

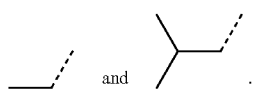

In some embodiments of the present invention, the moiety

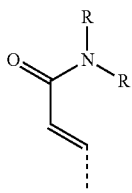

is selected from

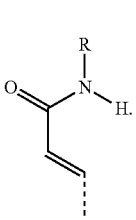

In some embodiments of the present invention, the structural unit is selected from
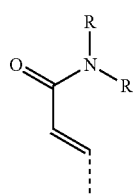
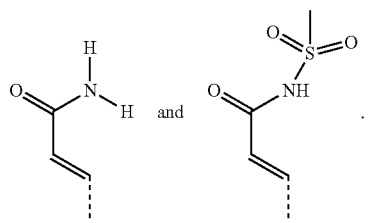
In some embodiments of the present invention, the compound is selected from the group consisting of
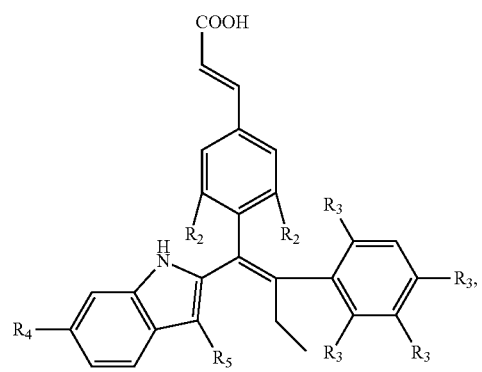
(II)
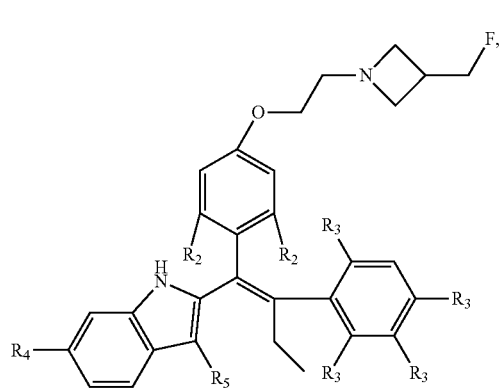
(III)
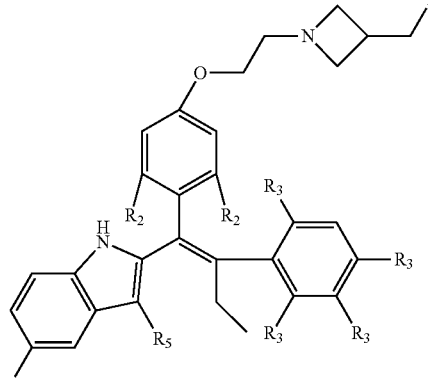
(IV)
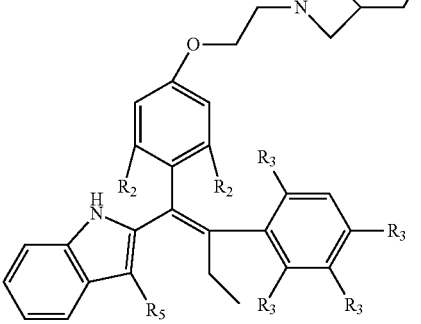
(V)
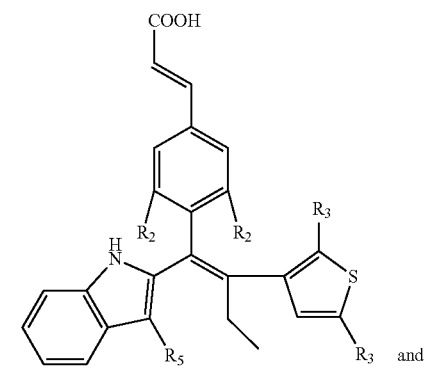
(VI)
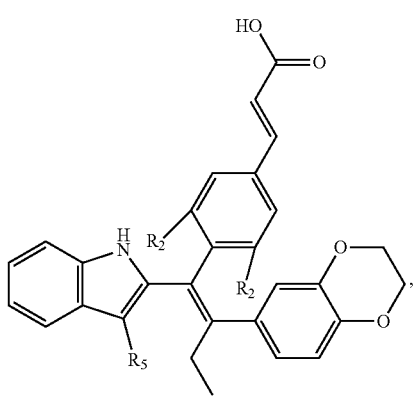
(VII)
wherein, $R_2$, $R_3$, $R_4$ and $R_5$ are defined as above.
In some embodiments of the present invention, the compound is selected from

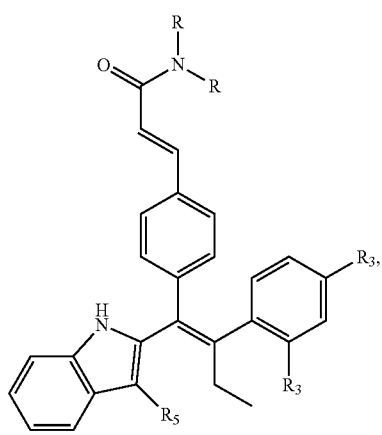
wherein, $R_3$, $R_5$ and R are defined as above.
The present invention also provides a compound or a pharmaceutically acceptable salt, wherein the compound is selected from the group consisting of
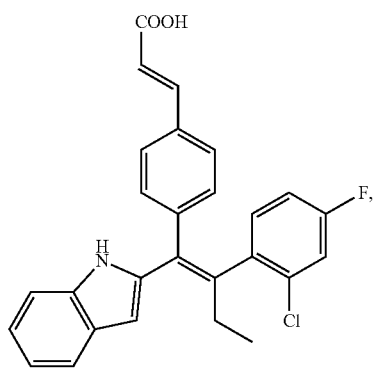
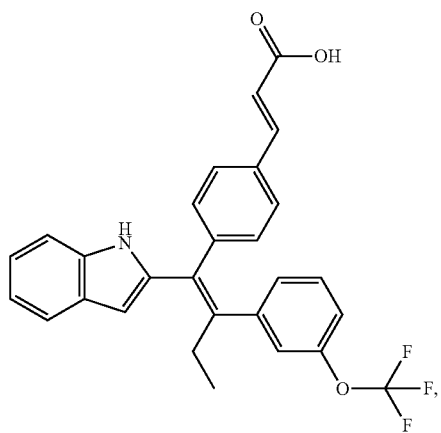
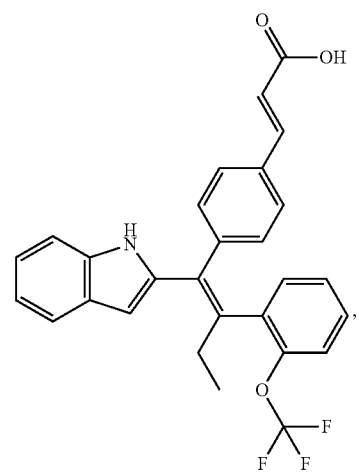
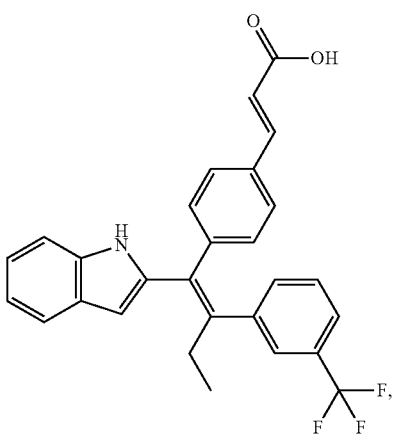
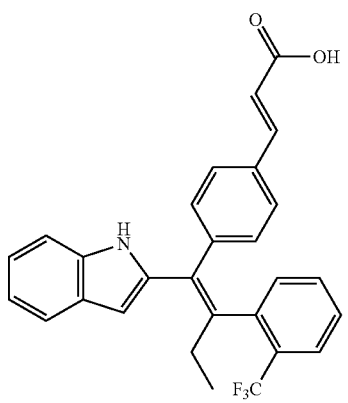

-continued
I-6
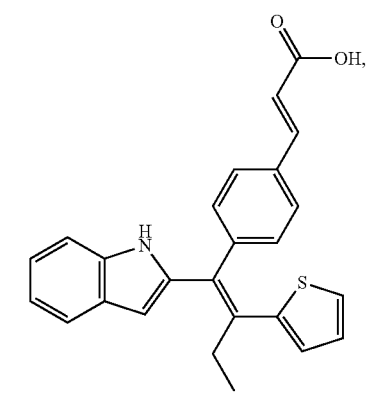
I-7
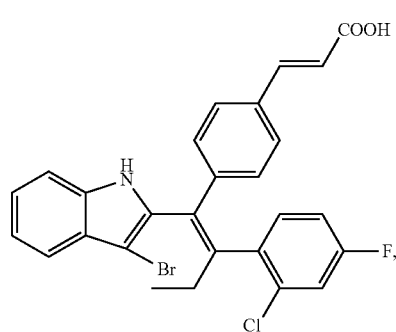
I-8
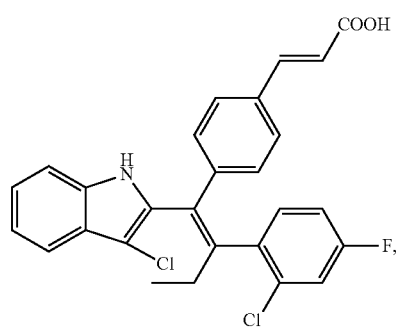
I-9
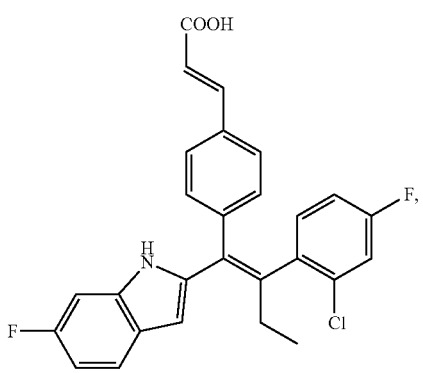
-continued
I-10
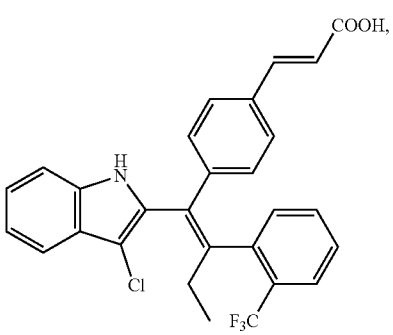
I-11
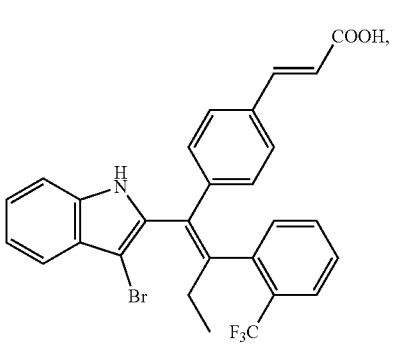
I-12
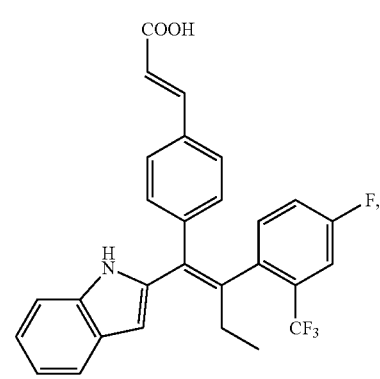
I-13
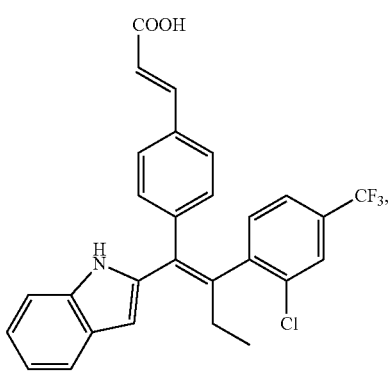

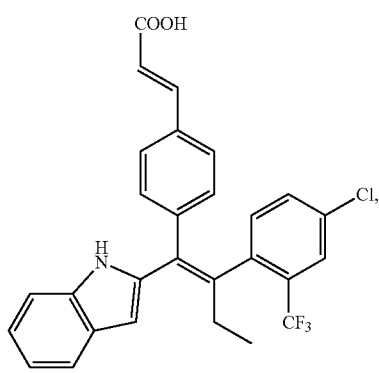
I-14
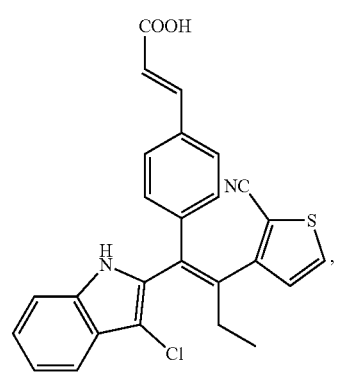
I-15
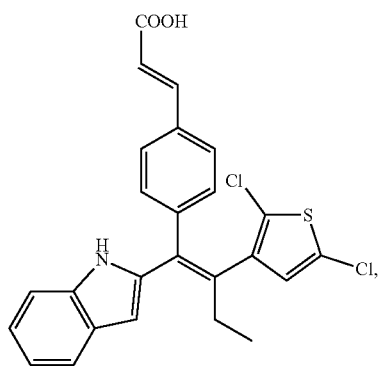
I-17
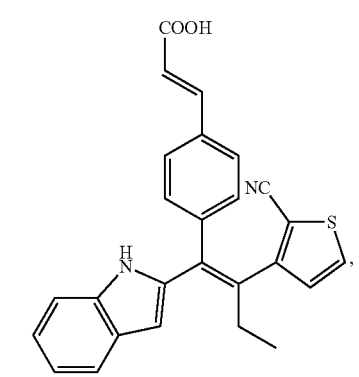
I-18
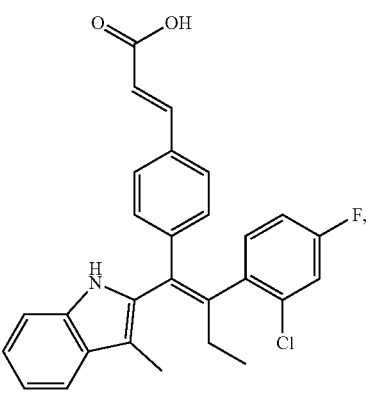
I-19
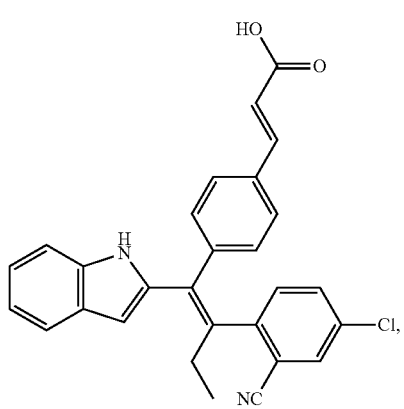
I-21
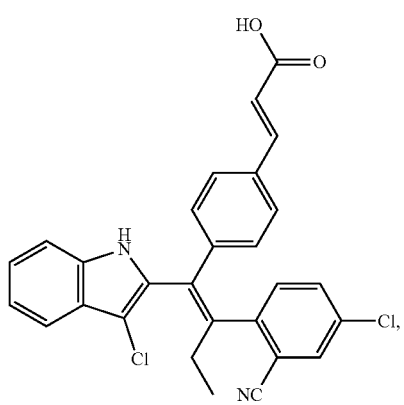
I-22
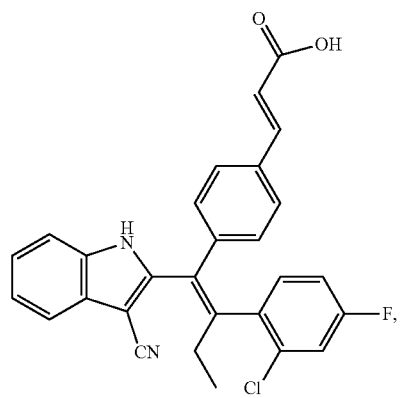
I-23

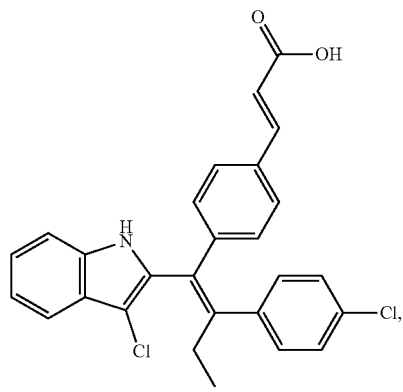
I-24
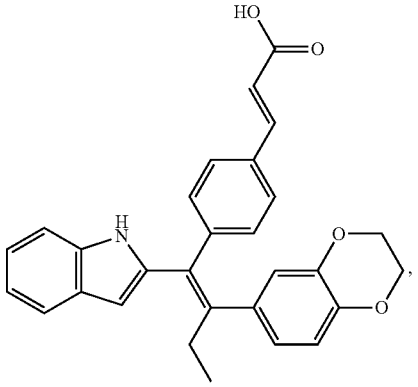
I-30
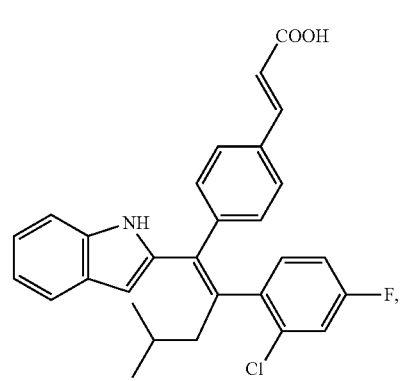
I-27
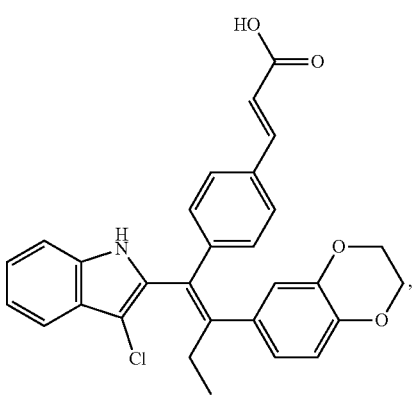
I-31
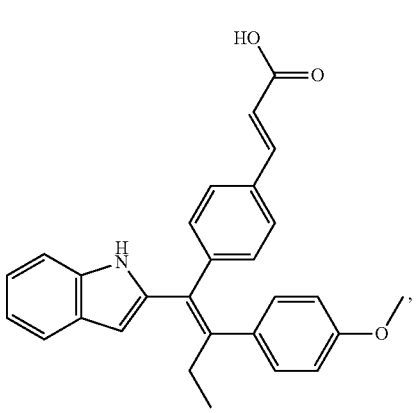
I-28
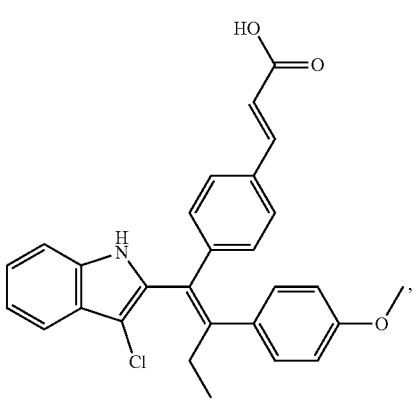
I-32
I-29
I-33

I-34
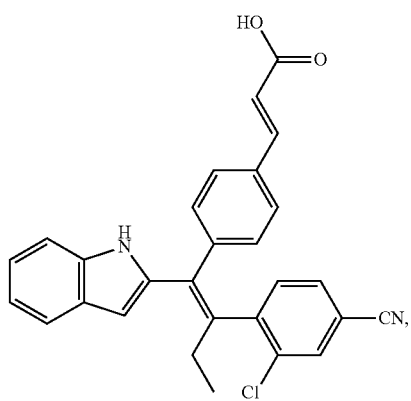
I-35
I-36
I-37
I-38
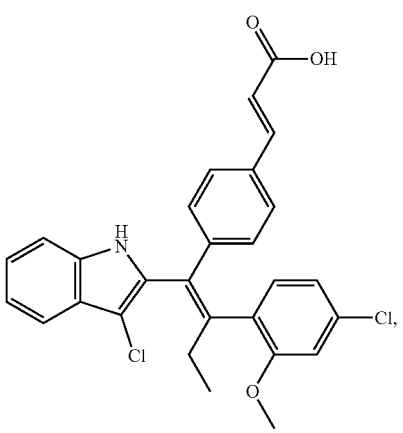
I-39
I-40
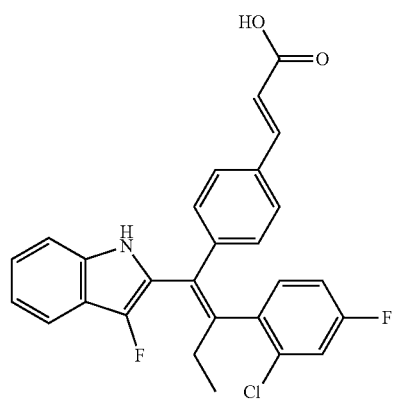
I-41
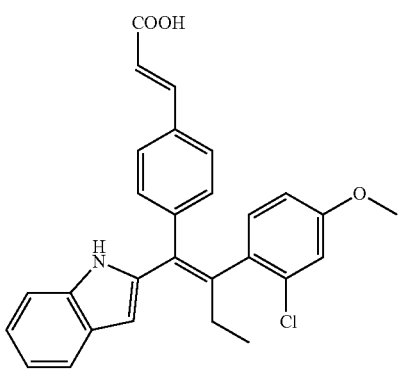

I-42 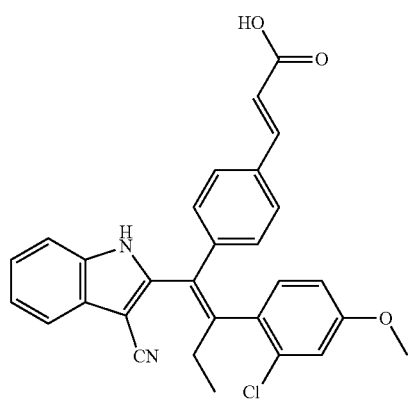
I-43 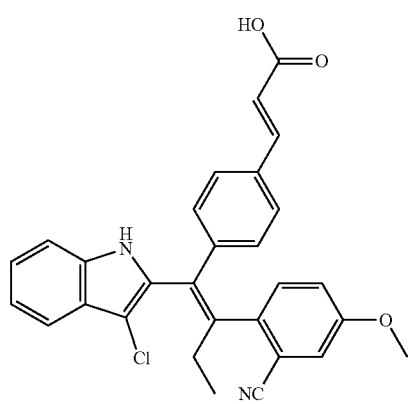
I-44 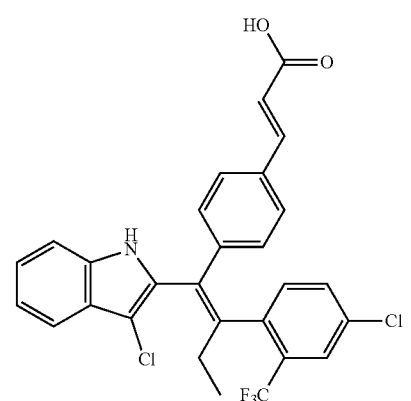
I-45 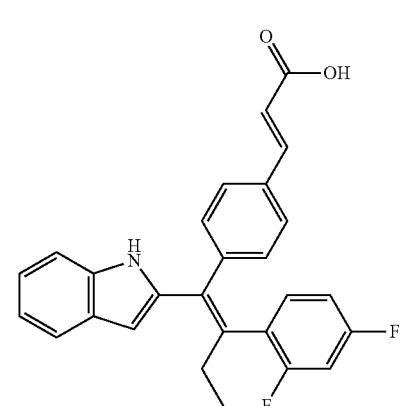
I-46 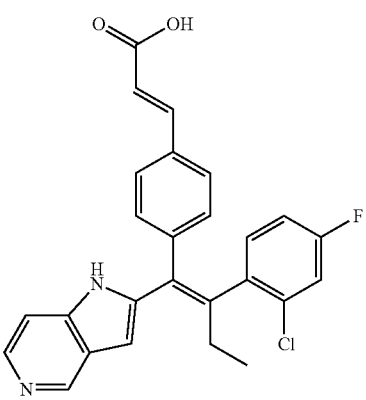
I-47 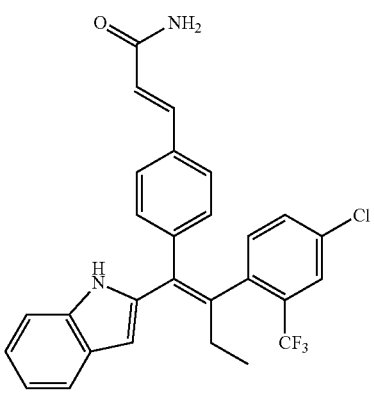
I-48 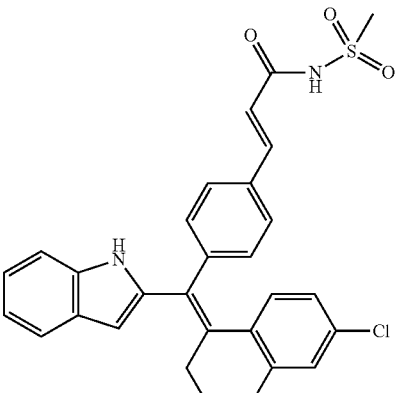
I-49 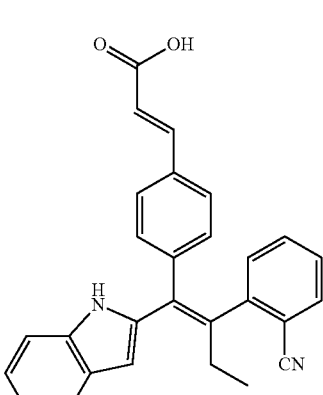

I-50
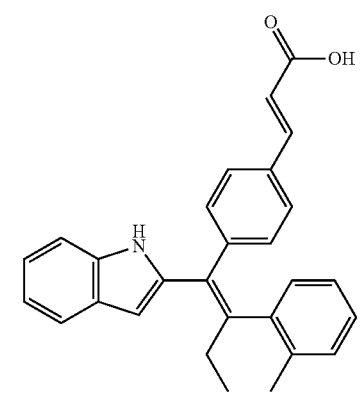
I-51
I-52
I-53
I-54
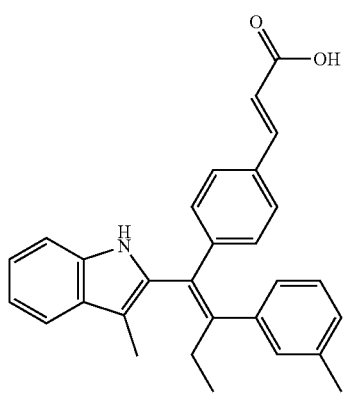
I-55
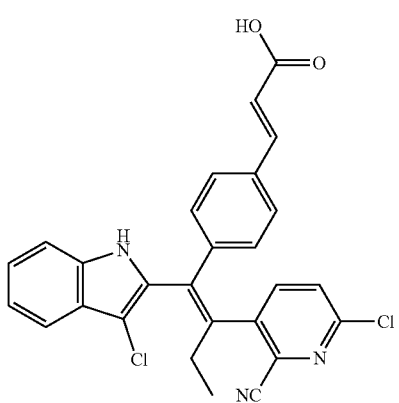
I-56
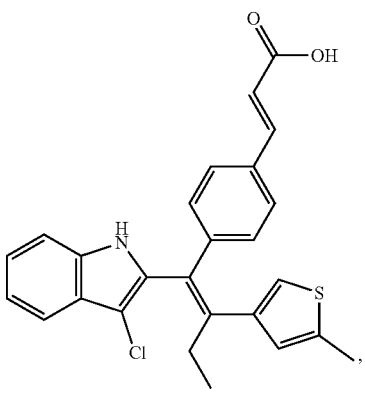
I-57
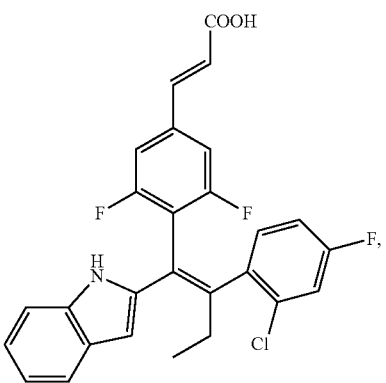

-continued
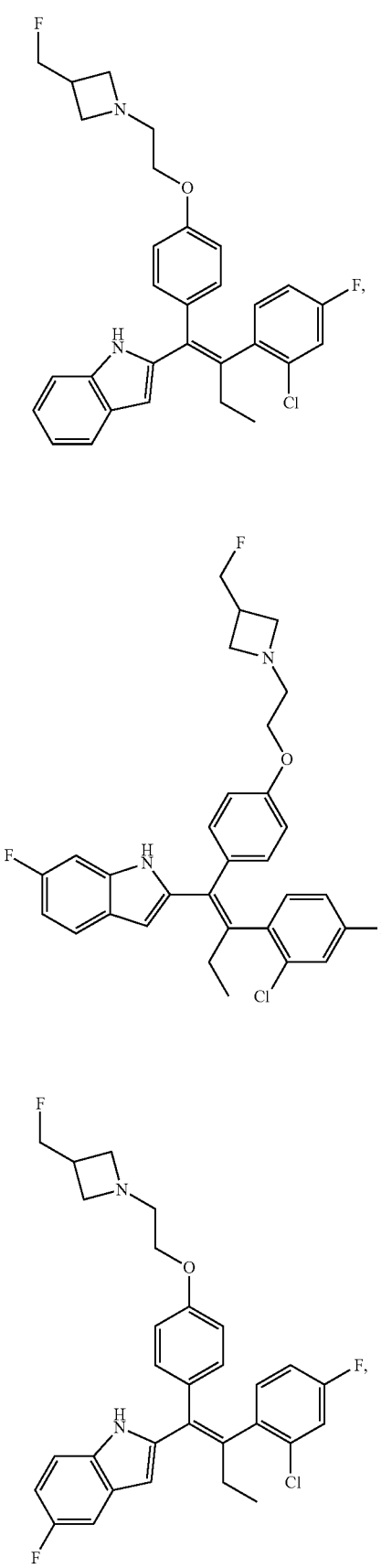
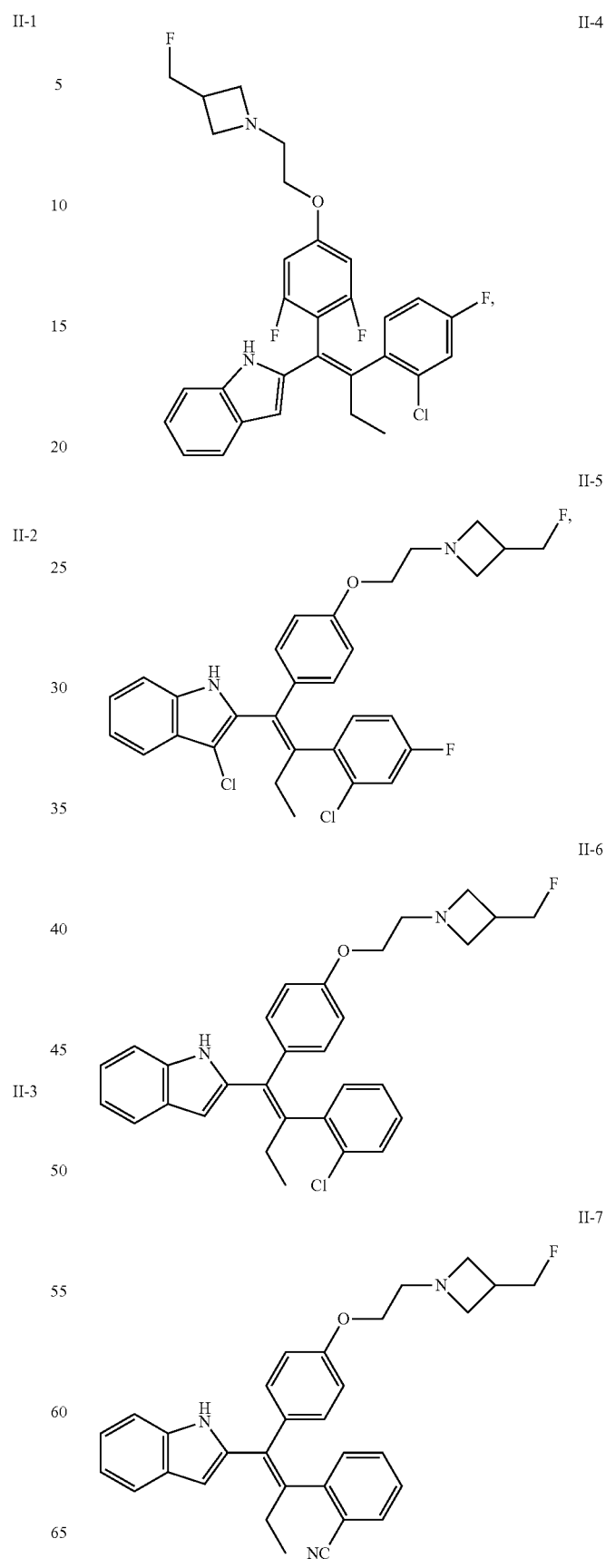

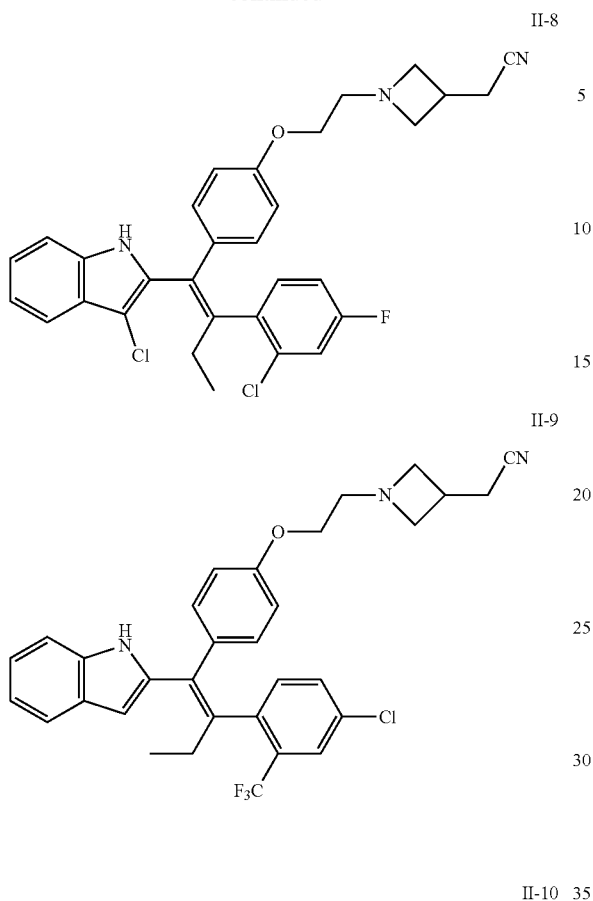

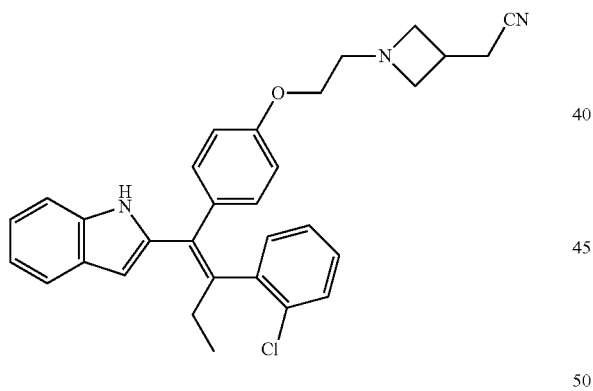

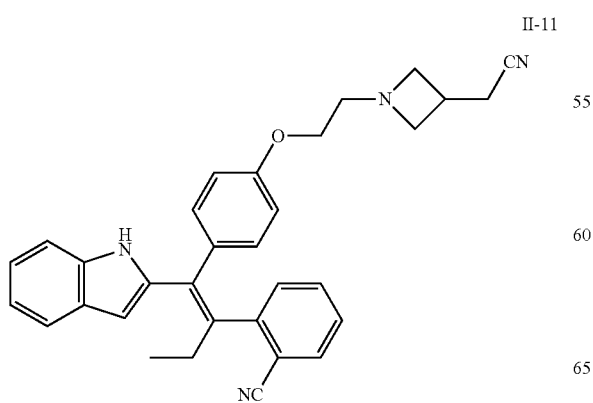

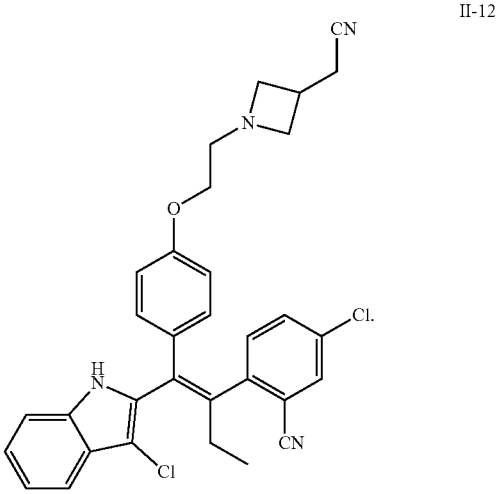

The present invention also provides a pharmaceutical composition comprising a therapeutically effective amount of the compound or the pharmaceutically acceptable salt thereof as defined above and a pharmaceutically acceptable carrier.

The present invention also provides a use of the compound or the pharmaceutically acceptable salt thereof as defined above or the pharmaceutical composition as defined above in preparing a medicament for treating a disorder associated with estrogen receptor.

In some embodiments of the present invention, the moiety

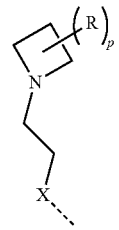

is selected from

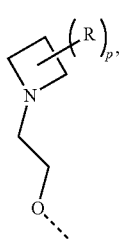

other variables are defined as above.

In some embodiments of the present invention, the moiety

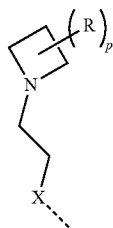

is selected from

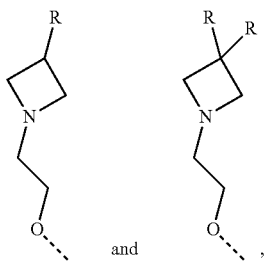

other variables are defined as above.

In some embodiments of the present invention, the moiety

is selected from the group consisting of

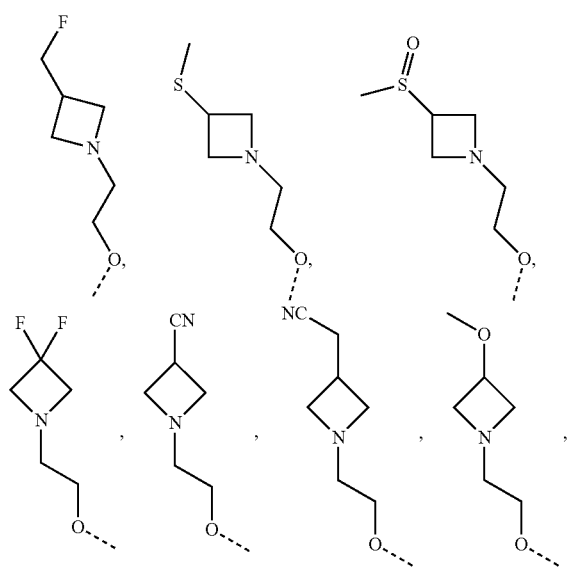

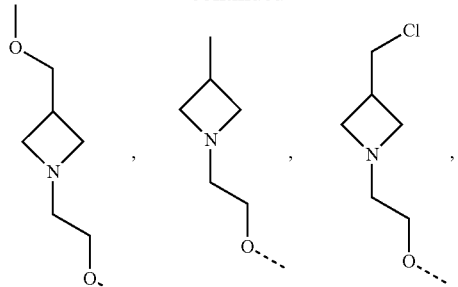

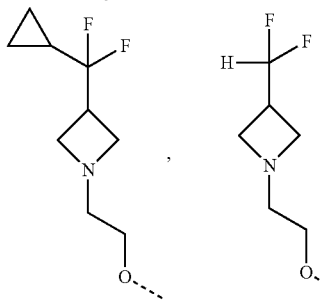

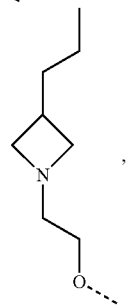

other variables are defined as above.

In some embodiments of the present invention, $R_2$ is selected from H, F, Cl, Br, I, CN, $NO_2$, OH, COOH, $NH_2$, or the group consisting of $C_{1-4}$ alkyl, $C_{1-4}$ alkoxy, $C_{1-4}$ alkylthio, NH($C_{1-4}$ alkyl), N,N-di($C_{1-3}$ alkyl)amino and $C_{3-6}$ cycloalkyl, each of which is optionally substituted with 1, 2 or 3 R, other variables are defined as above.

In some embodiments of the present invention, $R_3$ is selected from H, F, Cl, Br, I, CN, $NO_2$, OH, COOH, $NH_2$, or the group consisting of $C_{1-4}$ alkyl, $C_{1-4}$ alkoxy, $C_{1-4}$ alkylthio, NH($C_{1-4}$ alkyl), N,N-di($C_{1-3}$ alkyl)amino, $C_{3-6}$ cycloalkyl, 3-6 membered heterocycloalkyl, 5-6 membered aryl and 5-6 membered heteroaryl, each of which is optionally substituted with 1, 2 or 3 R, other variables are defined as above.

In some embodiments of the present invention, $R_3$ is selected from H, F, Cl, Br, I, CN, $NO_2$, OH, COOH, $NH_2$, or the group consisting of $CH_3$, $CH_3CH_2$, $CH_3O$, $CH_3CH_2$ and

each of which is optionally substituted with 1, 2 or 3 R, other variables are defined as above.

In some embodiments of the present invention, $R_3$ is selected from H, F, Cl, CN, $CH_3$, $CF_3$ and

other variables are defined as above.

In some embodiments of the present invention, $R_4$ and $R_5$ are each independently selected from H, F, Cl, Br, I, CN, $NO_2$, OH, COOH, $NH_2$, or the group consisting of $C_{1-4}$ alkyl, $C_{1-4}$ alkoxy, $C_{1-4}$ alkylthio, NH($C_{1-4}$ alkyl), N,N-di($C_{1-3}$ alkyl)amino and $C_{3-6}$ cycloalkyl, each of which is optionally substituted with 1, 2 or 3 R, other variables are defined as above.

In some embodiments of the present invention, $R_4$ and $R_5$ are each independently selected from the group consisting of H, F, Cl, Br, CN and $CH_3$, other variables are defined as above.

In some embodiments of the present invention, ring A is selected from the group consisting of phenyl, pyridyl, pyrazinyl, imidazolyl, pyrazolyl, oxazolyl, isoxazolyl, thiazolyl, isothiazolyl, thienyl, benzofuranyl, benzothienyl, indolyl, benzimidazolyl, benzothiazolyl, purinyl, quinolinyl and isoquinolinyl, other variables are defined as above.

In some embodiments of the present invention, the moiety

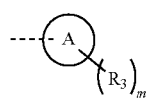

is selected from the group consisting of

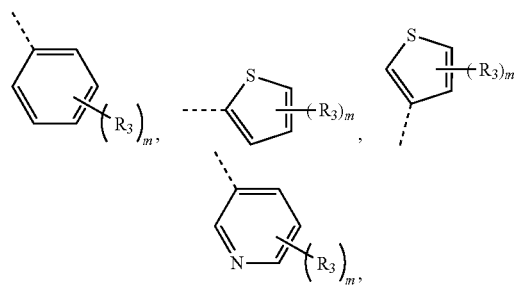

other variables are defined as above.

In some embodiments of the present invention, the moiety

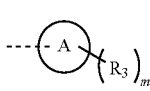

is selected from the group consisting of

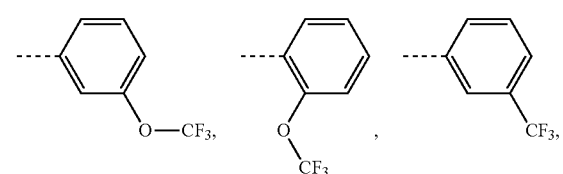

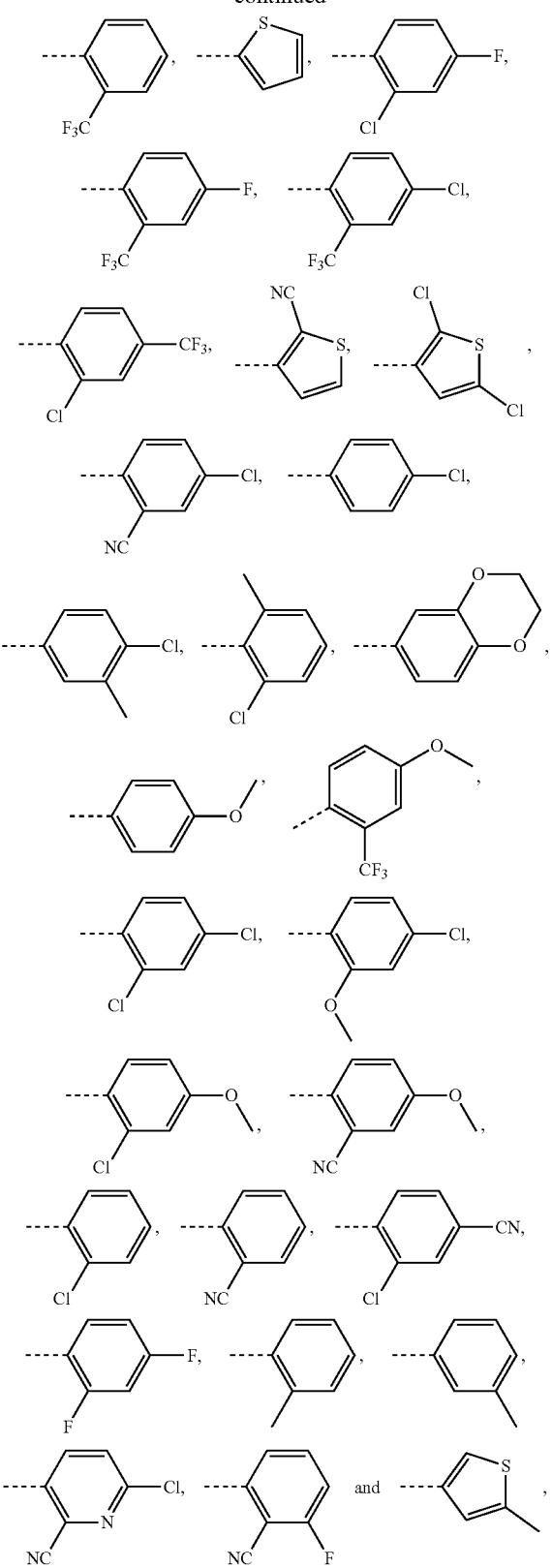

other variables are defined as above.

In some embodiments of the present invention, $R_6$ is selected from

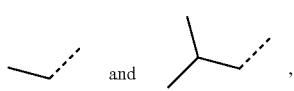

other variables are defined as above.

In some embodiments of the present invention, the moiety

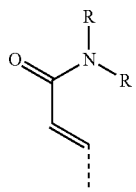

is selected from

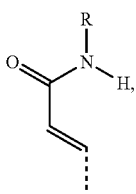

other variables are defined as above.

In some embodiments of the present invention, the moiety

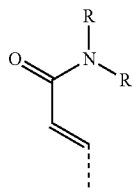

is selected from

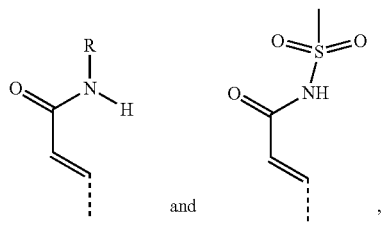

other variables are defined as above.

The above variables can be arbitrarily combined, then other embodiments of the present invention are obtained.

Advantageous Effect

The compound of the present invention is mainly used as an estrogen receptor down-regulator, which can effectively degrade the estrogen receptor and reduce its intracellular concentration, thereby blocking the estrogen signaling pathway and inhibiting the progression of related diseases. The pharmacophore of the compound of the present invention is 2-substituted indole. Compared with the prior art, the compound has a novel pharmacophore and exhibits a novel binding mode to the target. There is no hydrogen bond receptor on the left side of the structure of the compound, but the compound has an excellent intracellular estrogen receptor degradation activity. At the same time, due to the structural change, the metabolic site of the compound has been reduced, thus the compound is not easy to be metabolized inside the body and has a long half-life. The experimental data in vivo shows that compared with the prior art, the compound of the present invention has a higher exposure amount in animals, a higher drug concentration in the tumor site, and a higher plasma concentration in the brain tissue since it is easy to pass through the blood-brain barrier. The compound is expected to have a good therapeutic effect on metastatic cancer in the brain. The compound of the present invention may have a smaller clinical dose and dosing frequency than ARN-810, and it is easy to be administered and has lower toxic side effects.

DEFINITION AND DESCRIPTION

Unless otherwise indicated, the following terms and phrases used in this document are intended to have the following meanings. A specific term or phrase should not be considered indefinite or unclear in the absence of a particular definition, but should be understood in the ordinary sense. When a trade name appears herein, it is intended to refer to its corresponding commodity or active ingredient thereof.

The term "pharmaceutically acceptable" is used herein in terms of those compounds, materials, compositions, and/or dosage forms, which are suitable for use in contact with human and animal tissues within the scope of reliable medical judgment, with no excessive toxicity, irritation, allergic reaction or other problems or complications, commensurate with a reasonable benefit/risk ratio.

The term "pharmaceutically acceptable salt" refers to a salt of the compound of the present invention that is prepared by reacting the compound having a specific substituent of the present invention with a relatively non-toxic acid or base. When the compound of the present invention contains a relatively acidic functional group, a base addition salt can be obtained by bringing the neutral form of the compound into contact with a sufficient amount of base in a pure solution or a suitable inert solvent. The pharmaceutically acceptable base addition salt includes a salt of sodium, potassium, calcium, ammonium, organic amine or magnesium or similar salts. When the compound of the present invention contains a relatively basic functional group, an acid addition salt can be obtained by bringing the neutral form of the compound into contact with a sufficient amount of acid in a pure solution or a suitable inert solvent. Examples of the pharmaceutically acceptable acid addition salt include an inorganic acid salt, wherein the inorganic acid includes, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, and the like; and an organic acid salt, wherein the organic acid includes, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid, and the like; and an salt of amino acid (such as arginine and the like), and a salt of an organic acid such as glucuronic acid and the like (refer to Berge et al., "*Pharmaceutical*

Salts," *Journal of Pharmaceutical Science* 66: 1-19 (1977)). Certain specific compounds of the present invention that contain both basic and acidic functional groups can be converted to any base or acid addition salt.

Preferably, through bringing the salt into contact with a base or an acid in a conventional manner, then separating the parent compound, the neutral form of the compound is thereby regenerated. The difference between the parent form of the compound and its various salt forms lies in specific physical properties, such as different solubility in a polar solvent.

"Pharmaceutically acceptable salt" used herein belongs to a derivative of the compound of the present invention, wherein, the parent compound is modified by forming a salt with an acid or a base. Examples of the pharmaceutically acceptable salt include but are not limited to an inorganic acid or organic acid salt of a basic moiety such as amine, an alkali metal salt or an organic salt of an acidic moiety such as carboxylic acid, and the like. The pharmaceutically acceptable salt includes conventional non-toxic salt or quaternary ammonium salt of the parent compound, such as a salt formed by a non-toxic inorganic acid or an organic acid. The conventional non-toxic salt includes but is not limited to the salt derived from an inorganic acid and an organic acid, wherein the inorganic acid or organic acid is selected from the group consisting of 2-acetoxybenzoic acid, 2-hydroxyethanesulfonic acid, acetic acid, ascorbic acid, benzenesulfonic acid, benzoic acid, bicarbonate, carbonic acid, citric acid, edetic acid, ethanedisulfonic acid, ethanesulfonic acid, fumaric acid, glucoheptose, gluconic acid, glutamic acid, glycolic acid, hydrobromic acid, hydrochloric acid, hydroiodide, hydroxyl, hydroxynaphthalene, isethionic acid, lactic acid, lactose, dodecyl sulfonic acid, maleic acid, malic acid, mandelic acid, methanesulfonic acid, nitric acid, oxalic acid, pamoic acid, pantothenic acid, phenylacetic acid, phosphoric acid, polygalactanal acid, propionic acid, salicylic acid, stearic acid, subacetic acid, succinic acid, sulfamic acid, sulfanilic acid, sulfuric acid, tannin, tartaric acid and p-toluenesulfonic acid.

The pharmaceutically acceptable salt of the present invention can be prepared from the parent compound that contains an acidic or basic moiety by conventional chemical method. Generally, such salt can be prepared by reacting the free acid or base form of the compound with a stoichiometric amount of an appropriate base or acid in water or an organic solvent or a mixture thereof. Generally, non-aqueous media such as ether, ethyl acetate, ethanol, isopropanol or acetonitrile are preferred.

In addition to the salt form, the compound provided by the present invention also exists in prodrug form. The prodrug of the compound described herein is the compound that readily undergoes chemical change under physiological condition to be converted into the compound of the present invention. Additionally, the prodrug can be converted to the compound of the present invention by a chemical or biochemical method in vivo environment.

Certain compounds of the present invention can exist in an unsolvated form or a solvated form, including hydrated form. Generally, the solvated form is equivalent to the unsolvated form, and both are encompassed within the scope of the present invention.

Certain compounds of the present invention can have an asymmetric carbon atom (optical center) or a double bond. The racemate, diastereomer, geometric isomer and individual isomer are all encompassed within the scope of the present invention.

Unless otherwise specified, the absolute configuration of a stereogenic center is represented by a wedged solid bond ( ) and a wedged dashed bond ( ), a wavy line ( ) represents a wedged solid bond ( ) or a wedged dashed bond ( ), and the relative configuration of a stereogenic center is represented by a straight solid bond ( ) and a straight dashed bond ( ). When the compound described herein contains an olefinic double bond or other geometric asymmetric centers, E and Z geometric isomers are included unless otherwise specified. Likewise, all tautomeric forms are encompassed within the scope of the present invention.

The compound of the present invention may have a specific geometric or stereoisomeric form. The present invention contemplates all such compounds, including cis and trans isomer, (−)- and (+)-enantiomer, (R)- and (S)-enantiomer, diastereoisomer, (D)-isomer, (L)-isomer, and racemic mixture and other mixtures, for example, an enantiomer or diastereoisomer enriched mixture, all of which are encompassed within the scope of the present invention. The substituent such as alkyl may have an additional asymmetric carbon atom. All these isomers and mixtures thereof are encompassed within the scope of the present invention.

Optically active (R)- and (S)-isomer, or D and L isomer can be prepared using chiral synthesis or chiral reagents or other conventional techniques. If one kind of enantiomer of certain compound of the present invention is to be obtained, the pure desired enantiomer can be obtained by asymmetric synthesis or derivative action of chiral auxiliary followed by separating the resulting diastereomeric mixture and cleaving the auxiliary group. Alternatively, when the molecule contains a basic functional group (such as amino) or an acidic functional group (such as carboxyl), the compound reacts with an appropriate optically active acid or base to form a salt of the diastereomeric isomer which is then subjected to diastereomeric resolution through the conventional method in the art to give the pure enantiomer. In addition, the enantiomer and the diastereoisomer are generally isolated through chromatography which uses a chiral stationary phase and optionally combines with a chemical derivative method (for example, carbamate generated from amine).

The compound of the present invention may contain an unnatural proportion of atomic isotope at one or more than one atom(s) that constitute the compound. For example, the compound can be radiolabeled with a radioactive isotope, such as tritium ($^3H$), iodine-125 ($^{125}I$) or C-14 ($^{14}C$). All isotopic variations of the compound of the present invention, whether radioactive or not, are encompassed within the scope of the present invention.

The term "pharmaceutically acceptable carrier" refers to any agent or carrier medium which is capable of delivering an effective amount of the active substance of the present invention, does not interfere with the biological activity of the active substance and has no toxic side effect on the host or patient. The representative carrier includes water, oil, vegetable and mineral, cream base, lotion base, ointment base and the like. The base includes a suspending agent, a thickener, a penetration enhancer and the like. Their formulations are well known to the skilled in the cosmetic field or the topical pharmaceutical field. The additional information about the carrier can be referred to *Remington: The Science and Practice of Pharmacy,* 21*st Ed*, Lippincott, Williams & Wilkins (2005), the disclosure of which is incorporated herein by reference.

The term "excipient" generally refers to a carrier, a diluent and/or a medium required for formulating an effective pharmaceutical composition.

For a medicament or a pharmacologically active agent, the term "effective amount" or "therapeutically effective amount" refers to a nontoxic but sufficient amount to achieve a desired effect of the medicament or the agent. For the oral dosage form of the present invention, an "effective amount" of the active substance in the composition refers to an amount required for achieving a desired effect when combining with another active substance in the composition. The effective amount varies from person to person and is determined depending on the age and general condition of the recipient as well as the specific active substance. The appropriate effective amount in an individual case can be determined by the skilled in the art based on routine experiment.

The term "active ingredient", "therapeutic agent", "active substance" or "active agent" refers to a chemical entity which can effectively treat the target disorder, disease or condition.

"Optional" or "optionally" means that the subsequent event or condition may occur but not requisite, that the term includes the instance in which the event or condition occurs and the instance in which the event or condition does not occur.

The term "substituted" means one or more than one hydrogen atom(s) on a specific atom are substituted with the substituent, including deuterium and hydrogen variants, as long as the valence of the specific atom is normal and the substituted compound is stable. When the substituent is a ketone (i.e. =O), it means two hydrogen atoms are substituted. Positions on an aromatic ring can not be substituted with a ketone. The term "optionally substituted" means an atom can be substituted with a substituent or not, unless otherwise specified, the type and number of the substituent may be arbitrary as long as being chemically achievable.

When any variable (such as R) occurs in the constitution or structure of the compound more than once, the definition of the variable at each occurrence is independent. Thus, for example, if a group is substituted with 0-2 R, the group can be optionally substituted with up to two R, wherein the definition of R at each occurrence is independent. Moreover, a combination of the substituent and/or the variant thereof is allowed only when the combination results in a stable compound.

When the number of a linking group is 0, such as —(CRR)$_0$—, it means that the linking group is a single bond.

When one of the variable is selected from a single bond, it means that the two groups linked by the single bond are connected directly. For example, when L in A-L-Z represents a single bond, the structure of A-L-Z is actually A-Z.

When a substituent is vacant, it means that the substituent does not exist. For example, when X is vacant in A-X, the structure of A-X is actually A. When a substituent can be linked to more than one atoms on a ring, such substituent can be bonded to any atom of the ring. For example, the structural unit

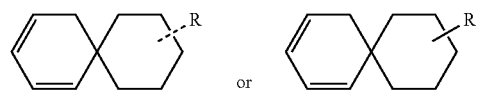

means that the substituent R can be located at any position on cyclohexyl or cyclohexadiene. When the enumerative substituent does not indicate by which atom it is linked to the group to be substituted, such substituent can be bonded by any atom thereof. For example, when pyridyl acts as a substituent, it can be linked to the group to be substituted by any carbon atom on the pyridine ring. When the enumerative linking group does not indicate the direction for linking, the direction for linking is arbitrary, for example, the linking group L contained in

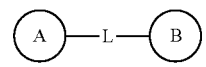

is -MW—, then -MW— can link ring A and ring B to form

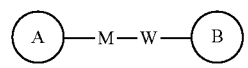

in the direction same as left-to-right reading order, and form

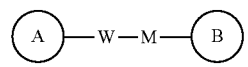

in the direction contrary to left-to-right reading order. A combination of the linking group, substituent and/or variants thereof is allowed only when such combination can result in a stable compound.

Unless otherwise specified, the term "hetero" represents a heteroatom or a heteroatom group (e.g., an atom group containing a heteroatom), including the atom except carbon (C) and hydrogen (H) and the atom group containing the above heteroatom, for example, including oxygen (O), nitrogen (N), sulfur (S), silicon (Si), germanium (Ge), aluminum (Al), boron (B), —O—, —S—, =O, =S, —C(=O)O—, —C(=O)—, —C(=S)—, —S(=O), —S(=O)$_2$—, and the group consisting of —C(=O)N(H)—, —N(H)—, —C(=NH)—, —S(=O)$_2$N(H)— and —S(=O)N(H)—, each of which is optionally substituted.

Unless otherwise specified, the term "ring" refers to a substituted or unsubstituted cycloalkyl, heterocycloalkyl, cycloalkenyl, heterocycloalkenyl, cycloalkynyl, heterocycloalkynyl, aryl or heteroaryl. The so-called ring includes a single ring, a ring assembly, a spiral ring, a fused ring or a bridged ring. The number of the atom on the ring is usually defined as the member number of the ring, for example, a "5-7 membered ring" means that 5 to 7 atoms are arranged on a ring. Unless otherwise specified, the ring optionally contains 1 to 3 heteroatoms. Therefore, a "5-7 membered ring" includes, for example, phenyl, pyridinyl and piperidinyl; on the other hand, the term "5-7 membered heterocycloalkyl ring" includes pyridyl and piperidinyl, but excluding phenyl. The term "ring" also includes a ring system containing at least one ring, wherein each ring independently meets the above definition.

Unless otherwise specified, the term "heterocycle" or "heterocyclo" refers to a stable monocyclic, bicyclic or tricyclic ring containing a heteroatom or a heteroatom group, which can be saturated, partially unsaturated or unsaturated (aromatic) and can contain carbon atoms and 1, 2, 3 or 4 ring heteroatoms independently selected from N, O and S, wherein any of the above heterocycle can be fused to a benzene ring to form a bicyclic ring. Nitrogen and sulfur heteroatoms can optionally be oxidized (i.e., NO and S(O)p, p is 1 or 2). Nitrogen atom can be substituted or unsubstituted (i.e., N or NR, wherein R is H or other substituents already defined herein). The heterocycle can be attached to the pendant group of any heteroatom or carbon atom to form a stable structure. If the resulting compound is stable, the heterocycle described herein may have a substitution at a carbon or nitrogen position. Nitrogen atom on the heterocycle is optionally quaternized. In a preferred embodiment, when the total number of S and O atom of the heterocycle is more than 1, the heteroatom is not adjacent to each other. In another preferred embodiment, the total number of S and O atom of the heterocycle is not more than 1. As used herein, the term "aromatic heterocyclic group" or "heteroaryl" refers to a stable 5-, 6- or 7-membered monocyclic or bicyclic or 7-, 8-, 9- or 10-membered bicyclic heterocyclic aromatic ring which contains carbon atoms and 1, 2, 3 or 4 ring heteroatoms independently selected from N, O and S. Nitrogen atom can be substituted or unsubstituted (i.e., N or NR, wherein R is H or other substituents already defined herein). Nitrogen and sulfur heteroatoms may optionally be oxidized (i.e., NO and S(O)p, p is 1 or 2). It is worth noting that the total number of S and O atom of an aromatic heterocycle is not more than one. The bridged ring is also included in the definition of the heterocycle. A bridged ring is formed when one or more than one atom (i.e, C, O, N or S) link two non-adjacent carbon or nitrogen atoms. A preferred bridged ring includes, but not limited to one carbon atom, two carbon atoms, one nitrogen atom, two nitrogen atoms and one carbon-nitrogen group. It is worth noting that a bridge always converts a monocyclic ring to a tricyclic ring. In a bridged ring, the substituent on the ring may also be present on the bridge.

Examples of the heterocyclic compound include, but are not limited to: acridinyl, azocinyl, benzimidazolyl, benzofuranyl, benzomercaptofuranyl, benzomercaptophenyl, benzoxazolyl, benzoxazolinyl, benzothiazolyl, benzotriazolyl, benzotetrazolyl, benzoisoxazolyl, benzoisothiazolyl, benzoimidazolinyl, carbazolyl, 4aH-carbazolyl, carbolinyl, chromanyl, chromene, cinnolinyl decahydroquinolinyl, 2H,6H-1,5,2-dithiazinyl, dihydrofuro[2,3-b]tetrahydrofuranyl, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isoindolyl, isoindolinyl, isoquinolinyl, isothiazolyl, isoxazolyl, methylenedioxyphenyl, morpholinyl, naphthyridinyl, octahydro-isoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, hydroxindolyl, pyrimidinyl, phenanthridinyl, phenanthrolinyl, phenazine, phenothiazine, benzoxanthinyl, phenoloxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyrido-oxazolyl, pyrido-imidazolyl, pyrido-thiazolyl, pyridinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, isothiazolylthienyl, thienyl, thieno-oxazolyl, thieno-thiazolyl, thieno-imidazolyl, thienyl, triazinyl, 1H-1,2,3-triazolyl, 2H-1,2,3-triazolyl, 1H-1,2,4-triazolyl, 4H-1,2,4-triazolyl, and xanthenyl. Also included are fused-ring compounds and spiro compounds.

Unless otherwise specified, the term "hydrocarbyl" or its hyponyms (e.g. alkyl, alkenyl, alkynyl, and aryl, etc.), by itself or as part of another substituent, refers to a linear, branched chain or cyclic hydrocarbon radical or any combination thereof. They can be fully saturated (e.g. alkyl), mono- or polyunsaturated (e.g. alkenyl, alkynyl, and aryl), can be mono-, di- or poly-substituted, can be monovalent (e.g. methyl), divalent (e.g. methylene) or multivalent (e.g. methenyl), can also include a divalent or multivalent group, have a specified number of carbon atom (for example, $C_1$-$C_{12}$ indicates 1 to 12 carbon atoms, $C_{1-12}$ is selected from $C_1$, $C_2$, $C_3$, $C_4$, $C_5$, $C_6$, $C_7$, $C_8$, $C_9$, $C_{10}$, $C_{11}$ and $C_{12}$; $C_{3-12}$ is selected from $C_3$, $C_4$, $C_5$, $C_6$, $C_7$, $C_8$, $C_9$, $C_{10}$, $C_{11}$ and $C_{12}$). The term "hydrocarbyl" includes, but is not limited to aliphatic hydrocarbyl and aromatic hydrocarbyl. The aliphatic hydrocarbyl includes linear and cyclic hydrocarbyl, specifically includes but not limited to alkyl, alkenyl, and alkynyl. The aromatic hydrocarbyl includes but is not limited to 6-12 membered aromatic hydrocarbyl such as phenyl, naphthyl and the like. In some embodiments, the term "hydrocarbyl" refers to a linear or branched group or a combination thereof which can be fully saturated, mono- or polyunsaturated, and can include a divalent or multivalent group. Examples of the saturated hydrocarbyl group include, but are not limited to, methyl, ethyl, n-propyl, isopropyl, n-butyl, tert-butyl, isobutyl, sec-butyl, cyclohexyl, (cyclohexyl)methyl, cyclopropylmethyl, and the homolog or isomer of n-amyl, n-hexyl, n-heptyl, n-octyl and other atom groups. The unsaturated hydrocarbyl has one or more than one double or triple bonds. Examples of the unsaturated alkyl include but are not limited to, vinyl, 2-propenyl, butenyl, crotyl, 2-isopentenyl, 2-(butadienyl), 2,4-pentadienyl, 3-(1,4-pentadienyl), ethynyl, 1- and 3-propynyl, 3-butynyl, and more higher homologs and isomers.

Unless otherwise specified, the term "heterohydrocarbyl" or its hyponyms (such as heteroalkyl, heteroalkenyl, heteroalkynyl, and heteroaryl, etc.), by itself or as part of another substituent, refers to a stable linear, branched or cyclic hydrocarbon group or any combination thereof, which has a specified number of carbon atoms and at least one heteroatom. In some embodiments, the term "heteroalkyl" by itself or in combination with another term refers to a stable linear chain, branched hydrocarbon radical or a combination thereof which has a specified number of carbon atoms and at least one heteroatom. In a specific embodiment, a heteroatom is selected from B, O, N and S, wherein nitrogen and sulfur atoms are optionally oxidized and the nitrogen atom is optionally quaternized. The heteroatom or heteroatom group can be located at any interior position of a heterohydrocarbyl, including the position where the hydrocarbyl attaches to the rest part of the molecule. But the terms "alkoxy", "alkylamino" and "alkylthio" (or thioalkyl) are used by the conventional meaning and refer to an alkyl group connected to the rest part of the molecule via an oxygen atom, an amino or a sulfur atom respectively. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —CH$_2$—CH=N—OCH$_3$ and —CH=CH—N(CH$_3$)—CH$_3$. Up to two consecutive heteroatoms can be present, such as, —CH$_2$—NH—OCH$_3$.

Unless otherwise specified, the term "cyclohydrocarbyl", "heterocyclohydrocarbyl" or its hyponyms (such as aryl, heteroaryl, cycloalkyl, heterocycloalkyl, cycloalkenyl, heterocycloalkenyl, cycloalkynyl, heterocycloalkynyl, etc.) by itself or in combination with another term refers to cyclized "hydrocarbyl" or "heterohydrocarbyl". Furthermore, for heterohydrocarbyl or heterocyclohydrocarbyl (e.g. heteroalkyl, and heterocycloalkyl), one heteroatom can occupy the position where the heterocycle attaches to the remainder position of the molecule. Examples of the cycloalkyl include, but are not limited to, cyclopentyl, cyclohexyl, 1-cyclohexenyl, 3-cyclohexenyl, cycloheptyl and the like. Non-limiting examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydro-thiophen-2-yl, tetrahydro-thiophen-3-yl, 1-piperazinyl and 2-piperazinyl.

Unless otherwise specified, the term "alkyl" refers to a linear chain or branched saturated hydrocarbon group, can be mono-substituted (e.g. —$CH_2F$) or poly-substituted (e.g. —$CF_3$), can be monovalent (e.g. methyl), divalent (e.g. methylene) or multivalent (e.g. methenyl). Examples of alkyl include methyl (Me), ethyl (Et), propyl (such as n-propyl and isopropyl), butyl (such as n-butyl, isobutyl, s-butyl, t-butyl), pentyl (such as n-pentyl, isopentyl, neo-pentyl) and the like.

Unless otherwise specified, the term "alkenyl" refers to an alkyl group having one or more than one carbon-carbon double bonds at any position on the chain, can be mono-substituted or poly-substituted, and can be monovalent, divalent or multivalent. Examples of alkenyl include ethenyl, propenyl, butenyl, pentenyl, hexenyl, butadienyl, pentadienyl, hexadienyl, and the like.

Unless otherwise specified, the term "alkynyl" refers to an alkyl group having one or more than one carbon-carbon triple bonds at any position on the chain, can be mono-substituted or poly-substituted, and can be monovalent, divalent or multivalent. Examples of alkynyl include ethynyl, propynyl, butynyl, pentynyl, hexynyl, and the like.

Unless otherwise specified, cycloalkyl includes any stable cyclic or polycyclic hydrocarbyl, and any carbon atom is saturated, can be mono-substituted or poly-substituted, and can be monovalent, divalent or multivalent. Examples of cycloalkyl include, but are not limited to, cyclopropyl, norbornanyl, [2.2.2]bicyclooctane, [4.4.0]bicyclodecanyl and the like.

Unless otherwise specified, cycloalkenyl includes any stable cyclic or polycyclic hydrocarbyl having one or more than one unsaturated carbon-carbon single bonds at any position on the ring, can be mono-substituted or poly-substituted, and can be monovalent, divalent or multivalent. Examples of the cycloalkenyl include, but are not limited to, cyclopentenyl, cyclohexenyl and the like.

Unless otherwise specified, cycloalkynyl includes any stable cyclic or polycyclic hydrocarbyl having one or more carbon-carbon triple bonds at any position on the ring, can be mono-substituted or poly-substituted, and can be monovalent, divalent or multivalent.

Unless otherwise specified, the term "halo" or "halogen" by itself or as part of another substituent refers to fluorine, chlorine, bromine or iodine atom. Furthermore, the term "haloalkyl" is meant to include monohaloalkyl and polyhaloalkyl. For example, the term "halo($C_1$-$C_4$)alkyl" is meant to include, but not limited to, trifluoromethyl, 2,2,2-trifluoroethyl, 4-chlorobutyl, 3-bromopropyl and the like. Examples of haloalkyl include, but not limited to trifluoromethyl, trichloromethyl, pentafluoroethyl and pentachloroethyl.

The term "alkoxy" represents any alkyl defined above having a specified number of carbon atoms attached by an oxygen bridge. Unless otherwise specified, $C_{1-6}$ alkoxy includes $C_1$, $C_2$, $C_3$, $C_4$, $C_5$ and $C_6$ alkoxy. Examples of alkoxy include, but not limited to methoxy, ethoxy, n-propoxy, isopropoxy, n-butoxy, sec-butoxy, tert-butoxy, n-pentyloxy and S-pentyloxy.

Unless otherwise specified, the term "aryl" refers to a polyunsaturated aromatic substituent, can be mono-, di- or poly-substituted, can be a monovalent, divalent or multivalent, can be a single ring or a multiple ring (e.g. one to three rings; wherein at least one ring is aromatic), which are fused together or connected covalently. The term "heteroaryl" refers to an aryl (or ring) containing one to four heteroatoms. In an illustrative example, the heteroatom is selected from B, O, N and S, wherein nitrogen and sulfur atoms are optionally oxidized and nitrogen atom is optionally quaternized. A heteroaryl may attach to the rest part of a molecule via a heteroatom. Non-limiting examples of aryl or heteroaryl include phenyl, naphthyl, biphenyl, pyrrolyl, pyrazolyl, imidazolyl, pyrazinyl, oxazolyl, phenyl-oxazolyl, isoxazolyl, thiazolyl, furanyl, thienyl, pyridyl, pyrimidinyl benzothiazolyl, purinyl, benzimidazolyl, indolyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl and 6-quinolyl. The substituent of any of the above aryl and heteroaryl ring system is selected from the acceptable substituent described below.

Unless otherwise specified, when combined with other terms (such as aryloxy, arylthio, arylalkyl), the aryl includes the aryl and heteroaryl ring as defined above. Thus, the term "aralkyl" is meant to include the group (e.g. benzyl, phenethyl, pyridylmethyl, etc.) where an aryl is attached to an alkyl, including an alkyl where the carbon atom (e.g. methylene) has been replaced by an atom such as oxygen, for example, phenoxymethyl, 2-pyridyloxy, 3-(1-naphthyloxy) propyl, and the like.

The term "leaving group" refers to a functional group or atom which can be replaced by another functional group or atom through a substitution reaction (such as affinity substitution reaction). For example, representative leaving groups include triflate; chlorine, bromine and iodine; sulfonate group, such as mesylate, tosylate, p-bromobenzenesulfonate, p-toluenesulfonates and the like; acyloxy, such as acetoxy, trifluoroacetoxy and the like.

The term "protecting group" includes, but is not limited to "amino protecting group", "hydroxy protecting group" or "thio protecting group". The term "amino protecting group" refers to a protecting group suitable for blocking the side reaction on the nitrogen of an amino. Representative amino protecting groups include, but are not limited to: formyl; acyl, such as alkanoyl (e.g. acetyl, trichloroacetyl or trifluoroacetyl); alkoxycarbonyl, such as tert-butoxycarbonyl (Boc); arylmethoxycarbonyl such as benzyloxycarbonyl (Cbz) and 9-fluorenylmethoxycarbonyl (Fmoc); arylmethyl such as benzyl (Bn), trityl (Tr), 1,1-bis-(4'-methoxyphenyl) methyl; silyl such as trimethylsilyl (TMS) and tert-butyldimethylsilyl (TBS) and the like. The term "hydroxy protecting group" refers to a protecting group suitable for blocking the side reaction on hydroxy. Representative hydroxy protecting groups include, but are not limited to: alkyl such as methyl, ethyl and tert-butyl; acyl such as alkanoyl (e.g. acetyl); arylmethyl such as benzyl (Bn), p-methoxybenzyl (PMB), 9-fluorenylmethyl (Fm), and diphenylmethyl (benzhydryl, DPM); silyl such as trimethylsilyl (TMS) and tert-butyl dimethyl silyl (TBS) and the like.

The compound of the present invention can be prepared by a variety of synthetic methods well known to the skilled in the art, including the following enumerative embodiment, the embodiment formed by the following enumerative embodiment in combination with other chemical synthesis methods and the equivalent replacement well known to the skilled in the art. The preferred embodiment includes, but is not limited to the embodiment of the present invention.

All of the solvents used in the present invention are commercially available. The reaction was generally carried out in an anhydrous solvent under inert nitrogen atmosphere. Proton nuclear magnetic resonance data was recorded on a Bruker Avance III 400 (400 MHz) spectrometer, and the chemical shift was represented by δ (ppm) at the low field of tetramethylsilane. The mass spectrum was measured on the Agilent 1200 Series Plus 6110 (&1956A). LC/MS or Shimadzu MS contains a DAD: SPD-M20A (LC) and Shimadzu Micromass 2020 detector. The mass spectrometer is equipped with an electrospray ion source (ESI) operating in positive or negative mode.

The present invention employs the following abbreviations: eq represents equivalent or equal; DCM represents dichloromethane; PE represents petroleum ether; DMF represents N,N-dimethylformamide; DMSO represents dimethyl sulfoxide; EtOAc or EA represents ethyl acetate; EtOH represents ethanol; MeOH represents methanol; Cbz represents benzyloxycarbonyl, which is an amine protecting group; Boc represents tert-butylcarbonyl, which is an amine protecting group; THF represents tetrahydrofuran; $Boc_2O$ represents di-tert-butyl dicarbonate; DBU represents 1,8-diazabicyclo[5.4.0]undec-7-ene; NBS represents N-bromosuccinamide; NCS represents N-chlorosuccinamide; HMPA represents hexamethylphosphoramide; LDA represents lithium diisopropylamide; DPPF or dppf represents bis(diphenylphosphino)ferrocene; MeCN represents acetonitrile; $BBr_3$ represents boron tribromide; Ad2nBuP represents di(adamantan-1-yl)(butyl)phosphine.

High performance liquid chromatography analysis was performed on a Shimadzu LC20AB system equipped with a Shimadzu SIL-20A autosampler and a Shimadzu DAD of SPD-M20A detector. The column used was a Xtimate C18, 3 μm, 2.1×300 mm. Method 0-60AB_6 min: a linear gradient was used, starting at 100% A (A: 0.0675% TFA in water) and ending at 60% B (B: 0.0625% TFA in MeCN) over 4.2 min, followed by additional 1 min elution with 60% B. The column was then re-equilibrated for 0.8 min to 100:0 with a total run time of 6 min. Method 10-80AB_6 min: a linear gradient is applied, starting at 90% A (A: 0.0675% TFA in water) and ending at 80% B (B: 0.0625% TFA in MeCN) over 4.2 min, followed by additional 1 min elution with 80% B. The column was then re-equilibrated for 0.8 min to 90:10 with a total run time of 6 min. Column temperature was 50° C., flow rate was 0.8 mL/min. The Diode Array Detector was scanned from 200-400 nm.

Thin layer chromatography (TLC) was performed on Sanpont-group GF254 silica gel plate. Spots were usually visualized by UV-irradiation, and other methods for visualizing spots on TLC plate were also used. In these methods, $I_2$ (1 g $I_2$ thoroughly mixed in 10 g silica gel), vanillin (1 g vanillin dissolved in 100 mL 10% $H_2SO_4$), ninhydrin (supplied by Aldrich), or a special reagent (25 g $(NH_4)_6Mo_7O_{24} \cdot 4H_2O$ and 5 g $(NH_4)_2Ce(IV)(NO_3)_6$ dissolved in 450 mL $H_2O$ and 50 mL conc.$H_2SO_4$) was used to visualize the compound spots. Flash column chromatography was performed on Silicycle 40-63 μm (230-400 mesh) silica gel, by the similar methods disclosed by Still, W. C.; Kahn, M; Mitra, M. *J. Org. Chem.* 1978, 43, 2923-2925. Eluent of flash column chromatography or TLC included mixed solvents of dichloromethane/methanol, ethyl acetate/methanol or ethyl acetate/n-hexane.

Preparative chromatography analysis was performed on Gilson-281 Prep LC 322 system with Gilson UV/VIS-156 detector. Column was Agella Venusil ASB Prep C18, 5 μm, 150×21.2 mm, Phenomenex Gemini C18, 5 μm, 150×30 mm, Boston Symmetrix C18, 5 μm, 150×30 mm, or Phenomenex Synergi C18, 4 μm, 150×30 mm. At a flow rate of about 25 mL/min, the compound was eluted with MeCN/$H_2O$ with a low gradient, wherein the water contained 0.05% HCl, 0.25% HCOOH or 0.5% $NH_3 \cdot H_2O$, and the total run time was 8-15 min.

SFC analysis was performed on an Agilent 1260 Infinity SFC system equipped with an Agilent 1260 autosampler and an Agilent DAD of 1260 detector. The column used was Chiralcel OD-H 250×4.6 mm I.D., 5 μm or Chiralpak AS-H 250×4.6 mm I.D., 5 μm or Chiralpak AD-H 250×4.6 mm I.D., 5 μm. Method OD-H_5_40_2.35 ML column was Chiralcel OD-H 250×4.6 mm I.D., 5 μm, mobile phase was 40% ethanol (0.05% DEA) in $CO_2$, flow rate was 2.35 mL/min, wavelength was 220 nm. Method AS-H_3_40_2.35 ML: column was Chiralpak AS-H 250×4.6 mm I.D., 5 μm, mobile phase was 40% methanol (0.05% DEA) in $CO_2$, flow rate was 2.35 mL/min, wavelength was 220 nm. Method OD-H_3_40_2.35M: column was Chiralcel OD-H 250×4.6 mm I.D., 5 μm, mobile phase was 40% methanol (0.05% DEA) in $CO_2$, flow rate was 2.35 mL/min, wavelength was 220 nm. Method AD-H_2_50_2.35 ML: column was Chiralpak AD-H 250×4.6 mm I.D., 5 μm, mobile phase was 50% methanol (0.1% MEA) in $CO_2$, flow rate was 2.35 mL/min, wavelength was 220 nm.

Preparative SFC analysis was performed on a Waters Thar 80 Pre-SFC System with a Gilson UV detector. The column used was Chiralcel OD-H 250×4.6 mm I.D., 5 μm or Chiralpak AD-H 250×4.6 mm I.D., 5 μm. A mobile phase of ethanol in $CO_2$ or methanol in $CO_2$ with a low gradient was used to elute the compound at a flow rate between 40-80 mL/min, wherein the ethanol or methanol contained 0.05% $NH_3 \cdot H_2O$ or 0.05% DEA or 0.1% MEA, and the total run time was 20-30 min.

Compounds are named manually or by ChemDraw® software, the commercially available compounds use their vendor directory names.

DETAILED DESCRIPTION OF THE PREFERRED EMBODIMENT

The present invention will be specifically described below by way of embodiments, but the scope of the present invention is not limited thereto.

It will be appreciated by the skilled in the art that the order of the reaction step in any reaction scheme may be varied in order to prepare the compound of the present invention, which is also encompassed within the scope of the invention.

Embodiment 1
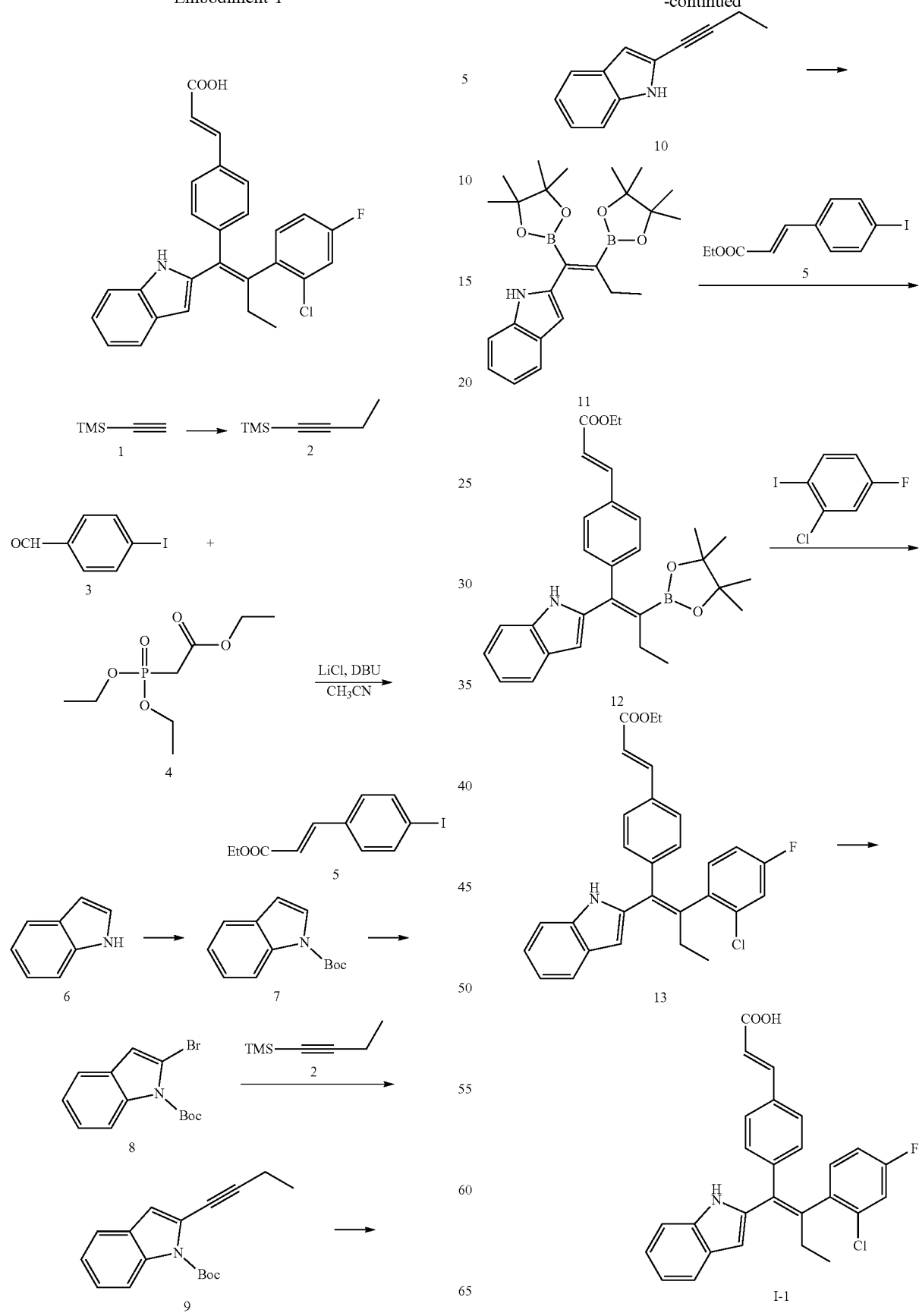

Step A: N-butyllithium (2.5M, 428.40 mL, 1.05 eq) was slowly added dropwise to a solution of 1 (100.00 g, 1.02 mol, 140.85 mL, 1.00 eq) in tetrahydrofuran (500 mL) over 1 hour at −75° C. under nitrogen atmosphere. The reaction solution was allowed to warm to 0° C. and stirred for 10 minutes, then cooled to −75° C., and hexamethylphosphoric triamide (201.06 g, 1.12 mol, 197.12 mL, 1.10 eq) was added over 1 hour. After the reaction solution was stirred at −75° C. for 1 hour, ethyl iodide (198.86 g, 1.27 mol, 101.98 mL, 1.25 eq) was added over 1 hour. The reaction solution was allowed to warm to 20° C. and stirred for 10 hours. Then 400 mL water was added, and the mixture was partitioned. The organic phase was washed three times with 400 mL water, dried over anhydrous sodium sulfate, filtered and purified by distillation to give the product 2 as a colorless liquid (65.00 g, 514.77 mmol, yield 50.47%).

Step B: Triethyl phosphonoacetate 4 (11.60 g, 51.72 mmol, 10.26 mL, 1.20 eq) and lithium chloride (3.65 g, 86.20 mmol, 1.77 mL, 2.00 eq) were added to a solution of 3 (10.00 g, 43.10 mmol, 1.00 eq) in 100 mL acetonitrile, then a solution of DBU (8.53 g, 56.03 mmol, 8.45 mL, 1.30 eq) in acetonitrile was added dropwise over 30 min at 0° C. under nitrogen atmosphere. After the reaction solution was stirred at 15° ° C. for 1 hour, 100 mL water was added, and the mixture was partitioned. The aqueous phase was extracted twice with 70 mL dichloromethane. The organic phase was combined, dried over anhydrous sodium sulfate, filtered and concentrated to give a crude product, which was purified by silica gel column chromatography (PE:EA=100:1-30:1) to give the product 5 as a yellow solid (12.00 g, 39.72 mmol, yield 92.16%).

Step C: Dimethylaminopyridine (3.65 g, 29.88 mmol, 0.10 eq) and Boc$_2$O (68.46 g, 313.70 mmol, 72.07 mL, 1.05 eq) were added to a solution of 6 (35.00 g, 298.76 mmol, 1.00 eq) in 400 mL dichloromethane. The reaction solution was stirred at 20° C. for 12 hours, then washed twice with 400 mL aqueous ammonium chloride solution. The organic phase was dried over anhydrous sodium sulfate, filtered and concentrated to give the product 7 as a colorless oil (60.00 g, 276.17 mmol, yield 92.44%).

Step D: Lithium diisopropylamide (2M, 75.95 mL, 1.10 eq) was slowly added dropwise to a solution of 7 (30.00 g, 138.08 mmol, 1.00 eq) in tetrahydrofuran (400 mL) at −75° C. under nitrogen atmosphere. The reaction solution was stirred at −75° C. for 30 minutes, then cyanogen bromide (55.40 g, 523.04 mmol, 38.47 mL, 3.79 eq) was added. The reaction solution was allowed to warm to 15° C. and stirred for 12 hours, then 400 mL water was added. After the mixture was partitioned, the organic phase was washed three times with 300 mL water, dried over anhydrous sodium sulfate and filtered to give a crude product, which was purified by silica gel column chromatography (PE:EA=1:0-50:1) to give the product 8 as a yellow oil (39.00 g, crude product).

Step E: Cesium carbonate (85.81 g, 263.38 mmol, 2.00 eq), cuprous iodide (1.25 g, 6.58 mmol, 0.05 eq), palladium acetate (1.48 g, 6.58 mmol, 0.05 eq) and 1,1'-bis(diphenylphosphino)ferrocene (3.65 g, 6.58 mmol, 0.05 eq) were added to a solution of 8 (39.00 g, 131.69 mmol, 1.00 eq) in 300 mL N,N-dimethylacetamide, followed by addition of 2 (33.26 g, 263.38 mmol, 2.00 eq) under nitrogen atmosphere. The reaction solution was stirred at 80° C. for 12 hours, then 1 L ethyl acetate and 1 L water were added. After the mixture was filtered and partitioned, the organic phase was washed three times with 1 L water, dried over anhydrous sodium sulfate, filtered and concentrated to give a crude product, which was purified by silica gel column chromatography (PE:EA=1:0-30:1) to give the product 9 as a yellow oil (27.00 g, crude product).

Step F: Potassium carbonate (69.27 g, 501.25 mmol, 5.00 eq) was added to a solution of 9 (27.00 g, 100.25 mmol, 1.00 eq) in 300 mL methanol and 15 mL water. The reaction solution was stirred at 70° C. for 12 hours, then filtered and concentrated. 300 mL ethyl acetate was added and washed twice with 300 mL water. The organic layer was dried over anhydrous sodium sulfate, filtered and concentrated to give a crude product, which was purified by silica gel column chromatography (PE:EA=100:1-30:1) to give the product 10 as a yellow solid (7.50 g, 44.32 mmol, yield 44.21%). MS [ESI, M+1]: 170.1.

Step G: diboron pinacol ester (4.50 g, 17.73 mmol, 1.00 eq) and tetrakis(triphenylphosphine)platinum (1.10 g, 886.50 umol, 0.05 eq) were added to a solution of 5 (3.00 g, 17.73 mmol, 1.00 eq) in 30 mL dimethyltetrahydrofuran. The reaction solution was stirred at 70° C. under nitrogen atmosphere for 5 hours, and then cooled to room temperature. The product 6 contained in the reaction solution was used in the next step without purification.

Step H: Cesium carbonate (11.55 g, 35.44 mmol, 2.00 eq), compound 5 (4.28 g, 14.18 mmol, 0.80 eq) and bis(triphenylphosphine)palladium dichloride (622.02 mg, 886.00 umol, 0.05 eq) were added to a solution of 10 (7.50 g, 17.72 mmol, 1.00 eq) in 70 mL dimethyltetrahydrofuran and 3 mL water. The reaction solution was stirred at 15° C. under nitrogen atmosphere for 12 hours. The product 11 contained in the reaction solution was used in the next step without purification.

Step I: 2-Chloro-4-fluoroiodobenzene (9.03 g, 35.22 mmol, 2.00 eq), potassium hydroxide solution (4M, 22.01 mL, 5.00 eq) and bis(triphenylphosphine)palladium dichloride (617.94 mg, 880.50 umol, 0.05 eq) were added to a solution of 11 (8.30 g, 17.61 mmol, 1.00 eq) in 100 mL dimethyltetrahydrofuran. The reaction solution was stirred at 70° C. under nitrogen atmosphere for 12 hours, then filtered through celite, and the filtrate was washed twice with 100 mL brine. The organic phase was dried over anhydrous sodium sulfate, filtered and concentrated to give a crude product, which was purified by silica gel column chromatography (PE:EA=40: 1-10:1) to give the product 13 as a yellow solid (4.50 g, 5.57 mmol, yield 31.65%, purity 58.7%). MS [ESI, M+1]: 474.3.

Step J: Lithium hydroxide (1.33 g, 55.73 mmol, 10.00 eq) was added to a solution of 13 (4.50 g, 5.57 mmol, 1.00 eq) in a mixed solvent of 30 mL methanol, 30 mL tetrahydrofuran and 10 mL water. The reaction solution was stirred at 35° ° C. for 1 hour, then 30 mL water was added. The reaction solution was adjusted to pH 5 with 1M hydrochloric acid, then extracted twice with 50 mL ethyl acetate. The organic phase was combined, washed twice with 60 mL water, dried over anhydrous sodium sulfate, filtered and concentrated to give a crude product, which was purified by preparative HPLC (formic acid system) to give the product I-1 (2.10 g, 4.69 mmol, yield 84.13%, purity 99.5%). MS [ESI, M+1]: 446.1.

$^1$H NMR EW3644-175-P1B (400 MHz, DMSO-d$_6$):δ 12.34 (s, 1H), 10.75 (s, 1H), 7.56 (d, J=7.6 Hz, 1H), 7.47-7.42 (m, 3H), 7.36 (dd, J=8.8 Hz, J=1.6 Hz, 1H), 7.30 (d, J=8.0 Hz, 1H), 7.25 (dd, J=8.8 Hz, J=6.4 Hz, 1H), 7.12 (dt, J=2.4 Hz, J=8.4 Hz, 1H), 7.06 (t, J=7.6 Hz, 1H), 7.01-6.96 (m, 3H), 6.57 (s, 1H), 6.41 (d, J=16.0 Hz, 1 H), 2.71-2.59 (m, 2 H), 0.99 (t, J=7.2 Hz, 3 H).

Embodiment 2

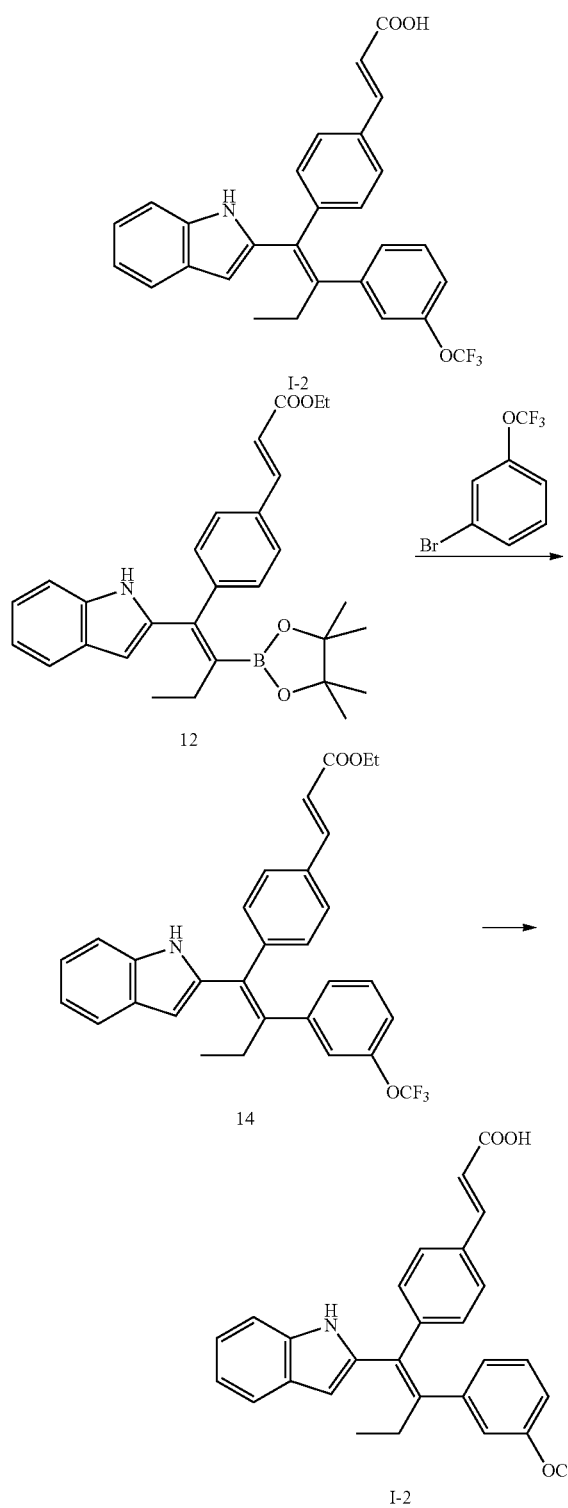

Step A: A solution of compound 12 (556.08 mg, 1.18 mmol, 1.00 eq), 3-trifluoromethoxybromobenzene (572.85 mg, 2.11 mmol, 1.80 eq), aqueous potassium hydroxide solution (4M, 1.64 mL, 5.60 eq), dichlorobis(triphenylphosphine)palladium (24.64 mg, 35.10 umol, 0.03 eq) in 20 mL 2-methyltetrahydrofuran was purged with nitrogen for three times. The reaction solution was stirred at 80° C. under nitrogen atmosphere for 24 hours, then diluted with 20 mL water, extracted twice with 50 mL ethyl acetate each time. The organic phase was combined, washed once with 50 mL saturated brine, dried over anhydrous sodium sulfate, filtered, concentrated, and purified by column chromatography to give the compound 14 as a yellow oil (200.00 mg), which was directly used in the next step.

Step B: Lithium hydroxide monohydrate (83.00 mg, 1.98 mmol, 5.00 eq) was added to a solution of compound 14 (200.00 mg, 408.56 umol, 1.00 eq) in 20 mL methanol and 6 mL water, the reaction solution was stirred at 30° C. for 3 hours, then poured into 100 mL water. The mixture was adjusted to pH 5-6 with 3 mol/L hydrochloric acid, then extracted twice with 100 mL dichloromethane each time. The organic phase was combined, dried over anhydrous sodium sulfate, filtrated and concentrated to give a crude product, which was purified by preparative chromatography (formic acid) to give I-2 (22.00 mg, 46.08 umol, yield 11.65%). MS [ESI, M+1]: 478.1.

$^1$H NMR (400 MHz, DMSO-$d_6$) δ 10.78 (br. s., 1H), 7.55 (d, J=7.2 Hz, 1H), 7.50-7.27 (m, 5H), 7.23 (d, J=7.6 Hz, 1H), 7.14 (d, J=7.6 Hz, 1H), 7.10-6.85 (m, 5H), 6.54 (br. s., 1H), 6.42 (d, J=16.0 Hz, 1H), 2.65-2.78 (m, 2H), 0.98 (t, J=6.8 Hz, 3H).

Embodiment 3

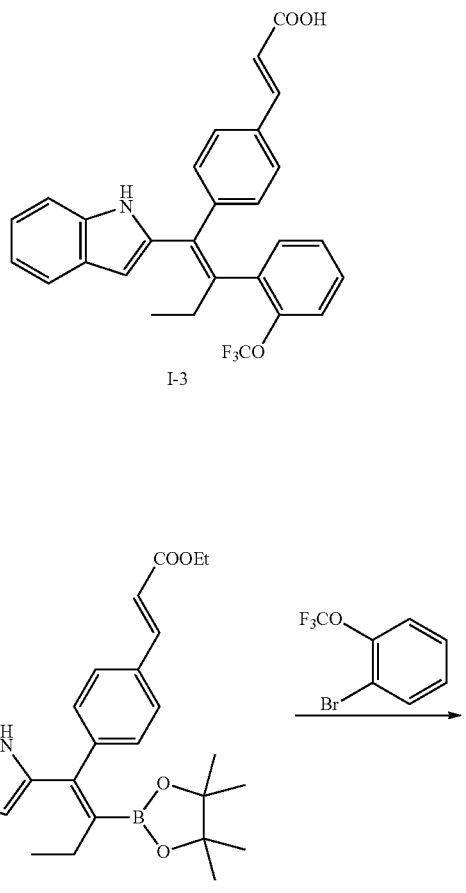

53

-continued

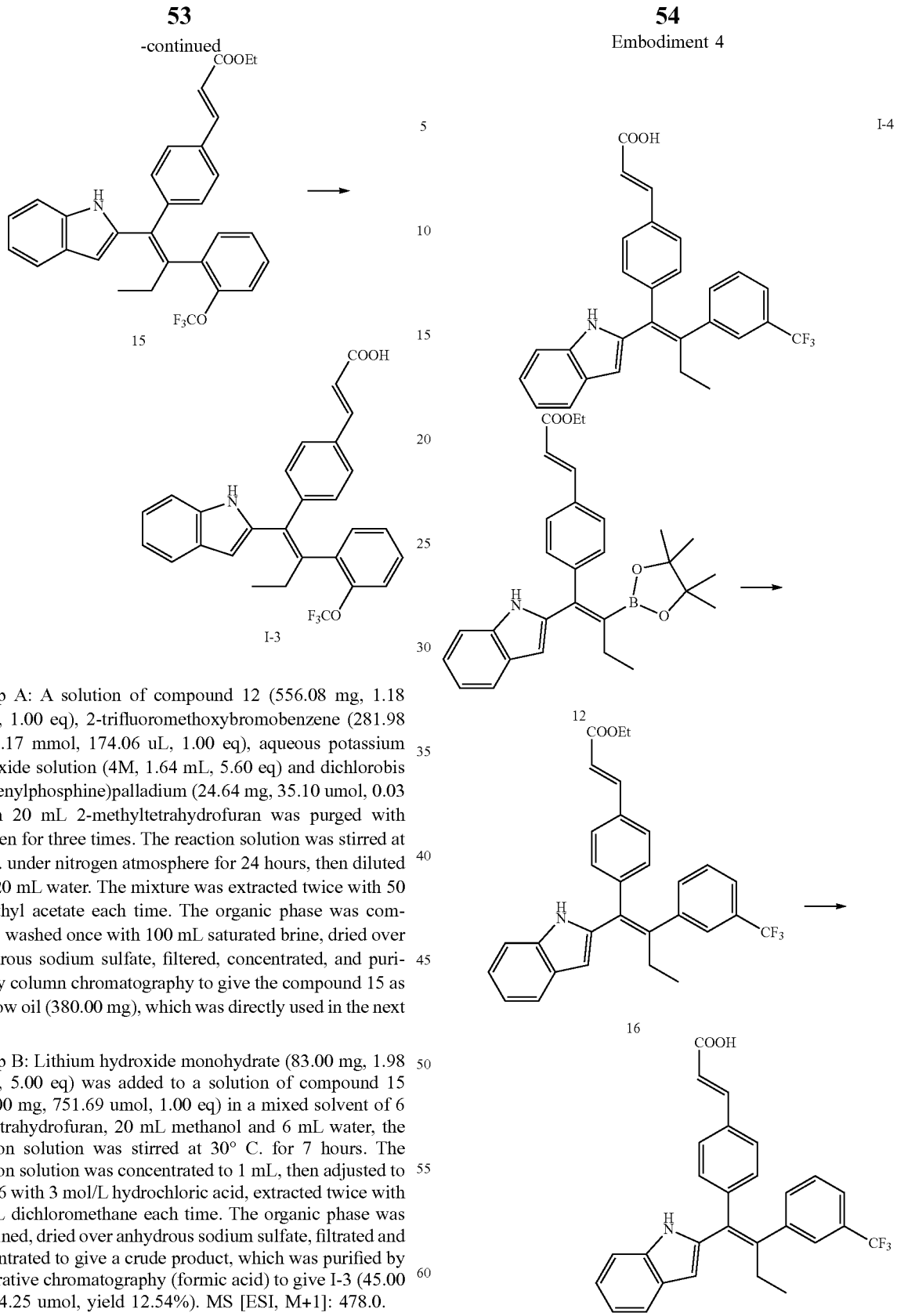

Step A: A solution of compound 12 (556.08 mg, 1.18 mmol, 1.00 eq), 2-trifluoromethoxybromobenzene (281.98 mg, 1.17 mmol, 174.06 uL, 1.00 eq), aqueous potassium hydroxide solution (4M, 1.64 mL, 5.60 eq) and dichlorobis (triphenylphosphine)palladium (24.64 mg, 35.10 umol, 0.03 eq) in 20 mL 2-methyltetrahydrofuran was purged with nitrogen for three times. The reaction solution was stirred at 80° C. under nitrogen atmosphere for 24 hours, then diluted with 20 mL water. The mixture was extracted twice with 50 mL ethyl acetate each time. The organic phase was combined, washed once with 100 mL saturated brine, dried over anhydrous sodium sulfate, filtered, concentrated, and purified by column chromatography to give the compound 15 as a yellow oil (380.00 mg), which was directly used in the next step.

Step B: Lithium hydroxide monohydrate (83.00 mg, 1.98 mmol, 5.00 eq) was added to a solution of compound 15 (380.00 mg, 751.69 umol, 1.00 eq) in a mixed solvent of 6 mL tetrahydrofuran, 20 mL methanol and 6 mL water, the reaction solution was stirred at 30° C. for 7 hours. The reaction solution was concentrated to 1 mL, then adjusted to pH 5-6 with 3 mol/L hydrochloric acid, extracted twice with 50 mL dichloromethane each time. The organic phase was combined, dried over anhydrous sodium sulfate, filtrated and concentrated to give a crude product, which was purified by preparative chromatography (formic acid) to give I-3 (45.00 mg, 94.25 umol, yield 12.54%). MS [ESI, M+1]: 478.0.

$^1$H NMR (400 MHz, DMSO-$d_6$) δ 10.77 (s, 1H), 7.57 (d, J=7.6 Hz, 1H), 7.50-7.37 (m, 3H), 7.36-7.15 (m, 5H), 7.11-6.97 (m, 2H), 6.92 (d, J=8.4 Hz, 2H), 6.57 (s, 1H), 6.42 (d, J=16.4 Hz, 1H), 2.80-2.60 (m, 2H), 0.97 (t, J=7.6 Hz, 3H).

54

Embodiment 4

Step A: 3-Trifluoromethyl iodobenzene (320.84 mg, 1.18 mmol, 169.76 uL, 2.00 eq), aqueous potassium hydroxide solution (4M, 737.19 uL, 5.00 eq) and bis(triphenylphosphine)palladium dichloride (20.70 mg, 29.49 umol, 0.05 eq) were added to a solution of 12 (278.00 mg, 589.75 umol, 1.00 eq) in 10 mL dimethyltetrahydrofuran. The reaction solution was stirred at 70° C. under nitrogen atmosphere for 12 hours, then 20 mL ethyl acetate was added. The mixture was filtered through celite, and the filtrate was washed twice with 30 mL saturated brine. The organic phase was dried over anhydrous sodium sulfate, filtered and concentrated to give a crude product, which was purified by silica gel column chromatography (PE:EA=20:1 to 10:1) to give the product 16 (200.00 mg, crude product) as a yellow slime. MS (ESI, M+1): 490.2.

Step B: Lithium hydroxide (97.85 mg, 4.09 mmol, 10.00 eq) was added to a solution of compound 16 (200.00 mg, 408.56 umol, 1.00 eq) in a mixed solvent of 2 mL methanol, 2 mL tetrahydrofuran and 2 mL water, the reaction solution was stirred at 30° C. for 1 hour. 10 mL water was added, then the mixture was adjusted to pH 5 with 1M hydrochloric acid and extracted twice with 10 mL ethyl acetate. The organic phase was combined, washed twice with 10 mL water, dried over anhydrous sodium sulfate, filtrated and concentrated to give a crude product, which was purified by preparative HPLC (formic acid system) to give the product I-4 (20.90 mg, 45.29 umol, yield 11.09%, purity 100%). MS (ESI, M+1): 462.2.

$^1$H NMR EW3644-177-P1B (400 MHz, DMSO-d$_6$): δ 10.77 (s, 1H), 7.56 (d, J=8.0 Hz, 1H), 7.51-7.46 (m, 3H), 7.40 (d, J=8.8 Hz, 4H), 7.30 (d, J=8.0 Hz, 1H), 7.06 (t, J=8.0 Hz, 1H), 6.99 (t, J=7.2 Hz, 1H), 6.90 (d, J=8.4 Hz, 2H), 6.55 (d, J=1.6 Hz, 1H), 6.40 (d, J=16.0 Hz, 1 H), 2.75 (q, J=7.2 Hz 2 H), 0.98 (t, J=7.2 Hz, 3 H).

Embodiment 5

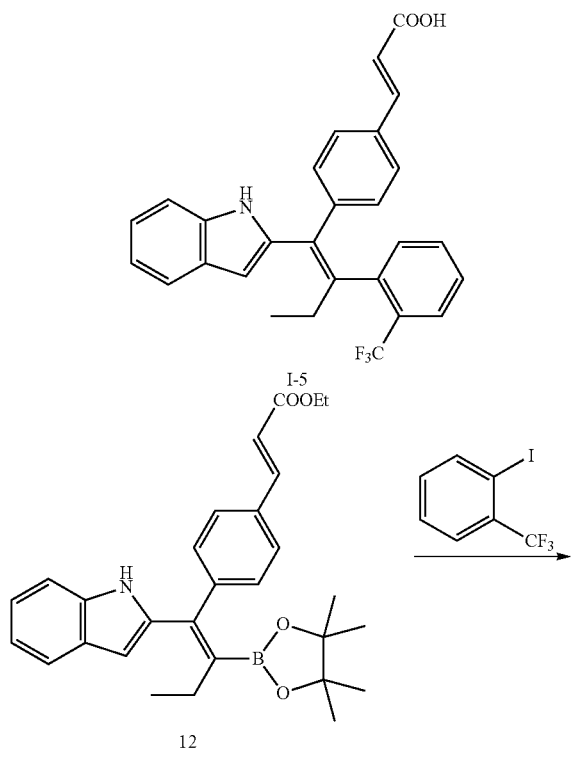

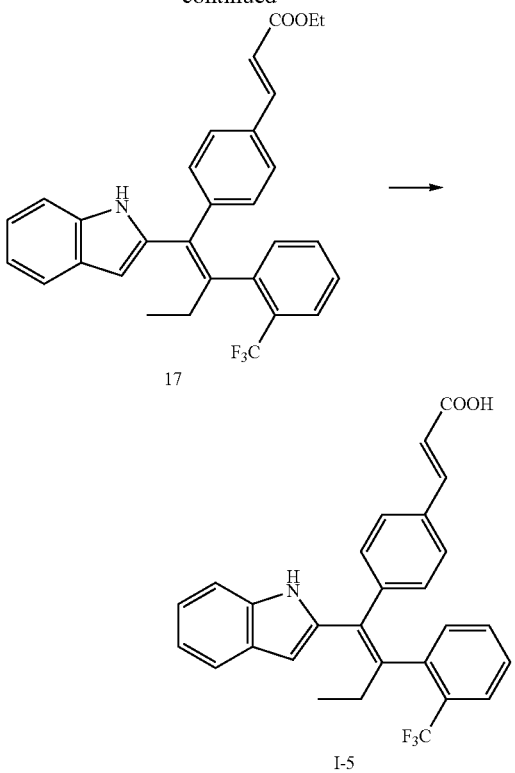

Step A: A solution of compound 12 (558.00 mg, 1.18 mmol, 1.00 eq), 2-trifluoromethyl iodobenzene (572.85 mg, 2.11 mmol, 1.80 eq), aqueous potassium hydroxide solution (4M, 1.64 mL, 5.60 eq) and dichlorobis(triphenylphosphine) palladium (24.64 mg, 35.10 umol, 0.03 eq) in 10 mL 2-methyltetrahydrofuran was purged with nitrogen for three times. The reaction solution was stirred at 80° C. under nitrogen atmosphere for 24 hours, then diluted with 30 mL water. The mixture was extracted twice with 50 mL ethyl acetate each time. The organic phase was combined, washed twice with 50 mL saturated brine each time, dried over anhydrous sodium sulfate, filtered, concentrated, and purified by column chromatography to give the compound 17 as a yellow oil (200.00 mg), which was directly used in the next step.

Step B: Lithium hydroxide monohydrate (85.71 mg, 2.04 mmol, 5.00 eq) was added to a solution of compound 17 (200.00 mg, 408.56 umol, 1.00 eq) in a mixed solvent of 6 mL tetrahydrofuran, 20 mL methanol and 6 mL water, the reaction solution was stirred at 30° C. for 3 hours. The reaction solution was concentrated to 1 mL, then adjusted to pH 5-6 with 3 mol/L hydrochloric acid, extracted twice with 50 mL dichloromethane each time. The organic phase was combined, dried over anhydrous sodium sulfate, filtrated and concentrated to give a crude product, which was purified by preparative chromatography (formic acid) to give the product I-5 (44.90 mg, 97.30 umol, yield 22.45%). MS [ESI, M+1]: 462.1.

$^1$H NMR (400 MHz, DMSO-d$_6$) δ 10.79 (s, 1H), 7.64 (d, J=8.0 Hz, 1H), 7.60-7.50 (m, 2H), 7.46-7.29 (m, 6H), 7.12-6.90 (m, 4H), 6.59-6.50 (m, 1H), 6.39 (d, J=16.0 Hz, 1H), 2.90-2.79 (m, 1H), 2.48-2.41 (m, 1H), 0.95 (t, J=7.6 Hz, 3H).

Embodiment 6

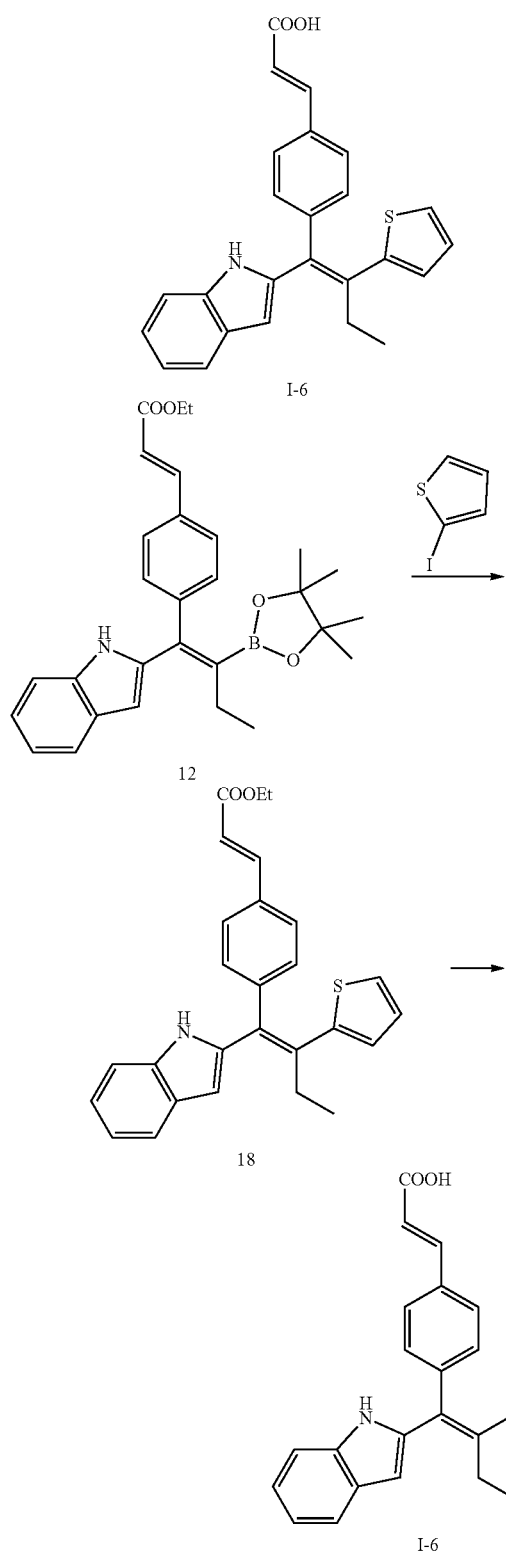

Step A: A solution of compound 12 (279.00 mg, 590.95 umol, 1.00 eq), 2-iodothiophene (247.74 mg, 1.18 mmol, 120.26 uL, 2.00 eq), aqueous potassium hydroxide solution (4M, 737.19 uL, 5.00 eq), dichlorobis(triphenylphosphine) palladium (20.70 mg, 29.49 umol, 0.05 eq) in 10 mL 2-methyltetrahydrofuran was purged with nitrogen for three times and stirred at 70° C. for 12 hours. The reaction solution was diluted with 20 mL ethyl acetate, filtered, and the filtrate was washed twice with 30 mL saturated brine each time, dried over anhydrous sodium sulfate, filtered, concentrated and purified by silica gel column chromatography (PE:EA=20:1 to 10:1) to give the compound 18 (200.00 mg) as a yellow jelly, which was directly used in the next step.

Step B: Lithium hydroxide (112.03 mg, 4.68 mmol, 10.00 eq) was added to a solution of compound 18 (200.00 mg, 467.77 umol, 1.00 eq) in a mixed solvent of 2 mL methanol, 2 mL tetrahydrofuran and 2 mL water, the reaction solution was stirred at 30° C. for 1 hour. Then 10 mL water was added, the mixture was adjusted to pH 5 with 1M hydrochloric acid, extracted twice with 10 mL ethyl acetate each time. The organic phase was combined, dried over anhydrous sodium sulfate, filtrated and concentrated to give a crude product, which was purified by preparative HPLC (formic acid system) to give the product I-6 (12.40 mg, 30.83 umol, yield 6.59%, purity 99.34%). MS [ESI, M+1]: 400.1.

$^1$H NMR (400 MHz, DMSO-$d_6$): δ 10.72 (s, 1H), 7.52 (d, J=8.0 Hz, 3H), 7.48 (d, J=16.0 Hz, 1H), 7.40 (dd, J=5.2 Hz, J=1.2 Hz, 1H), 7.28 (d, J=8.4 Hz, 1H), 7.09 (d, J=8.4 Hz, 2H), 7.04 (t, J=6.0 Hz, 1H), 6.97 (t, J=6.8 Hz, 1H), 6.91 (dd, J=3.6 Hz, J=4.8 Hz, 1H), 6.87 (dd, J=0.8 Hz, J=3.6 Hz, 1H), 6.49 (d, J=1.6 Hz, 1H), 6.46 (d, J=16.0 Hz, 1 H), 2.71 (q, J=7.2 Hz 2 H), 1.10 (t, J=7.2 Hz, 3 H); MS(ESI, M+1): 400.1.

Embodiment 7

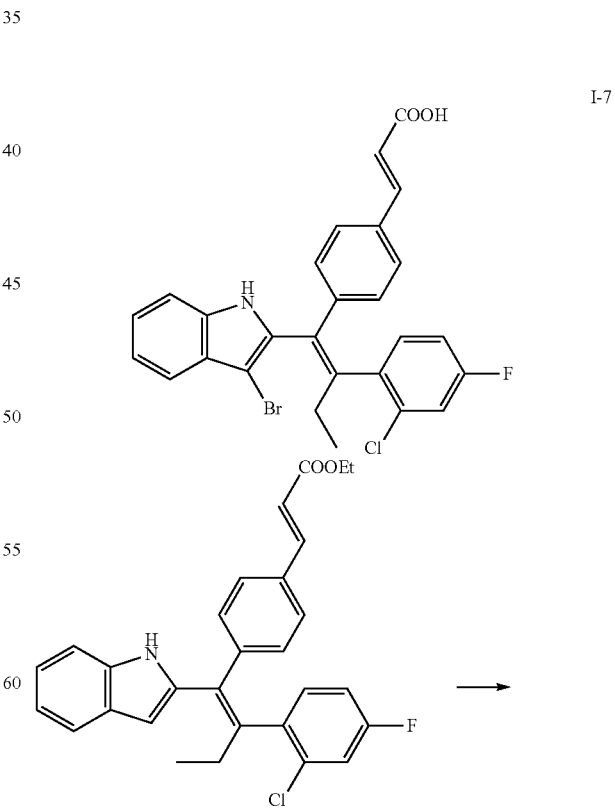

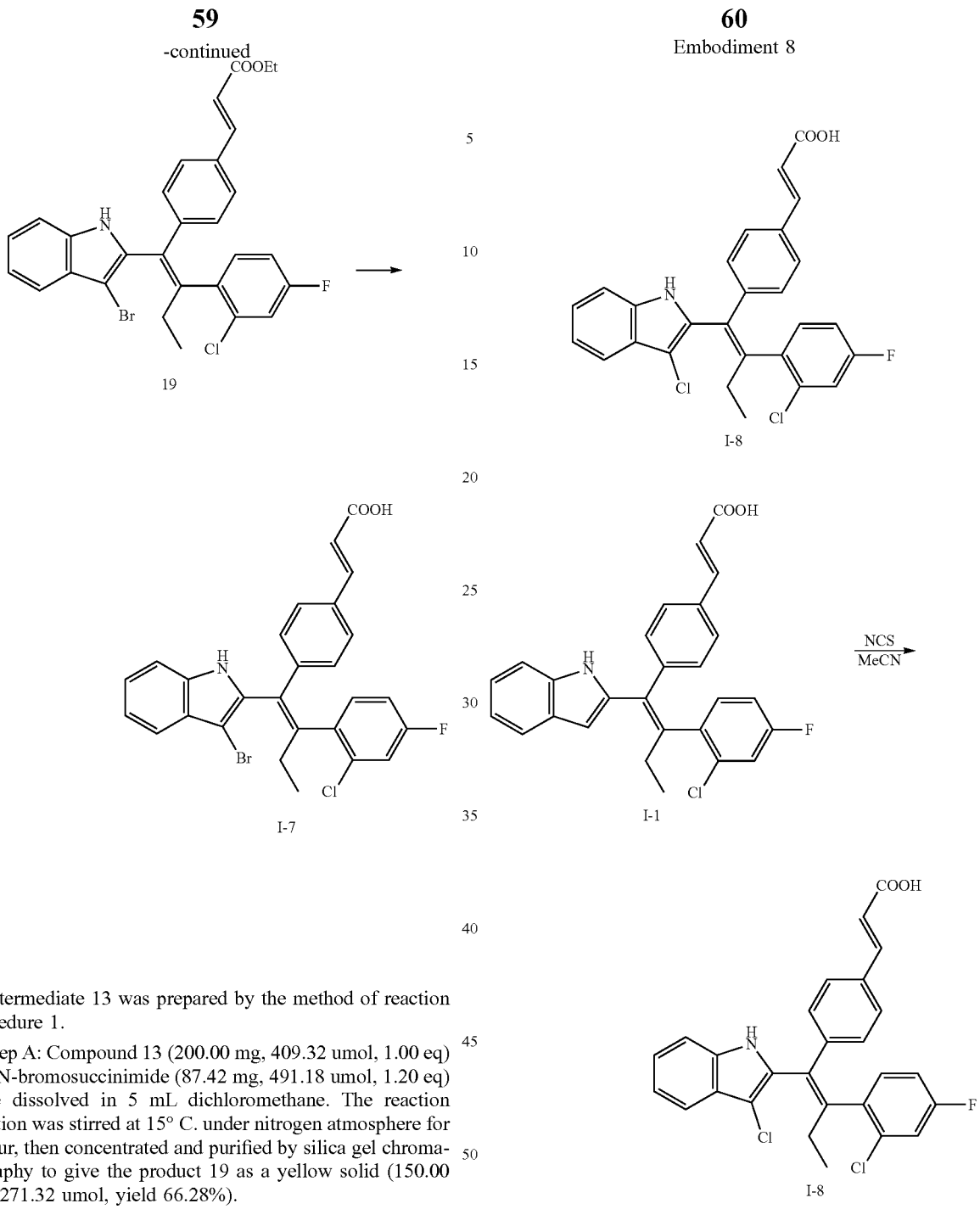

Embodiment 8

Intermediate 13 was prepared by the method of reaction procedure 1.

Step A: Compound 13 (200.00 mg, 409.32 umol, 1.00 eq) and N-bromosuccinimide (87.42 mg, 491.18 umol, 1.20 eq) were dissolved in 5 mL dichloromethane. The reaction solution was stirred at 15° C. under nitrogen atmosphere for 1 hour, then concentrated and purified by silica gel chromatography to give the product 19 as a yellow solid (150.00 mg, 271.32 umol, yield 66.28%).

Step C: Compound 19 (80.00 mg, 144.70 umol, 1.00 eq), lithium hydroxide (30.36 mg, 723.51 umol, 5.00 eq) were dissolved in a mixed solvent of 1 mL methanol, 1 mL tetrahydrofuran and 0.5 mL water. The reaction solution was stirred at 30° C. under nitrogen atmosphere for 3 hours. Then the reaction solution was adjusted to pH 5-6 with hydrochloric acid (1 mol/L) and filtered to give a crude product, which was purified by preparative chromatography (formic acid system) to give the product I-7 (61.00 mg, 116.23 umol, yield 80.32%, purity 99.29%). MS [ESI, M+1]=526.0.

$^1$H NMR (400 MHz, DMSO-$d_6$) δ: 11.66 (s, 1H), 7.51-7.35 (m, 6H), 7.30-7.24 (m, 1H), 7.22-7.09 (m, 3H), 7.01 (d, J=8.4 Hz, 2H), 6.39 (d, J=16.0 Hz, 1H), 2.47-2.32 (m, 2H), 0.88 (t, J=7.6 Hz, 3H).

Step A: Compound I-1 (150.00 mg, 336.39 umol, 1.00 eq) and N-chlorosuccinimide (53.90 mg, 403.67 umol, 1.20 eq) were dissolved in 5 mL acetonitrile. The reaction solution was stirred at 15° C. under nitrogen atmosphere for 6 hours. After completion of the reaction, the reaction solution was concentrated and purified by preparative chromatography (formic acid system) to give the product I-8 (10.00 mg, 21.56 umol, yield 11.78%, purity 97.65%). MS [ESI, M+1]$^+$=480.1.

$^1$H NMR (400 MHz, DMSO-$d_6$) δ 11.51 (s, 1H), 7.50 (d, J=8.0 Hz, 1H), 7.47-7.37 (m, 5H), 7.29 (dd, J=6.4, 8.4 Hz, 1H), 7.22-7.09 (m, 3H), 7.01 (d, J=8.4 Hz, 2H), 6.41 (d, J=16.4 Hz, 1H), 2.49-2.36 (m, 2H), 0.89 (t, J=7.6 Hz, 3H).

Embodiment 9

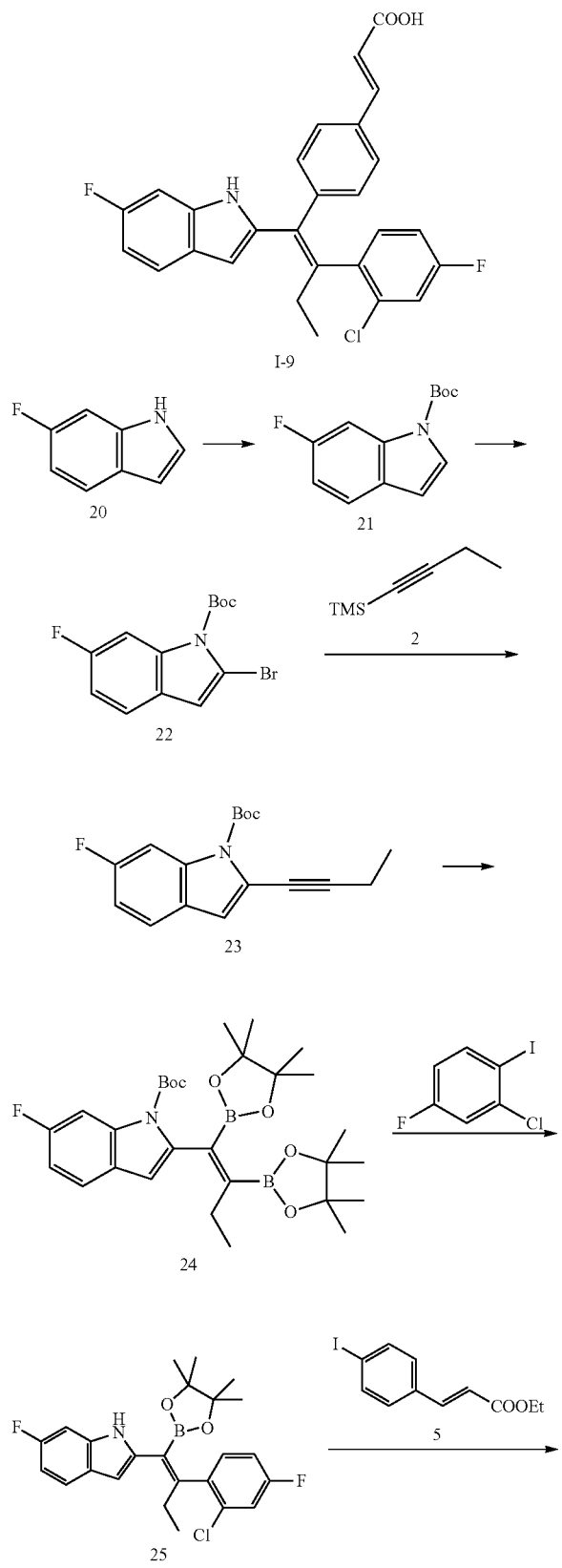

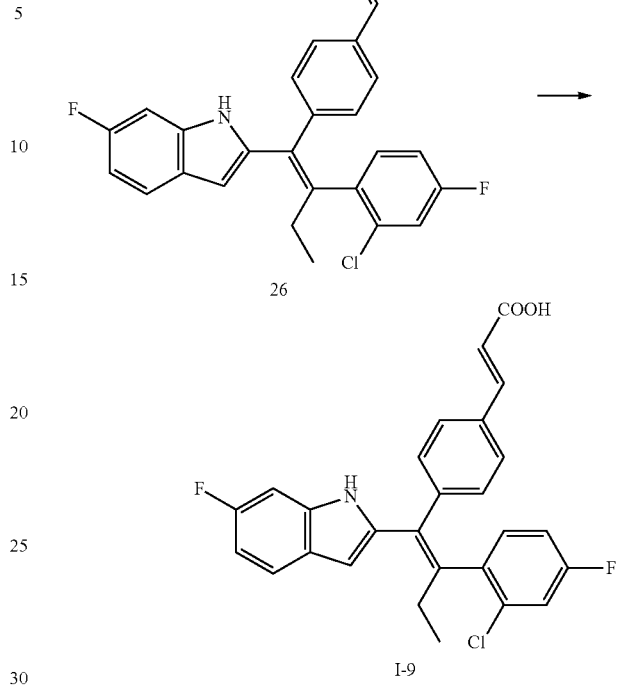

Step A: N,N-dimethylpyridine (406.83 mg, 3.33 mmol, 0.05 eq) and Boc₂O (15.00 g, 68.73 mmol, 15.79 mL, 1.03 eq) were added to a solution of 20 (9.00 g, 66.60 mmol, 1.00 eq) in 180 mL dichloromethane. The reaction solution was stirred at 15° C. for 12 hours, then quenched with 100 mL water at 0° C., extracted three times with 210 mL ethyl acetate. The organic phase was combined, washed with 200 mL saturated brine, dried over anhydrous sodium sulfate, filtrated, concentrated and purified by column chromatography to give the product 21 as a colorless oil (15.40 g, 65.46 mmol, yield 98.29%).

Step B: Lithium diisopropylamide (2M, 70.14 mL, 2.00 eq) was added dropwise to a solution of 21 (16.50 g, 70.14 mmol, 1.00 eq) in 300 mL tetrahydrofuran at −70° C. under nitrogen atmosphere. The reaction solution was stirred at −70° C. for 30 minutes, then cyanogen bromide (22.29 g, 210.42 mmol, 15.48 mL, 3.00 eq) was added to the reaction solution. The reaction solution was stirred at 15° C. for 12 hours, then quenched with 50 mL saturated aqueous ammonium chloride solution, diluted with 50 mL water and extracted with 300 mL ethyl acetate. The organic phase was combined, washed twice with 200 mL saturated brine, dried over anhydrous sodium sulfate, filtered and concentrated to give a crude product, which was purified by column chromatography to give the crude product 22 as a yellow oil (14.10 g, 44.88 mmol, yield 63.99%).

Step C: Compound 22 (12.00 g, 38.20 mmol, 1.00 eq), 1-trimethylsilylbutyne (9.65 g, 76.40 mmol, 2.00 eq), cuprous iodide (145.50 mg, 764.00 umol, 0.02 eq), cesium carbonate (16.30 g, 50.04 mmol, 1.31 eq), 1,1'-bis(diphenylphosphino)ferrocene (423.55 mg, 764.00 umol, 0.02 eq) and palladium acetate (171.53 mg, 764.00 umol, 0.02 eq) were dissolved in 100 mL N,N-dimethylacetamide, the reaction system was purged with nitrogen for three times, and the reaction solution was stirred at 80° C. under nitrogen atmosphere for 6 hours. After completion of the reaction, the reaction solution was quenched with 100 mL water, diluted with 100 mL ethyl acetate, filtered through celite, the filtrate was extracted three times with 300 mL ethyl acetate. The organic phase was combined, washed with 300 mL brine for three times, dried over anhydrous sodium sulfate, filtered, concentrated and purified by column chromatography to give the product 23 as a yellow oil (6.00 g, 20.88 mmol, yield 54.66%).

Step D: Compound 23 (6.00 g, 20.88 mmol, 1.00 eq), diboron pinacol ester (5.30 g, 20.88 mmol, 1.00 eq), tetrakis (triphenylphosphine)platinum (1.30 g, 1.04 mmol, 0.05 eq) were dissolved in 100 mL 2-methyltetrahydrofuran, the reaction system was purged with nitrogen for three times. The reaction solution was stirred at 80° C. under nitrogen atmosphere for 4 hours. After completion of the reaction, the reaction solution was quenched with 50 mL water at 0° C., then diluted with 100 mL ethyl acetate, filtered through celite, and the filtrate was extracted three times with 300 mL ethyl acetate. The organic phase was combined, washed with 100 mL brine, dried over anhydrous sodium sulfate, filtered, concentrated and purified by column chromatography to give the product 24 as a yellow oil (4.00 g, 7.17 mmol, yield 34.33%, purity 97%). MS [ESI, M+1]$^+$=542.3.

Step E: Compound 24 (515.46 mg, 923.75 umol, 1.00 eq), 2-chloro-4-fluoroiodobenzene (236.89 mg, 923.75 umol, 1.00 eq), cesium carbonate (601.95 mg, 1.85 mmol, 2.00 eq), dichlorobis(triphenylphosphine)palladium (64.84 mg, 92.38 umol, 0.10 eq) and 1.2 mL water were dissolved in 30 mL 2-methyltetrahydrofuran, and the reaction system was purged with nitrogen for three times. The reaction solution was stirred at 75° C. under nitrogen atmosphere for 12 hours. After completion of the reaction, the reaction solution was quenched with 30 mL water at 0° C., then diluted with 100 mL ethyl acetate, filtered through celite, and the filtrate was extracted three times with 90 mL ethyl acetate. The organic phase was combined, washed with 50 mL brine, dried over anhydrous sodium sulfate, filtered, concentrated and purified by silica gel column chromatography to give the product 25 as a yellow oil (500.00 mg), which was used directly in the next step. MS [ESI, M+1]$^+$=446.0.

Step F: Compound 25 (200.00 mg, 450.73 umol, 1.00 eq), compound 5 (292.84 mg, 901.46 umol, 2.00 eq), dichlorobis (triphenylphosphine)palladium (63.27 mg, 90.15 umol, 0.20 eq) and aqueous potassium hydroxide (4M, 631.02 uL, 5.60 eq) were dissolved in 5 mL 2-methyltetrahydrofuran, and the reaction system was purged with nitrogen for three times. The reaction solution was stirred at 80° C. under nitrogen atmosphere for 12 hours. After completion of the reaction, the reaction solution was quenched with 30 mL water at 0° C., then diluted with 30 mL ethyl acetate, filtered through celite, and the filtrate was extracted three times with 90 mL ethyl acetate. The organic phase was combined, washed with 50 mL brine, dried over anhydrous sodium sulfate, filtered, concentrated and purified by silica gel column chromatography to give the crude product 26 (90.00 mg), which was used directly in the next step. MS [ESI, M+1]$^+$=492.2.

Step G: Compound 26 (90.00 mg, 182.94 umol, 1.00 eq) and lithium hydroxide (38.38 mg, 914.70 umol, 5.00 eq) were dissolved in a mixed solvent of 2 mL methanol, 1 mL tetrahydrofuran and 0.5 mL water. The reaction solution was stirred at 25° C. for 12 hours, then concentrated to 3 mL, diluted with 20 mL water. The mixture was adjusted to pH 5-6 with hydrochloric acid (1 mol/L) and extracted with 200 mL dichloromethane. The organic phase was combined, concentrated and purified by preparative chromatography (formic acid system) to give the product I-9 (10.00 mg, 21.56 umol, yield 11.78%). MS [ESI, M+1]$^+$=464.2.

$^1$H NMR (400 MHz, DMSO-d$_6$) δ 10.82 (s, 1H), 7.56 (dd, J=5.6, 8.8 Hz, 1H), 7.48-7.32 (m, 4H), 7.25 (dd, J=6.4, 8.4 Hz, 1H), 7.12 (dt, J=2.4, 8.4 Hz, 1H), 7.05 (dd, J=2.0, 10.0 Hz, 1H), 6.96 (d, J=8.0 Hz, 2H), 6.91-6.81 (m, 1H), 6.60 (d, J=1.6 Hz, 1H), 6.41 (d, J=14.4 Hz, 1H), 2.70-2.59 (m, 2H), 1.00 (t, J=7.2 Hz, 3H).

Embodiment 10

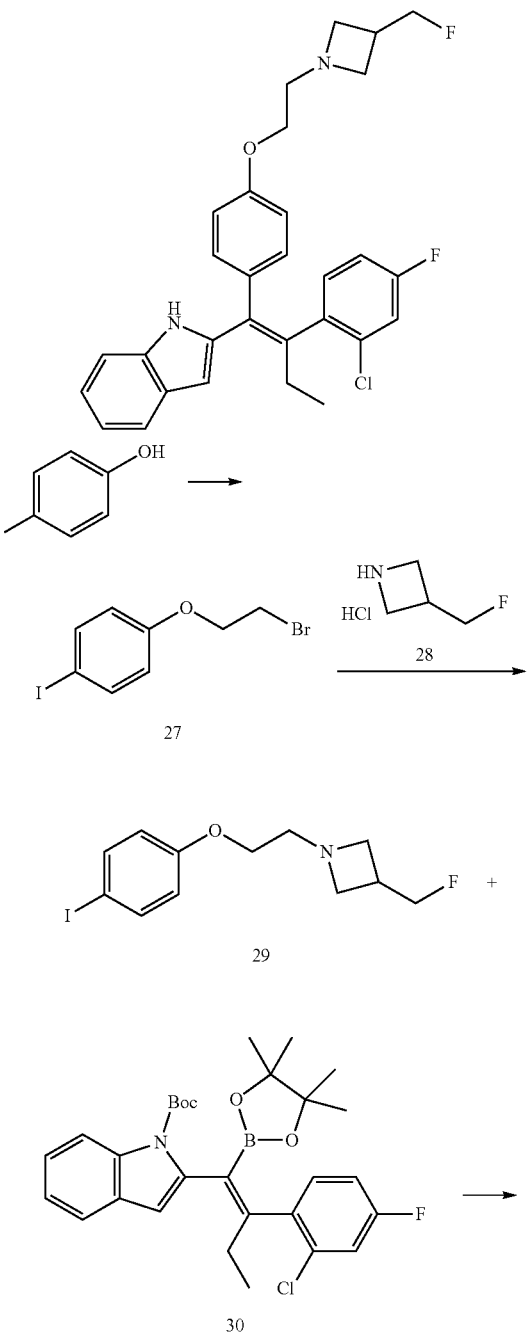

-continued

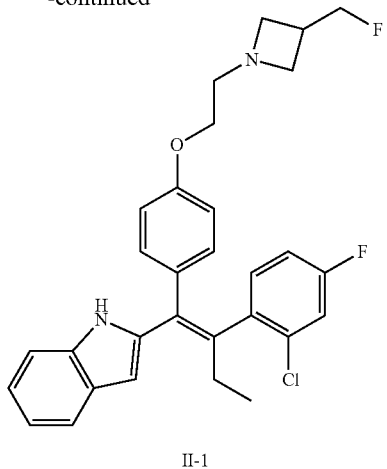

II-1

Intermediate 30 was prepared using a similar procedure to that described in Embodiment 9, but using indole as the raw material.

Step A: Cesium carbonate (6.52 g, 20.00 mmol, 4.00 eq) and 1,2-dibromoethane (4.70 g, 25.00 mmol, 1.89 mL, 5.00 eq) were added to a solution of p-iodophenol (1.10 g, 5.00 mmol, 1.00 eq) in acetonitrile (20.00 mL), the reaction solution was stirred at 85° C. for 24 hours, then concentrated under reduced pressure to remove the solvent, diluted with 20 mL water and extracted three times with 30 mL ethyl acetate each time. The organic phase was combined, washed with 30 mL saturated brine, dried over anhydrous sodium sulfate, filtered and concentrated to give a crude product, which was purified by silica gel column chromatography (PE/EA=100/1 to 20/1) to give the product 27 (1.40 g, 4.28 mmol, yield 85.64%).

Step B: Cesium carbonate (3.28 g, 10.08 mmol, 3.00 eq) and compound 28 (506.30 mg, 4.03 mmol, 1.20 eq) were added to a solution of compound 27 (1.10 g, 3.36 mmol, 1.00 eq) in acetonitrile (20.00 mL), the reaction solution was stirred at 85° C. for 12 hours, then diluted with 50 mL water and extracted three times with 50 mL ethyl acetate each time. The organic phase was combined, washed twice with 50 mL saturated brine each time, dried over anhydrous sodium sulfate, filtered, concentrated under reduced pressure to give a crude product, which was purified by silica gel column chromatography (DCM/MeOH=100/1 to 10/1) to give the product 29 (700.00 mg, 2.09 mmol, yield 62.16%).

Step C: Aqueous potassium hydroxide solution (4M, 190.17 uL, 4.00 eq) was added to a mixture of compound 30 (201.61 mg, 190.17 umol, 1.00 eq), compound 29 (127.47 mg, 380.34 umol, 2.00 eq) and dichlorobis(triphenylphosphine)palladium (133.48 mg, 190.17 umol, 1.00 eq), the reaction solution was purged with nitrogen and then stirred at 80° C. under nitrogen atmosphere for 12 hours. The reaction solution was concentrated to give a crude product, which was purified by preparative high performance liquid chromatography (formic acid system) to give the product II-1 (2.80 mg, 5.49 umol, yield 2.89%, purity 99.5%). MS(ESI, M+1): 507.1. $^1$H NMR (400 MHz, DMSO-$d_6$) δ 10.65 (s, 1H), 8.32 (s, 1H), 7.55 (d, J=7.6 Hz, 1H), 7.36 (dd, J=2.4, 8.8 Hz, 1H), 7.30 (d, J=8.0 Hz, 1H), 7.24-7.18 (m, 1H), 7.11 (dt, J=2.4, 8.4 Hz, 1H), 7.08-7.02 (m, 1H), 7.02-6.95 (m, 1H), 6.84 (d, J=8.8 Hz, 2H), 6.64 (d, J=8.8 Hz, 2H), 6.53 (s, 1H), 4.54 (d, J=6.4 Hz, 1H), 4.42 (d, J=6.4 Hz, 1H), 3.79 (t, J=5.2 Hz, 2H), 3.27 (t, J=7.2 Hz, 2H), 2.96 (t, J=6.4 Hz, 2H), 2.71-2.60 (m, 5H), 0.99 (t, J=7.2 Hz, 3H).

Embodiment 11

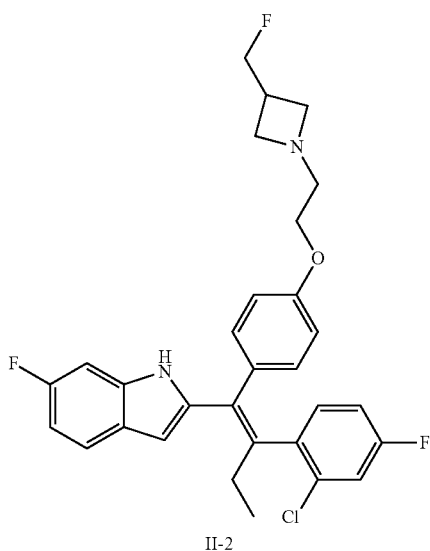

II-2

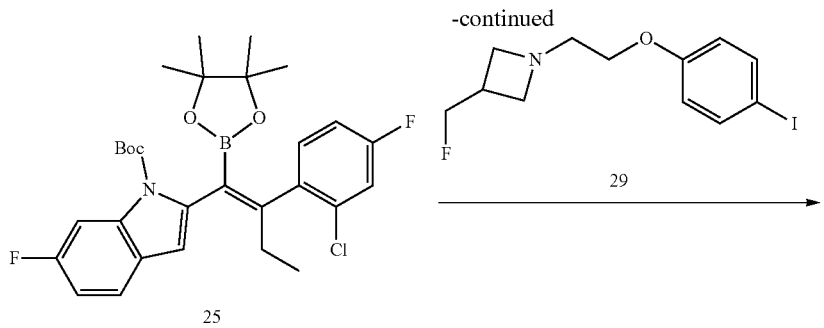

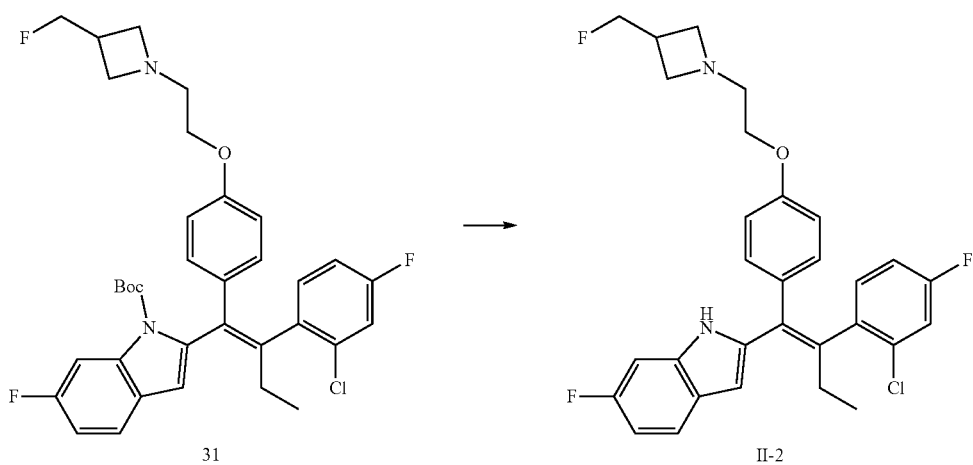

Step A: Compound 25 (340.00 mg, 625.18 umol, 1.00 eq) and compound 29 (419.07 mg, 1.25 mmol, 2.00 eq), dichlorobis(triphenylphosphine)palladium (219.41 mg, 312.59 umol, 0.50 eq) and aqueous potassium hydroxide solution (4M, 875.26 uL, 5.60 eq) were dissolved in 10 mL 2-methyltetrahydrofuran, the reaction system was purged with nitrogen for three times. The reaction solution was stirred at 80° C. under nitrogen atmosphere for 12 hours. After completion of the reaction, the reaction solution was cooled to 0° C., quenched with 30 mL water, diluted with 30 mL ethyl acetate, filtered through celite, and the filtrate was extracted three times with 20 mL ethyl acetate. The organic phase was combined, washed with 20 mL brine, dried over anhydrous sodium sulfate, filtered, concentrated under reduced pressure, and purified by preparative thin layer chromatography to give the crude product 31 as a yellow oil (110.00 mg, crude), which was used directly in the next step. MS [ESI, M−56]=625.2.

Step B: Trifluoroacetic acid (770.00 mg, 6.75 mmol, 500.00 uL, 42.22 eq) was added to a solution of compound 31 (90.00 mg, 152.37 umol, 1.00 eq) in 33 mL dichloromethane, and the reaction solution was stirred at 16° C. for 3 hours. The reaction solution was adjusted to pH 7 to 8 with saturated aqueous sodium bicarbonate solution, diluted with 20 mL water, extracted twice with 100 mL dichloromethane each time. The organic phase was combined, dried over anhydrous sodium sulfate, filtered, concentrated, and purified by preparative chromatography (formic acid system) to give the product II-2 (10.00 mg, 18.86 umol, yield 12.38%, purity 99.0%).

MS [ESI, M+1]$^+$=525.2.

$^1$H NMR (400 MHz, DMSO-d$_6$) δ=10.71 (s, 1H), 8.29 (br. s., 1H), 7.55 (dd, J=5.6, 8.4 Hz, 1H), 7.35 (dd, J=2.4, 8.8 Hz, 1H), 7.21 (dd, J=6.4, 8.4 Hz, 1H), 7.13-7.02 (m, 2H), 6.91-6.77 (m, 3H), 6.65 (d, J=8.8 Hz, 2H), 6.56 (d, J=1.2 Hz, 1H), 4.54 (d, J=6.4 Hz, 1H), 4.42 (d, J=6.4 Hz, 1H), 3.79 (t, J=5.2 Hz, 2H), 3.28 (t, J=6.8 Hz, 2H), 2.97 (t, J=6.4 Hz, 2H), 2.71-2.62 (m, 5H), 0.99 (t, J=7.6 Hz, 3H).

Embodiment 12
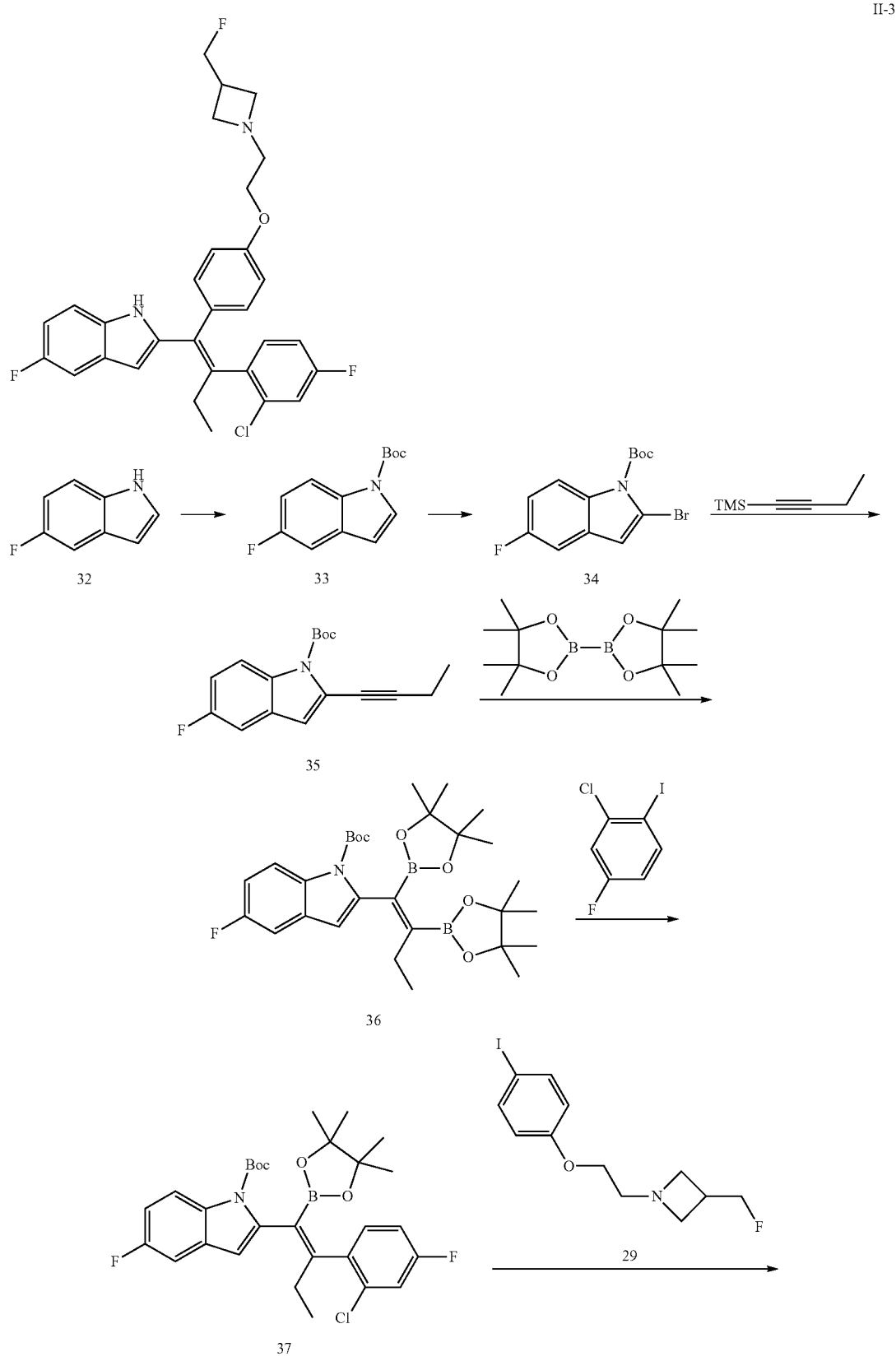

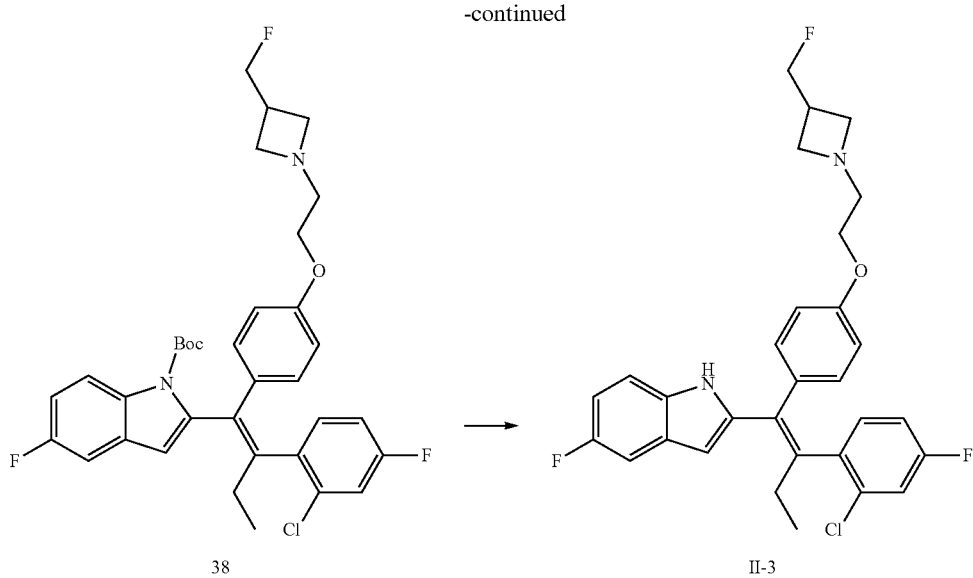

Step A: N,N-dimethylpyridine (135.61 mg, 1.11 mmol, 0.05 eq) and Boc₂O (4.89 g, 22.42 mmol, 1.01 eq) were added to a solution of 32 (3.00 g, 22.20 mmol, 1.00 eq) in 30 mL dichloromethane. The reaction solution was stirred at 10-15° C. for 12 hours, then quenched with 50 mL aqueous ammonium chloride solution at 0° C., extracted twice with 25 mL dichloromethane each time. The organic phase was combined, washed with 50 mL saturated brine, dried over anhydrous sodium sulfate, filtered, concentrated, and purified by silica gel column chromatography to give the product 33 as a white oil (5.20 g, 22.10 mmol, yield 99.57%).

Step B: Lithium diisopropylamide (2M, 14.96 mL, 1.10 eq) was added dropwise to a solution of 33 (6.40 g, 27.21 mmol, 1.00 eq) in 60 mL tetrahydrofuran at −70° C., after stirring at −70° C. for 30 minutes, a solution of cyanogen bromide (8.64 g, 81.62 mmol, 6.00 mL, 3.00 eq) in 20 mL tetrahydrofuran was added dropwise to the above solution. The reaction solution was stirred at 15° C. for 12 hours. Then 40 mL water and 40 mL ethyl acetate were successively added, and the mixture was partitioned in a separating funnel. The organic phase was washed three times with 120 mL water (40 mL each time), dried over anhydrous sodium sulfate, concentrated and filtrated to give a crude product, which was purified by column chromatography to give the product 34 as a yellow oil (7.80 g, 24.83 mmol, yield 91.25%).

Step C: Compound 34 (7.80 g, 24.83 mmol, 1.00 eq), 1-trimethylsilylbutyne (4.70 g, 37.24 mmol, 1.50 eq), cuprous iodide (236.43 mg, 1.24 mmol, 0.05 eq), cesium carbonate (10.52 g, 32.28 mmol, 1.30 eq), 1,1'-bis(diphenylphosphino)ferrocene (688.23 mg, 1.24 mmol, 0.05 eq) and palladium acetate (278.72 mg, 1.24 mmol, 0.05 eq) were dissolved in 80 mL N,N-dimethylacetamide, the reaction system was purged with nitrogen for three times, and the reaction solution was stirred at 80-90° C. under nitrogen atmosphere for 48 hours. After completion of the reaction, the reaction solution was diluted with 100 mL water, extracted twice with 100 mL ethyl acetate each time. The organic phase was combined, washed twice with 100 mL brine each time, dried over anhydrous sodium sulfate, filtered, concentrated, and purified by column chromatography to give the product 35 as a yellow oil (4.00 g, 13.92 mmol, yield 56.07%).

Step D: Compound 35 (4.00 g, 13.92 mmol, 1.00 eq), diboron pinacol ester (3.57 g, 14.06 mmol, 1.01 eq), tetrakis(triphenylphosphine)platinum (865.42 mg, 696.06 umol, 0.05 eq) were dissolved in 50 mL 2-methyltetrahydrofuran, the reaction system was purged with nitrogen for three times. The reaction solution was stirred at 70-80° C. under nitrogen atmosphere for 5 hours, then concentrated under reduced pressure to give a crude product, which was purified by column chromatography to give the product 36 as a yellow solid (2.10 g, 3.88 mmol, yield 27.87%).

Step E: Compound 36 (2.10 g, 3.88 mmol, 1.00 eq), 2-chloro-4-fluoroiodobenzene (994.93 mg, 3.88 mmol, 1.00 eq), cesium carbonate (2.53 g, 7.76 mmol, 2.00 eq) and dichlorobis(triphenylphosphine)palladium (272.32 mg, 387.98 umol, 0.10 eq) were dissolved in 10 mL 2-methyltetrahydrofuran, and the reaction system was purged with nitrogen for three times. The reaction solution was stirred at 70-80° C. under nitrogen atmosphere for 12 hours, then concentrated under reduced pressure, diluted with 50 mL water, extracted twice with 50 mL ethyl acetate each time. The organic phase was combined, washed with 30 mL saturated brine, dried over anhydrous sodium sulfate, filtered, concentrated, and purified by silica gel column chromatography to give the product 37 as a yellow oil (400.00 mg).

Step F: Compound 37 (200.00 mg, 367.76 umol, 1.00 eq), compound 29 (246.52 mg, 735.52 umol, 2.00 eq), dichlorobis(triphenylphosphine)palladium (25.81 mg, 36.78 umol, 0.10 eq) and aqueous potassium hydroxide solution (4M, 514.86 uL, 5.60 eq) were dissolved in 5 mL 2-methyltetrahydrofuran, and the reaction system was purged with nitrogen for three times. The reaction solution was stirred at 80° C. under nitrogen atmosphere for 12 hours, then concentrated under reduced pressure, and purified by preparative thin layer chromatography to give the crude product 38 (100.00 mg), which was used directly in the next step.

Step G: Trifluoroacetic acid (770.00 mg, 6.75 mmol, 500.00 uL, 42.22 eq) was added to a solution of compound 38 (100.00 mg, 159.97 umol, 1.00 eq) in 10 mL dichloromethane, and the reaction solution was stirred at 10-16° C. for 12 hours. The reaction solution was adjusted to pH 7-8 with aqueous sodium bicarbonate solution, diluted with 20 mL water, extracted twice with 25 mL dichloromethane each time. The organic phase was combined, dried over anhydrous sodium sulfate, filtered, concentrated, and purified by HPLC (formic acid system) to give the product II-3 (20.00 mg, 38.05 umol, yield 23.79%, purity 99.89%). MS (ESI, M+1): 525.2.

$^1$H NMR (400 MHz, DMSO-d$_6$) δ=10.75 (s, 1H), 7.34 (dd, J=2.8, 9.2 Hz, 1H), 7.31-7.25 (m, 2H), 7.20 (dd, J=6.4, 8.8 Hz, 1H), 7.13-7.07 (m, 1H), 6.88 (dt, J=2.6, 9.2 Hz, 1H), 6.83-6.80 (m, 2H), 6.65-6.62 (m, 2H), 6.52 (d, J=1.6 Hz, 1H), 4.53 (d, J=6.2 Hz, 1H), 4.41 (d, J=6.2 Hz, 1H), 3.78 (t, J=5.6 Hz, 2H), 3.28-3.23 (m, 3H), 2.94 (t, J=6.4 Hz, 2H), 2.68-2.59 (m, 4H), 0.97 (t, J=7.2 Hz, 3H).

Embodiment 13

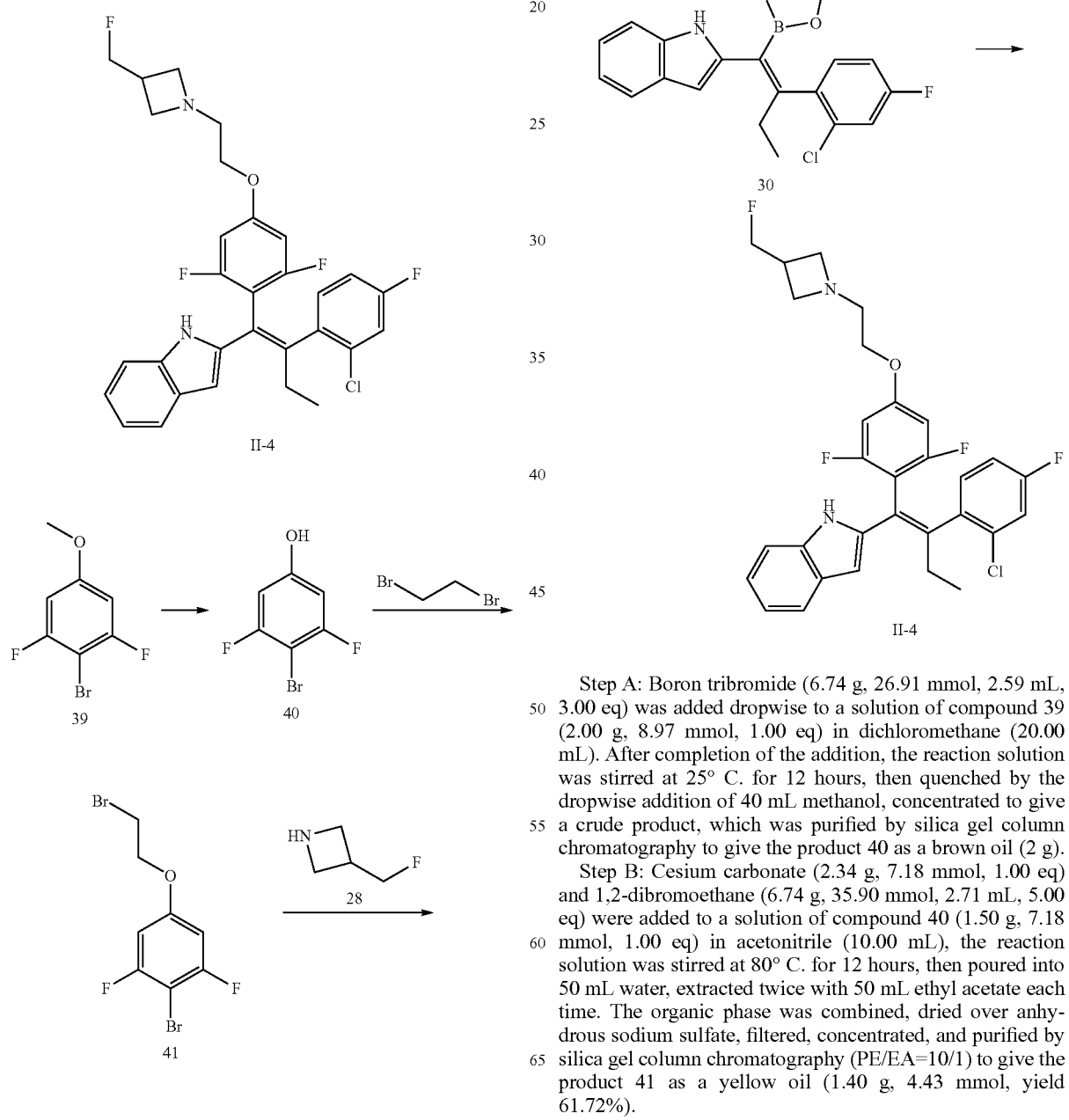

Step A: Boron tribromide (6.74 g, 26.91 mmol, 2.59 mL, 3.00 eq) was added dropwise to a solution of compound 39 (2.00 g, 8.97 mmol, 1.00 eq) in dichloromethane (20.00 mL). After completion of the addition, the reaction solution was stirred at 25° C. for 12 hours, then quenched by the dropwise addition of 40 mL methanol, concentrated to give a crude product, which was purified by silica gel column chromatography to give the product 40 as a brown oil (2 g).

Step B: Cesium carbonate (2.34 g, 7.18 mmol, 1.00 eq) and 1,2-dibromoethane (6.74 g, 35.90 mmol, 2.71 mL, 5.00 eq) were added to a solution of compound 40 (1.50 g, 7.18 mmol, 1.00 eq) in acetonitrile (10.00 mL), the reaction solution was stirred at 80° C. for 12 hours, then poured into 50 mL water, extracted twice with 50 mL ethyl acetate each time. The organic phase was combined, dried over anhydrous sodium sulfate, filtered, concentrated, and purified by silica gel column chromatography (PE/EA=10/1) to give the product 41 as a yellow oil (1.40 g, 4.43 mmol, yield 61.72%).

Step C: Cesium carbonate (2.06 g, 6.32 mmol, 4.00 eq) and compound 28 (768.02 mg, 4.74 mmol, 3.00 eq, 2HCl) were added to a solution of compound 41 (500.00 mg, 1.58 mmol, 1.00 eq) in acetonitrile (20.00 mL), the reaction solution was stirred at 70° C. for 1 hour, then diluted with 30 mL water, extracted with 30 mL ethyl acetate, dried over anhydrous sodium sulfate, filtered, concentrated to give a crude product, which was purified by preparative TLC (PE/EA=1/2) to give the product 42 as a yellow solid (400.00 mg, 1.23 mmol, yield 78.10%).

Step D: Potassium phosphate (2M, 1.64 mL, 4.00 eq) and Ad2nBuP Biphenyl (54.62 mg, 81.77 umol, 0.10 eq) were added to a solution of compound 42 (430.00 mg, 817.72 umol, 1.00 eq) and compound 30 (318.07 mg, 981.26 umol, 1.20 eq) in 8 mL tetrahydrofuran. The reaction solution was stirred at 80° C. under nitrogen atmosphere, then diluted with 50 mL water, extracted twice with 50 mL ethyl acetate each time for 36 hours, dried over anhydrous sodium sulfate, filtered, concentrated to give a crude product, which was purified by silica gel column chromatography (PE/EA=15/1 to 0/1) and preparative high performance liquid chromatography (formic acid system) to give the product II-4 (530.00 ug, 0.98 umol, yield 0.12%). MS(ESI, M+1): 543.1.

$^1$H NMR (400 MHz, DMSO-$d_6$) δ 10.70 (s, 1H), 7.52 (d, J=8.0 Hz, 1H), 7.35-7.31 (m, 2H), 7.26-7.20 (m, 1H), 7.15-7.10 (m, 1H), 7.10-7.03 (m, 1H), 7.01-6.95 (m, 1H), 6.50 (t, J=8.0 Hz, 3H), 4.54 (d, J=6.4 Hz, 1H), 4.42 (d, J=6.4 Hz, 1H), 3.84 (t, J=5.2 Hz, 2H), 3.28 (t, J=7.2 Hz, 2H), 2.95 (t, J=5.2 Hz, 2H), 2.90-2.75 (m, 2H), 2.74-2.60 (m, 3H), 1.03 (t, J=7.2 Hz, 3H).

Embodiment 14

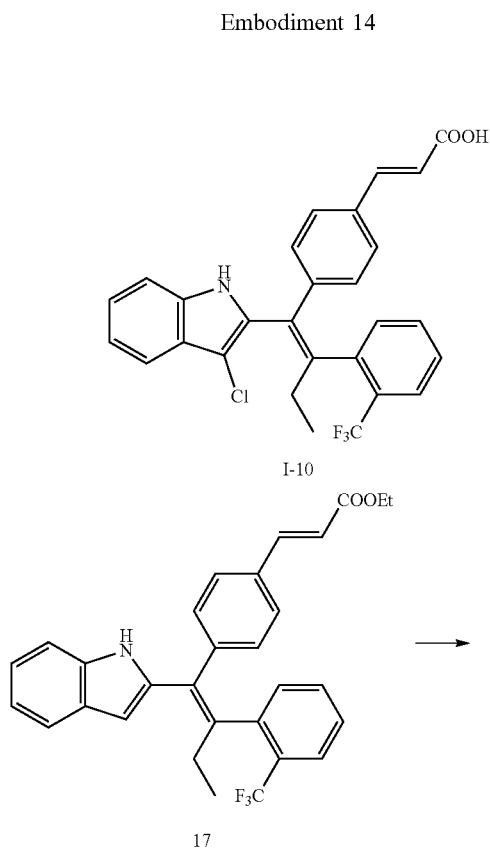

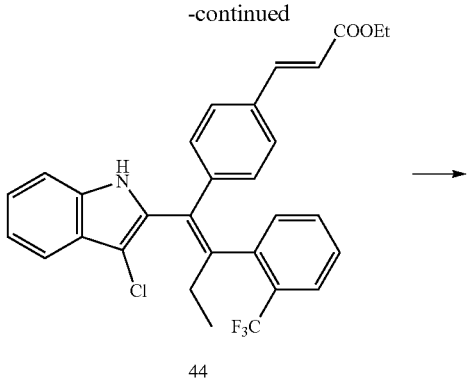

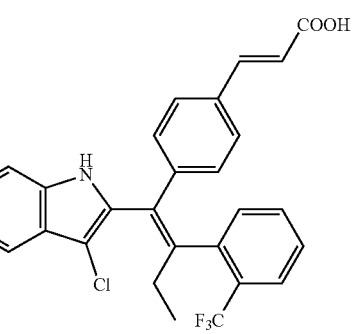

Step A: N-chlorosuccinimide (390.71 mg, 2.93 mmol, 1.10 eq) was added to a solution of the crude product 17 (1.30 g) in 10 mL acetonitrile, the reaction solution was stirred at 15° C. under nitrogen atmosphere for 5 hours, then quenched with 40 mL water, extracted three times with 120 mL ethyl acetate (40 mL each time). The organic phase was combined, washed with 100 mL saturated brine, dried over anhydrous sodium sulfate, filtered and concentrated to give the crude product 44 (1.4 g, crude).

Step B: Lithium hydroxide (319.96 mg, 13.35 mmol, 5.00 eq) was added to a solution of the crude product 44 (1.40 g) in a mixed solvent of 10 mL tetrahydrofuran, 10 mL methanol and 2.5 mL water, the reaction solution was stirred at 30° C. for 1 hour, then concentrated to 1 mL under reduced pressure, adjusted to pH 5-6 with 3M hydrochloric acid and filtered. The filter cake was dried and purified by preparative chromatography (formic acid system) to give the product I-10 (691.00 mg, 1.38 mmol, yield 51.66%, purity 99%).

$^1$H NMR (400 MHz, DMSO-$d_6$) δ 12.32 (br s, 1H), 11.48 (s, 1H), 7.71 (d, J=7.6 Hz, 1H), 7.64-7.57 (m, 1H), 7.53-7.45 (m, 2H), 7.43-7.30 (m, 5H), 7.22-7.10 (m, 2H), 6.97 (d, J=8.4 Hz, 2H), 6.37 (d, J=16.0 Hz, 1H), 2.57-2.51 (m, 1H), 2.38-2.29 (m, 1H), 0.86 (t, J=7.6 Hz, 3H). MS [ESI, M+1]: 496.1.

Embodiment 15

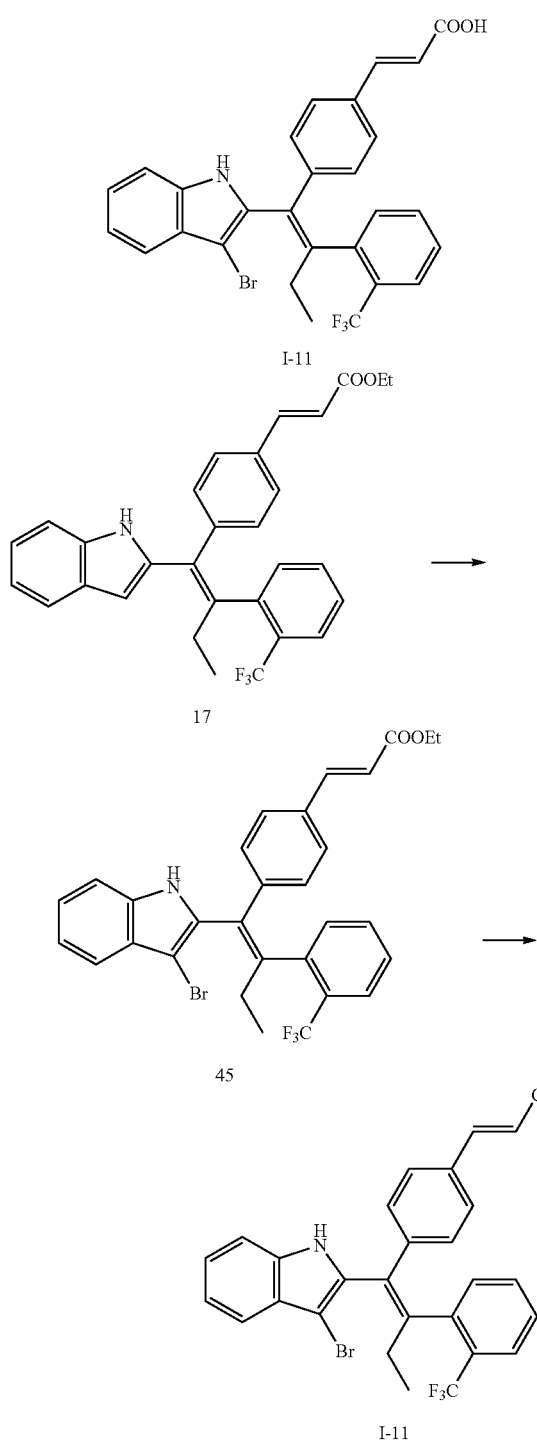

Step A: N-bromosuccinimide (520.77 mg, 2.93 mmol, 1.10 eq) was added to a solution of the crude product 17 (1.30 g, 2.66 mmol, 1.00 eq) in 10 mL acetonitrile, the reaction solution was stirred at 15° C. under nitrogen atmosphere for 5 hours, then quenched with 40 mL water, extracted three times with 120 mL ethyl acetate (40 mL each time). The organic phase was combined, washed with 100 mL saturated brine, dried over anhydrous sodium sulfate, filtered and concentrated to give the crude product 45 (1.6 g, crude), which was directly used in the next step.

Step B: Lithium hydroxide (336.50 mg, 14.05 mmol, 5.00 eq) was added to a solution of the crude product 45 (1.60 g, 2.8 mmol, 1.00 eq) in a mixed solvent of 10 mL tetrahydrofuran, 10 mL methanol and 2.5 mL water, the reaction solution was stirred at 30° C. for 1 hour. The reaction solution turned from deep yellow to brown, then concentrated to 1 mL under reduced pressure, adjusted to pH 5-6 with 3M hydrochloric acid and filtered. The filter cake was purified by preparative chromatography (formic acid system) and then lyophilized to give the product I-11 as a pale yellow solid (811.00 mg, 1.49 mmol, yield 52.88%, purity 99%).

Embodiment 16

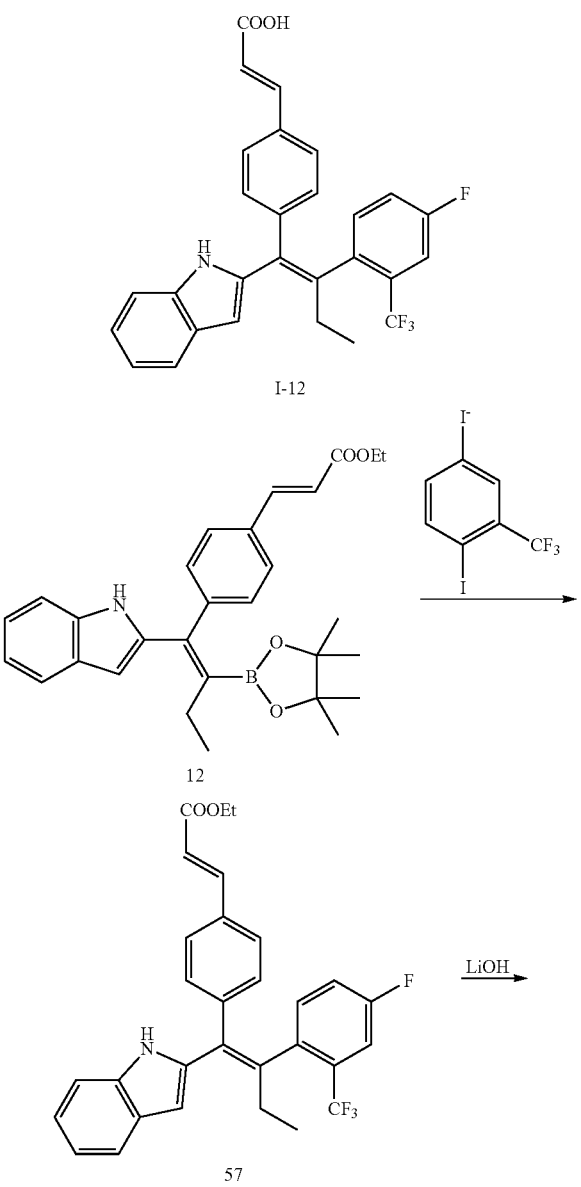

-continued

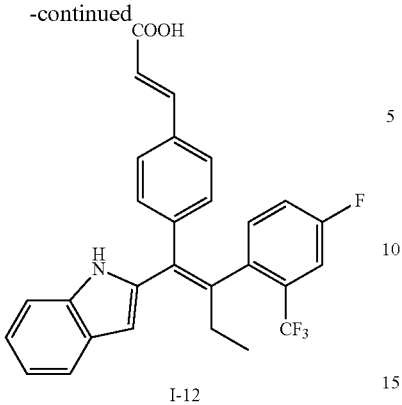

I-12

Step A: Diboron pinacol ester (329.61 mg, 1.30 mmol, 1.10 eq) and tetrakis(triphenylphosphine)platinum (73.53 mg, 59.09 umol, 0.05 eq) were added to a solution of compound 10 (200.00 mg, 1.18 mmol, 1.00 eq) in 2-methyltetrahydrofuran (5.00 mL), the reaction solution was purged three times with nitrogen and stirred at 70° C. under nitrogen atmosphere for 5 hours. After the reaction solution was cooled to 0° C., compound 5 (285.58 mg, 945.27 umol, 0.80 eq), cesium carbonate (769.97 mg, 2.36 mmol, 2.00 eq), 0.4 mL water, 5 mL 2-methyltetrahydrofuran and dichlorobis(triphenylphosphine)palladium (41.47 mg, 59.08 umol, 0.05 eq) were added, then the reaction solution was purged three times with nitrogen and stirred at 20° C. under nitrogen atmosphere for 12 hours. Then 4-fluoro-2-trifluoromethyl iodobenzene (678.60 mg, 2.34 mmol, 2.00 eq), aqueous potassium hydroxide solution (4M, 1.46 mL, 5.00 eq), dichlorobis(triphenylphosphine)palladium (41.06 mg, 58.50 umol, 0.05 eq) and 10 mL 2-methyltetrahydrofuran were added to the above solution, which was subsequently purged three times with nitrogen. After stirring at 70° C. under nitrogen atmosphere for 12 hours, the reaction solution was filtered, and the filtrate was directly concentrated and then purified by silica gel column chromatography (PE:EA=40:1 to 15:1) to give the compound 57 as a yellow solid (350.00 mg, 628.94 umol, yield 53.76%, purity 91.2%).

Step B: Lithium hydroxide monohydrate (263.90 mg, 6.29 mmol, 10.00 eq) was added to a solution of compound 57 (350.00 mg, 628.94 umol, 1.00 eq) in a mixed solvent of 3 mL tetrahydrofuran, 3 mL methanol and 3 mL water, the reaction solution was stirred at 35° C. for 1 hour. 10 mL water was added to the reaction solution, then the mixture was adjusted to pH 5 with 1 mol/L hydrochloric acid and extracted twice with 10 mL ethyl acetate each time. The organic phase was combined, washed twice with 10 mL water each time, dried over anhydrous sodium sulfate, filtered and concentrated to give a crude product, which was purified by preparative high performance liquid chromatography (formic acid system) to give the product I-12 (108.80 mg, 226.01 umol, yield 35.94%, purity 99.6%).

$^1$H NMR (400 MHz, DMSO-$d_6$): δ 10.78 (brs, 1H), 9.57-9.54 (m, 2H), 7.48-7.38 (m, 5H), 7.31 (d, J=7.6 Hz, 1H), 7.06 (dt, J=6.8 Hz, J=0.8 Hz, 1H), 6.99 (dt, J=6.8 Hz, J=0.8 Hz, 1H), 6.93 (d, J=8.0 Hz, 2H), 6.53 (d, J=1.6 Hz, 1H), 6.40 (d, J=16.0 Hz, 1H), 2.85-2.78 (m, 1 H), 2.47-2.39 (m, 1 H), 0.95 (t, J=7.6 Hz, 3 H). MS(ESI, M+1): 480.2.

Embodiment 17

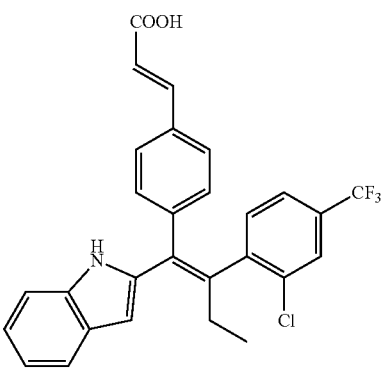

I-13

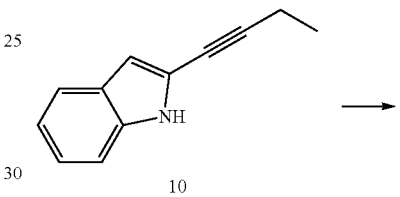

10

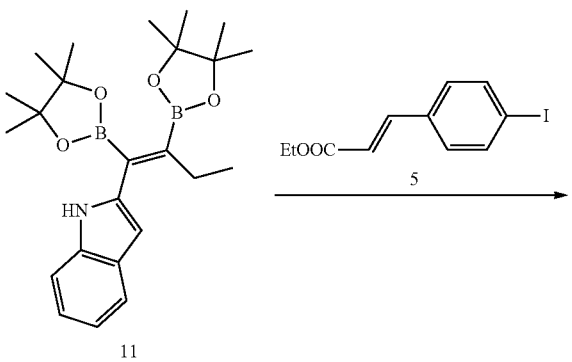

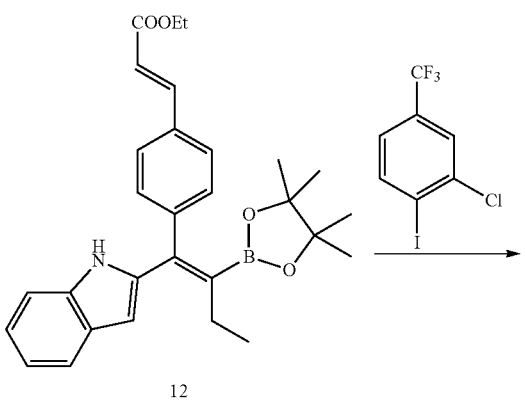

12

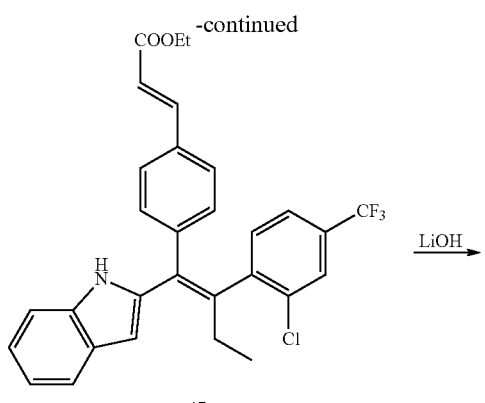

47

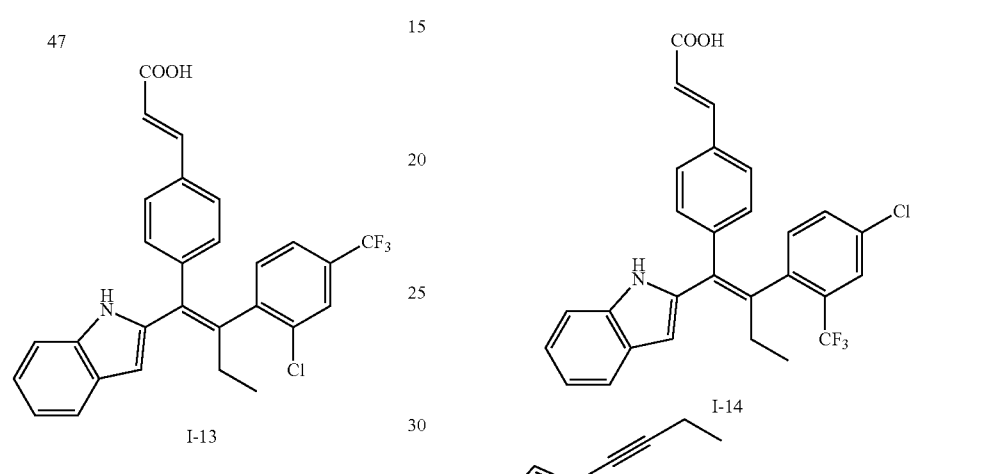

filtered and concentrated to give a crude product, which was purified by preparative high performance liquid chromatography (formic acid system) to give the product I-13 (135.30 mg, 267.64 umol, yield 18.98%, purity 98.10%).

$^1$H NMR (400 MHz, DMSO-d$_6$): δ 10.77 (brs, 1H), 7.81 (brs, 1H), 7.62 (dd, J=8.0 Hz, J=1.2 Hz, 1H), 7.57 (d, J=8.0 Hz, 1H), 7.47-7.40 (m, 4 H), 7.31 (d, J=8.0 Hz, 1H), 7.07 (dt, J=8.0 Hz, J=1.2 Hz, 1H), 7.02-6.96 (m, 3H), 6.61 (d, J=1.6 Hz, 1H), 6.41 (d, J=16.0 Hz, 1H), 2.75-2.62 (m, 2 H), 1.00 (t, J=7.6 Hz, 3H); MS(ESI, M+1): 496.2.

Embodiment 18

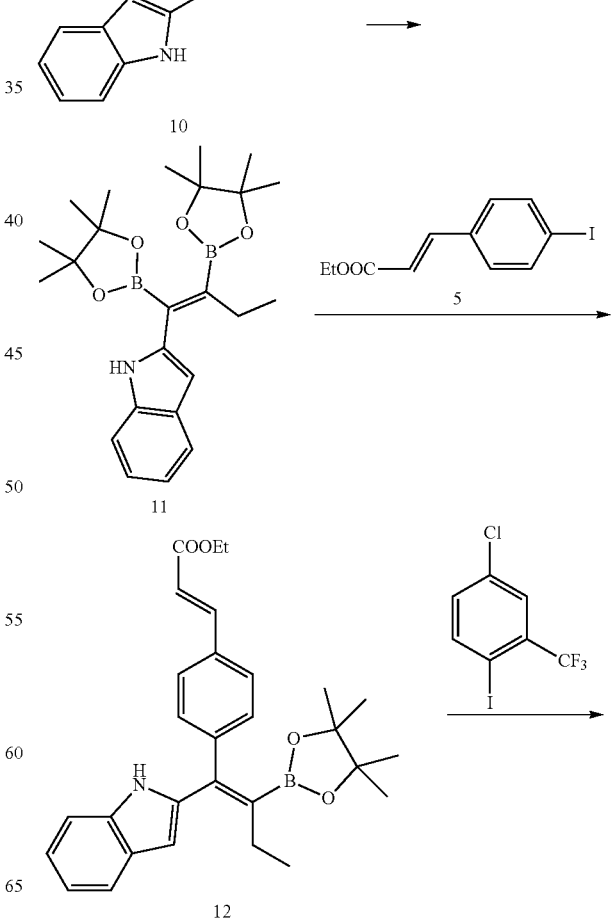

Step A: Diboron pinacol ester (329.61 mg, 1.30 mmol, 1.10 eq) and tetrakis(triphenylphosphine)platinum (73.53 mg, 59.09 umol, 0.05 eq) were added to a solution of compound 10 (200.00 mg, 1.18 mmol, 1.00 eq) in 2-methyltetrahydrofuran (5.00 mL), the reaction solution was purged three times with nitrogen and stirred at 70° C. under nitrogen atmosphere for 5 hours. After the reaction solution was cooled to 0° C., compound 5 (285.58 mg, 945.27 umol, 0.80 eq), cesium carbonate (769.97 mg, 2.36 mmol, 2.00 eq), 0.4 mL water, 5 mL 2-methyltetrahydrofuran and dichlorobis(triphenylphosphine)palladium (41.47 mg, 59.08 umol, 0.05 eq) were added, then the reaction solution was purged three times with nitrogen and stirred at 20° C. under nitrogen atmosphere for 12 hours. Then 2-chloro-4-trifluoromethyl iodobenzene (717.09 mg, 2.34 mmol, 2.00 eq), aqueous potassium hydroxide (4M, 1.46 mL, 5.00 eq), dichlorobis(triphenylphosphine)palladium (41.06 mg, 58.50 umol, 0.05 eq) and 10 mL 2-methyltetrahydrofuran were added to the reaction solution, which was subsequently purged three times with nitrogen. After stirring at 70° C. under nitrogen atmosphere for 12 hours, the reaction solution was filtered through celite, concentrated and purified by silica gel column chromatography (PE:EA=40:1 to 15:1) to give the compound 47 as a yellow jelly (738.00 mg), which was directly used in the next step.

Step B: Lithium hydroxide monohydrate (591.64 mg, 14.10 mmol, 10.00 eq) was added to a solution of compound 47 (738.80 mg, 1.41 mmol, 1.00 eq) in a mixed solvent of 3 mL methanol, 3 mL tetrahydrofuran and 3 mL water, the reaction solution was stirred at 35° C. for 1 hour. 10 mL water was added to the reaction solution, then the resulting solution was adjusted to pH 5 with 1 mol/L hydrochloric acid, extracted twice with 10 mL ethyl acetate each time. The organic phase was combined, washed twice with 10 mL water each time, dried over anhydrous sodium sulfate,

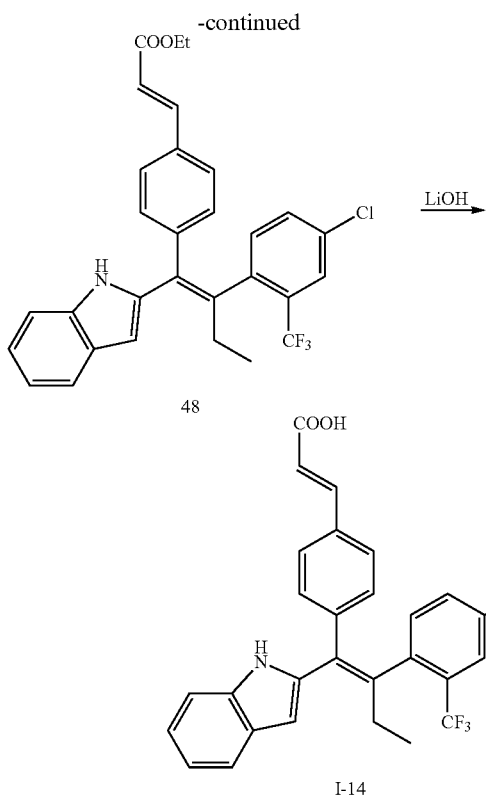

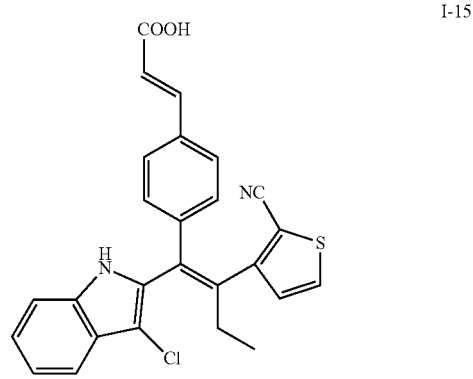

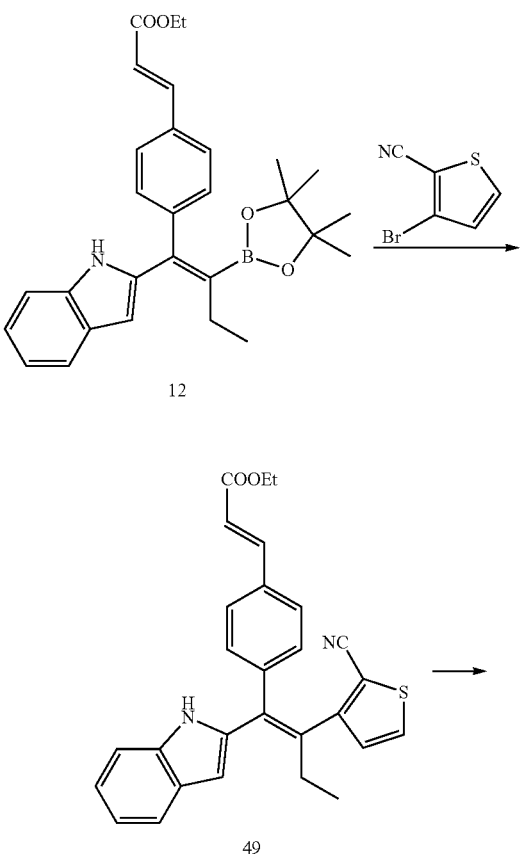

purified by preparative high performance liquid chromatography (formic acid system) to give the product I-14 (735.10 mg, 1.48 mmol, yield 29.77%, purity 99.6%).

$^1$H NMR (400 MHz, DMSO-$d_6$): δ 12.33 (brs, 1H), 10.77 (brs, 1H), 7.73 (d, J=2.0 Hz, 1H), 7.65 (dd, J=8.4 Hz, J=2.0 Hz, 1H), 7.55 (d, J=8.0 Hz, 1H), 7.45-7.37 (m, 4H), 7.31 (d, J=8.0 Hz, 1H), 7.06 (t, J=7.2 Hz, 1H), 6.99 (t, J=7.2 Hz, 1H), 6.94 (d, J=8.0 Hz, 2H), 6.53 (d, J=1.2 Hz, 1H), 6.40 (d, J=16.0 Hz, 1H), 2.87-2.78 (m, 1 H), 2.47-2.41 (m, 1 H), 0.94 (t, J=7.6 Hz, 3 H). MS (ESI, M+1 ): 496.0.

Embodiment 19

Step A: Diboron pinacol ester (1.65 g, 6.50 mmol, 1.10 eq) and tetrakis(triphenylphosphine)platinum (367.64 mg, 295.50 umol, 0.05 eq) were added to a solution of compound 10 (1.09 g, 5.91 mmol, 1.00 eq) in 2-methyltetrahydrofuran (20.00 mL), the reaction solution was purged three times with nitrogen and stirred at 70° C. under nitrogen atmosphere for 5 hours. After the reaction solution was cooled to 0° C., compound 5 (1.43 g, 4.73 mmol, 0.80 eq), cesium carbonate (3.85 g, 11.82 mmol, 2.00 eq), 1.2 mL water, 10 mL 2-methyltetrahydrofuran and dichlorobis(triphenylphosphine)palladium (207.34 mg, 295.50 umol, 0.05 eq) were added, then the reaction solution was purged three times with nitrogen and stirred at 20° C. under nitrogen atmosphere for 12 hours. Then 4-chloro-2-trifluoromethyl iodobenzene (3.63 g, 11.84 mmol, 2.00 eq), aqueous potassium hydroxide solution (4M, 7.40 mL, 5.00 eq) and dichlorobis(triphenylphosphine)palladium (207.72 mg, 296.00 umol, 0.05 eq) were added to the reaction solution, which was subsequently purged three times with nitrogen. After stirring at 70° C. under nitrogen atmosphere for 12 hours, the reaction solution was filtered, concentrated and purified by silica gel column chromatography (PE:EA=50:1 to 5:1) to give the compound 48 as a yellow jelly (2.60 g), which was directly used in the next step.

Step B: Lithium hydroxide monohydrate (2.08 g, 49.60 mmol, 10.00 eq) was added to a solution of compound 48 (2.60 g, 4.96 mmol, 1.00 eq) in a mixed solvent of 20 mL methanol, 20 mL tetrahydrofuran and 20 mL water, the reaction solution was stirred at 35° C. for 1 hour. 60 mL water was added to the reaction solution, then the mixture was adjusted to pH 5 with 1 mol/L hydrochloric acid, extracted twice with 60 mL ethyl acetate each time. The organic phase was combined, washed twice with 50 mL water each time, dried over anhydrous sodium sulfate, filtered and concentrated to give a crude product, which was

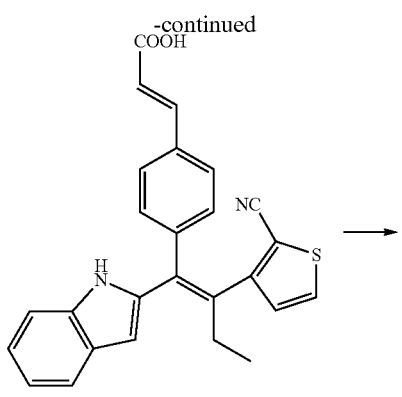

50

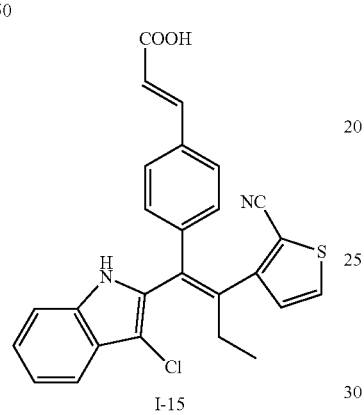

I-15

Step A: 3-Bromo-2-cyanothiophene (195.55 mg, 1.04 mmol, 2.00 eq) and aqueous potassium hydroxide solution (4M, 520.00 uL, 4.00 eq) were added to a solution of compound 12 (300.00 mg, 519.95 umol, 1.00 eq) in 2-methyltetrahydrofuran (10.00 mL), after the reaction system was purged with nitrogen for three times, dichlorobis(triphenylphosphine)palladium (18.25 mg, 26.00 umol, 0.05 eq) was added. The reaction solution was stirred at 70° C. under nitrogen atmosphere for 12 hours, then diluted with 20 mL ethyl acetate, filtered through celite. The filtrate was washed three times with 20 mL brine each time, dried over anhydrous sodium sulfate, filtered and concentrated to give the compound 49 as a brown jelly (400.00 mg, crude product).

Step B: Lithium hydroxide monohydrate (370.86 mg, 8.84 mmol, 10.00 eq) was added to a solution of compound 49 (400.00 mg, 883.84 umol, 1.00 eq) in a mixed solvent of 2 mL methanol, 2 mL tetrahydrofuran and 2 mL water, the reaction solution was stirred at 45° C. for 1 hour, then adjusted to pH 5 with 1 mol/L hydrochloric acid. 20 mL ethyl acetate was added, then washed twice with 20 mL brine each time, dried over anhydrous sodium sulfate, filtered and concentrated to give a crude product, which was purified by preparative high performance liquid chromatography (formic acid system) to give the intermediate 50 (75.00 mg, 163.0716.12 umol, yield 18.45%, purity 92.3%).

Step C: N-chlorosuccinimide (26.13 mg, 195.68 umol, 1.20 eq) was added to a solution of compound 50 (75.00 mg, 163.07 umol, 1.00 eq) in acetonitrile (5.00 mL), the reaction solution was stirred at 30° C. for 14 hours, then concentrated and purified by preparative high performance liquid chromatography (formic acid system) to give I-15 (7.40 mg, 16.12 umol, yield 9.89%, purity 100%).

$^1$H NMR (400 MHz, DMSO-d$_6$): δ 11.46 (brs, 1H), 8.03 (d, J=5.2 Hz, 1H), 7.51 (d, J=7.6 Hz, 1H), 7.44 (d, J=8.4 Hz, 2H), 7.40 (d, J=16.4 Hz, 1H), 7.37 (d, J=8.0 Hz, 1H), 7.31 (d, J=5.2 Hz, 1H), 7.19 (dt, J=7.2 Hz, J=1.2 Hz, 1H), 7.13 (dt, J=8.0 Hz, J=1.2 Hz, 1H), 6.92 (d, J=8.4 Hz, 2H), 6.42 (d, J=16.0 Hz, 1H), 2.50-2.46 (m, 2H), 0.94 (t, J=7.6 Hz, 3 H). MS (ESI, M+1, M+23): 459.0, 481.1.

Embodiment 20

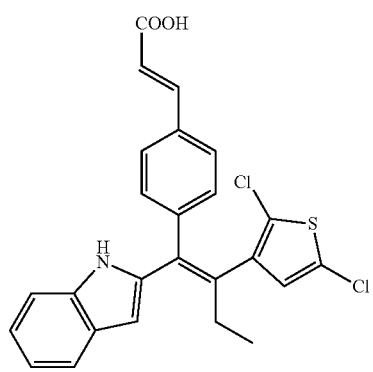

I-17

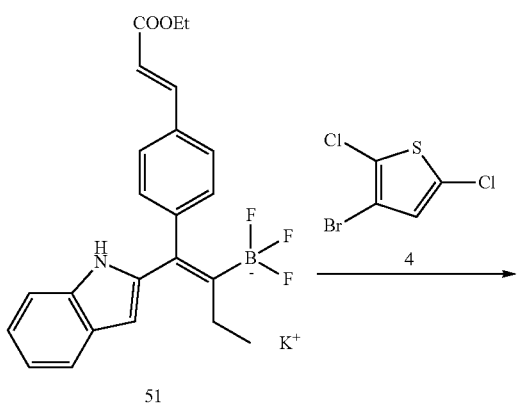

51

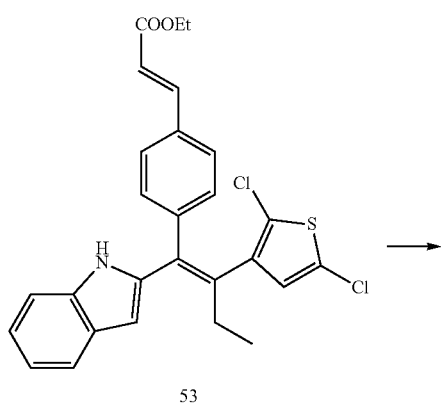

53

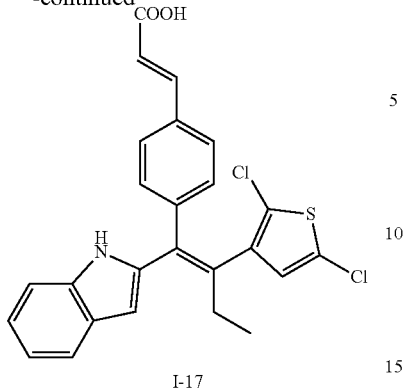

I-17

Step A: Bis(diphenylphosphino)ferrocene dichloropalladium (7.94 mg, 10.86 umol, 0.05 eq) was added to a solution of 51 (100.00 mg, 217.14 umol, 1.00 eq), 2,5-dichloro-3-bromothiophene (70.50 mg, 304.00 umol, 1.40 eq), aqueous sodium hydroxide solution (4M, 217.14 uL, 4.00 eq) in 2-methyltetrahydrofuran (10 mL) in a 100 mL three-necked flask. After the reaction system was purged with nitrogen under reduced pressure, the reaction solution was stirred at 70° C. (internal temperature 60° C.) for 12 hours, then turned from yellow to brown. 30 mL ethyl acetate was added to the reaction solution, and the resulting mixture was filtered through celite. The filtrate was washed three times with 30 mL saturated brine each time, dried over anhydrous sodium sulfate, filtered and concentrated to give the product 53 as a brown solid (200.00 mg, crude product), which was directly used in the next step.

Step B: Lithium hydroxide monohydrate (169.04 mg, 4.03 mmol, 10.00 eq) was added to a solution of compound 53 (200.00 mg, 402.86 umol, 1.00 eq) in a mixed solvent of 2 mL methanol, 2 mL tetrahydrofuran and 2 mL water in a 100 mL single-neck flask, the reaction solution was stirred at 45° C. for 1 hour and turned from yellow to brown, then adjusted to pH 1 with 1 mol/L hydrochloric acid. 30 mL ethyl acetate and 30 mL water were added, then the resulting mixture was partitioned. The organic phase was washed twice with 30 mL saturated brine each time, dried over anhydrous sodium sulfate, filtered and concentrated to give a crude product, which was purified by preparative high performance liquid chromatography (formic acid system) to give I-17 (36.00 mg, 76.71 umol, yield 19.04%, purity 99.8%). $^1$H NMR (400 MHz, DMSO-$d_6$): δ 10.73 (brs, 1H), 7.70 (d, J=3.6 Hz, 1H), 7.53 (d, J=8.0 Hz, 3H), 7.45 (d, J=16.0 Hz, 1H), 7.29 (d, J=8.0 Hz, 1H), 7.10-7.04 (m, 3H), 6.98 (t, J=7.6 Hz, 1H), 6.91 (d, J=3.6 Hz, 1H), 6.54 (brs, 1H), 6.47 (d, J=16.0 Hz, 1H), 2.75 (q, J=7.2 Hz, 2H), 2.43 (s, 3H), 1.11 (t, J=7.6 Hz, 3 H). MS (ESI, M+1): 468.0.

Embodiment 21

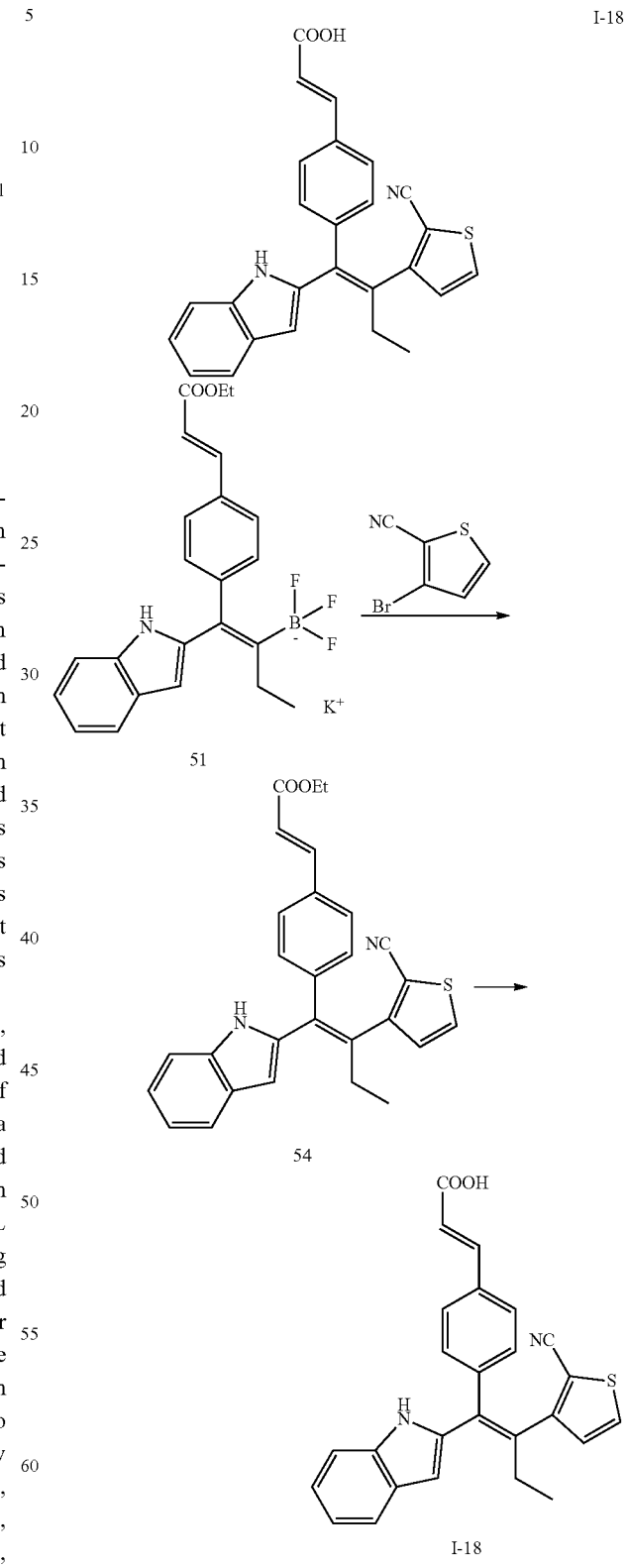

Step A: Bis(diphenylphosphino)ferrocene dichloropalladium (7.94 mg, 10.86 umol, 0.05 eq) was added to a solution of 51 (100.00 mg, 217.14 umol, 1.00 eq), 3-bromo-2-cyanothiophene (57.17 mg, 304.00 umol, 1.40 eq), aqueous sodium hydroxide solution (4M, 217.14 uL, 4.00 eq) in 2-methyltetrahydrofuran (10 mL) in a 50 mL three-necked flask. After the reaction system was purged with nitrogen under reduced pressure, the reaction solution was stirred at 70° C. for 12 hours, then turned from yellow to brown. 30 mL ethyl acetate was added to the reaction solution, and the mixture was filtered through celite. The filtrate was washed three times with 30 mL saturated brine each time, dried over anhydrous sodium sulfate, filtered and concentrated to give the product 54 as a brown solid (200.00 mg, crude product), which was directly used in the next step.

Step B: Lithium hydroxide monohydrate (185.43 mg, 4.42 mmol, 10.00 eq) was added to a solution of compound 54 (200.00 mg, 402.86 umol, 1.00 eq) in a mixed solvent of 2 mL methanol, 2 mL tetrahydrofuran and 2 mL water in a 100 mL single-neck flask, the reaction solution was stirred at 45° C. for 1 hour and turned from yellow to brown, then adjusted to pH 1 with 1 mol/L hydrochloric acid. 30 mL ethyl acetate and 30 mL water were added, then the mixture was partitioned. The organic phase was washed twice with 30 mL saturated brine each time, dried over anhydrous sodium sulfate, filtered and concentrated to give a crude product, which was purified by preparative high performance liquid chromatography (formic acid system) to give I-18 (24.70 mg, 57.95 umol, yield 13.11%, purity 99.6%).

$^1$H NMR (400 MHz, DMSO-d$_6$): δ 10.78 (brs, 1H), 7.99 (d, J=5.2 Hz, 1H), 7.57 (d, J=8.0 Hz, 1H), 7.49-7.45 (m, 3H), 7.31-7.28 (m, 2H), 7.07 (t, J=7.2 Hz, 1H), 7.00 (t, J=7.2 Hz, 1H), 6.93 (d, J=8.4 Hz, 2H), 6.58 (d, J=1.2 Hz, 1H), 6.45 (d, J=16.0 Hz, 1H), 2.71 (q, J=7.6 Hz, 2H), 1.02 (t, J=7.6 Hz, 3 H). MS (ESI, M+1): 425.1.

Embodiment 22

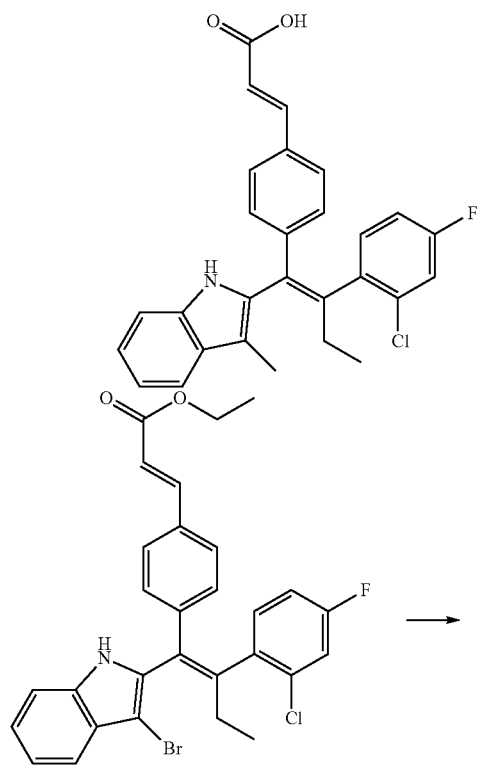

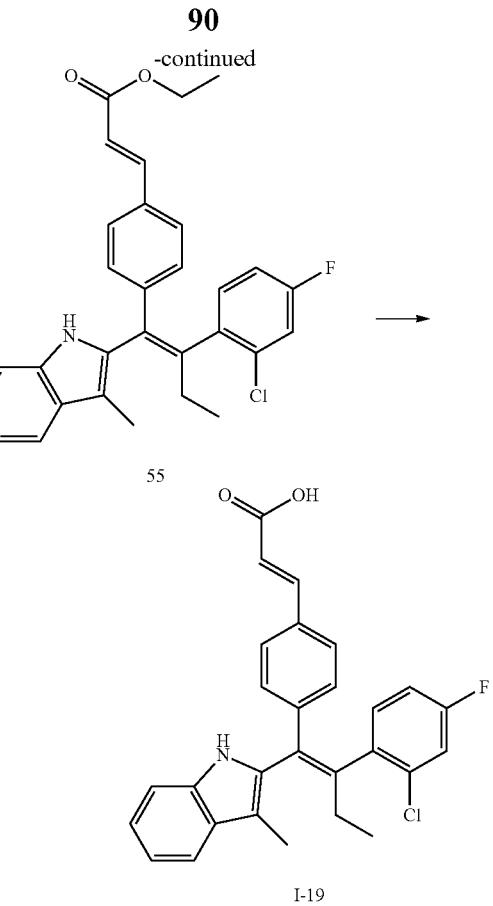

Step A: 19 (50.00 mg, 90.44 umol, 1.00 eq), 2,4,6-trimethylboroxine (34.06 mg, 271.32 umol, 37.84 uL, 3.00 eq), cesium carbonate (88.40 mg, 271.32 umol, 3.00 eq) and 3 mL dioxane were added to a single-neck round bottom flask. After the reaction system was purged with nitrogen, Pd(dppf)Cl$_2$.DCM (7.39 mg, 9.04 umol, 0.1 eq) was added, and the reaction system was purged with nitrogen again. The yellow emulsible mixture was stirred at 120° C. for 1 hour and turned from bright yellow to dark yellow. The reaction solution was filtered and concentrated to give a crude product, which was purified by preparative TLC (PE:EA=5:1) to give the intermediate 55 (25.00 mg, 51.23 umol, yield 56.65%). MS (ESI, M+1): 488.1.

Step B: Lithium hydroxide monohydrate (6.45 mg, 153.69 umol, 3.00 eq) was added to a solution of compound 55 (25.00 mg, 51.23 umol, 1.00 eq) in a mixed solvent of 2 mL tetrahydrofuran, 2 mL methanol and 2 mL water, the colorless transparent solution was stirred at 20° C. for 72 hours, then concentrated under reduced pressure, diluted with 10 mL water, adjusted to pH 1-2 with 1 mol/L hydrochloric acid, extracted three times with 20 mL ethyl acetate, washed with 20 mL saturated brine, dried over anhydrous sodium sulfate, filtered and concentrated to give a crude product, which was purified by preparative TLC (PE:EA=3:1) to give the product I-19 (20.00 mg, 43.44 umol, yield 84.79%, purity 99.9%).

$^1$H NMR (400 MHz, DMSO-d$_6$) δ 10.80 (s, 1H), 8.30 (s, 1H), 7.49 (d, J=7.6 Hz, 1H), 7.43-7.32 (m, 5H), 7.30 (d, J=8.0 Hz, 1H), 7.18 (dt, J=2.4, 8.5 Hz, 1H), 7.07 (dt, J=1.2, 7.6 Hz, 1H), 7.03-6.95 (m, 3H), 6.39 (d, J=16.0 Hz, 1H), 2.43 (q, J=7.6 Hz, 2H), 2.29 (s, 3H), 0.86 (t, J=7.6 Hz, 3H); MS (ESI, M+1): 460.1.

Embodiment 23

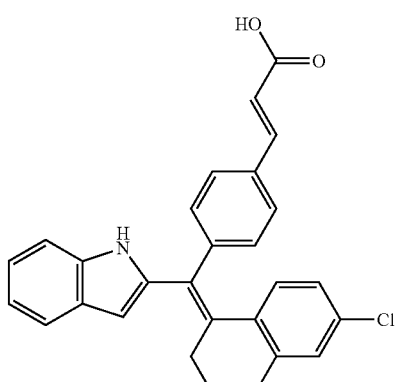

Embodiment 24

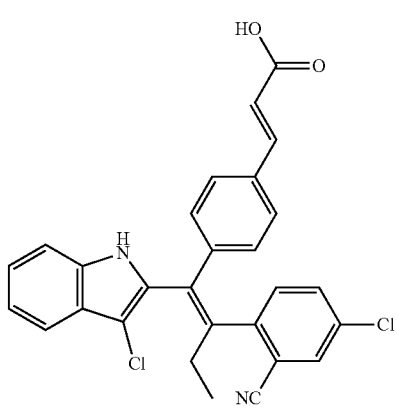

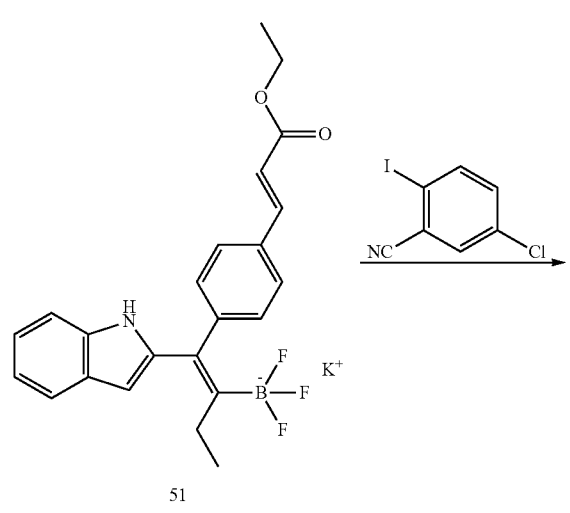

Step A: 51 (101.68 mg, 221.57 umol, 1.00 eq), 5-chloro-2-iodobenzonitrile (70.05 mg, 265.88 umol, 1.20 eq), Pd(dppf)Cl$_2$ (8.11 mg, 11.08 umol, 0.05 eq) and 2-methyltetrahydrofuran (5.00 mL) were added to a three-necked round bottom flask, after the reaction system was purged with nitrogen, 4M sodium hydroxide (221.57 uL, 4.00 eq) was added, and the reaction system was purged with nitrogen again. The reaction solution was heated to 68° C. and stirred for 10 hours, then filtered. The filter cake was washed with 10 mL ethyl acetate and the filtrate was concentrated to give intermediate 63 (125.00 mg), which was directly used in the next step. MS (ESI, M+1): 481.2.

Step B: 63 (125.00 mg, 259.88 umol, 1.00 eq), tetrahydrofuran (2.00 mL) and methanol (2.00 mL) were added to a single-neck round bottom flask, followed by addition of lithium hydroxide monohydrate (32.71 mg, 779.64 umol, 3.00 eq) and water (2.00 mL). The reaction solution was stirred at 30° C. for 12 hours, then concentrated to remove the solvent. 5 mL water was added to the reaction solution, and the resulting mixture was adjusted to pH 3 with 2M hydrochloric acid, extracted twice with 20 mL ethyl acetate each time. The organic phase was combined, washed with saturated brine, dried over anhydrous sodium sulfate, filtered and concentrated to give a crude product, which was purified by preparative high performance liquid chromatography (formic acid system) to give the product I-21 (32.00 mg, 70.51 umol, yield 27.13%, purity 99.8%). $^1$H NMR (400 MHz, DMSO-$d_6$) δ=10.77 (s, 1H), 7.88 (d, J=2.0 Hz, 1H), 7.75 (dd, J=2.0, 8.4 Hz, 1H), 7.61 (dd, J=8.0, 12.0 Hz, 2H), 7.49-7.37 (m, 3H), 7.31 (br d, J=8.0 Hz, 1H), 7.08 (br t, J=7.2 Hz, 1H), 7.04-6.99 (m, 1H), 6.94 (br d, J=8.0 Hz, 2H), 6.62 (s, 1H), 6.44 (br d, J=16.0 Hz, 1H), 2.95-2.57 (m, 2H), 1.03 (br t, J=7.2 Hz, 3H); MS (ESI, M+1): 453.1.

Step C:

I-21 (80.00 mg, 176.63 umol, 1.00 eq), 3 mL dichloromethane, 6 mL acetonitrile and NCS (25.94 mg, 194.29 umol, 1.10 eq) were added to a single-neck round bottom flask under nitrogen atmosphere. The reaction solution was stirred at 25° C. for 1 hour, then quenched with 10% sodium thiosulphate (20 mL). 20 mL dichloromethane was added, and the mixture was partitioned, the aqueous phase was extracted three times with 10 mL dichloromethane each time. The organic phase was combined, washed with 20 mL saturated brine, dried over anhydrous sodium sulfate, filtered and concentrated to give a crude product, which was purified by preparative high performance liquid chromatography (formic acid system) to give the product I-22 (25.00 mg, 50.99 umol, yield 28.87%, purity 99.4%). $^1$H NMR (400 MHz, DMSO-$d_6$) δ=11.47 (br s, 1H), 7.94 (br s, 1H), 7.78 (br d, J=8.0 Hz, 1H), 7.60-7.49 (m, 2H), 7.48-7.36 (m, 4H), 7.25-7.09 (m, 2H), 6.96 (br d, J=7.2 Hz, 2H), 6.41 (br d, J=15.6 Hz, 1H), 2.61-2.53 (m, 2H), 0.93 (br t, J=6.8 Hz, 3H); MS (ESI, M+1): 487.0.

Embodiment 25

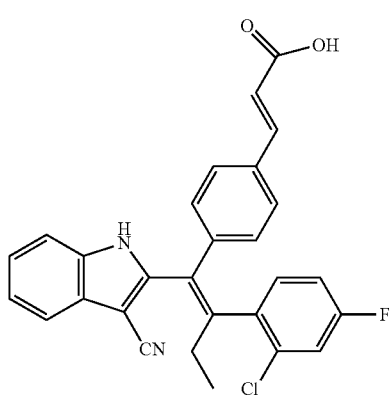

I-23

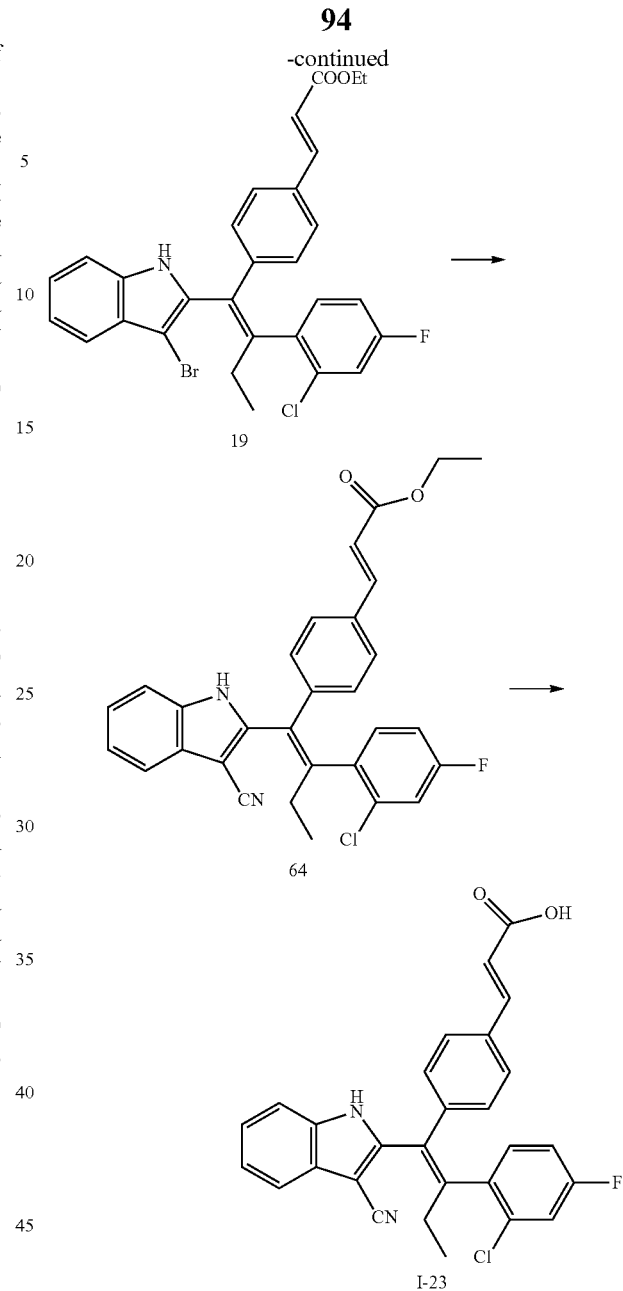

Step A: Compound 19 (50.00 mg, 85.92 umol, 1.00 eq) and CuCN (23.08 mg, 257.75 umol, 3.00 eq) were dissolved in NMP (2.00 mL). The reaction solution was purged with nitrogen, stirred at 180° C. for 2 hours under microwave irradiation and turned from green to black. After completion of the reaction, water (20 mL) was added, and the mixture was adjusted to pH 10 with aqueous NaHCO$_3$ (2 mL) and extracted with ethyl acetate (20 mL*3). The organic phase was combined, washed with saturated brine (30 mL), dried over anhydrous sodium sulfate, filtered and concentrated to give a crude product, which was purified by preparative TLC (PE:EA=5:1) to give the product 64 as a yellow oil (10.00 mg, 16.43 umol, yield 19.13%, purity 82%). MS (ESI, M+1): 499.1.

Step B: Compound 64 (80.00 mg, 160.33 umol, 1.00 eq) was dissolved in a mixed solvent of tetrahydrofuran (1.50 mL), ethanol (1.50 mL) and water (1.50 mL), followed by addition of LiOH.H$_2$O (20.18 mg, 480.99 umol, 3.00 eq), then the reaction solution was stirred at 30° C. for 12 hours. The reaction was incomplete, then sodium hydroxide (9.62 mg, 240.50 umol, 1.50 eq) and ethanol (1.50 mL) were added to the reaction solution. The yellow reaction solution was stirred at 45° C. for 3 hours. After completion of the reaction, the reaction solution was concentrated to give a crude product, then water (1 mL) and 3 mol/L HCl were added to the crude product to adjust pH to 4. Then a solid precipitated, which was isolated by filtration. The solid was purified by preparative chromatography (formic acid system) to give the product I-23 (25.90 mg, 54.45 umol, yield 33.96%, purity 99%). MS (ESI, M+1): 471.0.

$^1$H NMR (400 MHz, DMSO-$d_6$) δ 12.36 (br s, 1H), 7.65 (d, J=6.8 Hz, 1H), 7.52 (d, J=8.0 Hz, 1H), 7.48-7.41 (m, 3H), 7.37 (br d, J=16.0 Hz, 1H), 7.34-7.25 (m, 3H), 7.25-7.17 (m, 1H), 7.01 (d, J=8.4 Hz, 2H), 6.41 (br d, J=16.4 Hz, 1H), 2.46-2.40 (m, 1H), 2.46-2.40 (m, 1H), 0.94 (t, J=7.6 Hz, 3H).

Embodiment 26

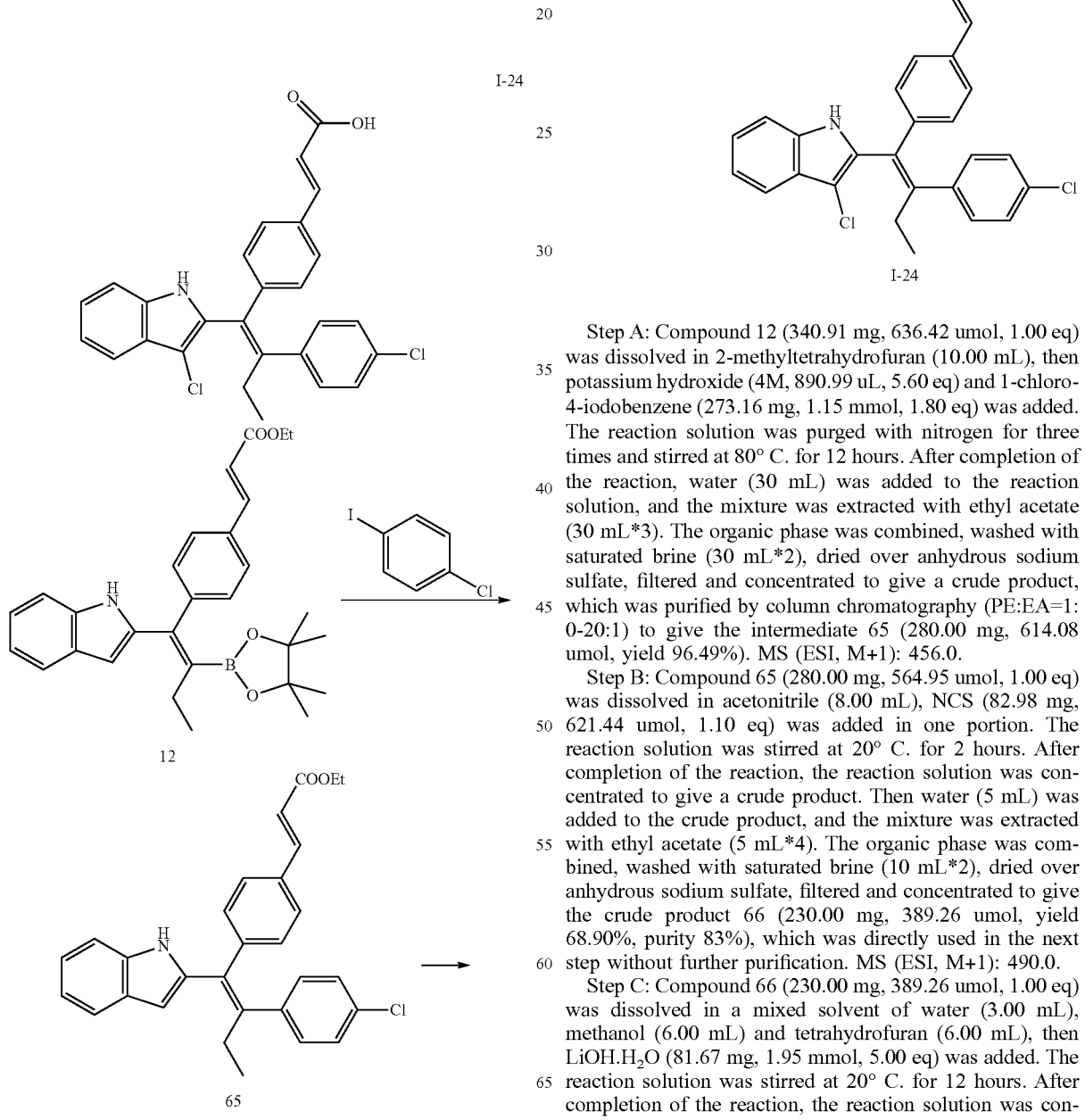

Step A: Compound 12 (340.91 mg, 636.42 umol, 1.00 eq) was dissolved in 2-methyltetrahydrofuran (10.00 mL), then potassium hydroxide (4M, 890.99 uL, 5.60 eq) and 1-chloro-4-iodobenzene (273.16 mg, 1.15 mmol, 1.80 eq) was added. The reaction solution was purged with nitrogen for three times and stirred at 80° C. for 12 hours. After completion of the reaction, water (30 mL) was added to the reaction solution, and the mixture was extracted with ethyl acetate (30 mL*3). The organic phase was combined, washed with saturated brine (30 mL*2), dried over anhydrous sodium sulfate, filtered and concentrated to give a crude product, which was purified by column chromatography (PE:EA=1: 0-20:1) to give the intermediate 65 (280.00 mg, 614.08 umol, yield 96.49%). MS (ESI, M+1): 456.0.

Step B: Compound 65 (280.00 mg, 564.95 umol, 1.00 eq) was dissolved in acetonitrile (8.00 mL), NCS (82.98 mg, 621.44 umol, 1.10 eq) was added in one portion. The reaction solution was stirred at 20° C. for 2 hours. After completion of the reaction, the reaction solution was concentrated to give a crude product. Then water (5 mL) was added to the crude product, and the mixture was extracted with ethyl acetate (5 mL*4). The organic phase was combined, washed with saturated brine (10 mL*2), dried over anhydrous sodium sulfate, filtered and concentrated to give the crude product 66 (230.00 mg, 389.26 umol, yield 68.90%, purity 83%), which was directly used in the next step without further purification. MS (ESI, M+1): 490.0.

Step C: Compound 66 (230.00 mg, 389.26 umol, 1.00 eq) was dissolved in a mixed solvent of water (3.00 mL), methanol (6.00 mL) and tetrahydrofuran (6.00 mL), then LiOH.H$_2$O (81.67 mg, 1.95 mmol, 5.00 eq) was added. The reaction solution was stirred at 20° C. for 12 hours. After completion of the reaction, the reaction solution was concentrated, adjusted to pH 4 with 3 mol/L HCl (1 mL), filtered to give a solid, which was dissolved in 1 mL DMF and purified by preparative chromatography (formic acid system) to give the product I-24 as a yellow solid (41.00 mg, 81.58 umol, yield 20.96%, purity 92%), but the purity was not enough. The product was purified by alkaline preparative chromatography, but the purity was still not enough, then purified by preparative TLC (dichloromethane:ethyl acetate=10:1) to give the product I-24 (9.70 mg, 20.56 umol, yield 25.20%, purity 98%).

1H NMR (400 MHz, DMSO-d$_6$) δ 11.47 (s, 1H), 7.50 (d, J=7.6 Hz, 1H), 7.47-7.30 (m, 6H), 7.25-7.16 (m, 3H), 7.16-7.10 (m, 1H), 6.93 (d, J=8.4 Hz, 2H), 6.40 (d, J=16.0 Hz, 1H), 2.48-2.40 (m, 2H), 0.90 (t, J=7.6 Hz, 3H). MS (ESI, M+1): 462.0.

Embodiment 27

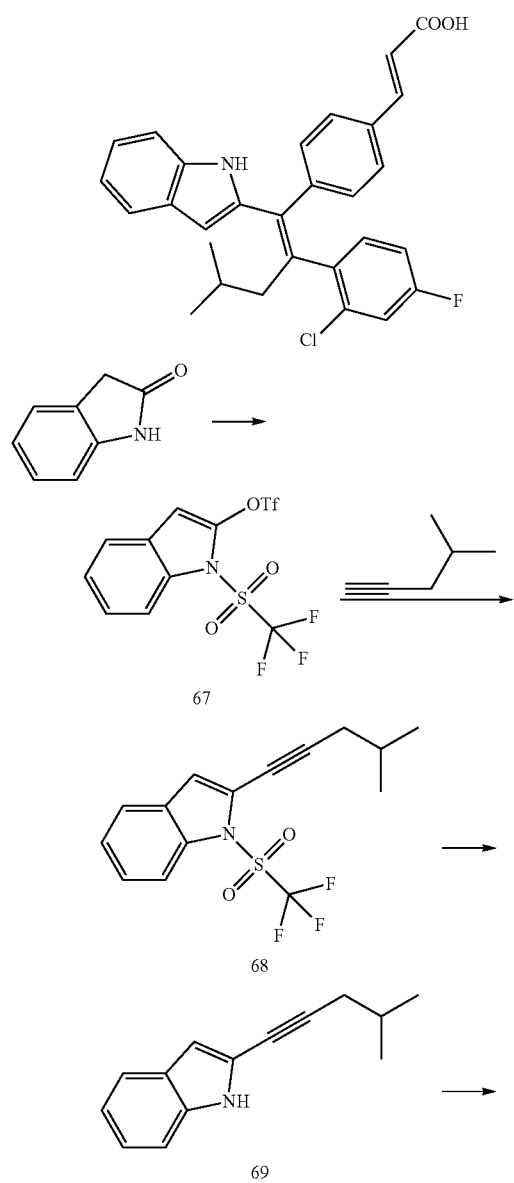

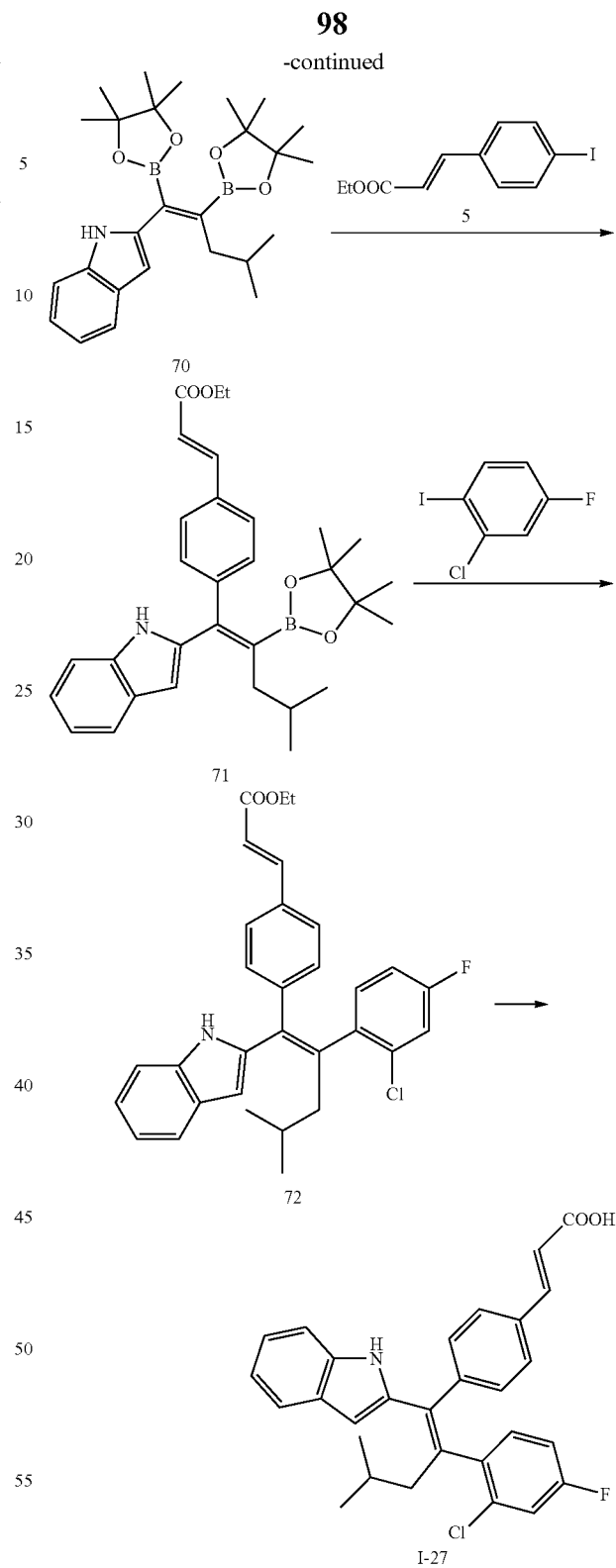

Step A: Trifluoromethanesulfonic anhydride (19.07 g, 67.59 mmol, 11.15 mL, 3.00 eq) was slowly added dropwise to a solution of oxindole (3.00 g, 22.53 mmol, 1.00 eq) and triethylamine (22.80 g, 225.30 mmol, 31.23 mL, 10.00 eq) in 100 mL 2-methyltetrahydrofuran at −78° C. under nitrogen atmosphere in a reaction flask. The reaction solution was stirred for more than 2 hours, and turned from colorless to orange. Then 4-methyl-1-pentyne (3.70 g, 45.06 mmol, 5.29 mL, 2.00 eq), triethylamine (22.80 g, 225.30 mmol, 31.23 mL, 10.00 eq), tetrakis(triphenylphosphine)platinum (2.60 g, 2.25 mmol, 0.10 eq) and cuprous iodide (429.08 mg, 2.25 mmol, 0.10 eq) were added. The reaction solution was purged with nitrogen, warmed to 15° C. and stirred under nitrogen atmosphere for 12 hours. The gray suspension turned into a black solution. The reaction solution was quenched by saturated aqueous ammonium chloride solution (300 mL), extracted three times with 100 mL ethyl acetate each time. The organic phase was washed with saturated brine (100 mL), dried over anhydrous sodium sulfate, filtered, concentrated under reduced pressure to give a residue, which was purified by silica gel column chromatography (EA:PE=0-5%) to give the compound 68 (4.90 g, 14.88 mmol, yield 66.04%).

Step B: Potassium carbonate (3.78 g, 27.32 mmol, 2.00 eq) was added to a solution of compound 68 (4.50 g, 13.66 mmol, 1.00 eq) in 50 mL tetrahydrofuran and 50 mL methanol. The reaction solution was stirred at 25° C. for 12 hours and the colorless mixture turned from yellow to brown. 200 mL ethyl acetate and 200 mL water were added to the reaction solution. The mixture was partitioned in a separatory funnel. The organic phase was washed three times with 100 mL water each time, dried over anhydrous sodium sulfate, filtered and concentrated under reduced pressure to give the compound 69 (2.60 g, 13.18 mmol, yield 96.48%).

Step C: Tetrakis(triphenylphosphine)platinum (126.29 mg, 101.50 umol, 0.05 eq) was added to a solution of compound 69 (400.00 mg, 2.03 mmol, 1.00 eq) and diboron pinacol ester (515.50 mg, 2.03 mmol, 1.00 eq) in 10 mL 2-methyltetrahydrofuran. The reaction solution was stirred at 70° C. for 5 hours and gradually turned from yellow to brown. The reaction solution of compound 70 in 10 mL 2-methyltetrahydrofuran was directly used in the next step.

Step D: Compound 5 (490.63 mg, 1.62 mmol, 0.80 eq), 10 mL 2-methyltetrahydrofuran and 3 mL water were added to the solution of compound 70 (915.96 mg, 2.03 mmol, 1.00 eq) in 10 mL 2-methyltetrahydrofuran. Then cesium carbonate (1.32 g, 4.06 mmol, 2.00 eq) and bis(triphenylphosphine)palladium dichloride (142.49 mg, 203.00 umol, 0.10 eq) were quickly added to the mixture at 0° C. The reaction solution was stirred at 25° C. under nitrogen atmosphere for 12 hours and gradually turned from yellow to brown. The reaction solution of compound 71 in 20 mL 2-methyltetrahydrofuran was directly used in the next step.

Step E: 2-Chloro-4-fluoro-iodobenzene (621.61 mg, 2.42 mmol, 1.20 eq) and 10 mL 2-methyltetrahydrofuran were added to the solution of compound 71 (1.01 g, 2.02 mmol, 1.00 eq) in 20 mL 2-methyltetrahydrofuran, then aqueous potassium hydroxide solution (4M, 2.53 mL, 5.00 eq) and bis(triphenylphosphine)palladium dichloride (70.89 mg, 101.00 umol, 0.05 eq) were added at 25° C. The reaction solution was stirred at 70° C. for 12 hours, then filtered, and 30 mL ethyl acetate and 30 mL water were added. The mixture was partitioned with a separatory funnel. The organic phase was washed with 30 mL brine, dried over anhydrous sodium sulfate, filtered, concentrated under reduced pressure to give a crude product, which was purified by silica gel column chromatography (PE:EA=1:0 to 20:1) to give the intermediate 72 (500.00 mg, crude product).

Step F: Lithium hydroxide monohydrate (417.91 mg, 9.96 mmol, 10.00 eq) was added to a solution of compound 72 (500.00 mg, 995.98 umol, 1.00 eq) in tetrahydrofuran (5.00 mL), methanol (5.00 mL) and water (5.00 mL) at 25° C., The mixture was stirred at 40° C. for 1 hour and turned from yellow to brown, then adjusted to pH 3 with 1M HCl, and 20 mL water was added. The mixture was extracted twice with 20 mL ethyl acetate each time. The organic phase was combined, washed twice with 20 mL brine each time, dried over anhydrous sodium sulfate, filtered, concentrated to give a crude product, which was purified by preparative high performance liquid chromatography (formic acid system) to give the product I-27 (150.00 mg, 307.62 umol, yield 30.89%, purity 97.2%).

$^1$H NMR (400 MHz, DMSO-$d_6$): δ 10.78 (brs, 1H), 7.56 (d, J=7.6 Hz, 1H), 7.48-7.38 (m, 3H), 7.34 (dd, J=2.4 Hz, J=9.2 Hz, 1H), 7.31-7.25 (m, 2H), 7.11 (dt, J=2.4 Hz, J=8.4 Hz, 1H), 7.08-7.03 (m, 1H), 7.01-6.96 (m, 3H), 6.52 (d, J=1.2 Hz, 1H), 6.40 (d, J=16.0 Hz, 1H), 2.62-2.53 (m, 2H), 1.55-1.45 (m, 1H), 0.87 (d, J=6.8 Hz, 3H), 0.84 (d, J=6.8 Hz, 3H). MS(ESI, M+1): 474.1.

Embodiment 28

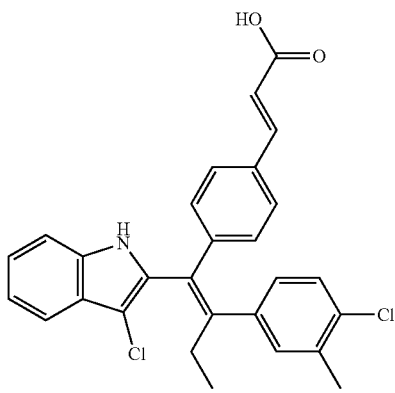

I-28

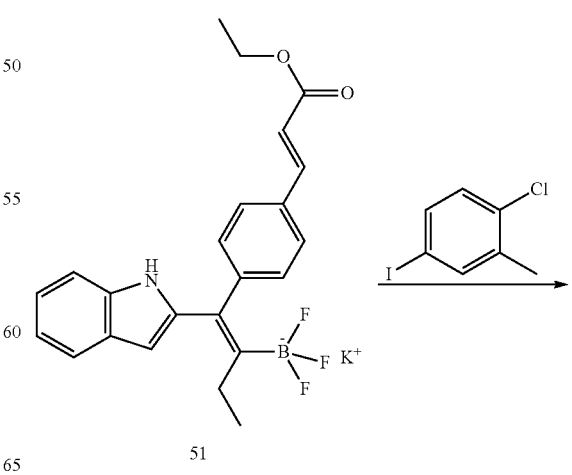

51

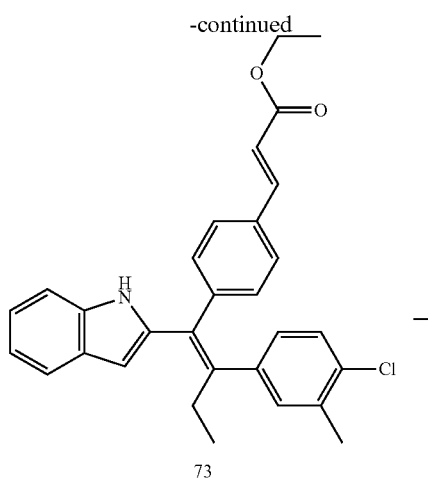

73

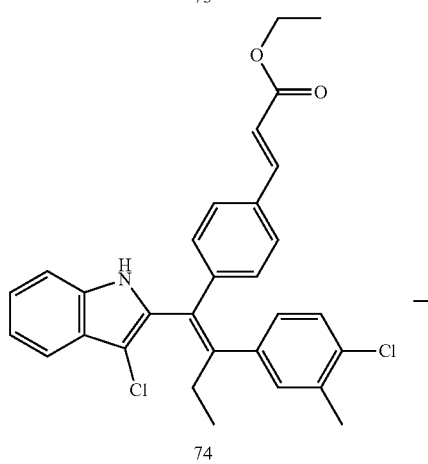

74

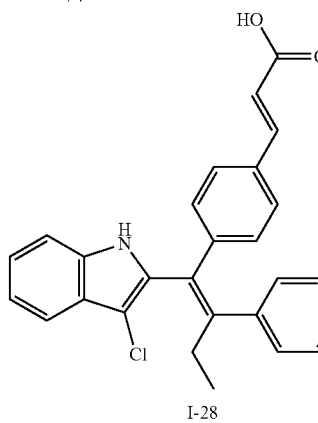

I-28

Step A: NaOH (4M, 443.13 uL, 4.00 eq) was added to a solution of compound 51 (200.00 mg, 443.13 umol, 1.00 eq), 4-chloro-1-iodo-2-toluene (156.63 mg, 620.38 umol, 1.40 eq), Pd(dppf)Cl$_2$ (16.21 mg, 22.16 umol, 0.05 eq) in 12 mL 2-methyltetrahydrofuran, the reaction solution was purged with nitrogen for three times, then stirred at 65° C. for 12 hours, gradually turned from yellow to black. 20 mL water was added to the above solution, and the mixture was extracted three times with ethyl acetate (20 mL*3). The organic phase was combined, washed with 20 mL saturated brine, dried over anhydrous sodium sulfate and filtered. The filtrate was concentrated under reduced pressure to give a crude product, which was purified by silica gel column chromatography (400 mesh, PE:EA=1:0 to 20:1) to give the compound 73 (170.00 mg, 325.53 umol, yield 73.46%, purity 90%).

Step B: NCS (38.35 mg, 287.23 umol, 1.00 eq) was added to a solution of compound 73 (150.00 mg, 287.23 umol, 1.00 eq) in acetonitrile (6.00 mL) and dichloromethane (14.00 mL). The yellow solution was stirred at 30° C. for 1.5 hours. Then 30 mL water was added to the reaction solution, and the mixture was extracted twice with ethyl acetate (30 mL*2). The organic phase was combined, washed twice with saturated brine (20 mL*2), dried over anhydrous sodium sulfate, filtered, concentrated under reduced pressure to give a crude product, which was purified by silica gel column chromatography (PE:EA=1:0 to 10:1) to give the intermediate 74 (170.00 mg, crude).

Step C: LiOH.H$_2$O (70.70 mg, 1.69 mmol, 5.00 eq) was added to a solution of compound 74 (170.00 mg, 337.00 umol, 1.00 eq) in water (2.00 mL), tetrahydrofuran (2.00 mL) and ethanol (2.00 mL). The yellow solution was stirred at 30° C. for 1.5 hours, then concentrated under reduced pressure to give a residue. 1 mL water was added to the residue, the resulting solution was adjusted to pH 4 with 3M hydrochloric acid. A solid precipitated, which was isolated by filtration and then dissolved in 3 mL DMF and purified by preparative high performance liquid chromatography (formic acid system) to give the product I-28 (46.50 mg, 96.63 umol, yield 28.67%, purity 99%).

$^1$H NMR (400 MHz, DMSO-d$_6$) δ 11.46 (s, 1H), 7.50 (d, J=7.6 Hz, 1H), 7.46-7.37 (m, 4H), 7.31-7.23 (m, 2H), 7.22-7.09 (m, 2H), 7.00-6.91 (m, 3H), 6.40 (d, J=16.0 Hz, 1H), 2.45 (q, J=7.6 Hz, 2H), 2.27 (s, 3H), 0.90 (t, J=7.6 Hz, 3H). MS (ESI, M+1): 476.0.

Embodiment 29

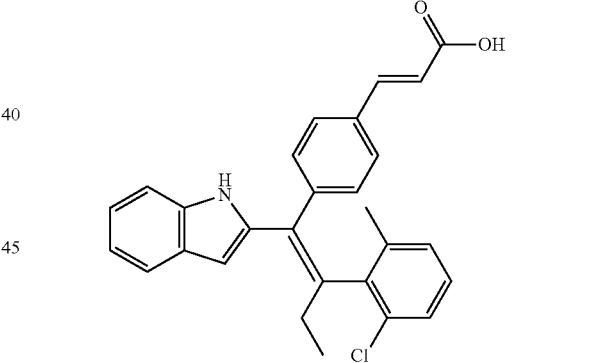

I-29

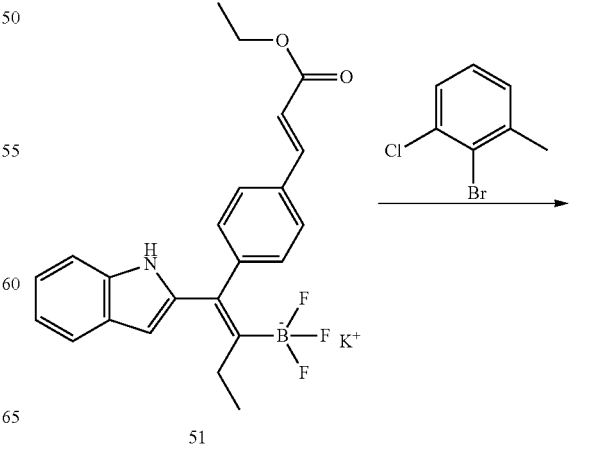

51

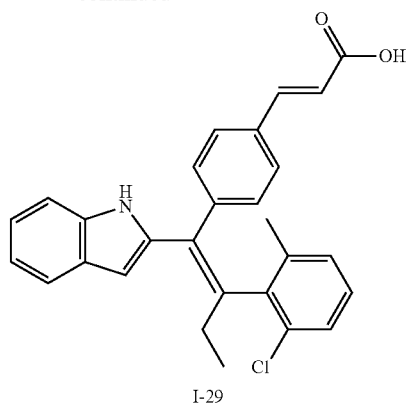

I-29

Sodium hydroxide (34.87 mg, 871.64 umol, 4.00 eq) was added to a mixture of compound 51 (100.00 mg, 217.91 umol, 1.00 eq), 2-bromo-3-chlorotoluene (62.69 mg, 305.07 umol, 1.40 eq) and 2-methyltetrahydrofuran (10.00 mL) in a single-neck flask, followed by addition of 1,1'-bis(diphenylphosphino)ferrocene palladium chloride (7.97 mg, 10.90 umol, 0.05 eq) under nitrogen atmosphere. The reaction solution was stirred at 70° C. for 16 hours. After completion of the reaction, the reaction solution was adjusted to pH 1 with hydrochloric acid (3M) at room temperature, then extracted with ethyl acetate (20 mL). The organic phase was concentrated to give a crude product, which was purified by preparative liquid phase chromatography (prep. HPLC: formic acid) to give the product I-29 (5.30 mg, 11.79 umol, yield 5.41%, purity 98.3%).

MS (ESI, M+1): 442.0.

$^1$H NMR (400 MHz, DMSO-$d_6$) δ=10.80 (s, 1H), 8.40 (s, 1H), 7.57 (d, J=7.3 Hz, 1H), 7.39-7.27 (m, 5H), 7.16-7.11 (m, 1H), 7.09-7.04 (m, 2H), 7.03-6.97 (m, 3H), 6.61 (d, J=1.4 Hz, 1H), 6.38 (d, J=15.9 Hz, 1H), 2.62-2.56 (m, 2H), 2.16 (s, 3H), 1.00 (t, J=7.5 Hz, 3H).

Embodiment 30

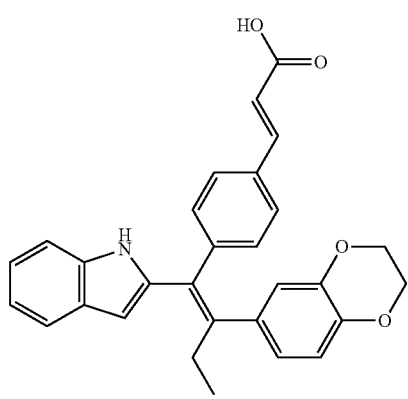

I-30

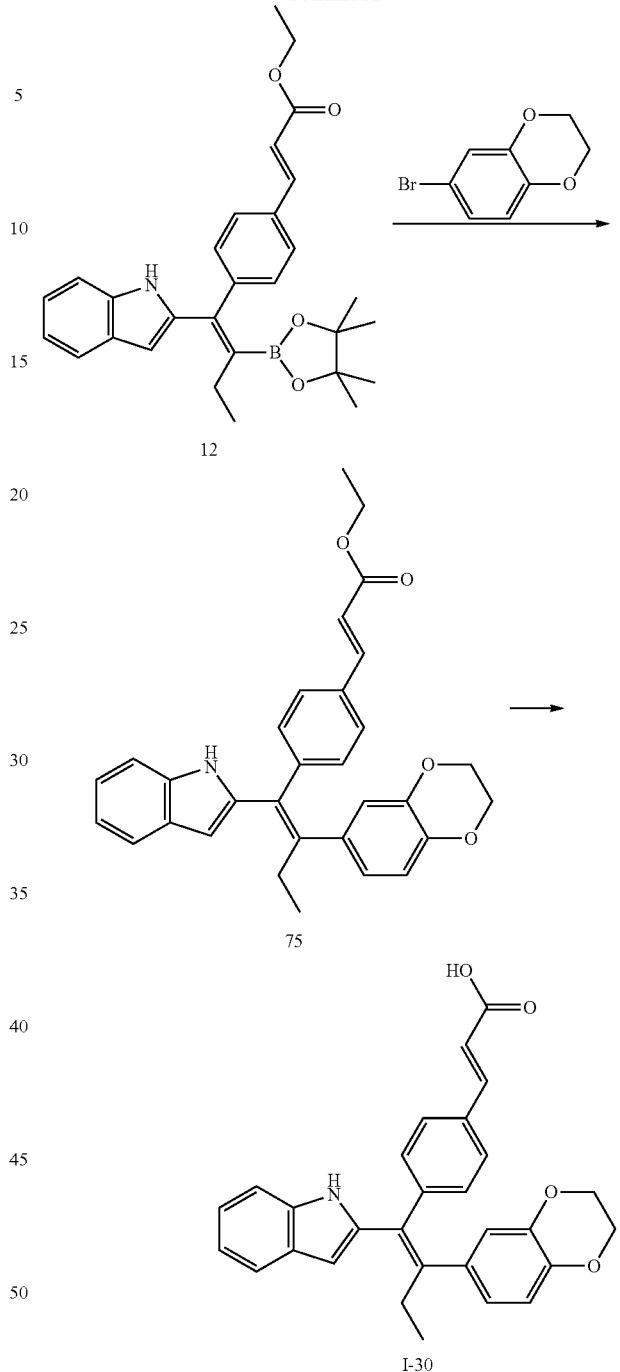

I-30

Step A: Compound 12 (100.00 mg, 212.13 umol, 1.00 eq) and 6-bromo-1,4-benzodioxan (68.42 mg, 318.19 umol, 42.76 uL, 1.50 eq) were weighed and dissolved in 2-methyltetrahydrofuran (4.00 mL) under nitrogen atmosphere, followed by addition of potassium hydroxide (66.65 mg, 1.19 mmol, 5.60 eq) (dissolved in 500.00 uL water) and dichlorobis(triphenylphosphine)palladium(II) (7.44 mg, 10.61 umol, 0.05 eq), the reaction solution was stirred at 75° C. for 16 hours. After completion of the reaction, the reaction solution was filtered through silica gel (100-200 mesh), the silica gel was washed with ethyl acetate (30 mL), the filtrate was combined and concentrated to give the crude product 75 as a dark brown oil (210.00 mg), which was directly used in the next step.

Step B: Lithium hydroxide monohydrate (36.75 mg, 875.78 umol, 2.00 eq) was added to a solution of the crude product 75 (210.00 mg) in tetrahydrofuran (4.00 mL), methanol (1.00 mL) and water (1.00 mL), the reaction solution was stirred at 25° C. for 4 hours. After completion of the reaction, the reaction solution was adjusted to pH 1 with hydrochloric acid (3M) at room temperature, then extracted with ethyl acetate (30 mL). The organic phase was washed with saturated brine (10 mL*2), concentrated to give a crude product, which was purified by preparative liquid phase chromatography (prep. HPLC: formic acid) to give the product I-30 (27.95 mg, 61.67 umol, yield 14.08%, purity 99.63%).

MS (ESI, M+1): 452.0.

$^1$H NMR (400 MHz, DMSO-d$_6$) δ=10.72 (s, 1H), 7.53 (d, J=7.8 Hz, 1H), 7.50-7.40 (m, 3H), 7.28 (d, J=8.0 Hz, 1H), 7.09-6.90 (m, 4H), 6.72-6.64 (m, 2H), 6.55 (dd, J=1.9, 8.3 Hz, 1H), 6.47 (d, J=1.4 Hz, 1H), 6.42 (d, J=16.1 Hz, 1H), 4.19 (s, 4H), 2.60 (q, J=7.2 Hz, 2H), 0.96 (t, J=7.3 Hz, 3H).

Embodiment 31

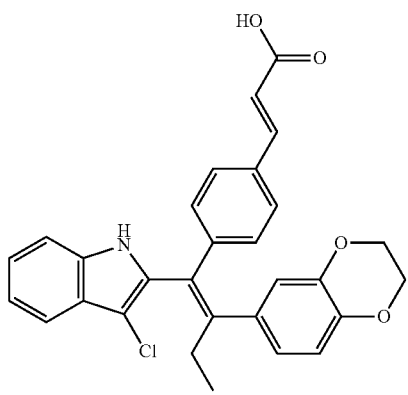

I-30

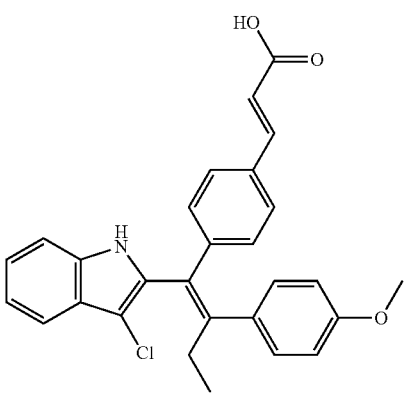

I-31

Compound I-30 (160.00 mg, 287.85 umol, 1.00 eq) was weighed and dissolved in acetonitrile (2.00 mL), N-chlorosuccinimide (38.44 mg, 287.85 umol, 1.00 eq) was added in portions, the reaction solution was stirred at 25° C. for 2 hours. After completion of the reaction, a saturated aqueous sodium thiosulfate solution (3 mL) was added to the reaction solution, the mixture was stirred for a few minutes, then extracted with dichloromethane (30 mL*1). The organic phase was concentrated to give a crude product, which was purified by preparative liquid phase chromatography (prep. HPLC: formic acid) to give the product I-31 as a yellow solid (25.82 mg, 51.84 umol, yield 18.01%, purity 97.56%).

$^1$H NMR (400 MHz, DMSO-d$_6$) δ=11.43 (s, 1H), 8.40 (s, 1H), 7.48 (d, J=7.9 Hz, 1H), 7.41-7.33 (m, 4H), 7.20-7.10 (m, 2H), 6.94 (d, J=8.3 Hz, 2H), 6.77-6.68 (m, 2H), 6.66-6.61 (m, 1H), 6.38 (d, J=15.9 Hz, 1H), 4.21 (s, 4H), 2.39 (q, J=7.3 Hz, 2H), 0.89 (t, J=7.4 Hz, 3H); MS (ESI, M+1): 486.1.

Embodiment 32

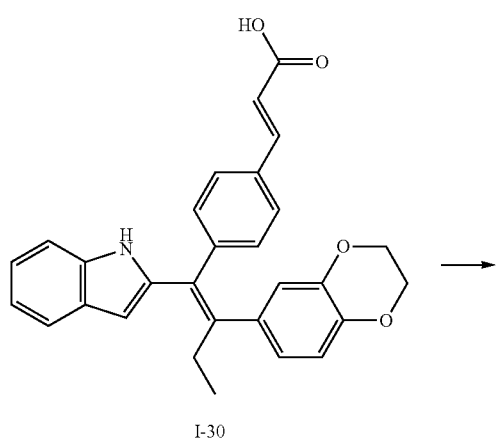

Embodiment 33

-continued

I-32

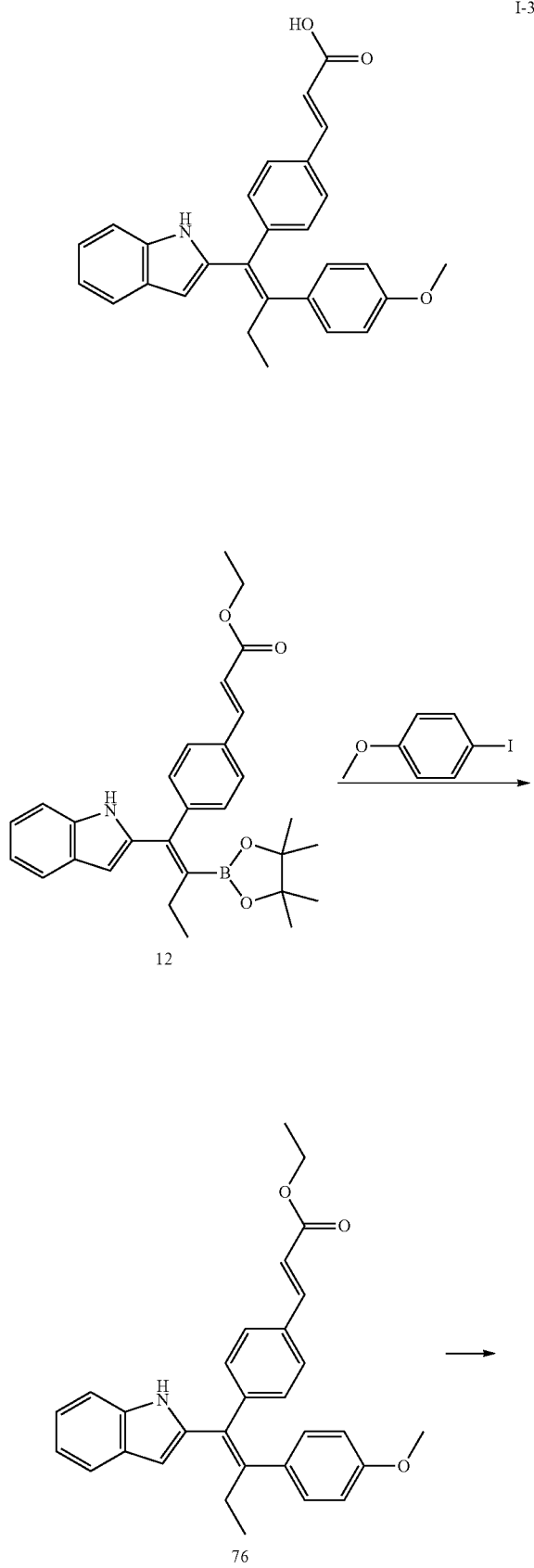

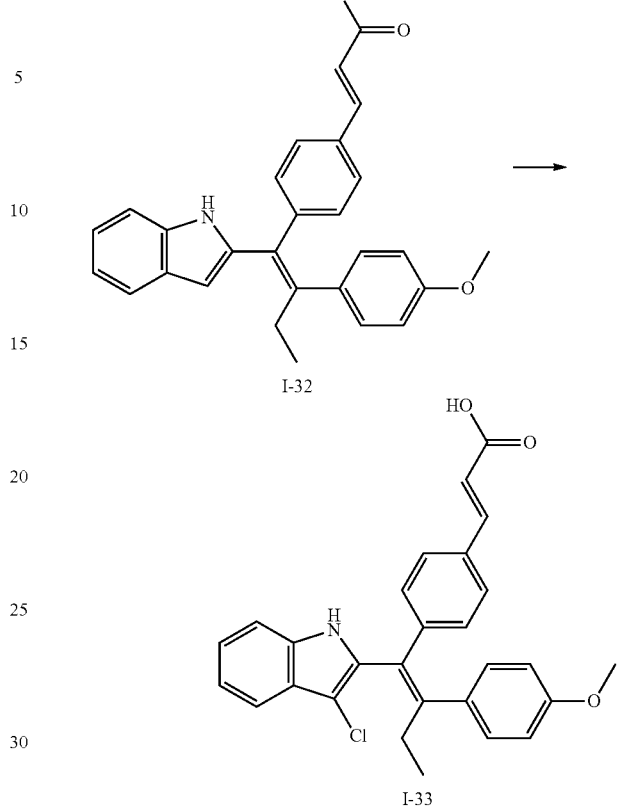

Step A: Compound 12 (100.00 mg, 212.13 umol, 1.00 eq) and 4-iodoanisole (74.47 mg, 318.19 umol, 1.50 eq) were weighed and dissolved in 2-methyltetrahydrofuran (4.00 mL) under nitrogen atmosphere, followed by addition of potassium hydroxide (66.65 mg, 1.19 mmol, 5.60 eq) (dissolved in 500.00 uL water) and dichlorobis(triphenylphosphine)palladium(II) (7.44 mg, 10.61 umol, 0.05 eq), the reaction solution was stirred at 75° C. for 16 hours. After completion of the reaction, the reaction solution was filtered through silica gel (100-200 mesh), the silica gel was washed with ethyl acetate (30 mL*1), the filtrate was combined and concentrated to give a crude product as a dark brown oil, which was purified by silica gel plate (PE/EA=10/1) to give the intermediate 76 (50.00 mg).

Step B: Lithium hydroxide monohydrate (25.09 mg, 597.90 umol, 15.00 eq) was added to a solution of the crude product 76 (50.00 mg) in a mixed solvent of tetrahydrofuran (2.00 mL), methanol (0.50 mL) and water (0.50 mL), the reaction solution was stirred at 25° C. for 4 hours. After completion of the reaction, the reaction solution was adjusted to pH 1 with hydrochloric acid (3M) at room temperature, then extracted with ethyl acetate (30 mL*1). The organic phase was concentrated to give the crude product I-32 as a yellow solid (68.00 mg).

Step C: Compound I-32 (68.00 mg) was weighed and dissolved in acetonitrile (2.00 mL) and dichloromethane (2.00 mL), N-chlorosuccinimide (10.72 mg, 80.28 umol, 0.50 eq) was added in portions, the reaction solution was stirred at 25° C. for 2 hours. After completion of the reaction, a saturated aqueous sodium thiosulfate solution (3 mL) was added to the reaction solution, the resulting mixture was stirred for a few minutes, then extracted with dichloromethane (30 mL*1). The organic phase was concentrated to give a crude product, which was purified by preparative liquid phase chromatography (prep. HPLC: formic acid) to give the product I-33 (8.71 mg, 18.39 umol, yield 11.45%, purity 96.67%).

MS (ESI, M+1): 458.1.

¹H NMR (400 MHz, DMSO-$d_6$) δ=11.44 (s, 1H), 8.42 (s, 1H), 7.48 (d, J=7.7 Hz, 1H), 7.40-7.29 (m, 4H), 7.20-7.16 (m, 1H), 7.15-7.09 (m, 3H), 6.92 (d, J=8.2 Hz, 2H), 6.84 (d, J=8.7 Hz, 2H), 6.36 (d, J=15.9 Hz, 1H), 3.73 (s, 3H), 2.43 (m, J=7.5 Hz, 2H), 0.89 (t, J=7.3 Hz, 3H).

Embodiment 34

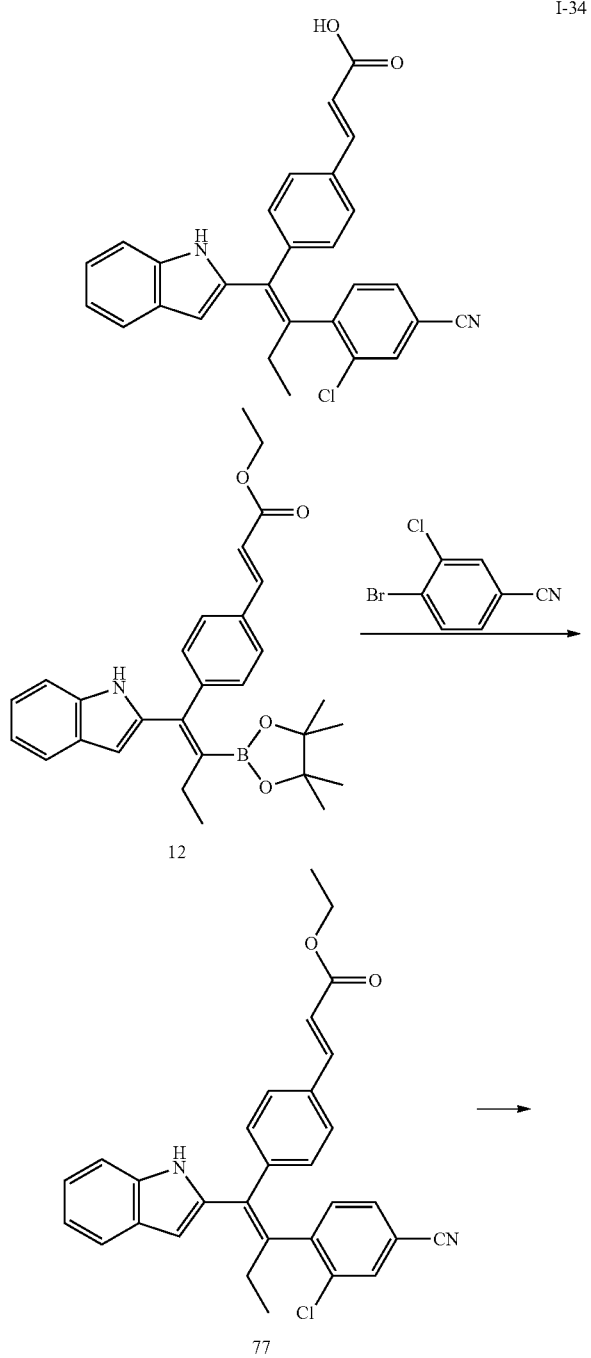

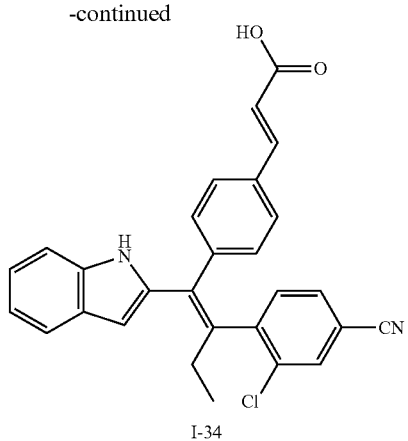

Step A: Compound 12 (200.00 mg, 339.42 umol, 1.00 eq) and 4-bromo-3-chlorobenzonitrile (110.21 mg, 509.13 umol, 1.50 eq) were weighed and dissolved in 2-methyltetrahydrofuran (8.00 mL) under nitrogen atmosphere, followed by addition of potassium hydroxide (106.65 mg, 1.90 mmol, 5.60 eq) (dissolved in 1.00 mL water) and dichlorobis(triphenylphosphine)palladium(II) (11.91 mg, 16.97 umol, 0.05 eq), the reaction solution was stirred at 75° C. for 8 hours. After completion of the reaction, the reaction solution was concentrated to remove 2-methyltetrahydrofuran, extracted with ethyl acetate (30 mL*1), dried, concentrated to give a crude product, which was purified by preparative TLC (PE/EA=5/1), further by preparative liquid phase chromatography (prep. HPLC: formic acid) to to give the intermediate 77 (8.00 mg, 15.76 umol, yield 4.64%, purity 94.75%).

Step B: Lithium hydroxide monohydrate (5.00 mg, 119.16 umol, 7.56 eq) was added to a solution of the compound 77 (8.00 mg) in a mixed solvent of tetrahydrofuran (2.00 mL), methanol (0.50 mL) and water (0.50 mL), the reaction solution was stirred at 25° C. for 4 hours. Under the same condition, additional lithium hydroxide monohydrate (5.00 mg, 119.16 umol, 7.56 eq) was added, and the reaction was allowed to continue for another 2 hours. After completion of the reaction, the reaction solution was adjusted to pH 1 with hydrochloric acid (4M) under an ice bath, then concentrated, extracted with ethyl acetate (15 mL*1). The organic phase was concentrated to give a crude product, which was purified by preparative liquid phase chromatography (prep. HPLC: formic acid) to give the product I-34 (3.60 mg, 7.88 umol, yield 50.02%, purity 99.18%).

MS (ESI, M+1): 453.0.

¹H NMR (400 MHz, DMSO-$d_6$) δ 10.77 (s, 1H), 8.38 (s, 1H), 7.99 (d, J=1.5 Hz, 1H), 7.73 (dd, J=1.6, 7.9 Hz, 1H), 7.57 (d, J=7.8 Hz, 1H), 7.46 (d, J=8.1 Hz, 1H), 7.43-7.29 (m, 4H), 7.11-7.05 (m, 1H), 7.04-6.94 (m, 3H), 6.61 (d, J=1.5 Hz, 1H), 6.40 (d, J=16.0 Hz, 1H), 2.74-2.67 (m, 2H), 1.00 (t, J=7.5 Hz, 3H).

Embodiment 35

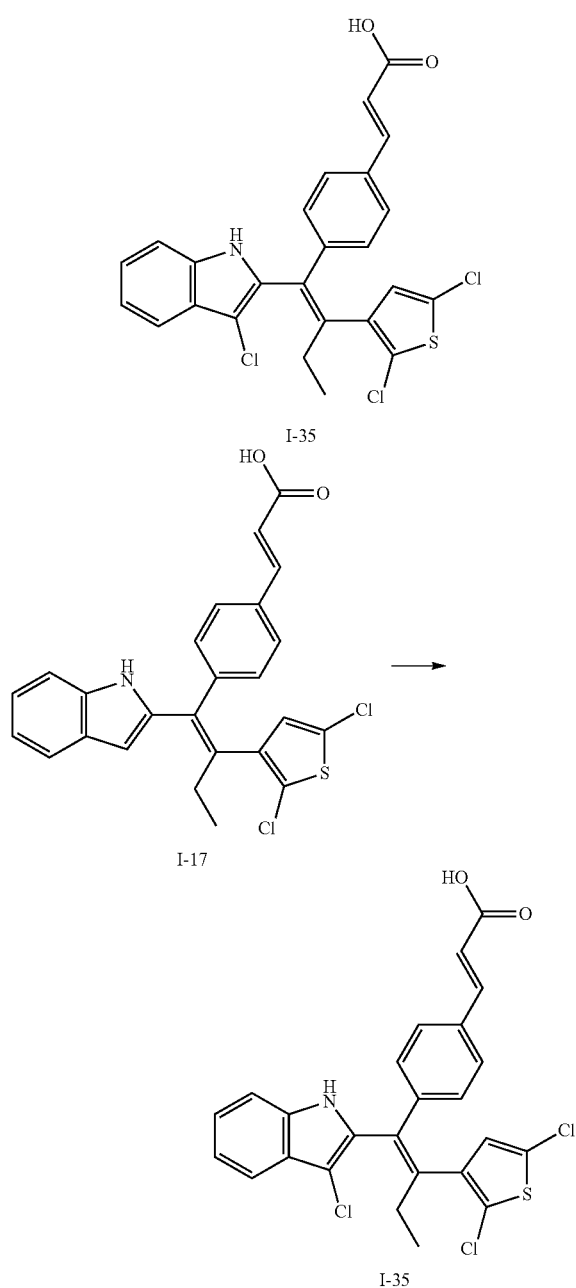

Compound I-17 (70.00 mg, 124.04 umol, 1.00 eq) was weighed and dissolved in acetonitrile (4.00 mL) and dichloromethane (4.00 mL), N-chlorosuccinimide (11.59 mg, 86.83 umol, 0.70 eq) was added in portions, the reaction solution was stirred at 25° C. for 2 hours. After completion of the reaction, a saturated aqueous sodium thiosulfate solution (2 mL) was added to the reaction solution, the mixture was stirred for a few minutes, then extracted with dichloromethane (30 mL*1). The organic phase was concentrated to give a crude product, which was purified by preparative TLC plate (dichloromethane/ethyl acetate=1/1, with a small amount of acetic acid) to give a yellow solid 2 (20.00 mg, 35.25 umol, yield 28.42%, purity 88.63%). The solid 2 was purified by preparative TLC (100% ethyl acetate), further by preparative liquid phase chromatography (formic acid) to give the product I-35 as a yellow solid (8.00 mg, 15.64 umol, yield 47.38%, purity 98.3%).

$^1$H NMR (400 MHz, CHLOROFORM-d) δ=7.88 (s, 1H), 7.72-7.64 (m, 2H), 7.36-7.29 (m, 3H), 7.28-7.21 (m, 2H), 7.05 (d, J=8.4 Hz, 2H), 6.72 (s, 1H), 6.38 (d, J=16.0 Hz, 1H), 2.53 (q, J=7.6 Hz, 2H), 1.05 (t, J=7.6 Hz, 3H); MS (ESI, M+1): 502.0.

Embodiment 36

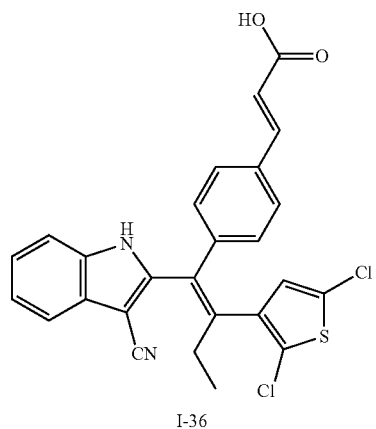

I-36

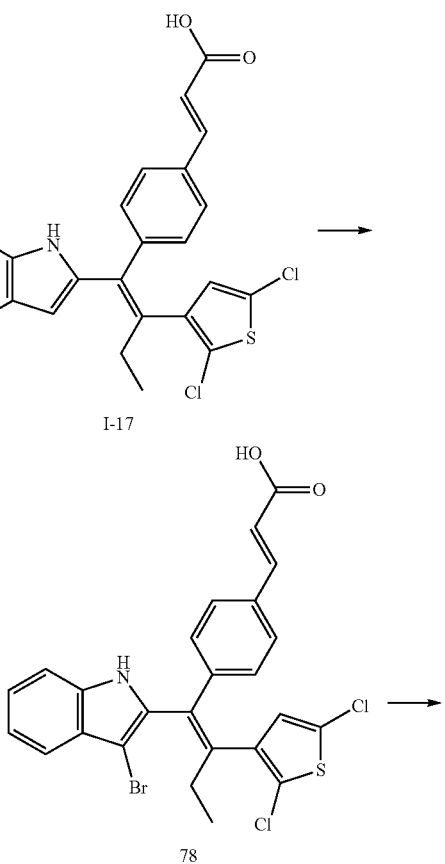

-continued

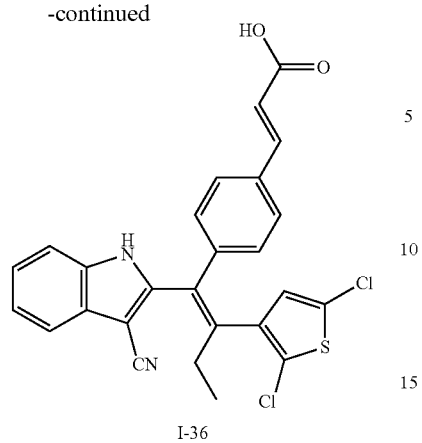

I-36

Step A: Compound I-17 (93.00 mg, 198.55 umol, 1.00 eq) was weighed and dissolved in acetonitrile (4.00 mL) and dichloromethane (4.00 mL), N-chlorosuccinimide (24.74 mg, 138.98 umol, 0.70 eq) was added in portions, the reaction solution was stirred at 25° C. for 1 hour. After completion of the reaction, a saturated aqueous sodium thiosulfate solution (3 mL) was added to the reaction solution, the mixture was stirred for a few minutes, then extracted with dichloromethane (30 mL*1). The organic phase was concentrated to give a crude product, which was purified by preparative TLC (dichloromethane/ethyl acetate=1/1, with a small amount of acetic acid) to give the intermediate 78 (95.00 mg, 151.02 umol, yield 76.06%, purity 87%).

Step B: Compound 78 (95.00 mg, 168.38 umol, 1.00 eq) was dissolved in N-methylpyrrolidone (2.00 mL) in a microwave tube, followed by addition of copper cyanide (31.06 mg, 346.86 umol, 75.76 uL, 2.06 eq), the reaction solution was stirred at 180° C. for 1.5 hours under microwave irradiation. Under the same condition, additional copper cyanide (30.16 mg, 336.76 umol, 73.56 uL, 2.00 eq) was added to the reaction solution and the reaction was allowed to continue for 2 hours. Under the same condition, additional copper cyanide (45.24 mg, 505.14 umol, 110.34 uL, 3.00 eq) was added to the reaction solution and the reaction was allowed to continue for 2 hours. After completion of the reaction, the reaction solution was poured into ice water (20 mL), extracted with ethyl acetate (50 mL*2). The organic phase was dried over anhydrous sodium sulfate, filtered and concentrated to give a crude product, which was purified by preparative liquid chromatography (prep. HPLC: formic acid) to give the product I-36 as a yellow solid (7.18 mg, 13.75 umol, yield 8.16%, purity 94.46%).

$^1$H NMR (400 MHz, DMSO-d$_6$) δ=12.28 (s, 1H), 7.66 (d, J=7.1 Hz, 1H), 7.55 (d, J=8.3 Hz, 2H), 7.52-7.46 (m, 2H), 7.33-7.24 (m, 3H), 7.00 (d, J=8.3 Hz, 2H), 6.47 (d, J=16.0 Hz, 1H), 2.44-2.39 (m, 2H), 0.98 (t, J=7.4 Hz, 3H); MS (ESI, M+1): 493.0.

Embodiment 37

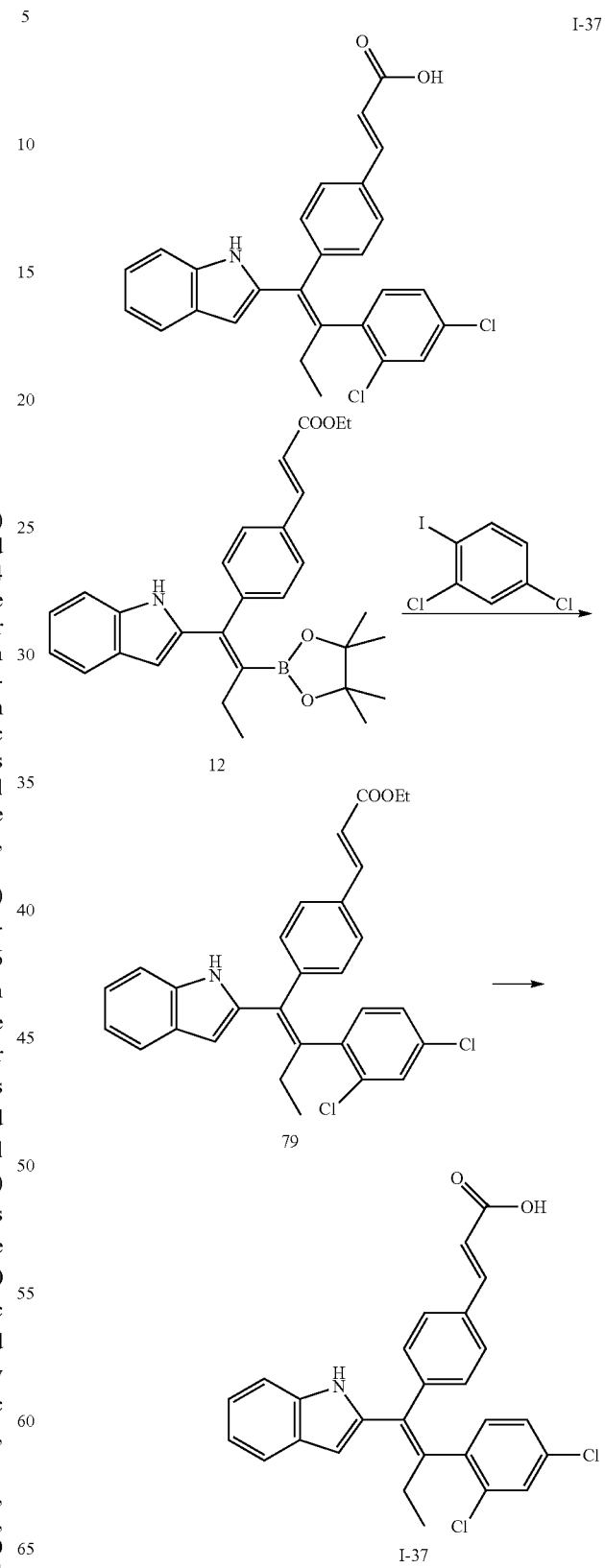

Step A: Compound 12 (300.00 mg, 560.05 umol, 1.00 eq) and 2,4-dichloro-1-iodobenzene (275.11 mg, 1.01 mmol, 1.80 eq), 2-methyltetrahydrofuran (10.00 mL) and aqueous potassium hydroxide solution (4M, 784.06 uL, 5.60 eq) were added to a 100 mL three-necked flask with magnetic stirring. After the reaction system was purged with nitrogen for three times, Pd(PPh$_3$)$_2$Cl$_2$ (11.79 mg, 16.80 umol, 0.03 eq) was added. The reaction system was purged with nitrogen for three times again, then the reaction solution was stirred at 80° C. for 12 hours, and eventually turned from yellow to black. After completion of the reaction, water (30 mL) was added to the reaction solution and the mixture was extracted with dichloromethane (30 mL*3). The organic phase was combined, washed with saturated brine (30 mL*2), dried over anhydrous sodium sulfate, filtered and concentrated to give a crude product, which was purified by column chromatography (PE:EA=1:0 to 20:1) to give the compound 79 (330.00 mg, crude). MS (ESI, M+1): 490.0.

Step B: Compound 79 (330.00 mg, 672.89 umol, 1.00 eq) was dissolved in a mixed solvent of water (4.00 mL), methanol (8.00 mL) and tetrahydrofuran (8.00 mL). LiOH.H$_2$O (141.17 mg, 3.36 mmol, 5.00 eq) was added to the above solution, which subsequently turned from yellow to light green. The reaction solution was stirred at 20° C. for 12 hours. After the completion of reaction, the reaction solution was evaporated to give a residue. Then 3 mol/L HCl (1.5 mL) was added to the residue to adjust the pH of the resulting solution to 5, the solution was filtered to give a filter cake, which was purified by preparative chromatography (formic acid) to give the product I-37 (33.70 mg, 71.43 umol, yield 10.62%, purity 98%).

$^1$H NMR (400 MHz, DMSO-d$_6$) δ 10.74 (s, 1H), 8.31 (br s, 1H), 7.62-7.49 (m, 2H), 7.44-7.35 (m, 3H), 7.34-7.27 (m, 2H), 7.23 (d, J=8.0 Hz, 1H), 7.10-7.03 (m, 1H), 7.02-6.93 (m, 3H), 6.57 (d, J=1.2 Hz, 1H), 6.40 (d, J=16.0 Hz, 1H), 2.75-2.58 (m, 2H), 0.99 (t, J=7.2 Hz, 3H); MS (ESI, M+1): 462.0.

Embodiment 38

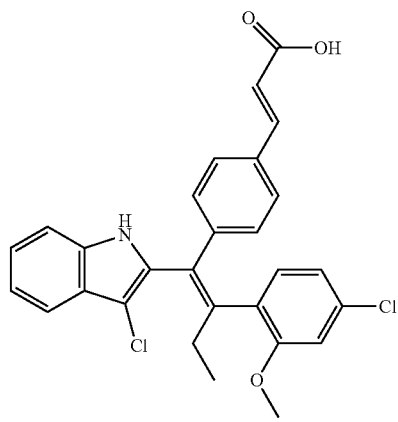

I-38

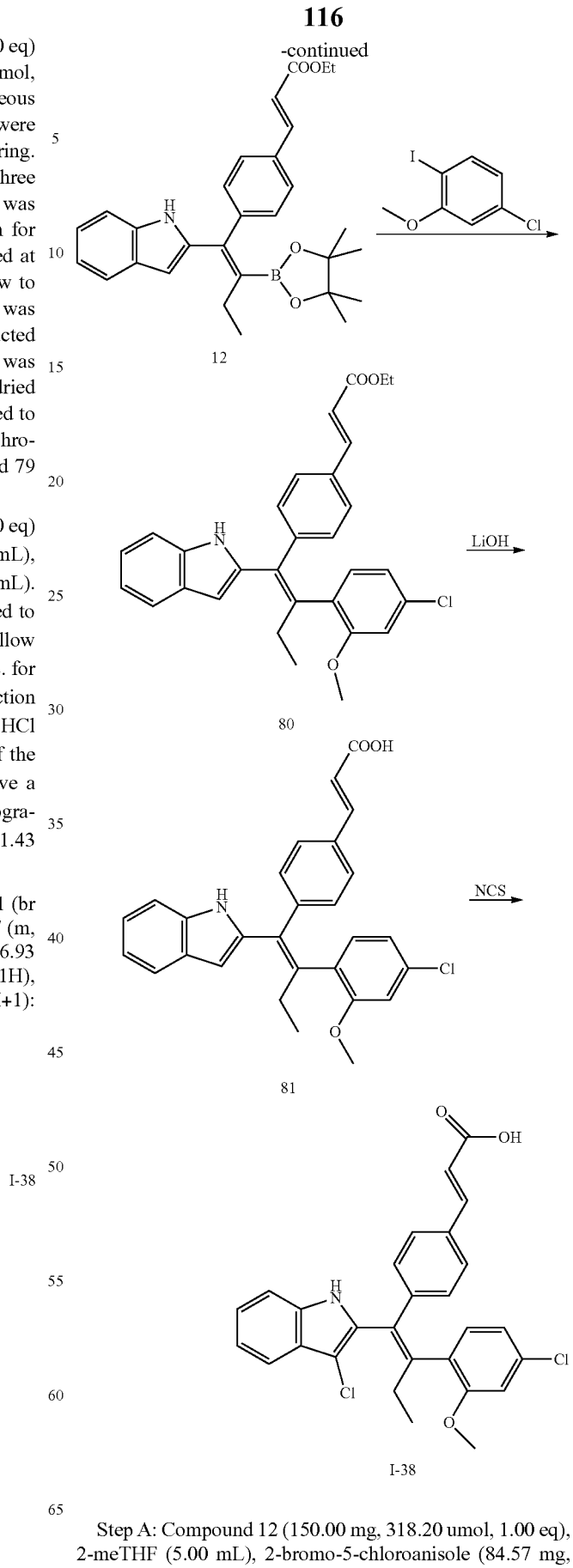

Step A: Compound 12 (150.00 mg, 318.20 umol, 1.00 eq), 2-meTHF (5.00 mL), 2-bromo-5-chloroanisole (84.57 mg, 381.84 umol, 1.20 eq), water (1.00 mL) and NaOH (50.91 mg, 1.27 mmol, 4.00 eq) were added successively to a single-neck flask with a magnetic stirrer. The resulting mixture was purged with N₂ for three times. Then Pd(dppf)Cl₂ (23.28 mg, 31.82 umol, 0.10 eq) was added to the mixture under nitrogen atmosphere. The reaction solution was stirred at 75° C. for 7 h. 10 mL EA and 10 mL water were added to the reaction solution. The organic phase was washed with 10 mL water, dried over Na₂SO₄, filtered and concentrated under reduced pressure to give the crude product (162.00 mg), which was directly used in the next step base on the theoretical yield.

Step B: Compound 80 (154.65 mg, 318.20 umol, 1.00 eq), THF (3.00 mL), MeOH (1.00 mL), water (1.00 mL) and LiOH (22.86 mg, 954.60 umol, 3.00 eq) were successively added to a single-neck flask with a magnetic stirrer. The resulting black solution was stirred at 45° C. for 4 h. 2 mL 1N HCl was added to the reaction solution, followed by addition of 10 mL water, then extracted with 30 mL EtOAc (10 mL*3). The organic phase was combined, dried over Na₂SO₄, filtered and concentrated under reduced pressure to give a crude product, which was purified by preparative chromatography (formic acid) to give the compound 81 (28.00 mg, 61.14 umol, yield 19.21%).

Compound 81 (28.00 mg, 61.14 umol, 1.00 eq) and CH₃CN (3.00 mL) were successively added to a single-neck flask with a magnetic stirrer to give a yellow solution, followed by addition of NCS (8.16 mg, 61.14 umol, 1.00 eq). The resulting solution was stirred at 30° C. for 4 h. Then the reaction was quenched with 5 mL Na₂S₂O₃ at 25° C., and 20 mL water was added. The mixture was extracted with 60 mL EtOAc (20 mL*3). The organic phase was combined, washed with 30 mL water, dried over Na₂SO₄, filtered and concentrated under reduced pressure to give a crude product, which was purified by preparative chromatography (formic acid) to give I-38 (18.10 mg, 36.43 umol, yield 59.58%, purity 99.1%), MS (ESI, M+1): 492.1.

¹H NMR (400 MHz, DMSO-d₆) δ 11.44 (s, 1H), 7.50 (d, J=8.0 Hz, 1H), 7.41-7.36 (m, 4H), 7.20-7.10 (m, 3H), 6.95-6.88 (m, 4H), 6.37 (d, J=16.0 Hz, 1H), 3.82 (s, 3H), 2.01-1.98 (m, 2H), 086-0.83 (m, 3H).

Embodiment 39

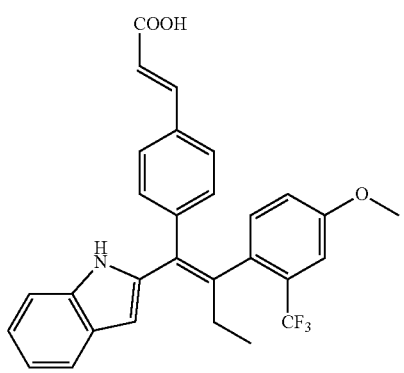

I-39

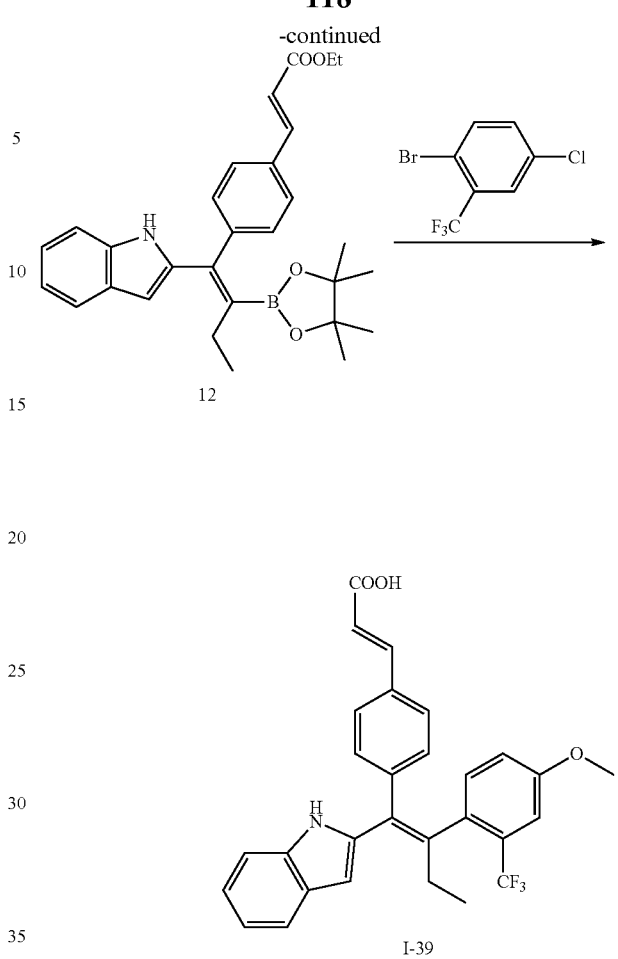

Compound 12 (110.00 mg, 190.65 umol, 1.00 eq) and 2-trifluoromethyl-4-chlorobromobenzene (53.7 mg, 210 umol, 1.1 eq.) were dissolved in 4 mL dimethyltetrahydrofuran in a 100 mL single-neck flask, followed by addition of sodium hydroxide solution (4M, 142.99 uL, 3.00 eq) and Pd(PPh₃)₂Cl₂ (6.69 mg, 9.53 umol, 0.05 eq). The reaction system was purged with nitrogen for three times, and the reaction solution was stirred at 70° C. under nitrogen atmosphere for 16 hours. After completion of the reaction, the reaction solution was concentrated to give a residue, which was purified by preparative TLC (PE:EtOAc=0:1) to give a crude product. The crude product was further purified by preparative HPLC (FA) to give I-39.

¹H NMR (400 MHz, CHLOROFORM-d) δ=7.72 (s, 1H), 7.67 (d, J=7.8 Hz, 1H), 7.60 (d, J=15.8 Hz, 1H), 7.28-7.24 (m, 2H), 7.21-7.12 (m, 2H), 7.08 (d, J=2.6 Hz, 1H), 7.05-6.99 (m, 3H), 6.90 (dd, J=2.6, 8.7 Hz, 1H), 6.72 (d, J=1.5 Hz, 1H), 6.35 (d, J=15.9 Hz, 1H), 3.81 (s, 3H), 3.03 (m, J=7.5, 13.9 Hz, 1H), 2.65-2.57 (m, 1H), 1.08 (t, J=7.5 Hz, 3H); MS (ESI, M+1): 492.5.

Embodiment 40

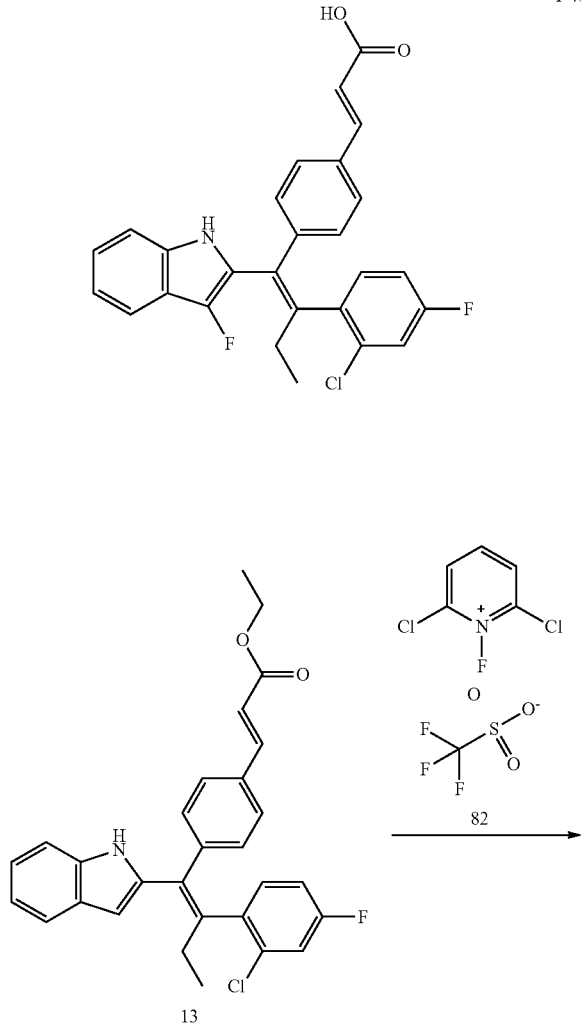

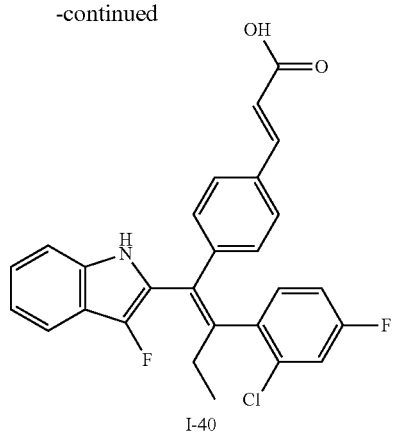

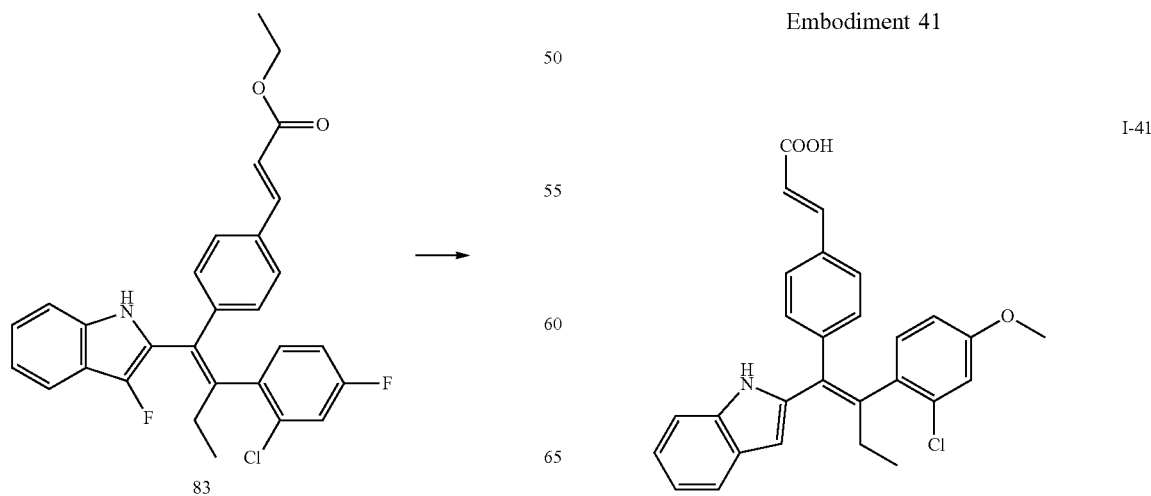

Step A: Compound 13 (1 g, 2.11 mmol, 1 eq) and dichloromethane (20 mL) were added to a 100 mL single-neck flask with a magnetic stirrer. The solution was purged with nitrogen and cooled to 0° C., followed by addition of compound 82 (1.00 g, 3.16 mmol, 1.5 eq) at 0° C. The resulting dark green solution was stirred at 25° C. under nitrogen atmosphere for 16 hours. 15 mL saturated aqueous sodium bicarbonate solution containing 10% sodium thiosulfate was added, and the resulting mixture was stirred for 10 minutes. The aqueous phase was extracted three times with 30 mL dichloromethane each time. The organic phase was combined, washed with 20 mL saturated brine, dried over anhydrous sodium sulfate, filtered, concentrated and purified by silica gel column chromatography (EA/PE=0%-20%) to give the product 83 as a yellow solid.

Step B: Compound 3 (1 g, (0.15 g, 304.91 umol, 1 eq), 2 mL ethanol and 3 mL tetrahydrofuran were added to a 100 mL single-neck flask with a magnetic stirrer, followed by addition of a solution of lithium hydroxide monohydrate (38.38 mg, 914.72 umol, 3 eq) in 1 mL water. The resulting yellow solution was stirred at 50° C. under nitrogen atmosphere for 2 hours, then concentrated and diluted with 10 mL water, adjusted pH to 5-6 with 1M hydrochloric acid, extracted three times with 20 mL ethyl acetate each time. The organic phase was combined, washed with 20 mL saturated brine, dried over anhydrous sodium sulfate, filtered, concentrated and purified by preparative high performance liquid chromatography to give I-40. $^1$H NMR (400 MHz, DMSO-$d_6$) δ 10.73 (s, 1H), 7.55 (d, J=8.0 Hz, 1H), 7.45-7.27 (m, 6H), 7.19-7.11 (m, 2H), 7.10-7.04 (m, 1H), 6.95 (d, J=8.4 Hz, 2H), 6.40 (d, J=16.0 Hz, 1H), 2.64-2.56 (m, 2H), 0.93 (t, J=7.6 Hz, 3H).

Embodiment 41

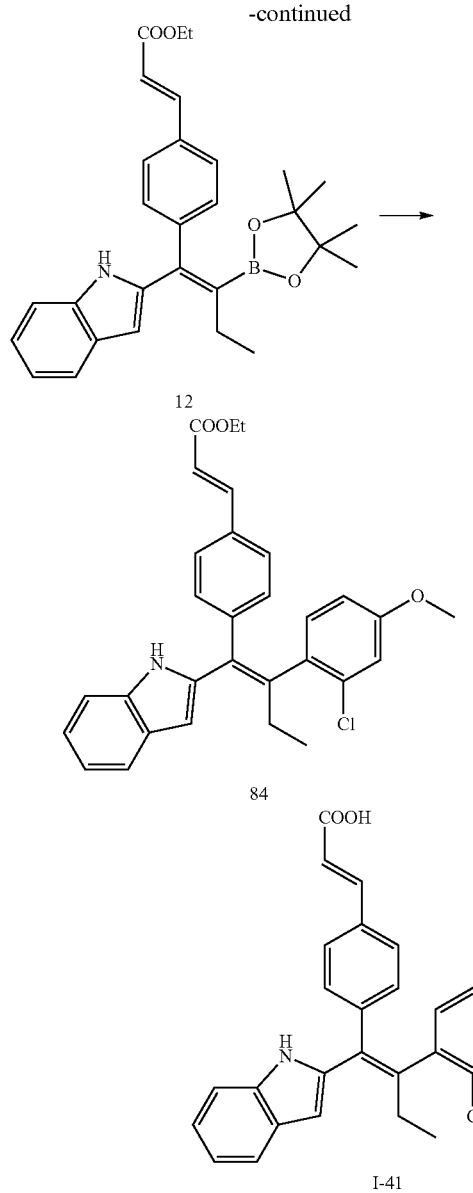

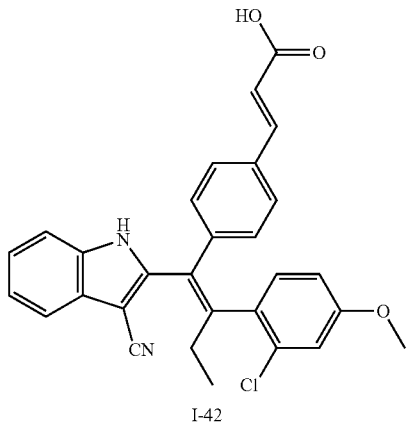

3 mL THF, 3 mL methanol and 3 mL water in a flask. The reaction solution was stirred at 45° C. for 1 hour and remained brown. After completion of the reaction, the reaction solution was adjusted to pH 1 with 1M hydrochloric acid, followed by addition of 20 mL ethyl acetate. The organic phase was washed twice with 20 mL saturated brine each time, dried over anhydrous sodium sulfate, filtered and concentrated under reduced pressure to give a crude product, which was purified by preparative high performance liquid chromatography (formic acid system) to give the compound I-41. $^1$H NMR (400 MHz, DMSO-d$_6$): δ 10.72 (brs, 1H), 7.54 (d, J=7.6 Hz, 1H), 7.43-7.39 (m, 3H), 7.29 (d, J=8.0 Hz, 1H), 7.08-6.94 (m, 6H), 6.80 (dd, J=8.8 Hz, J=2.8 Hz, 1H), 6.54 (d, J=1.2 Hz, 1H), 6.39 (d, J=16.0 Hz, 1H), 3.71 (s, 3H), 2.66-2.55 (m, 2H), 0.98 (t, J=7.2 Hz, 3 H). MS (ESI, M+1): 458.1.

Embodiment 42

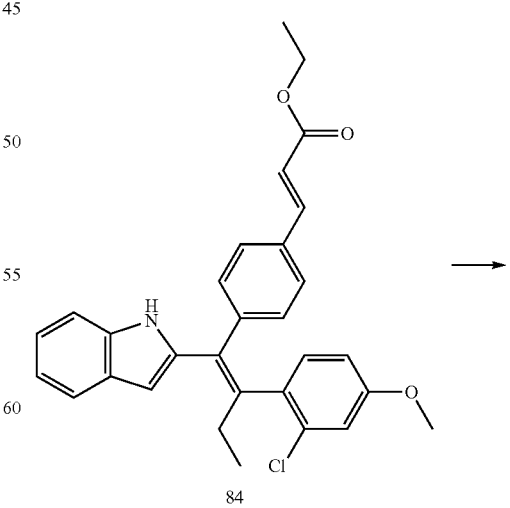

Step A: Compound 1 (400.00 mg, 693.27 umol, 1.00 eq), 2-chloro-4-methoxybromobenzene (230.32 mg, 1.04 mmol, 1.50 eq) and 10 mL 2-methyltetrahydrofuran were added to a 100 mL single-neck flask, followed by successive addition of aqueous potassium hydroxide solution (4M, 693.27 uL, 4.00 eq) and bis(triphenylphosphine)palladium dichloride (24.33 mg, 34.66 umol, 0.05 eq). The reaction solution was purged with nitrogen, then heated to 70° C. and stirred for 12 hours. The reaction solution turned from yellow to brown. After completion of the reaction, 20 mL ethyl acetate was added to the reaction solution, and the resulting mixture was filtered through celite. The filtrate was washed three times with 20 mL saturated brine each time, dried over anhydrous sodium sulfate, filtered and concentrated under reduced pressure to give the crude product 84 as a brown jelly (570.00 mg, crude product), which was directly used in the next step.

Step B: Lithium hydroxide monohydrate (490.93 mg, 11.70 mmol, 10.00 eq) was added to a solution of compound 84 (570.00 mg, 1.17 mmol, 1.00 eq) in a mixed solvent of

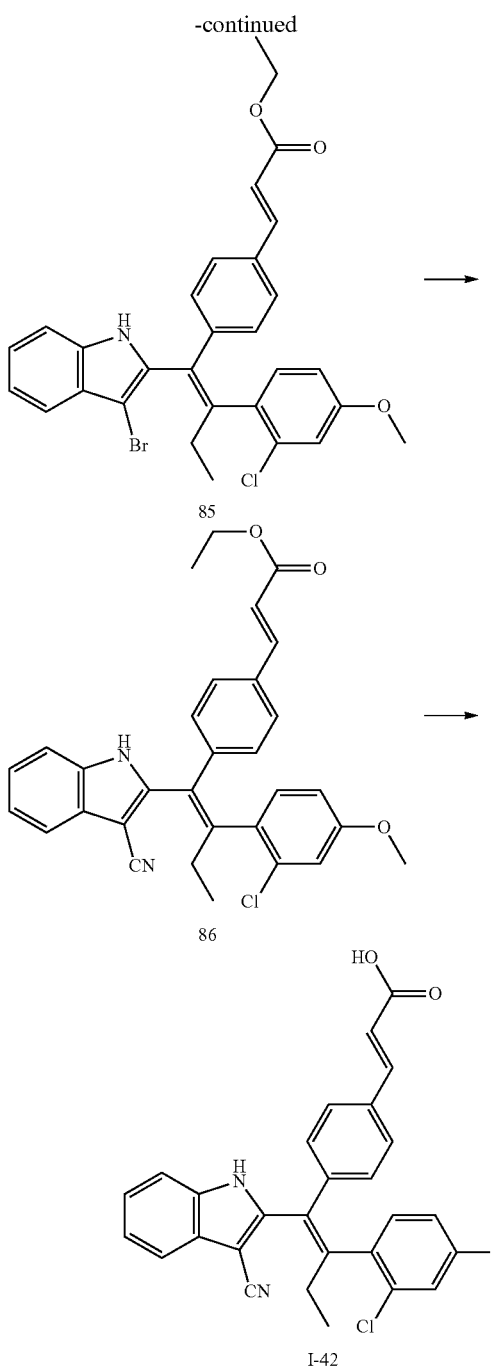

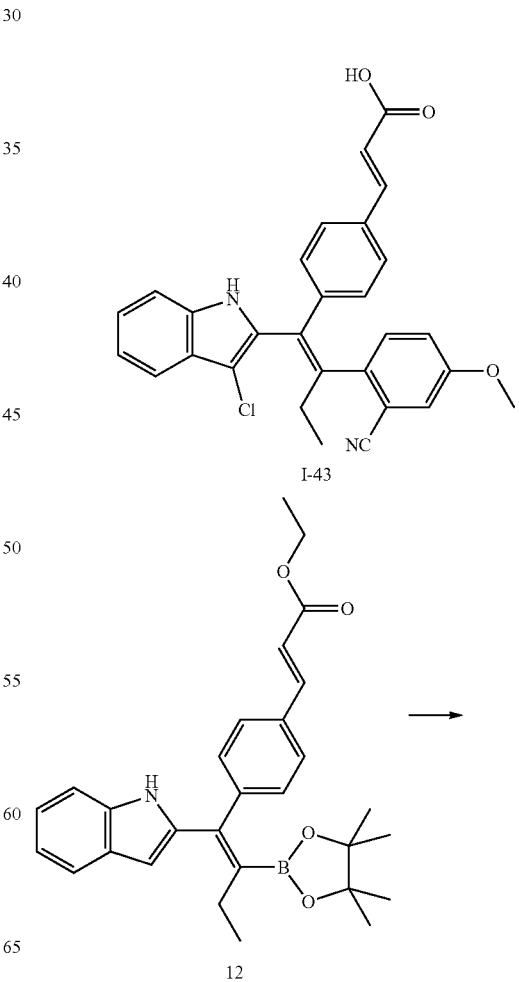

temperature, and additional cuprous cyanide (57.07 mg, 637.28 umol, 139.20 uL, 2.00 eq) was added, and the resulting reaction solution was heated to 180° C. under microwave irradiation and stirred for another 2 hours. The reaction solution was cooled to room temperature, poured into 20 mL water, extracted with ethyl acetate and concentrated to give a crude product, which was purified by preparative HPLC to give the intermediate 86 (30.00 mg, 54.60 umol, yield 17.13%, purity 93%).

Step C: Lithium hydroxide (12.32 mg, 293.61 umol, 5.38 eq) was added to a solution of intermediate 86 (30.00 mg, 54.60 umol, 1.00 eq) in a mixed solvent of tetrahydrofuran (4.00 mL), methanol (1.00 mL) and water (1.00 mL). The reaction solution was stirred for 4 hours, then adjusted to pH 1 with 4M HCl, concentrated in vacuum and extracted with ethyl acetate. The organic phase was combined, dried over sodium sulfate and concentrated to give a crude product, which was purified by preparative HPLC to give I-42. $^1$H NMR (400 MHz, DMSO-$d_6$): δ 12.32 (s, 1H), 7.66 (d, J=8.8 Hz, 1H), 7.50 (d, J=8.0 Hz, 1H), 7.55-7.40 (m, 3H), 7.33-7.23 (m, 2H), 7.15 (d, J=8.8 Hz, 1H), 7.10-7.00 (m, 3H), 6.91 (dd, J=4.8 Hz, J=16 Hz, 1H), 6.42 (d, J=16 Hz, 1H), 3.75 st, 3H), 2.53-2.31 (m, 2H), 0.93 (t, J=7.2 Hz, 3 H). (ESI, M+1): 483.1.

Embodiment 43

Step A: A solution of NBS (42.85 mg, 240.74 umol, 0.90 eq) in dichloromethane (1 mL) was added to a solution of compound 84 (130.00 mg, 267.49 umol, 1.00 eq) in dichloromethane (4.00 mL) and acetonitrile (4.00 mL). The reaction solution was stirred for 1 hour, then quenched with aqueous sodium thiosulfate solution and extracted with dichloromethane. The organic phase was dried over sodium sulfate and concentrated to give the intermediate 85 (180 mg, crude product), which was directly used in the next step.

Step B: A solution of intermediate 85 (180.00 mg, 318.64 umol, 1.00 eq) and cuprous cyanide (171.22 mg, 1.91 mmol, 417.61 uL, 6.00 eq) in N-methylpyrrolidone (2.00 mL) were heated to 180° C. under microwave irradiation and stirred for 2 hours. Then the reaction solution was cooled to room

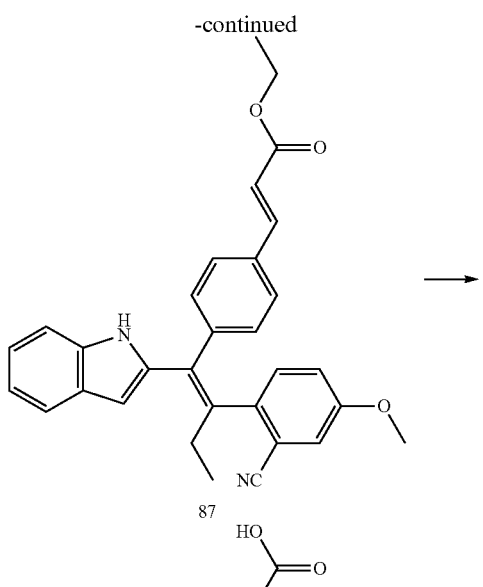

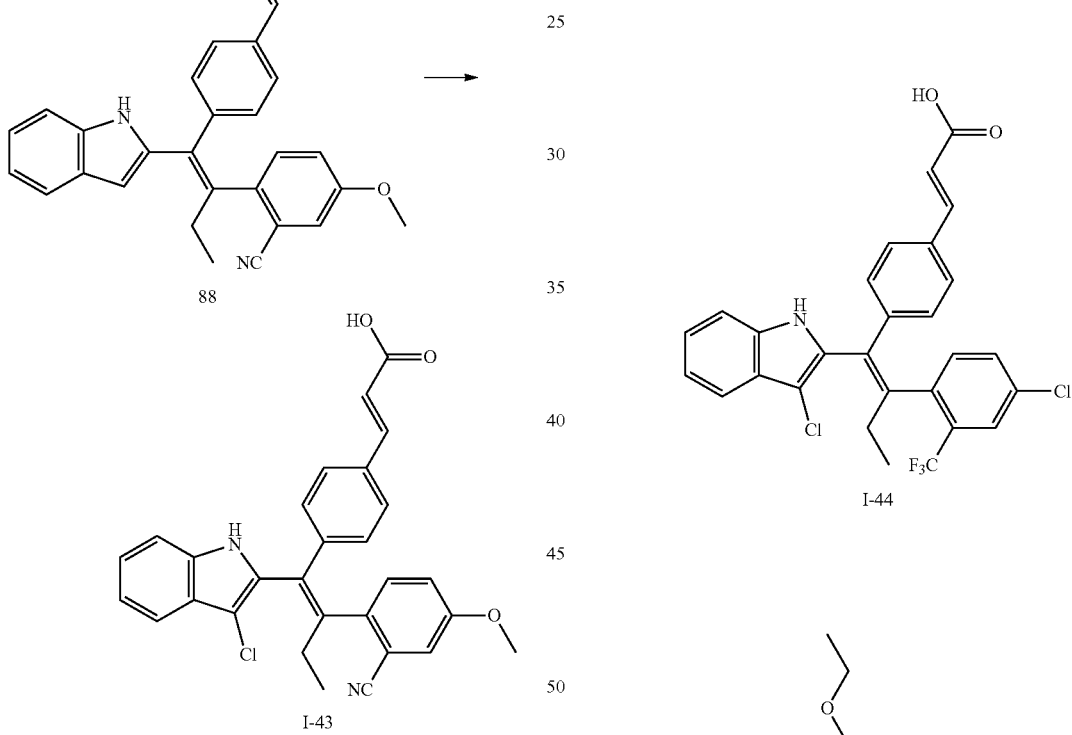

heated to 45° C. and stirred for 3 hours. The reaction solution was cooled to room temperature, adjusted to pH 5 with 2M HCl, diluted with water, extract with ethyl acetate, dried over sodium sulfate, concentrated and purified by silica gel column chromatography to give the intermediate 88.

Step B: NCS (20.49 mg, 153.45 umol, 1.00 eq) was added to a solution of intermediate 88 (70.00 mg, 153.45 umol, 1.00 eq) in acetonitrile (3.00 mL). The reaction solution was stirred at 20° C. for 3 hours, then quenched with aqueous sodium thiosulfate solution (10 mL), adjusted to pH 5 with 2M HCl, extracted with dichloromethane. The organic phase was combined, dried over sodium sulfate and concentrated to give a crude product, which was purified by preparative HPLC to give the product I-43. $^1$H NMR (400 MHz, DMSO-$d_6$): δ 11.43 (s, 1H), 7.52 (d, J=8.4 Hz, 1H), 7.42-7.39 (m, 5H), 7.37-7.35 (m, 1H), 7.31 (d, J=2.4 Hz, 1H), 7.27-7.15 (m, 2H), 6.94 (d, J=8.4 Hz, 2H), 6.39 (d, J=16.0 Hz, 1H), 3.78 (s, 3H), 2.58-2.41 (m, 2H), 0.91 (t, J=7.6 Hz, 3H); MS (ESI, M+1): 483.1.

Embodiment 44

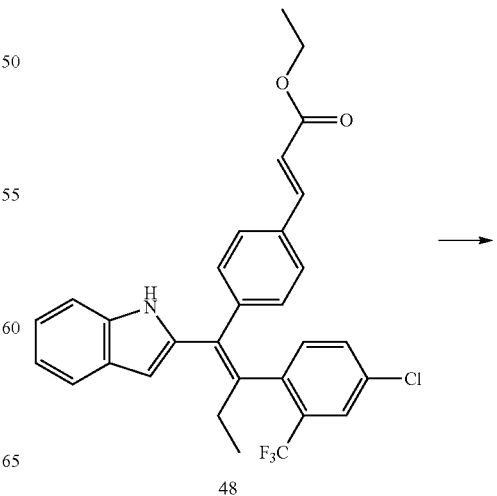

Step A: KOH (4M, 259.66 uL, 3.06 eq) and Pd(Ph$_3$P)$_2$Cl$_2$ (47.65 mg, 67.88 umol, 0.20 eq) were added to a solution of the intermediate 12 (200.00 mg, 339.42 umol, 1.00 eq) and 2-bromo-5-methoxyphenyl cyanide (108.00 mg, 509.13 umol, 1.50 eq) in 2-methyltetrahydrofuran. The reaction solution was stirred at 65° C. under nitrogen atmosphere for 13 hours, then cooled to room temperature, and additional Pd(Ph$_3$P)$_2$Cl$_2$ (20.00 mg, 33 umol, 0.10 eq) was added. The reaction solution was heated to 65° C. and stirred for another 3 hours to give 87, which was directly used in the next step. The reaction solution was cooled to room temperature, then methanol (6.00 mL) and water (3.00 mL) were added and the resulting mixture was stirred at 35° C. for 2 hours. Lithium hydroxide (15 mg) was added, the reaction solution was

127

-continued

128

Embodiment 45

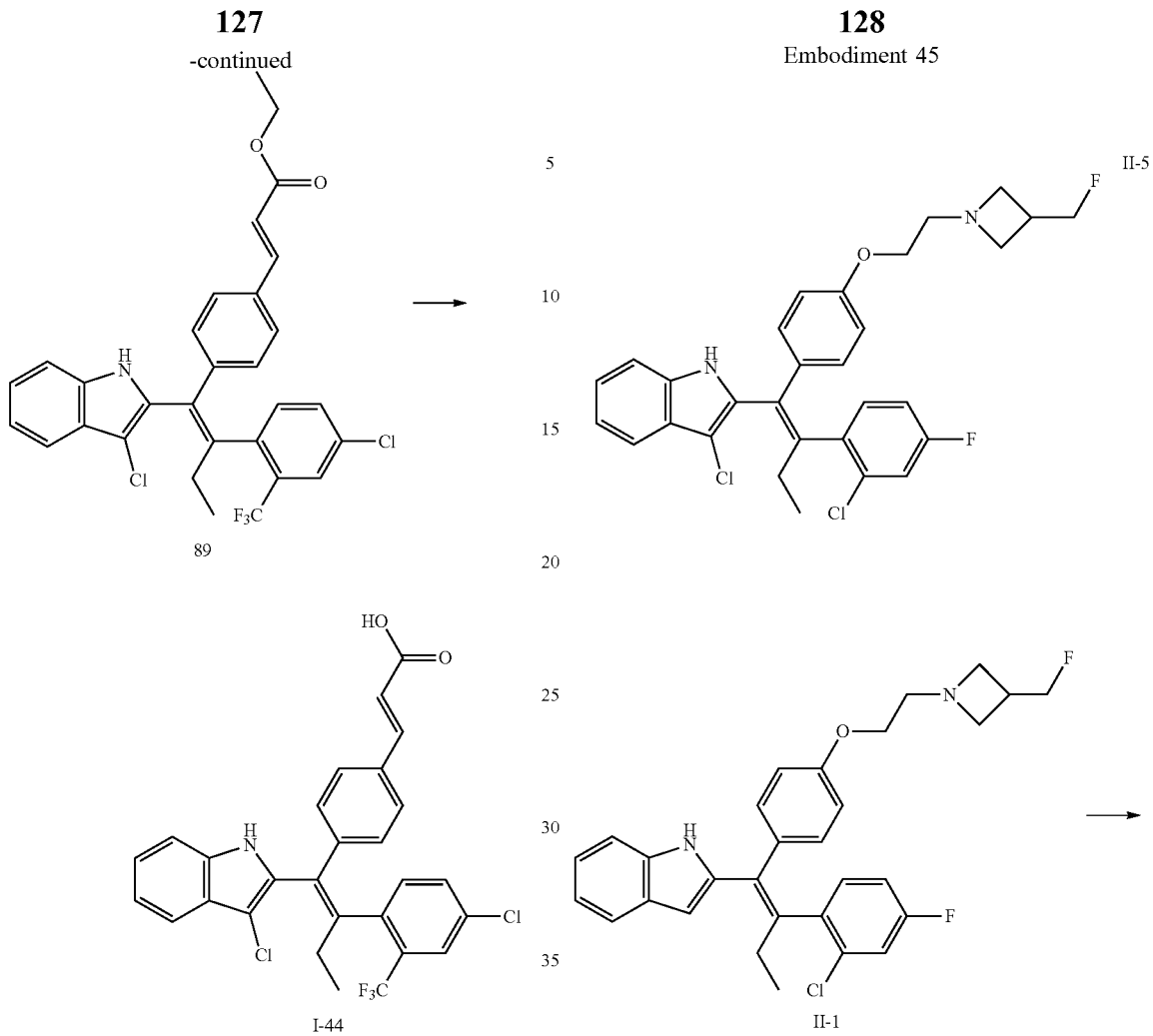

Step A: NCS (15.80 mg, 118.33 umol, 1.00 eq) was added to a solution of 48 (62.00 mg, 118.33 umol, 1.00 eq) in acetonitrile (3.00 mL) and dichloromethane (5.00 mL). The reaction solution was stirred at 15° C. for 5 hours. Additional NCS (4.00 mg, 29.96 umol, 0.25 eq) was added and the reaction solution was stirred for another 1 hour, then quenched with aqueous sodium thiosulfite solution (20 mL), extracted with ethyl acetate. The organic phase was washed with saturated brine, dried over sodium sulfate to give the intermediate 89 (66.00 mg, crude product), which was used directly in the next step.

Step B: LiOH (14.88 mg, 354.57 umol, 3.00 eq) was added to a solution of the intermediate 89 (66.00 mg, 118.19 umol, 1.00 eq) in a mixed solvent of methanol (3.00 mL), tetrahydrofuran (3.00 mL) and water (3.00 mL). The reaction solution was stirred at 15° C. for 12 hours and concentrated. The residue was diluted with water (10 mL), adjusted to pH 5 with 2M HCl, extracted with dichloromethane. The organic phase was combined, washed with saturated brine, dried over sodium sulfate and concentrated to give a crude product, which was purified by preparative HPLC to give I-44. $^1$H NMR (400 MHz, DMSO-$d_6$): δ 11.51 (s, 1H), 7.81 (d, J=2.0 Hz, 1H), 7.73 (d, J=12 Hz, 1H), 7.49 (d, J=9.6 Hz, 1H), 7.46-7.35 (m, 5H), 7.22-7.13 (m, 2H), 6.97 (d, J=8.4 Hz, 2H), 6.39 (s, J=16.0 Hz, 1H), 2.55-2.47 (m, 1H), 2.38-2.25 (m, 1H), 0.87 (t, J=7.2 Hz, 3H); MS (ESI, M+1): 530.1.

Step A: NCS (9.48 mg, 71.00 umol, 0.9 eq) was added to a mixture of compound II-1 (0.04 g, 78.89 umol, 1 eq) and dichloromethane (4 mL) in a single-neck flask with a magnetic stirrer. The yellow solution was stirred at 15° C. for 2 hours, then concentrated to give a crude product, which was purified by preparative high performance liquid chromatography to give II-5.

Embodiment 46

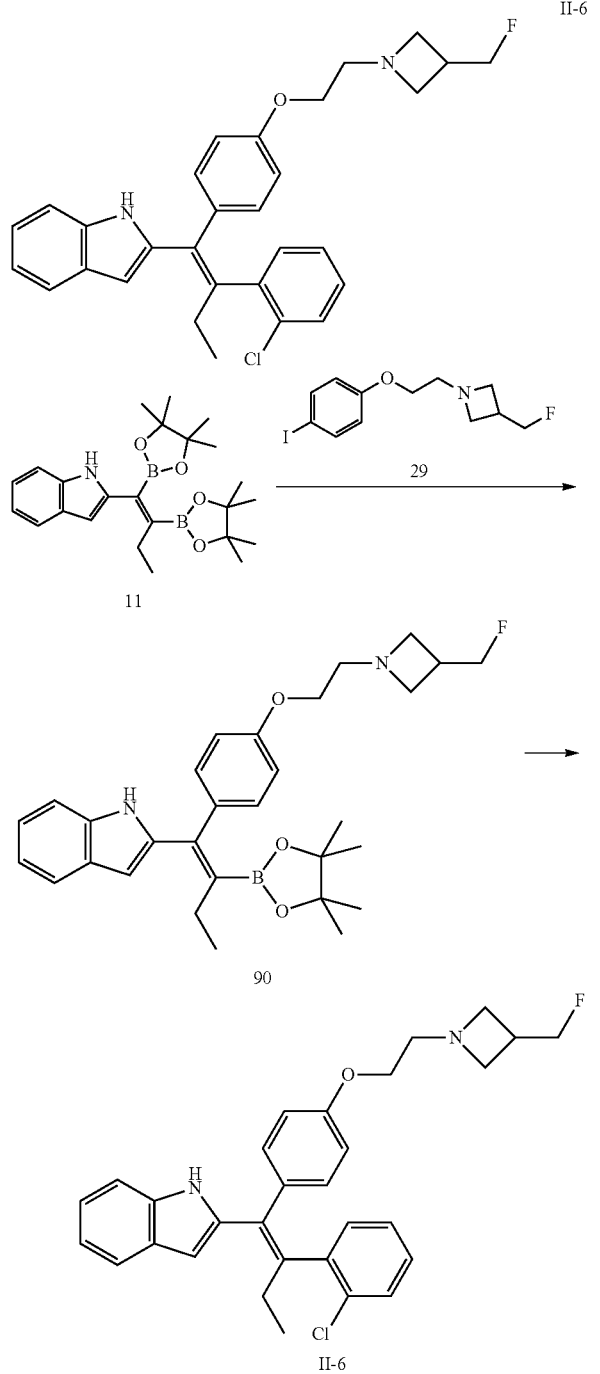

Step A: Aqueous sodium hydroxide solution (4M), 1.00 mL, 4.00 eq) was added to a mixture of compound 11 (423.16 mg, 1.00 mmol, 1.00 eq) (a solution of 10 mL 2-methyltetrahydrofuran) and compound 29 (402.19 mg, 1.20 mmol, 1.20 eq) in a three-necked flask, followed by addition of bis(diphenylphosphino)ferrocene dichloropalladium (36.50 mg, 50.00 umol, 0.05 eq) under nitrogen atmosphere. The reaction solution was stirred at 60° C. for 4 hours. After completion of the reaction, the reaction solution was directly used in the next step without further posttreatment based on the theoretical yield for 90.

Step B: Dichlorobis(tripheny/phosphine)palladium(II) (42.12 mg, 60.00 umol, 4.00 eq) and 1-chloro-2-iodobenzene (291.14 mg, 1.20 mmol, 1.20 eq) under nitrogen atmosphere in a three-necked flask. The reaction solution was added at 70° C. under nitrogen atmosphere for 4 hours. After completion of the reaction, water (40 mL) and ethyl acetate (30 mL) were added to the reaction solution, then extracted with ethyl acetate (20 mL*3). The organic phase was combined, washed with water (30 mL), dried over sodium sulfate, filtered and concentrated to give a crude product, which was purified by preparative liquid chromatography (prep. HPLC: formic acid) to give II-6.

$^1$H NMR (400 MHz, DMSO-$d_6$) δ=10.65 (s, 1H), 8.35 (s, 1H), 7.54-6.84 (m, 10H), 6.62-6.54 (m, 3H), 4.493 (dd, J=6.4 Hz, 48 Hz, 2H), 3.78 (d, J=5.2 Hz, 2H), 2.95 (t, J=6.4 Hz, 2H), 2.68-2.51 (m, 6H), 0.99 (t, J=7.6 Hz, 3H); MS (ESI, M+1): 489.1.

Embodiment 47

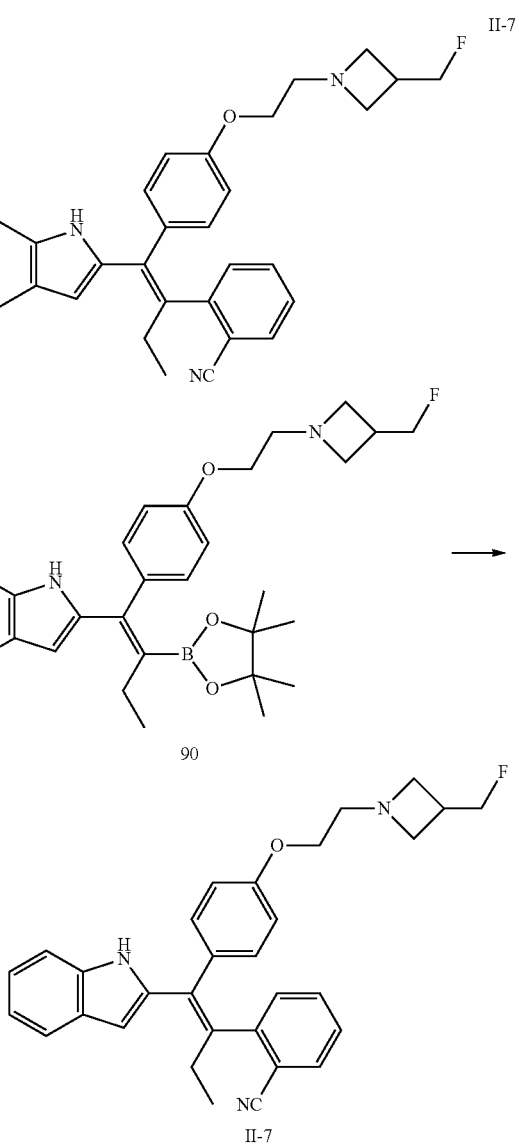

Step A: 2-Iodobenzonitrile (329.79 mg, 1.44 mmol, 1.20 eq) was added to a mixture of compound 90 (605.33 mg, 1.20 mmol, 1.00 eq) (a solution in 10 mL 2-methyltetrahydrofuran), water (2.00 mL) and sodium hydroxide (192.00 mg, 4.80 mmol, 4.00 eq) in a single-neck flask, which was then purged with $N_2$ for three times. Bis(triphenylphosphine) palladium chloride (42.11 mg, 60.00 umol, 0.05 eq) was added under nitrogen atmosphere. The reaction solution was stirred at 70° C. for 7 hours. After completion of the reaction, the reaction solution was diluted with 40 mL water, extracted with 45 mL ethyl acetate (15 mL*3). The organic phase was combined, washed with 40 mL water, dried over $Na_2SO_4$, filtered and concentrated to give a crude product, which was purified by preparative chromatography (formic acid system) to give the compound II-7. $^1$H NMR (400 MHz, DMSO-$d_6$) δ 10.65 (s, 1H), 8.27 (s, 1H), 7.66-7.51 (m, 4H), 7.38-7.30 (m, 2H), 7.06-7.00 (m, 2H), 6.81 (d, J=8.8 Hz, 2H), 6.62 (d, J=8.8 Hz, 2H), 6.57 (d, J=1.6 Hz, 1H), 4.54 (d, J=6.0 Hz, 1H), 4.42 (d, J=6.0 Hz, 1H), 3.78 (t, J=5.6 Hz, 2H), 2.96 (t, J=5.6 Hz, 2H), 2.68-2.63 (m, 6H), 2.03-1.96 (m, 1H), 1.01 (t, J=7.6 Hz, 3H); MS (ESI, M+1): 480.3.

Embodiment 48

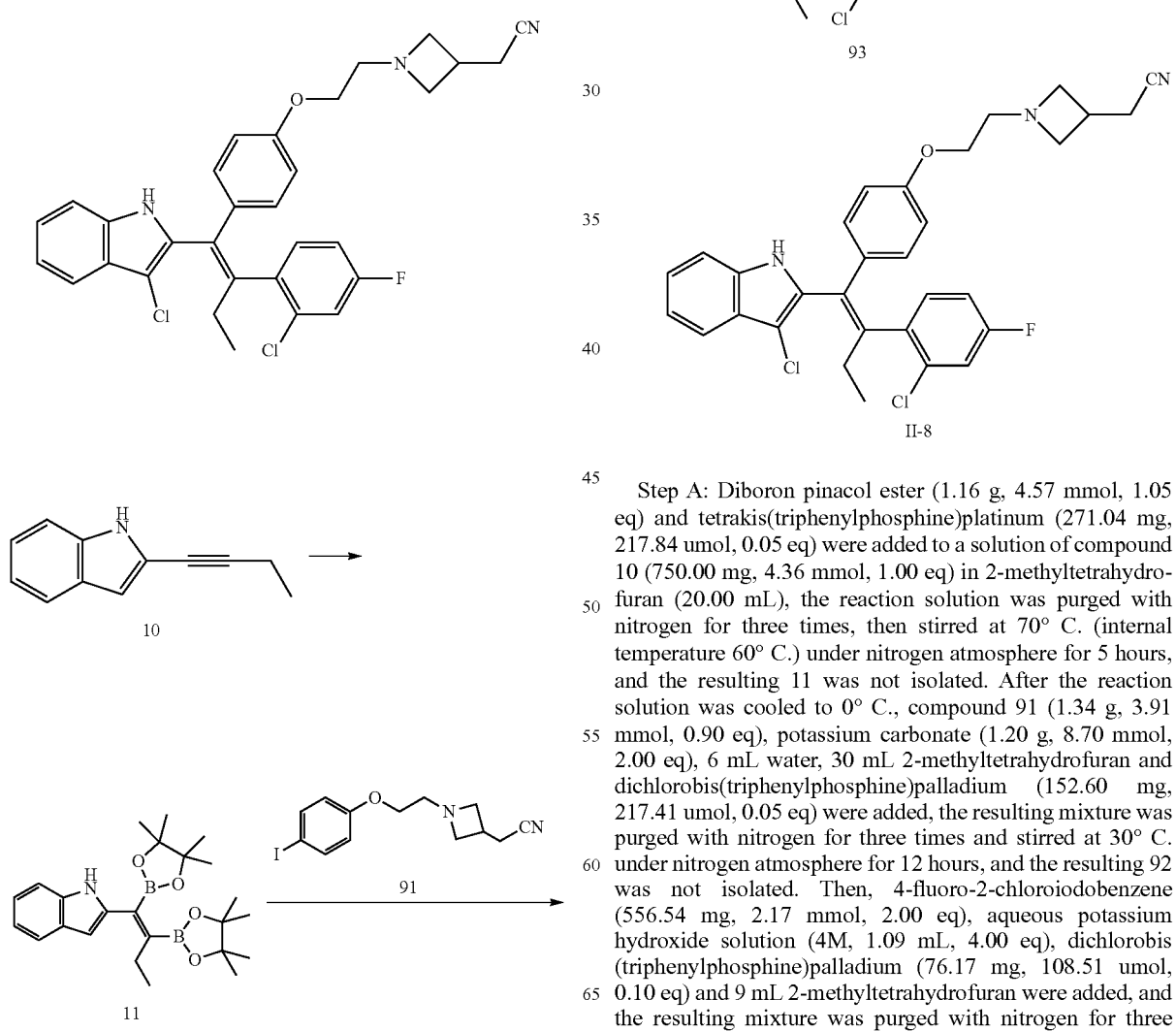

Step A: Diboron pinacol ester (1.16 g, 4.57 mmol, 1.05 eq) and tetrakis(triphenylphosphine)platinum (271.04 mg, 217.84 umol, 0.05 eq) were added to a solution of compound 10 (750.00 mg, 4.36 mmol, 1.00 eq) in 2-methyltetrahydrofuran (20.00 mL), the reaction solution was purged with nitrogen for three times, then stirred at 70° C. (internal temperature 60° C.) under nitrogen atmosphere for 5 hours, and the resulting 11 was not isolated. After the reaction solution was cooled to 0° C., compound 91 (1.34 g, 3.91 mmol, 0.90 eq), potassium carbonate (1.20 g, 8.70 mmol, 2.00 eq), 6 mL water, 30 mL 2-methyltetrahydrofuran and dichlorobis(triphenylphosphine)palladium (152.60 mg, 217.41 umol, 0.05 eq) were added, the resulting mixture was purged with nitrogen for three times and stirred at 30° C. under nitrogen atmosphere for 12 hours, and the resulting 92 was not isolated. Then, 4-fluoro-2-chloroiodobenzene (556.54 mg, 2.17 mmol, 2.00 eq), aqueous potassium hydroxide solution (4M, 1.09 mL, 4.00 eq), dichlorobis (triphenylphosphine)palladium (76.17 mg, 108.51 umol, 0.10 eq) and 9 mL 2-methyltetrahydrofuran were added, and the resulting mixture was purged with nitrogen for three times and stirred at 60° C. under nitrogen atmosphere for 12 hours. Then 20 mL ethyl acetate was added, and the mixture was filtered. the filtrate was washed three times with 20 mL saturated brine each time, dried over anhydrous sodium sulfate, filtered, concentrated and purified by preparative high performance liquid chromatography (formic acid system) to give the compound 93 as a yellow solid (41.10 mg, 71.26 umol, yield 6.54%, purity 97.1%). MS (ESI, M+23): 536.1.

J=7.6 Hz, 1H), 7.42-7.37 (m, 2H), 7.26 (dd, J=8.8 Hz, J=6.4 Hz, 1H), 7.19-7.10 (m, 3H), 6.92 (d, J=8.4 Hz, 2H), 6.64 (d, J=8.8 Hz, 2H), 3.77 (t, J=5.6 Hz, 2H), 3.33 (t, J=7.2 Hz, 2H), 2.91 (t, J=7.6 Hz, 2H), 2.71 (d, J=6.8 Hz, 2H), 2.65-2.59 (m, 3H), 2.43-2.37 (m, 2H), 0.92 (t, J=7.6 Hz, 3 H). MS (ESI, M+1): 548.1.

Embodiment 49

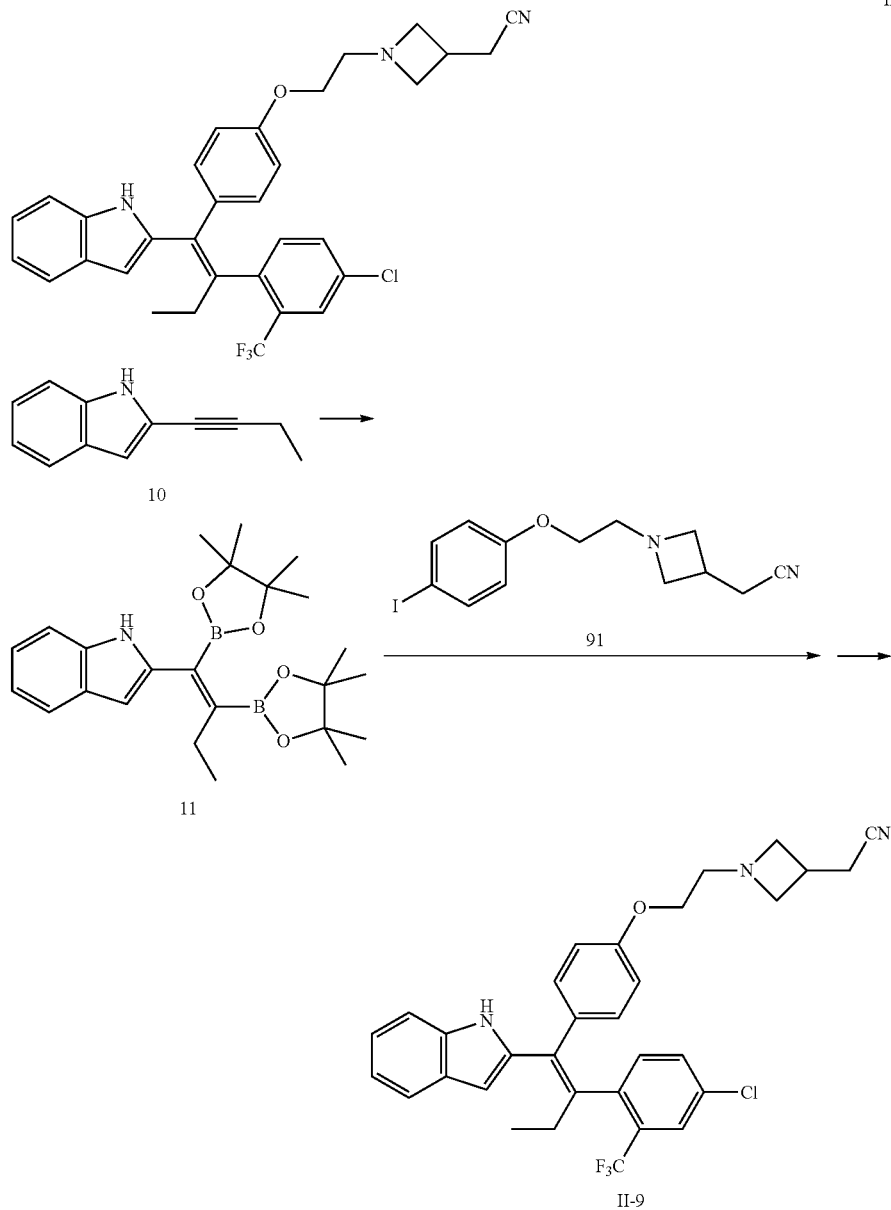

Step B: N-chlorosuccinimide was added to a solution of compound 93 (41.10 mg, 77.64 umol, 1.00 eq) in 10 mL acetonitrile, and the reaction solution was stirred at 30° C. for 10 hours. After completion of the reaction, the reaction solution was directly concentrated to give a crude product, which was purified by preparative high performance liquid chromatography (formic acid system) to give II-8. $^1$H NMR (400 MHz, DMSO-d$_6$): δ 11.42 (s, 1H), 8.36 (s, 1H), 7.49 (d, Step A: Diboron pinacol ester (147.80 mg, 582.03 umol, 1.05 eq) and tetrakis(triphenylphosphine)platinum (34.48 mg, 27.72 umol, 0.05 eq) were added to a solution of compound 10 (100.00 mg, 554.31 umol, 1.00 eq) in 2-methyltetrahydrofuran (10.00 mL), the reaction solution was purged with nitrogen for three times, then stirred at 70° C. under nitrogen atmosphere for 5 hours, and the resulting 11 was not isolated. After the reaction solution was cooled to 0°

C., compound 91 (238.50 mg, 497.68 umol, 0.90 eq), potassium carbonate K$_2$CO$_3$ (152.91 mg, 1.11 mmol, 2.00 eq), 2.5 mL water, 10 mL 2-methyltetrahydrofuran and dichlorobis(triphenylphosphine)palladium (19.41 mg, 27.65 umol, 0.05 eq) were added, the resulting mixture was purged with nitrogen for three times and stirred at 30° C. under nitrogen atmosphere for 12 hours, and the resulting 92 was not isolated. Then, 4-chloro-2-trifluoromethyl iodobenzene (338.89 mg, 1.11 mmol, 2.00 eq), aqueous potassium hydroxide solution (4M, 552.93 uL, 4.00 eq), dichlorobis (triphenylphosphine)palladium (19.40 mg, 27.65 umol, 0.05 eq) and 10 mL 2-methyltetrahydrofuran were added, and the resulting mixture was purged with nitrogen for three times and stirred at 70° C. under nitrogen atmosphere for 12 hours. Then 20 mL ethyl acetate was added, and the mixture was filtered. The filtrate was washed three times with 20 mL saturated brine each time, dried over anhydrous sodium sulfate, filtered, concentrated and purified by preparative high performance liquid chromatography (formic acid system) to give the compound II-9. $^1$H NMR (400 MHz, DMSO-d$_6$): δ 10.67 (s, 1H), 8.38 (s, 1H), 7.71 (d, J=1.6 Hz, 1H), 7.63 (dd, J=8.4 Hz, J=1.6 Hz, 1H), 7.53 (d, J=8.0 Hz, 1H), 7.32 (dd, J=8.0 Hz, J=12.0 Hz, 2H), 7.04 (t, J=7.2 Hz, 1H), 6.98 (t, J=7.2 Hz, 1H), 6.80 (d, J=8.8 Hz, 2H), 6.63 (d, J=8.4 Hz, 2H), 6.48 (d, J=0.8 Hz, 1H), 3.77 (t, J=5.6 Hz, 2H), 3.33 (t, J=7.2 Hz, 2H), 2.92 (t, J=7.6 Hz, 2H), 2.84-2.77 (m, 1H), 2.71 (d, J=6.8 Hz, 2H), 2.66-2.61 (m, 3H), 2.45-2.38 (m, 1H), 0.93 (t, J=7.6 Hz, 3 H). MS (ESI, M+23): 564.2.

Embodiment 50

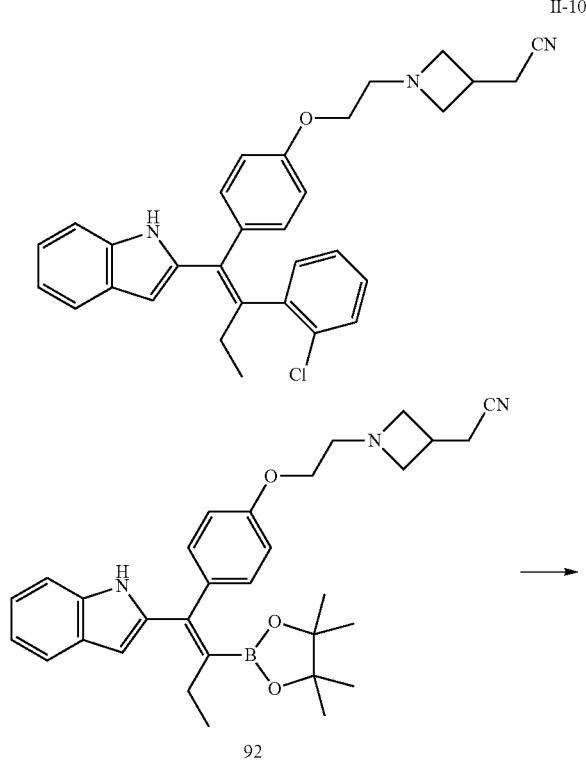

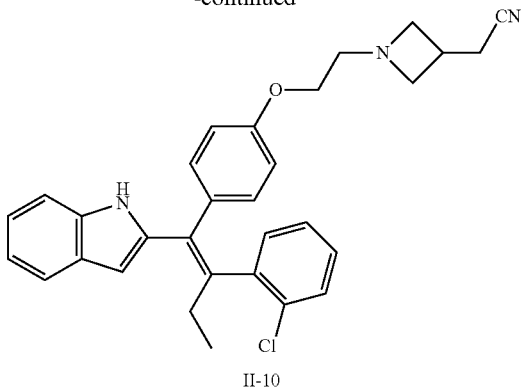

Step A: 1-Chloro-2-iodobenzene (517.50 mg, 2.17 mmol, 2.00 eq), potassium aqueous hydroxide (4M, 1.09 mL, 4.00 eq) and 2-methyltetrahydrofuran (5.00 mL) was added to a solution of compound 92 (555.00 mg, 1.09 mmol, 1.00 eq) in 2-methyltetrahydrofuran (7.50 mL), the reaction system was purged with nitrogen for three times, then dichlorobis (triphenylphosphine)palladium (38.08 mg, 54.26 umol, 0.05 eq) was added. The reaction solution was stirred at 70° C. under nitrogen atmosphere for 12 hours, then diluted with 20 mL ethyl acetate and filtered. The filtrate was washed three times with 20 mL brine each time, dried over anhydrous sodium sulfate, filtered, concentrated and purified by preparative HPLC (formic acid system) to give the compound II-10. $^1$H NMR (400 MHz, DMSO-d$_6$): δ 10.64 (brs, 1H), 8.29 (brs, 1H), 7.54 (d, J=8.0 Hz, 1H), 7.37-7.34 (m, 1H), 7.29 (d, J=8.0 Hz, 1H), 7.21-7.18 (m, 2H), 7.14-7.12 (m, 1H), 7.04 (dt, J=7.2 Hz, J=1.2 Hz, 1H), 6.97 (dt, J=8.0 Hz, J=1.2 Hz, 1H), 6.90-6.82 (m, 2H), 6.61-6.59 (m, 2H), 6.53 (d, J=1.2 Hz, 1H), 3.76 (t, J=5.6 Hz, 2 H), 3.33 (t, J=7.2 Hz, 2 H), 2.92 (t, J=7.2 Hz, 2 H), 2.71 (d, J=6.8 Hz, 2 H), 2.67-2.55 (m, 5H), 0.97 (t, J=7.6 Hz, 3 H). MS (ESI, M+1): 496.2.

Embodiment 51

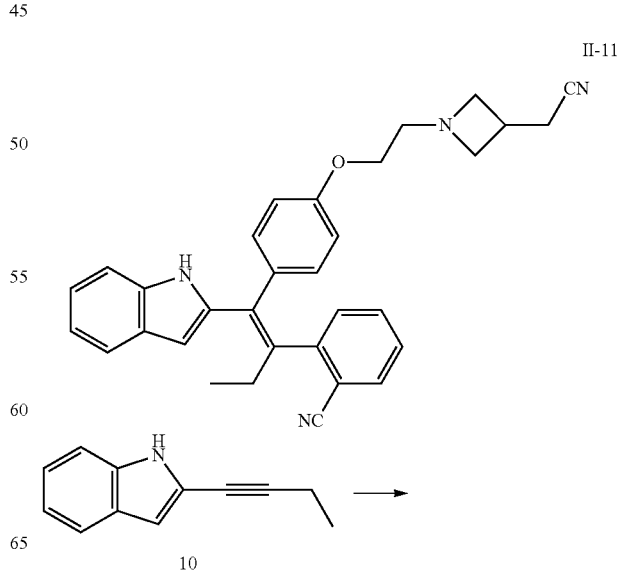

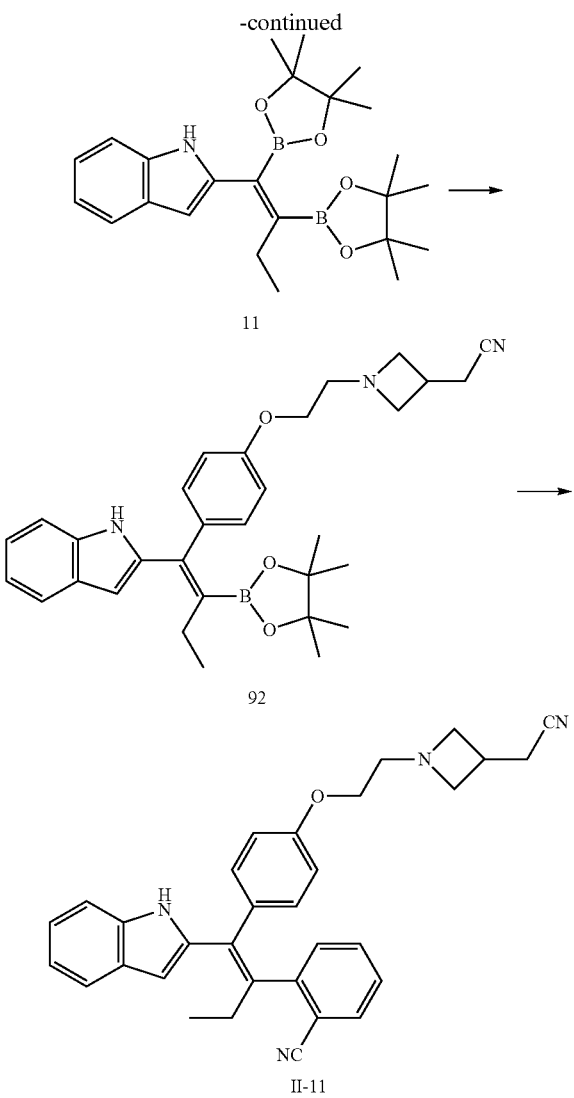

time, dried over anhydrous sodium sulfate, filtered, concentrated and purified by preparative high performance liquid chromatography (formic acid system) to give the compound II-11. $^1$H NMR (400 MHz, DMSO-$d_6$): δ 10.65 (s, 1H), 8.28 (s, 1H), 7.65-7.61 (m, 2H), 7.56 (d, J=7.6 Hz, 1H), 7.50 (d, J=7.6 Hz, 1H), 7.35 (dt, J=7.6 Hz, J=0.8 Hz, 1H), 7.30 (d, J=8.0 Hz, 1H), 7.05 (dt, J=8.0 Hz, J=1.2 Hz, 1H), 6.99 (dt, J=8.0 Hz, J=1.2 Hz, 1H), 6.80 (d, J=8.8 Hz, 2H), 6.61 (d, J=8.8 Hz, 2H), 6.56 (d, J=1.6 Hz, 1H), 3.77 (t, J=5.2 Hz, 2H), 3.34 (t, J=7.2 Hz, 2H), 2.92 (t, J=6.8 Hz, 2H), 2.71 (d, J=7.2 Hz, 2H), 2.67-2.57 (m, 3H), 2.52-2.50 (m, 2H), 1.00 (t, J=7.6 Hz, 3 H); MS (ESI, M+1, M+23): 492.2, 509.1.

Embodiment 52

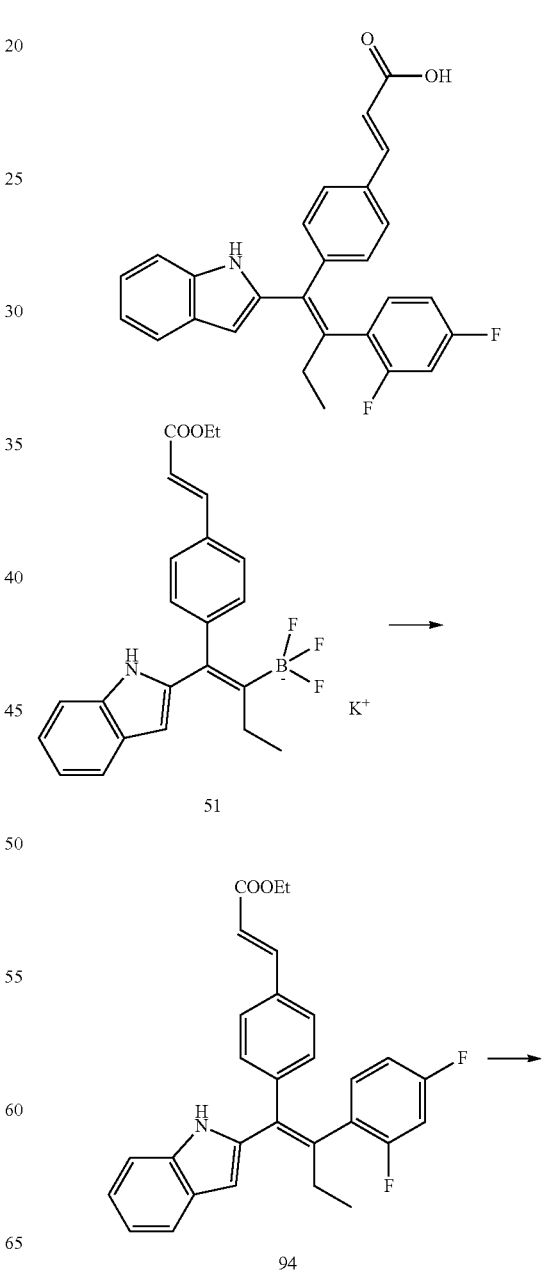

Step A: Diboron pinacol ester (147.80 mg, 582.03 umol, 1.05 eq) and tetrakis(triphenylphosphine)platinum (34.48 mg, 27.72 umol, 0.05 eq) were added to a solution of compound 10 (100.00 mg, 554.31 umol, 1.00 eq) in 2-methyltetrahydrofuran (10.00 mL), the reaction solution was purged with nitrogen for three times, then stirred at 70° C. under nitrogen atmosphere for 5 hours, and the resulting 11 was not isolated. After the reaction solution was cooled to 0° C., compound 91 (238.50 mg, 497.68 umol, 0.90 eq), potassium carbonate $K_2CO_3$ (152.91 mg, 1.11 mmol, 2.00 eq), 2.5 mL water, 10 mL 2-methyltetrahydrofuran and dichlorobis(triphenylphosphine)palladium (19.41 mg, 27.65 umol, 0.05 eq) were added, the resulting mixture was purged with nitrogen for three times and stirred at 30° C. under nitrogen atmosphere for 12 hours, and the resulting 92 was not isolated. Then, 2-iodobenzonitrile (253.26 mg, 1.11 mmol, 2.00 eq), aqueous potassium hydroxide solution (4M, 552.93 uL, 4.00 eq), dichlorobis(triphenylphosphine)palladium (19.40 mg, 27.65 umol, 0.05 eq) and 5 mL 2-methyltetrahydrofuran were added, and the resulting mixture was purged with nitrogen for three times and stirred at 70° C. under nitrogen atmosphere for 12 hours. Then 20 mL ethyl acetate was added, and the mixture was filtered. The filtrate was washed three times with 20 mL saturated brine each

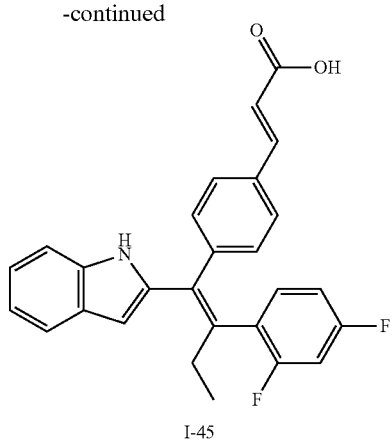

I-45

A solution of 51 (100.00 mg, 218.58 umol, 1.00 eq), 2,4-difluoroiodobenzene (73.44 mg, 306.01 umol, 1.40 eq) and bis(diphenylphosphino)ferrocene dichloropalladium (7.94 mg, 10.86 umol, 0.05 eq) in 2-methyltetrahydrofuran (15 mL) was purged with nitrogen, followed by addition of aqueous sodium hydroxide (4M, 218.58 uL, 4.00 eq). The reaction solution was stirred at 65° C. for 12 hours and turned from yellow to black. The resulting 15 mL black solution containing compound 94, the theoretical amount of which was 150 mg, was directly used in the next step. The above 15 mL black solution containing compound 94, the theoretical amount of which was 150 mg, and methanol (8.00 mL) were stirred at 30° C. for 15 hours. 20 mL was added to the reaction solution, then the mixture was filtered. The filtrate was adjusted to pH 4 with 3M hydrochloric acid, then extracted three times with 20 mL ethyl acetate. The organic phase was combined, washed once with 20 mL saturated brine, filtered, dried over anhydrous sodium sulfate and concentrated to give a crude product, which was dissolved in 3 mL acetonitrile and purified by high performance liquid chromatography (formic acid system) to give I-45. $^1$H NMR (400 MHz, DMSO-$d_6$) δ 10.76 (s, 1H), 7.55 (d, J=7.6 Hz, 1H), 7.47-7.38 (m, 3H), 7.33-7.19 (m, 2H), 7.15-6.91 (m, 6H), 6.54 (d, J=1.6 Hz, 1H), 6.41 (d, J=16.4 Hz, 1H), 2.63 (q, J=7.2 Hz, 2H), 0.99 (t, J=7.6 Hz, 3H). MS (ESI, M+1): 430.1.

Embodiment 53

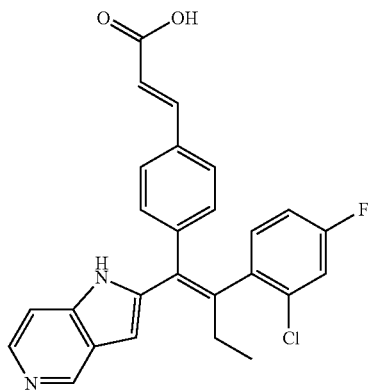

I-46

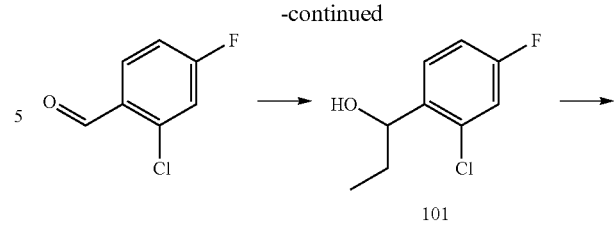

101

98

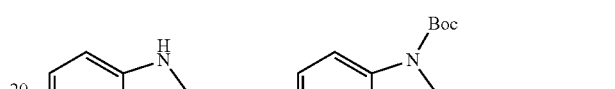

95

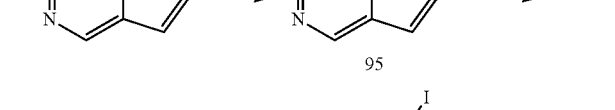

96

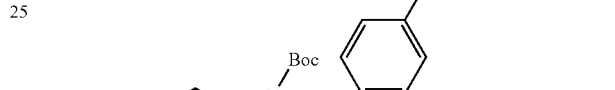

97

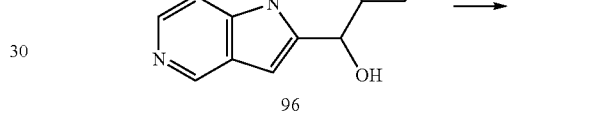

98

99

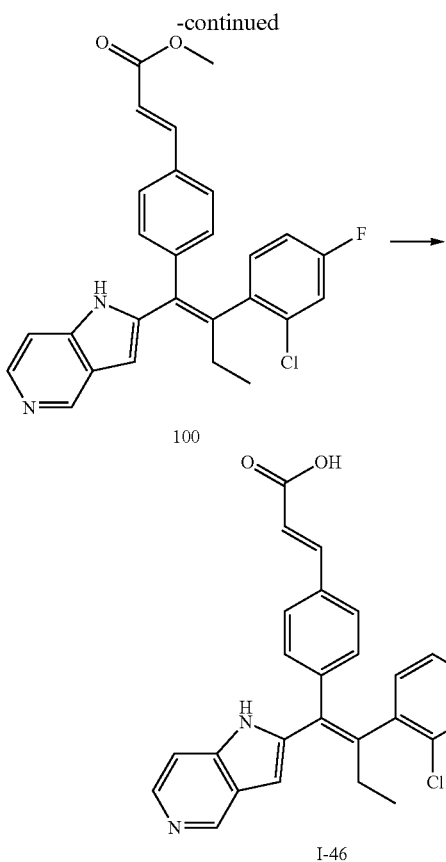

Step A: A solution of 2-chloro-4-fluorobenzaldehyde (5.00 g, 31.53 mmol, 1.00 eq) in 12 mL tetrahydrofuran was cooled to −20° C., followed by addition of ethylmagnesium bromide (2M, 17.34 mL, 1.10 eq) under nitrogen atmosphere. The reaction solution was warmed to 0° C. and then stirred at 20° C. for 12 hours. The reaction solution was quenched with saturated 15 mL aqueous ammonium chloride solution at 0° C., diluted with 10 mL water, partitioned, the aqueous phase was extracted three times with 50 mL ethyl acetate each time. The organic phase was combined, washed with saturated brine, dried over anhydrous sodium sulfate, filtered and concentrated to give a crude product, which was purified by silica gel column chromatography (EA/PE=0% to 30%) to give the product 101 as a yellow oil.

Step B: 101 (1.70 g, 9.01 mmol, 1.00 eq) and 50 mL dichloromethane were added to a single-neck round bottom flask, then cooled to 0° C. and Dess Martin reagent (6.11 g, 14.42 mmol, 4.46 mL, 1.60 eq) was added under nitrogen atmosphere. The reaction solution was stirred at 0° C. for 1 hour, then quenched with saturated aqueous sodium bicarbonate solution containing 15% sodium thiosulfate (20 mL) and filtered. The filtrate was partitioned, and the aqueous phase was extracted three times with 50 mL dichloromethane each time. The organic phase was combined, washed with saturated brine, dried over anhydrous sodium sulfate, filtered, concentrated and purified by silica gel column chromatography (EA/PE=0% to 10%) to give 98.

Step C: 5-Azaindole (10.00 g, 84.65 mmol, 1.00 eq), Boc$_2$O (19.40 g, 88.88 mmol, 20.42 mL, 1.05 eq) and 200 mL dichloromethane were added to a single-neck round bottom flask, followed by addition of DMAP (1.03 g, 8.47 mmol, 0.10 eq) under nitrogen atmosphere. The reaction solution was stirred at 20° C. for 12 hours, then concentrated and purified by silica gel column chromatography (EA/PE=0%-40%) to give 95. $^1$H NMR (400 MHz, CHLOROFORM-d) δ 8.89 (s, 1H), 8.47 (d, J=6.0 Hz, 1H), 7.98 (d, J=5.6 Hz, 1H), 7.61 (d, J=3.6 Hz, 1H), 6.65 (d, J=3.6 Hz, 1H), 1.69 (s, 9H).

Step D: 95 (1.00 g, 4.58 mmol, 1.00 eq) was dissolved in 10 mL tetrahydrofuran and cooled to −78° C. LDA (2M, 2.75 mL, 1.20 eq) was added dropwise, and the mixture was maintained below −70° C. for 30 minutes, then a solution of 4-iodobenzaldehyde (1.06 g, 4.58 mmol, 1.00 eq) in 5 mL tetrahydrofuran was added dropwise at −70° C. and the reaction solution was stirred at this temperature for 1 hour. The reaction solution was slowly quenched with 10 mL saturated aqueous ammonium chloride solution, then diluted with 10 mL water, partitioned, and the aqueous phase was extracted three times with 30 mL ethyl acetate each time. The organic phase was combined, washed with 20 mL saturated brine, dried over anhydrous sodium sulfate, filtered and concentrated to give a crude product, which was purified by silica gel column chromatography (EA/PE=20%-100%) to give the product 96 as a yellow solid. MS (ESI, M+1): 450.9.

Step E: 96 (6.10 g, 13.55 mmol, 1.00 eq) and 100 mL tetrahydrofuran were added to a single-neck round bottom flask, followed by addition of manganese dioxide (11.78 g, 135.50 mmol, 10.00 eq). The reaction solution was stirred at 70° C. for 72 hours, then filtered. The filter cake was washed with 30 mL dichloromethane. The filtrate was concentrated and purified by silica gel column chromatography (methanol/dichloromethane=0%-10%), and further purified by preparative high performance liquid chromatography (basic) to give the product 97 as a yellow solid. MS (ESI, M+1): 349.0.

Step D: Zinc powder (657.39 mg, 10.05 mmol, 14.00 eq) was added to 5 mL tetrahydrofuran, followed by dropwise addition of titanium tetrachloride (817.26 mg, 4.31 mmol, 472.40 uL, 6.00 eq) at 30° C. Then a solution of 97 (250.00 mg, 718.10 umol, 1.00 eq) and 98 (415.41 mg, 2.23 mmol, 3.10 eq) in tetrahydrofuran (20.00 mL) was added. The reaction solution was stirred at 70° C. for 14 hours and turned bright yellow. The reaction solution was cooled to room temperature, quenched with 20 mL saturated aqueous sodium bicarbonate solution, filtered to remove the yellow solid and partitioned. The aqueous phase was extracted three times with 20 mL ethyl acetate each time. The organic phase was combined, washed with brine, dried over anhydrous sodium sulfate, filtered. The filtrate was filtered, concentrated and purified by silica gel column chromatography (methanol/dichloromethane=0%-5%) to give the product 99. MS (ESI, M+1): 503.0.

Step F: 99 (230.00 mg, 457.48 umol, 1.00 eq), methyl acrylate (196.92 mg, 2.29 mmol, 205.13 uL, 5.00 eq), 1 mL triethylamine, POT (69.62 mg, 228.74 umol, 0.50 eq) and 3 mL DMF were added to a three-necked round bottom flask, followed by addition of palladium acetate (30.81 mg, 137.24 umol, 0.30 eq) under nitrogen atmosphere. The reaction solution was purged with nitrogen, and stirred at 110° C. for 2 hours. Then the reaction solution was filtered, and the filter cake was washed with 20 mL dichloromethane. The filtrate was concentrated to give 100 (250.00 mg, crude). MS (ESI, M+1): 461.1.

Step F: Lithium hydroxide monohydrate (57.35 mg, 1.37 mmol, 3.00 eq) was added to a solution of 100 (210.00 mg, 455.60 umol, 1.00 eq) in a mixed solvent of 5 mL tetrahydrofuran, 5 mL methanol and 5 mL water. The yellow suspension was stirred at 20° C. for 36 hours, then concentrated under reduced pressure, diluted with 10 mL water, and adjusted to pH 4-5 with citric acid. A solid precipitated, which was collected and purified by preparative high performance liquid chromatography (formic acid) to give the product I-46. $^1$H NMR (400 MHz, DMSO-d$_6$) δ=12.75 (s, 1H), 9.31 (s, 1H), 8.43 (d, J=6.8 Hz, 1H), 7.86 (d, J=6.4 Hz, 1H), 7.51-7.43 (m, 3H), 7.39 (dd, J=2.4, 8.8 Hz, 1H), 7.32 (dd, J=6.4, 8.4 Hz, 1H), 7.20-7.13 (m, 2H), 7.01 (d, J=8.0 Hz, 2H), 6.45 (d, J=16.0 Hz, 1H), 2.61 (q, J=7.2 Hz, 2H), 1.00 (br t, J=7.6 Hz, 3H); MS (ESI, M+1): 447.0.

Embodiment 54

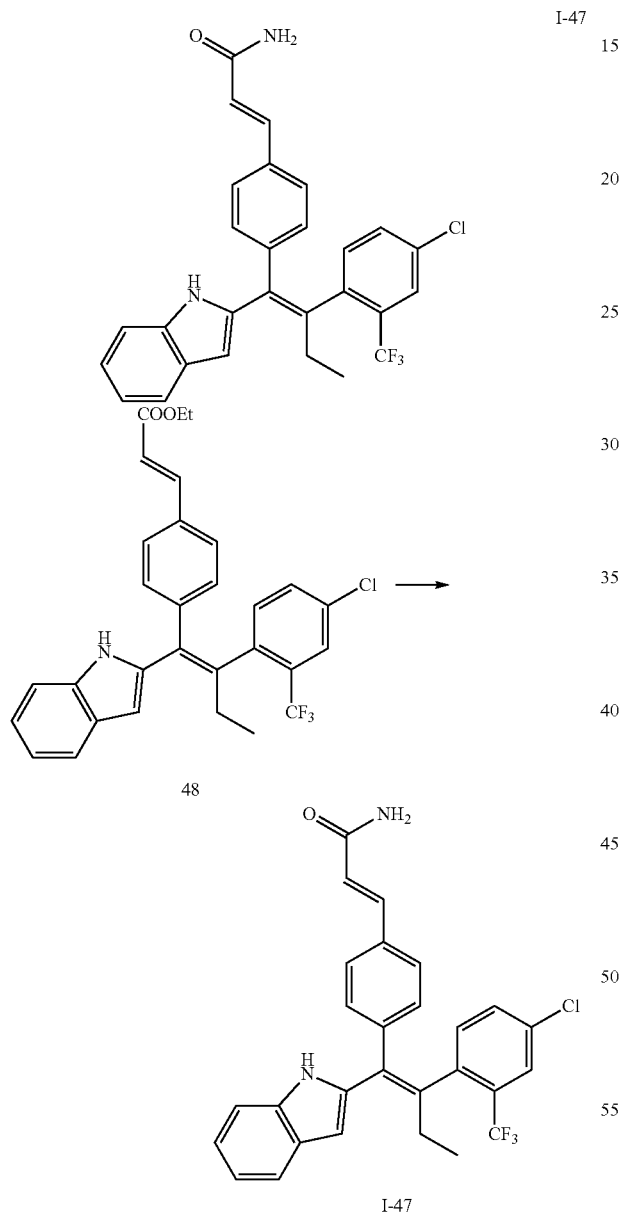

Step A: DMF (5.00 mL) was added a 50 mL single-neck flask, followed by addition of compound 48 (100.00 mg, 190.85 umol, 1.00 eq) and formamide (51.58 mg, 1.15 mmol, 45.64 uL, 6.00 eq). A solution of sodium methoxide in methanol (0.5M, 1.15 mL, 3.00 eq) was added to the solution. The reaction solution was stirred at 100° C. for 2 hours and turned from yellow to brown. After completion of the reaction, 30 mL ethyl acetate was added, then washed three times with 30 mL saturated brine each time. The organic phase was dried over anhydrous sodium sulfate, filtered and concentrated and purified by preparative high performance liquid chromatography (formic acid system) to give the product I-47. $^1$H NMR (400 MHz, DMSO-d$_6$): δ 10.76 (brs, 1H), 7.72 (d, J=2.0 Hz, 1H), 7.65 (dd, J=8.4 Hz, J=2.0 Hz, 1H), 7.55 (d, J=7.6 Hz, 1H), 7.44 (brs, 1H), 7.38 (d, J=8.4 Hz, 1H), 7.32-7.27 (m, 3H), 7.25 (d, J=15.6 Hz, 1H), 7.08-6.97 (m, 3H), 6.93 (d, J=8.0 Hz, 2H), 6.52 (d, J=1.6 Hz, 1H), 6.47 (d, J=16.0 Hz, 1H), 2.85-2.80 (m, 1H), 2.47-2.44 (m, 1H), 0.94 (t, J=7.6 Hz, 3 H). MS (ESI, M+1): 495.2.

Embodiment 55

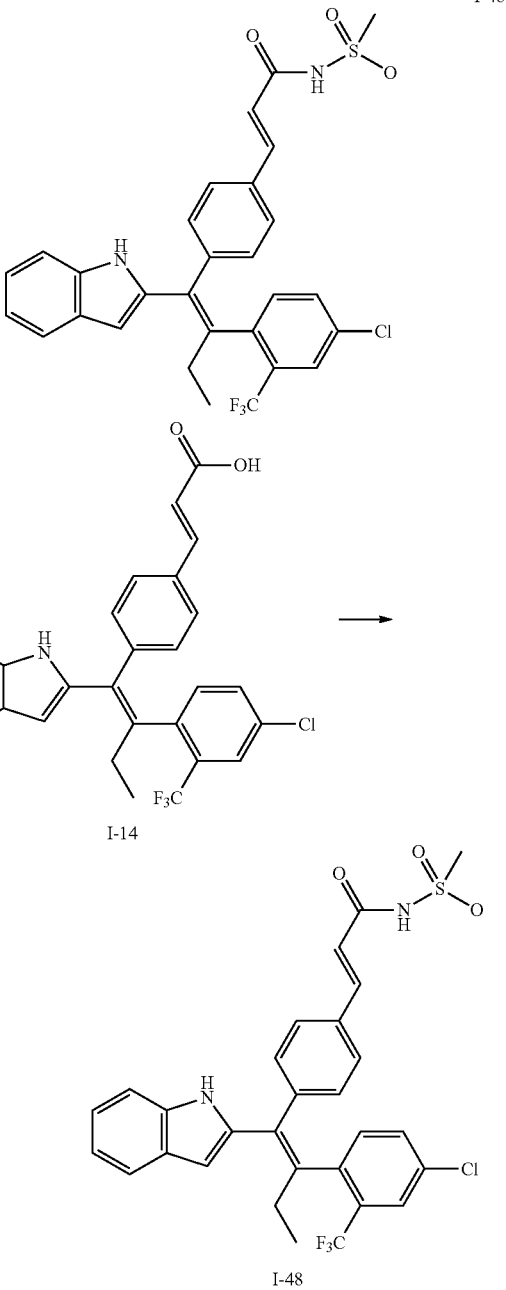

Step A: Compound I-14 (100.00 mg, 177.45 umol, 1.00 eq), EDCI (51.03 mg, 266.17 umol, 1.50 eq) and DMAP (49.86 mg, 408.13 umol, 2.30 eq) were dissolved in dichloromethane (7.00 mL), followed by addition of methylsulfonamide (50.64 mg, 532.34 umol, 3.00 eq). The black reaction solution was stirred at 30° C. for 12 hours. After completion of the reaction, water (10 mL) was added, then extracted with ethyl acetate (10 mL*3). The organic phase was combined, washed once with 15 mL brine, dried over anhydrous sodium sulfate, filtered and concentrated to give a crude product, which was purified by preparative chromatography (formic acid) to give the product I-48. $^1$H NMR (400 MHz, DMSO-d$_6$) δ 10.80 (s, 1H), 8.15 (s, 1H), 7.75 (d, J=2.4 Hz, 1H), 7.66 (dd, J=2.0, 8.4 Hz, 1H), 7.57 (d, J=8.0 Hz, 1H), 7.45-7.29 (m, 5H), 7.11-6.91 (m, 4H), 6.54 (d, J=2.0 Hz, 1H), 6.46 (d, J=15.4 Hz, 1H), 3.13 (s, 3H), 2.89-2.78 (m, 1H), 2.46 (br d, J=7.6 Hz, 1H), 0.95 (t, J=7.6 Hz, 3H); MS (ESI, M+1): 573.1.

Embodiment 56

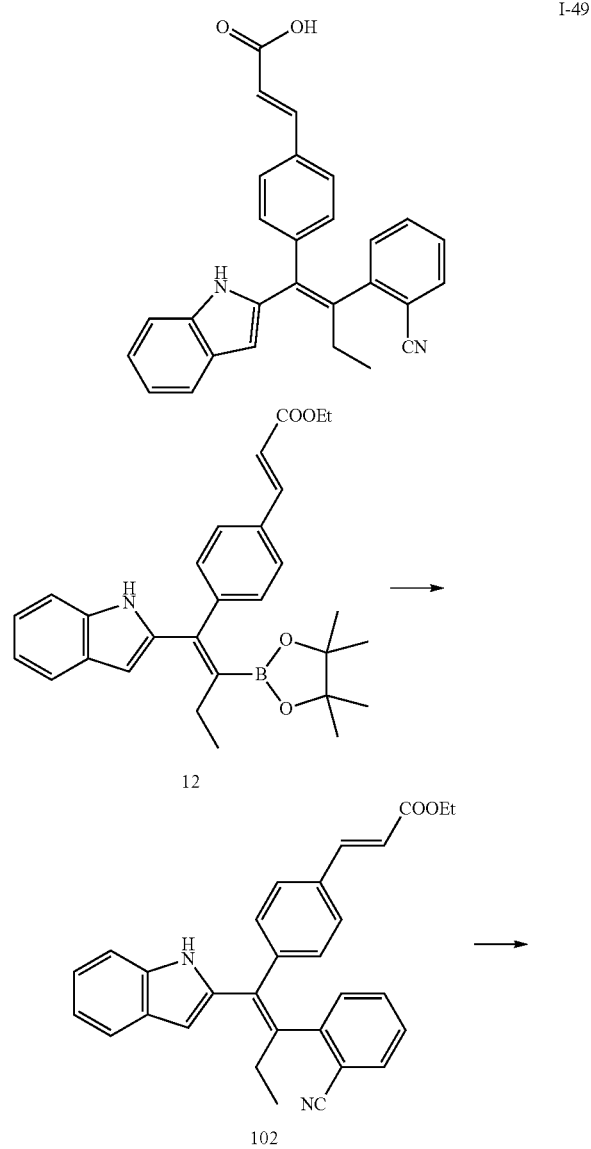

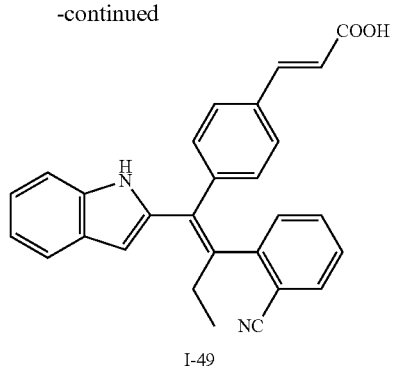

Step A: Compound 12 (272.73 mg, 509.13 umol, 1.00 eq), 2-cyano bromobenzene (139.01 mg, 763.70 umol, 1.50 eq), dichlorobis(triphenylphosphine)palladium (107.21 mg, 152.74 umol, 0.30 eq), aqueous potassium hydroxide (4M, 712.78 uL, 5.60 eq) were dissolved in 20 mL 2-methyltetrahydrofuran, the reaction solution was purged with nitrogen for three times, then stirred at 75° C. under nitrogen atmosphere for 7 hours. The reaction solution turned from yellow to dark brown and a black solid precipitated. The reaction solution was filtered through celite, and the filtrate was concentrated and purified to give the crude product 102 as a dark brown oil (250.00 mg, crude product), which was directly used in the next step without further purification.

Step B: Compound 102 (250.00 mg, 559.86 umol, 1.00 eq), lithium hydroxide (67.04 mg, 2.80 mmol, 5.00 eq) were dissolved in a mixed solvent of 10 mL methanol, 5 mL tetrahydrofuran and 5 mL water. The reaction solution was stirred at 30° C. for 1 hour, then concentrated to 1 ml, adjusted to pH 5-6 with hydrochloric acid (3 mol/L), extracted twice with 100 mL dichloromethane (50 mL each time). The organic phase was combined, dried, filtered, concentrated under reduced pressure, and purified by preparative chromatography (formic acid system) to give the product I-49 as a yellow solid. $^1$H NMR (400 MHz, DMSO-d$_6$) δ 10.76 (s, 1H), 7.69-7.62 (m, 2H), 7.60-7.55 (m, 2H), 7.44-7.39 (m, 3H), 7.38-7.29 (m, 2H), 7.07 (t, J=7.6 Hz, 1H), 7.03-6.98 (m, 1H), 6.94 (d, J=8.0 Hz, 2H), 6.61 (s, 1H), 6.41 (d, J=16.0 Hz, 1H), 2.81-2.67 (m, 2H), 1.02 (br t, J=7.2 Hz, 3H); MS [ESI, M+1]:419.2.

Embodiment 57

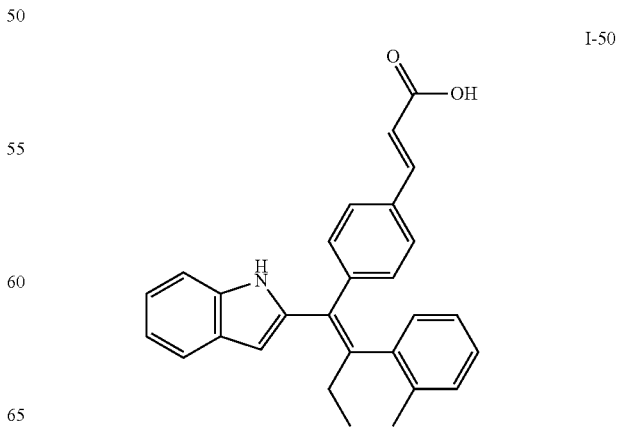

I-50 was prepared using the intermediate 12 (227.27 mg, 424.27 mg, 1.00 eq) and o-methyliodobenzene (185.01 mg, 848.54 umol, 108.19 uL, 2.00 eq) as raw material through a similar procedure to that described in preparing I-49.

The crude product was purified by preparative high performance liquid chromatography (formic acid system) to give the product I-50.

$^1$H NMR (400 MHz, DMSO-$d_6$): δ 10.81 (brs, 1H), 7.54 (d, J=8.0 Hz, 1H), 7.39 (d, J=16.0 Hz, 1H), 7.34 (d, J=8.4 Hz, 2H), 7.30 (dd, J=8.0 Hz, J=0.8 Hz, 1H), 7.18 (dt, J=7.6 Hz, J=1.6 Hz, 1H), 7.14-7.03 (m, 4H), 6.99 (dt, J=7.2 Hz, J=1.2 Hz, 1H), 6.89 (d, J=8.4 Hz, 2H), 6.53 (d, J=1.2 Hz, 1H), 6.36 (d, J=16.0 Hz, 1H), 2.59-2.54 (m, 2H), 2.08 (s, 3H), 0.95 (t, J=7.6 Hz, 3 H). MS (ESI, M+1): 408.1.

Embodiment 58

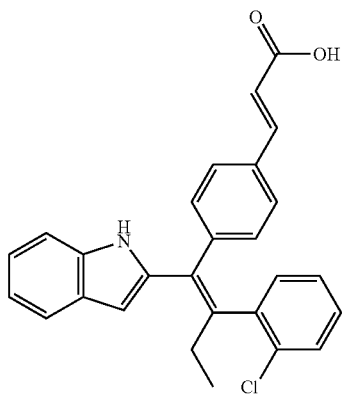

I-51

I-51 was prepared using the intermediate 12 (327.27 mg, 610.96 umol, 1.00 eq) and o-chloroiodobenzene (291.37 mg, 1.22 mmol, 2.00 eq) as raw material through a similar procedure to that described in preparing I-49.

The crude product was purified by preparative chromatography (formic acid system) to give the product I-51. MS [ESI, M+1]$^+$: 428.1, $^1$H NMR (400 MHz, DMSO-$d_6$) δ=10.74 (s, 1H), 7.56 (d, J=8.0 Hz, 1H), 7.42-7.35 (m, 4H), 7.30 (d, J=8.2 Hz, 1H), 7.24-7.15 (m, 3H), 7.09-6.94 (m, 4H), 6.57 (d, J=1.2 Hz, 1H), 6.38 (d, J=16.0 Hz, 1H), 2.75-2.59 (m, 1H), 2.75-2.56 (m, 1H), 1.00 (t, J=7.5 Hz, 3H).

Embodiment 59

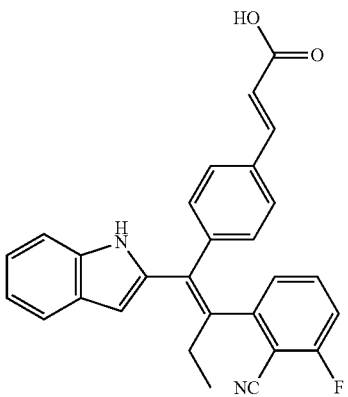

I-52

I-52 was prepared using the intermediate 51 (101.68 mg, 221.57 umol, 1.00 eq) and 2-cyano-3-fluoroiodobenzene (65.68 mg, 265.88 umol, 1.20 eq) as raw material through a similar procedure to that described in preparing I-28.

The crude product was purified by preparative high performance liquid chromatography (formic acid system) to give the product I-52. $^1$H NMR (400 MHz, DMSO-$d_6$) δ=10.79 (s, 1H), 8.34 (br s, 1H), 7.79-7.68 (m, 1H), 7.60 (d, J=7.6 Hz, 1H), 7.47-7.39 (m, 3H), 7.34 (dd, J=8.0, 16.8 Hz, 3H), 7.11-7.06 (m, 1H), 7.04-6.99 (m, 1H), 6.95 (d, J=8.0 Hz, 2H), 6.62 (d, J=1.2 Hz, 1H), 6.43 (d, J=16.0 Hz, 1H), 2.89-2.68 (m, 2H), 1.05 (t, J=7.4 Hz, 3H). MS (ESI, M+1): 437.1.

Embodiment 60

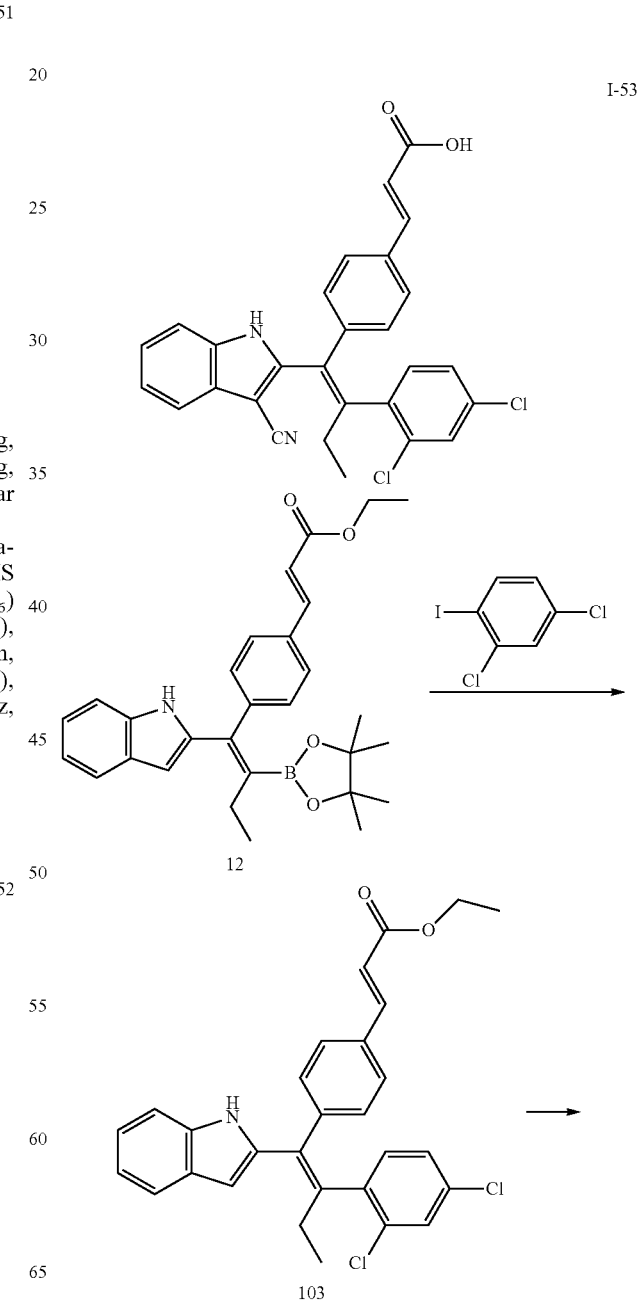

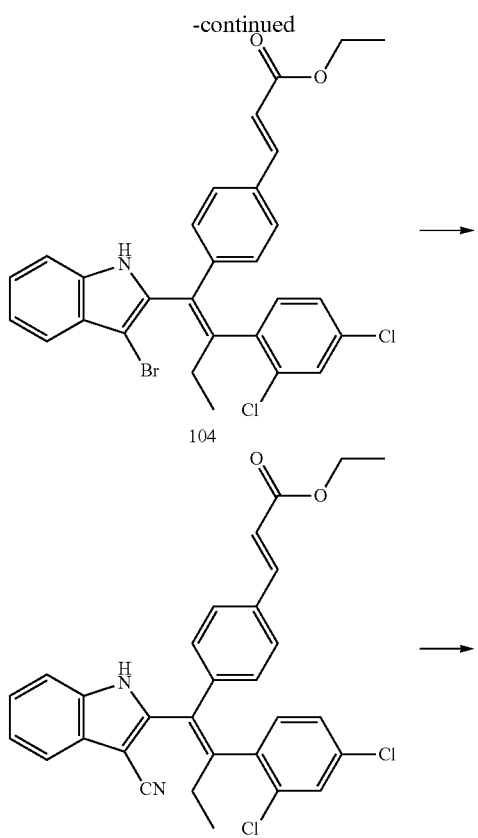

104

105

I-53

Step C: Cuprous cyanide (100.00 mg, 1.1.2 mmol, 243.90 uL, 21.46 eq) was added to a solution of compound 104 (125.00 mg, 52.04 umol, 1.00 eq) in 5 mL NMP. The reaction solution was stirred at 180° C. under microwave irradiation for 3 hours. Then the reaction solution was adjusted to pH 9-10 with 20 mL aqueous sodium bicarbonate, extracted with ethyl acetate, washed with saturated brine, dried over anhydrous sodium sulfate and concentrated to give 105.

Step D: Lithium hydroxide monohydrate (75.00 mg, 1.79 mmol, 10.24 eq) was added to a solution of compound 105 (90.00 mg, 174.61 umol, 1.00 eq) in a mixed solvent of 2 mL THF, 0.5 mL water and 2 mL methanol. The reaction solution was stirred at 25° C. for 9 hours. 10 mL water was added to the reaction solution, then the resulting solution was adjusted to pH 3-4 with 1M hydrochloric acid, extracted with ethyl acetate, concentrated to give a crude product, which was purified by preparative high performance liquid chromatography to give I-53. $^1$H NMR (400 MHz, CDCl3): δ 8.50 (s, 1H), 7.80-7.34 (m, 5H), 7.26-7.75 (m, 1H), 7.64 (d, J=16.0 Hz, 1H), 7.42-7.27 (m, 5H), 7.16 (dd, J=2.0 Hz, J=9.6 Hz, 1H), 7.08 (t, J=4.8 Hz, 3 H), 6.31 (d, J=16.0 Hz, 1 H), 2.78-2.65 (m, 1H), 7.26-7.75 (m, 1H), 7.63-2.51 (m, 1H), 1.05 (t, J=7.6 Hz, 3 H); MS (ESI, M+1): 487.2.

Embodiment 61

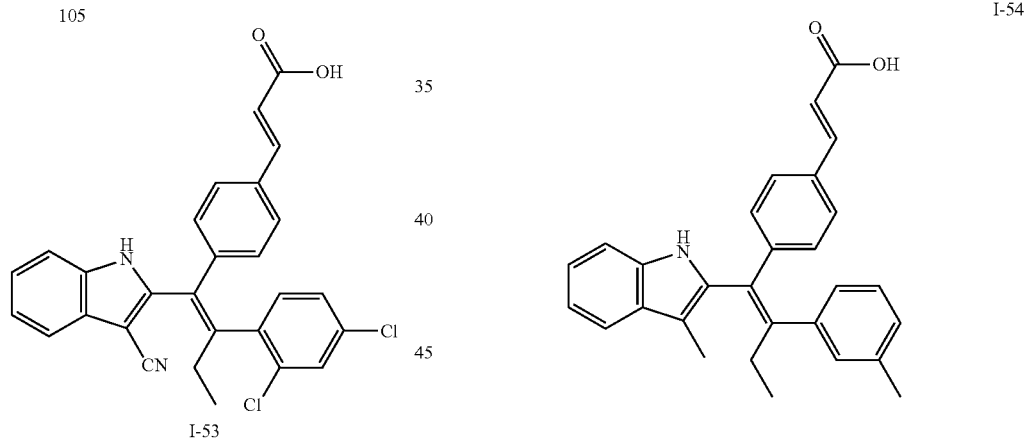

I-54

51

Step A: Bis(triphenylphosphine) palladium dichloride (30.00 mg, 42.74 umol, 0.5 eq) was added a solution of compound 12 (500.00 mg, 848.55 umol, 1.00 eq), 2,4-dichloroiodobenzene (250.00 mg, 916.43 umol, 1.08 eq), potassium hydroxide (450.00 mg, 8.02 mmol, 9.45 eq) in 2-methyltetrahydrofuran (8.00 mL) at 25° C. under nitrogen atmosphere. The reaction solution was stirred at 70° C. for 18 hours, then filtered, extracted, and purified by silica gel column chromatography to give 103.

Step B: NBS (115.00 mg, 646.14 umol, 1.02 eq) was added to a solution of compound 103 (330.00 mg, 632.52 umol, 1.00 eq) in 5 mL acetonitrile. The reaction solution was stirred at 25° C. for 10 minutes, then 5 mL dichloromethane was added and the reaction solution was stirred at 25° C. for another 50 minutes. The reaction solution was extracted, partitioned, dried over anhydrous sodium sulfate and concentrated to give the product 104 as a yellow solid.

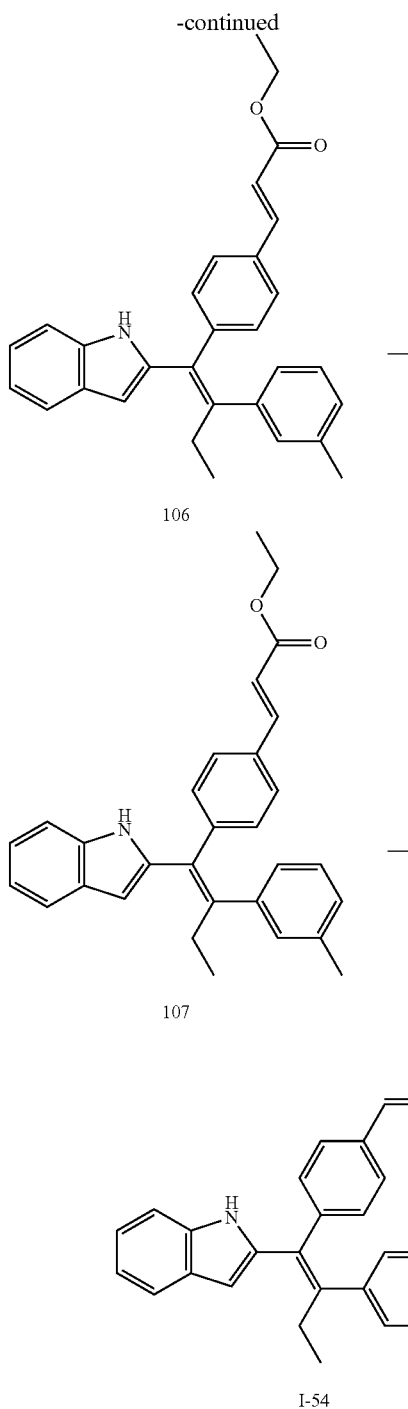

106

107

I-54

Step A: Intermediate 106 was prepared using intermediate 51 (200.00 mg, 443.13 umol, 1.00 eq) and m-methyliodobenzene (135.26 mg, 620.38 umol, 79.56 uL, 1.40 eq) as raw material through a similar procedure to that described in preparing intermediate 54.

Step B: Intermediate 107 was prepared using intermediate 106 (400.00 mg) and NBS (168.35 mg, 945.91 umol, 1.03 eq) as raw material through a similar procedure to that described in preparing intermediate 19.

Step C: I-54 was prepared using intermediate 107 (400.00 mg, 1 eq) and trimethylboroxine (300.13 mg, 2.39 mmol, 333.48 uL, 3.00 eq) as raw material through a similar procedure to that described in preparing I-19. $^1$H NMR (400 MHz, DMSO-d$_6$) δ 10.78 (s, 1H), 7.48 (d, J=7.6 Hz, 1H), 7.37-7.27 (m, 4H), 7.13-6.89 (m, 8H), 6.37 (d, J=16 Hz, 1H), 2.42 (t, J=7.6 Hz, 2H), 2.23 (s, 3H), 2.19 (s, 3H), 0.86 (t, J=7.6 Hz, 3H); MS (ESI, M+1): 422.2.

Embodiment 62

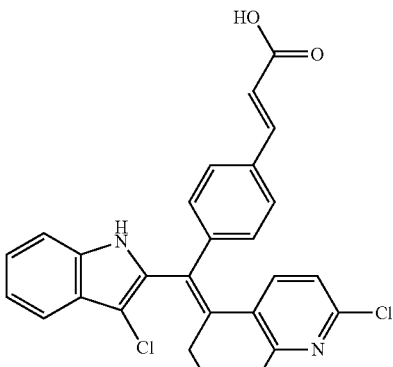

I-55

I-55 was prepared using intermediate 51 (300.00 mg, 0.656 mmol, 1.00 eq) and 2-chloro-5-bromo-6-cyanopyridine (214.21 mg, 985.10 umol, 1.5 eq) as raw material through a similar procedure to that described in preparing I-28.

The crude product was purified by preparative high performance liquid chromatography (formic acid system) to give the product I-55. $^1$H NMR (400 MHz, DMSO-d$_6$): δ 11.46 (brs, 1H), 8.25 (d, J=8.4 Hz, 1H), 7.94 (d, J=8.4 Hz, 1H), 7.61-7.34 (m, 5H), 7.26-7.13 (m, 2H), 6.96 (d, J=7.6 Hz, 1H), 6.45 (brs, 1H), 2.58 (q, J=7.2 Hz, 2H), 0.98 (t, J=7.2 Hz, 3 H). MS (ESI, M+1): 488.0.

Embodiment 63

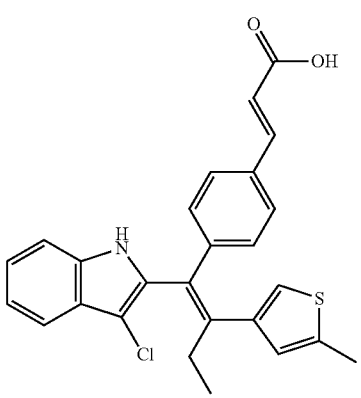

I-56

I-56 was prepared using intermediate 12 (1000 mg, 1.85 mmol, 1.00 eq) and 5-methyl-3-bromothiophene (588.21 mg, 3.32 mumol, 1.8 eq) as raw material through a similar procedure to that described in preparing I-24.

The crude product was purified by preparative high performance liquid chromatography (formic acid system) to give the product I-56. $^1$H NMR (400 MHz, DMSO-d$_6$) δ

11.43 (s, 1H), 7.53-7.43 (m, 4H), 7.36 (d, J=8.0 Hz, 1H), 7.22-7.09 (m, 2H), 7.06-6.98 (m, 3H), 6.53 (s, 1H), 6.44 (d, J=16 Hz, 1H), 2.39 (q, J=7.2 Hz, 2H), 2.34 (s, 3H), 0.96 (t, J=7.2 Hz, 3H); MS (ESI, M+1): 448.0.

Embodiment 64

I-57

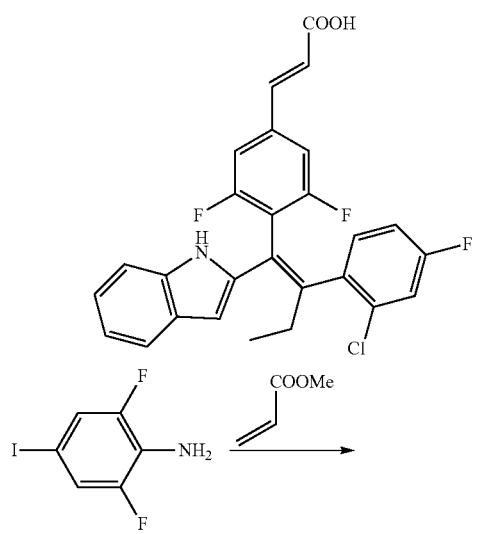

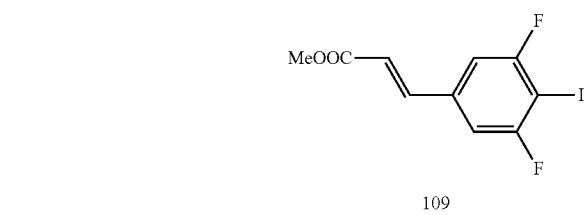

108

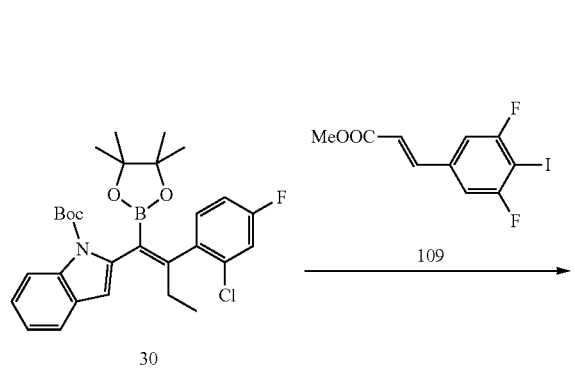

30

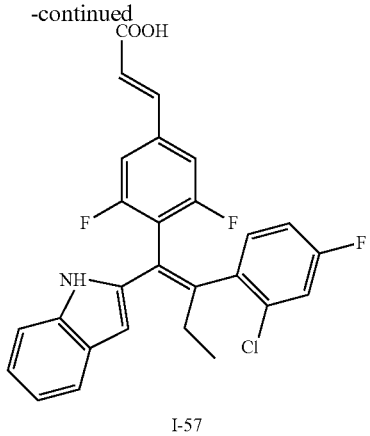

I-57

Step A: Methyl acrylate (25.32 g, 294.10 mmol, 26.38 mL, 5.00 eq), triethylamine (11.90 g, 117.64 mmol, 16.30 mL, 2.00 eq) and 1,1'-bis(diphenylphosphino)ferrocene palladium chloride (2.15 g, 2.94 mmol, 0.05 eq) were added to a solution of 2,6-difluoro-4-iodoaniline (15.00 g, 58.82 mmol, 1.00 eq) in 100 mL N,N-dimethylformamide. The reaction solution was stirred at 80° C. under nitrogen atmosphere for 12 hours. Then 400 mL ethyl acetate was added, and the mixture was filtered through celite. The filtrate was washed three times with 400 mL water. The organic phase was dried over anhydrous sodium sulfate, filtered and concentrated to give a crude product, which was purified by silica gel column chromatography to give intermediate 108.

Step B: Iodine (19.64 g, 77.40 mmol, 15.59 mL, 3.00 eq) was added to a solution of 108 (5.50 g, 25.80 mmol, 1.00 eq) in 50 mL acetonitrile, followed by addition of tert-butyl nitrite (3.99 g, 38.70 mmol, 4.59 mL, 1.50 eq) at 0° C. under nitrogen atmosphere. The reaction solution was stirred at 15° C. under nitrogen atmosphere for 12 hours. Then 150 mL ethyl acetate was added, and the mixture was filtered through celite. The filtrate was washed twice with 200 mL saturated aqueous sodium sulfite. The organic phase was dried over anhydrous sodium sulfate, filtered and concentrated to give a crude product, which was purified by silica gel column chromatography to give intermediate 109.

Step C: Aqueous potassium hydroxide solution (4M, 3.33 mL, 5.00 eq) and bis(triphenylphosphine)palladium dichloride (93.44 mg, 133.00 umol, 0.05 eq) were added to a solution of 30 (1.40 g, 2.66 mmol, 1.00 eq) in 30 mL dimethyltetrahydrofuran. The reaction solution was stirred at 70° C. under nitrogen atmosphere for 12 hours, then filtered through celite. The filtrate was neutralized to pH 5 with hydrochloric acid (1M). 40 mL water was added, then extracted twice with 30 mL ethyl acetate. The organic phase was combined, washed twice with 30 mL water, dried over anhydrous sodium sulfate, filtered and concentrated to give a crude product, which was purified by preparative HPLC (formic acid system) to give the product I-57. MS(ESI, M+1): 482.1 $^1$H NMR EW3644-119-P1E (400 MHz, DMSO-d$_6$): δ 12.52 (brs, 1H), 10.81 (s, 1H), 7.54 (d, J=8.0 Hz, 1H), 7.45 (d, J=16.4 Hz, 1H), 7.36-7.32 (m, 4H), 7.23 (ddd, J=2.0 Hz, J=6.4 Hz, J=8.8 Hz, 1 H), 7.13 (dt, J=2.8 Hz, J=8.4 Hz, 1 H), 7.07 (dt, J=1.2 Hz, J=7.2 Hz, 1 H), 6.99 (dt, J=0.8 Hz, J=8.0 Hz, 1 H), 6.59 (d, J=16.0 Hz, 1 H), 6.55 (d, J=1.2 Hz, 1 H), 2.88-2.81 (m, 2 H), 1.05 (t, J=7.6 Hz, 3 H).

Embodiment 65

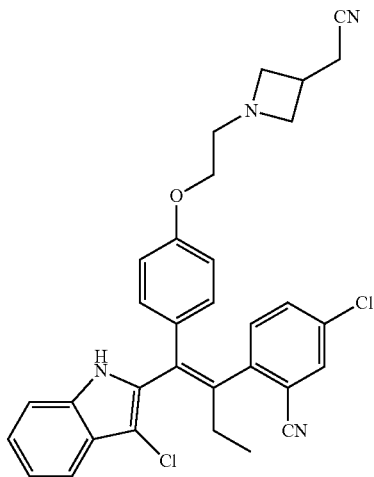

II-12 was prepared using intermediate 10 (500.00 mg, 2.92 mmol, 1.00 eq) and intermediate (920 mg, 2.56 mmol, 0.9 eq) and o-cyano-p-chlorobromobenzene (922 mg, 4.26 mmol) as raw material through a similar procedure to that described in preparing II-8.

The crude product was purified by preparative high performance liquid chromatography (formic acid system) to give the product I-56. $^1$H NMR (400 MHz, DMSO-d$_6$) δ=11.37 (s, 1H), 7.94 (d, J=2.4 Hz, 1H), 7.78-7.75 (m, 1H), 7.53-7.51 (m, 2H), 7.39-7.37 (m, 1H), 7.20-7.08 (m, 2H), 6.82 (d, J=8.8 Hz, 2H), 6.66 (d, J=8.8 Hz, 2H), 3.78 (t, J=5.2 Hz, 2H), 3.35-3.31 (m, 2H), 2.29 (t, J=5.2 Hz, 2H), 2.72-2.70 (m, 2H), 2.56-2.55 (m, 5H), 0.90 (t, J=7.6 Hz, 3H); MS (ESI, M+1): 555.2.

Effect Embodiment 1

(1) MCF-7 Cell Proliferation Inhibition Assay

Experimental Reagent:

RPMI 1640 medium, fetal bovine serum, Promega CellTiter-Glo reagent. The cell line MCF-7 was purchased from The European Collection of Authenticated Cell Cultures (ECACC). Envision Multilabel Reader (PerkinElmer).

Experimental Method:

MCF-7 cells were seeded in black 384-well plates at 600 cells per well in 30 mL cell suspension. The cell plate was placed in a carbon dioxide incubator overnight.

The test compound was diluted 5-fold to the 10th concentration with Epmotion, that was diluting from 2.5 mM to 1.28 nM, each concentration set two replicated wells. 198 μL medium was added to the intermediate plate, the compound with gradient concentrations was transferred to the intermediate plate at 2 μL per well according to the corresponding position, then mixing and transferring to the cell plate at 20 μL per well. The cell plate was incubated in a carbon dioxide incubator for 6 days.

Promega CellTiter-Glo reagent was added to the cell plate at 25 μL per well, cells were incubated for 10 minutes at room temperature to stabilize the luminescence signal, which was measured using PerkinElmer Envision Multilabel Reader.

Data Analysis:

The original data was converted to the inhibition rate using the equation (Max−Ratio)/(Max−Min)*100%, and the value of IC$_{50}$ could be obtained by curve fitting with four parameters. (Model 205 in XLFIT5, iDBS)

(2) ER Degradation Assay in MCF-7 Cells

Experimental Reagent:

RPMI 1640 medium, fetal bovine serum, PBS, 16% paraformaldehyde, Triton, blocking solution, estrogen receptor antibody, near-infrared goat anti-rabbit secondary antibody, DRAQ5 dye. The cell line MCF-7 was purchased from The European Collection of Authenticated Cell Cultures (ECACC). Odyssey infrared fluorescence scanning imaging system.

Experimental Method:

MCF-7 cells were seeded in black 384-well plates at 3200 cells per well in 30 mL cell suspension. The cell plate was placed in a carbon dioxide incubator for 4 days.

The test compound was diluted 5-fold to the 10th concentration with Epmotion, fulvestrant was diluted from 0.25 mM to 0.128 nM, other compounds were diluted from 2.5 mM to 1.28 nM, each concentration set two replicated wells. 198 μL medium was added to the intermediate plate, the compound with gradient concentrations was transferred to the intermediate plate at 2 μL per well according to the corresponding position, then mixing and transferring to the cell plate at 20 μL per well. The cell plate was incubated in a carbon dioxide incubator for 20 hours.

After 8% paraformaldehyde was added to the cell plate at 50 μL per well, the cell plate was incubated at room temperature for 30 minutes, then washed twice with PBS. After pat dry, 50 μL PBS containing 0.1% Triton was added, and the cell plate was incubated at room temperature for 15 minutes, then washed with PBS for five times. After 50 μL blocking solution was added, the cell plate was incubated at room temperature for 1 hour. After pat dry, 50 uL blocking solution containing 0.1% estrogen receptor antibody was added, and the cell plate was incubated at 4° C. overnight. The next day, after the primary antibody was brushed down, the cell plate was washed with PBS for five times, then a blocking solution containing 0.1% near-infrared goat anti-rabbit secondary antibody and 0.05% DRAQ5 dye was added. The cell plate was incubated at room temperature for 1 hour, washed with PBS for five times. After pat dry, the cell plate was measured using Odyssey infrared fluorescence scanning imaging system.

Data Analysis:

The original data was converted to the inhibition rate using the equation (Max−Ratio)/(Max−Min)*100%, and the value of IC$_{50}$ could be obtained by curve fitting with four parameters. (Model 205 in XLFIT5, iDBS)

TABLE 1 screening test results in vitro

| Compound | anti-proliferation in MCF-7 cells (nM) | ER degradation assay in MCF-7 cells IC$_{50}$ (nM) |
| --- | --- | --- |
| I-1 | 38.5 | 20.8 |
| I-2 | 282 | 68 |
| I-3 | 206 | 93 |
| I-4 | 325 | 131 |
| I-5 | 8.04 | 5.87 |
| I-6 | 321 | 64 |
| I-7 | 9.52 | 7.88 |
| I-8 | 5.59 | 4.49 |
| I-9 | 167 | 93.67 |
| I-10 | 13 | 9.95 |
| I-11 | 8.53 | 2.44 |
| I-12 | 13 | 5.59 |
| I-13 | 27 | 5.83 |

TABLE 1-continued screening test results in vitro

| Compound | anti-proliferation in MCF-7 cells (nM) | ER degradation assay in MCF-7 cells $IC_{50}$ (nM) |
|---|---|---|
| I-14 | 4.11 | 2 |
| I-15 | 7.56 | 2.25 |
| I-17 | 8.29 | 6.23 |
| I-18 | 22 | 38 |
| I-19 | 4.78 | 1.26 |
| I-21 | 14 | 18 |
| I-22 | 0.86 | 0.81 |
| I-23 | 4.84 | 2.6 |
| I-24 | 21.5 | 7.56 |
| I-27 | 8.36 | 13 |
| I-28 | 69 | 64 |
| I-29 | 30 | 42 |
| I-30 | 48 | 20 |
| I-31 | 3.66 | 2.66 |
| I-32 | 61 | 30 |
| I-33 | 2.86 | 2.35 |
| I-34 | 49 | 31 |
| I-35 | 20 | 5.13 |
| I-36 | 6.84 | 1.78 |
| I-37 | 11 | 9 |
| I-40 | 2.31 | 2.84 |
| I-41 | 3.91 | 2.54 |
| I-42 | 0.77 | 1.57 |
| I-43 | 1.56 | 0.70 |
| I-44 | 5.84 | 12 |
| I-45 | 103 | 178 |
| I-46 | 393 | 220 |
| I-47 | 4.27 | 4.13 |
| I-48 | 4.88 | 5.77 |
| I-49 | 42 | 29 |
| I-50 | 33 | 9 |
| I-51 | 9.24 | 9 |
| I-52 | 40 | 49 |
| I-53 | 4.35 | 2.02 |
| I-54 | 23 | 4.89 |
| I-55 | 2.42 | 2.82 |
| I-56 | 35 | 18 |
| I-57 | 32 | 18.5 |
| II-1 | 4.57 | 5.36 |
| II-2 | 7.75 | 34.34 |
| II-3 | 6.77 | 12.5 |
| II-4 | 6.86 | 26 |
| II-5 | 7.23 | 5.25 |
| II-6 | 2.46 | 5.28 |
| II-7 | 2.61 | 3.41 |
| II-8 | 5 | 26 |
| II-9 | 51 | 23 |
| II-10 | 3.92 | 9.88 |
| II-11 | 7.43 | 3.93 |
| II-12 | 1.56 | 5.51 |

Conclusion:

The compound of the present invention exhibits excellent in vitro activity.

Effect Embodiment 2: Evaluation of In Vitro DMPK Properties (1) The results of in vitro DMPK properties are shown in table 2:

TABLE 2 results of in vitro DMPK properties

| Compound | ARN-810 | I-1 |
|---|---|---|
| plasma protein binding rate (Human/CD-1 mouse) | NA (too high to be detected) | 97.2%/98.8% |
| inhibition of CYP enzymes ($IC_{50}$, μM) 1A2/2C9/2C19/2D6/3A4 | 13.7/0.664/0.884/ 23.6/24.6 | 25.5/10.1/40.4/ 43.4/25.1 |

Conclusion:

Compound I-1 of the present invention is superior to oral selective estrogen receptor down-regulator ARN-810 which is in clinical phase II in terms of plasma protein binding rate (PPB) and drug-drug interaction (DDI).

(2) The results of in vivo PK properties are shown in table 3:

TABLE 3 results of in vivo PK properties

| | Compound | | | |
|---|---|---|---|---|
| | ARN-810 | | I-1 | |
| | Cassette PK | | | |
| | i.V. (1 mpk) | P.O (2.5 mpk) | i.V. (1 mpk) | P.O (2.5 mpk) |
| $C_0$ (For i.v.) [$C_{max}$ (For P.O)/$T_{max}$] (nM) | 1639 | 924/0.417 | 3479 | 2147/3.33 |
| $T_{1/2}$ (hr) | 1.35 | 3.49 | 2.81 | 3.18 |
| Vdss (L/Kg) | 1.93 | N.D. | 0.992 | N.D. |
| Cl (mL/min/Kg) | 18.9 | N.D. | 3.61 | N.D. |
| $AUC_{0-last}$ (nm/hr) | 1987 | 3277 | 10378 | 18327 |
| F % | | 66 | | 70.6 |

Conclusion:

Compound I-1 of the present invention is superior to oral selective estrogen receptor down-regulator ARN-810 in clinical phase II in terms of oral peak plasma concentration Cmax, half-life, clearance rate (CL), AUC and oral bioavailability.

Effect Embodiment 3: Evaluation of In Vivo Pharmacodynamics

The purpose of this experiment was to evaluate antitumor activity of oral selective estrogen receptor down-regulator ARN-810 in clinical phase II and compound I-1 on MCF-7 breast cancer cell xenograft model in BALB/c nude mice (Beijing Vital River Laboratory Animal Technology Co., Ltd., 10 animals per experimental group). In this experiment, mice inoculated with MCF-7 breast cancer cells were orally administered with ARN-810 at a dose of 10/30 mg/kg, with compound I-1 at a dose of 30 mg/kg, and the inhibitory activity of the test drug on the tumor growth was evaluated.

Mice were inoculated subcutaneously with 0.36 mg estrogen sustained release tablet (60 days release) on the left shoulder three days before inoculation. When cells were in the logarithmic growth phase, cells were harvested, counted and adjusted to $10 \times 10^7$ cells/mL, then an equal volume of Matrigel was added, mixing for inoculation. 0.2 mL MCF-7 tumor cell suspension ($10 \times 10^6$) was inoculated subcutaneously into the right shoulder of each mouse. On the 7th day after tumor cell inoculation, mice were grouped and administrated once a day, with an average tumor volume of 169 mm³ and a body weight of 23.33 g. Tumor volume and body weight were measured twice a week after grouping, and the tumor growth rate (T/C) and tumor growth inhibition rate (TGI) were calculated based on the last measuring data on the 17th day after grouping. The results are as follows:

TABLE 4 evaluation of antitumor activity

| Group | test compound | tumor volumn (mm³)a 17th day after grouping | T/C (%) | TGI (%) | P |
|---|---|---|---|---|---|
| 1 | ARN-810 | 290 ± 38 | 43.4 | 75.7 | <0.001 |
| 2 | I-1 | 201 ± 27 | 30.1 | 93.6 | <0.001 | aMean ± SEM.

Conclusion:

The antitumor activity of oral administration of I-1 at a dose of 30 mg/kg is superior to that of oral administration of oral selective estrogen receptor down-regulator ARN-810 in clinical phase II at a dose of 10/30 mg/kg.

Effect Embodiment 4: Evaluation of Drug Distribution in Tissues

On the 20th day after grouping, the sample was collected from plasma, tumor, breast and brain of the mice at four time points (2-3 mice each time point) which was respectively 0.5 hour, 1.5 hours, 6 hours and 24 hours after administration. The blood (0.5 mL) was collected using a 1.5 mL EDTA-K2 anticoagulation tube, immediately centrifuged at 4000 rpm, 4° C. for 10 minutes to prepare plasma, the plasma sample was stored at −80° C. for determination of drug concentration. The tumor was collected using a 2 mL cryotube, and the brain was collected using a 5 mL cryotube, the samples were immediately put into liquid nitrogen for quike freeze. All samples were stored at −80° C. for determination of drug concentration after sampling. The result was converted based on corresponding AUC to compare the drug distribution.

The result was shown in table 5.

TABLE 5 evaluation of drug distribution in tissues
AUC0-last (nmol · h/kg)

| Compound | molecular weight | dose (μmol/kg) | plasma | tumor | brain |
|---|---|---|---|---|---|
| ARN-810 | 446.91 | 67.3 | 33545 | 11368 | 3490 |
| I-1 | 445.91 | 67.3 | 118937 | 55487 | 43167 |

Conclusion:

The distribution of compound I-1 in tumor tissue is much better than that of ARN-810, which is consistent with its better antitumor activity;

The distribution of compound I-1 in brain tissue is much better than that of ARN-810, indicating that it will have excellent activity to treat metastatic ER-positive breast cancer in brain.

What is claimed is:

1. A compound represented by formula (I), a pharmaceutically acceptable salt or a hydrate thereof,

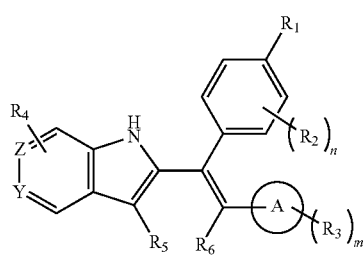

(I)

wherein, $R_1$ is selected from

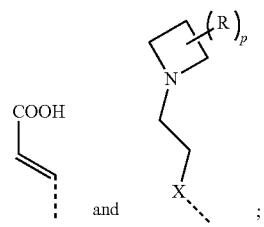

COOH and

X is selected from single bond, O and S;

Y and Z are CH;

ring A is selected from 5-10 membered aryl and 5-10 membered heteroaryl;

$R_2$ is selected from H, halogen, CN, $NO_2$, OH, COOH, $NH_2$, or the group consisting of $C_{1-6}$ alkyl, $C_{1-6}$ heteroalkyl, $C_{3-6}$ cycloalkyl and 3-6 membered heterocycloalkyl, each of which is optionally substituted with 1, 2, or 3 R;

$R_3$ is selected from H, halogen, CN, $NO_2$, OH, COOH, $NH_2$, or the group consisting of $C_{1-6}$ alkyl, $C_{1-6}$ heteroalkyl, $C_{3-6}$ cycloalkyl and 3-6 membered heterocycloalkyl, each of which is optionally substituted with 1, 2, or 3 R;

$R_4$ and $R_5$ are each independently selected from H, halogen, CN, $NO_2$, OH, COOH, $NH_2$, or the group consisting of $C_{1-6}$ alkyl, $C_{1-6}$ heteroalkyl, $C_{3-6}$ cycloalkyl and 3-6 membered heterocycloalkyl, each of which is optionally substituted with 1, 2, or 3 R;

$R_6$ is selected from the group consisting of $C_{1-6}$ alkyl, $C_{1-6}$ heteroalkyl, $C_{3-6}$ cycloalkyl and 3-6 membered heterocycloalkyl, each of which is optionally substituted with 1, 2, or 3 R;

R is selected from H, F, Cl, Br, I, OH, CN, $NH_2$, COOH, C(=O)$NH_2$, or the group consisting of $C_{1-8}$ alkyl, $C_{1-8}$ heteroalkyl, $C_{3-6}$ cycloalkyl, 3-6 membered heterocycloalkyl and $C_{3-6}$ cycloalkyl-$C_{1-3}$ alkyl-, each of which is optionally substituted with 1, 2, or 3 R';

n is selected from 0, 1, 2, 3 and 4;

m is selected from 0, 1, 2, 3 and 4;

P is selected from 0, 1, 2 and 3;

or, when m is 2, $R_3$ and $R_3$ are connected together to form a 5-6 membered ring;

R' is selected from the group consisting of F, Cl, Br, I, OH, CN, $NH_2$, COOH, Me, Et, $CF_3$, $CHF_2$, $CH_2F$, $NHCH_3$ and $N(CH_3)_2$;

"hetero" represents a heteroatom or a heteroatom group, which is selected from the group consisting of —C(=O)N(R)—, —N(R)—, —S(=O)$_2$N(R)—, —S(=O) N(R)—, —O—, —S—, =O, =S, —O—N=, —C(=O)O—, —C(=O)—, —C(=S)—, —S(=O)—, —S(=O)$_2$— and —N(R)C(=O)N(R)—;

in any of the above cases, the number of the heteroatom or the heteroatom group is independently selected from 1, 2 and 3.

2. A compound represented by formula (I), a pharmaceutically acceptable salt or a hydrate thereof,

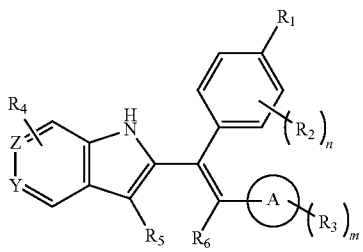

(I)

wherein,
$R_1$ is selected from

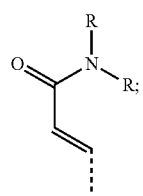

Y and Z are CH;
ring A is selected from 5-10 membered aryl and 5-10 membered heteroaryl;
$R_2$ is selected from H, halogen, CN, $NO_2$, OH, COOH, $NH_2$, or the group consisting of $C_{1-6}$ alkyl, $C_{1-6}$ heteroalkyl, $C_{3-6}$ cycloalkyl and 3-6 membered heterocycloalkyl, each of which is optionally substituted with 1, 2, or 3 R;
$R_3$ is selected from H, halogen, CN, $NO_2$, OH, COOH, $NH_2$, or the group consisting of $C_{1-6}$ alkyl, $C_{1-6}$ heteroalkyl, $C_{3-6}$ cycloalkyl and 3-6 membered heterocycloalkyl, each of which is optionally substituted with 1, 2, or 3 R;
$R_4$ and $R_5$ are each independently selected from H, halogen, CN, $NO_2$, OH, COOH, $NH_2$, or the group consisting of $C_{1-6}$ alkyl, $C_{1-6}$ heteroalkyl, $C_{3-6}$ cycloalkyl and 3-6 membered heterocycloalkyl, each of which is optionally substituted with 1, 2, or 3 R;
$R_6$ is selected from the group consisting of $C_{1-6}$ alkyl, $C_{1-6}$ heteroalkyl, $C_{3-6}$ cycloalkyl and 3-6 membered heterocycloalkyl, each of which is optionally substituted with 1, 2, or 3 R;
R is selected from H, F, Cl, Br, I, OH, CN, $NH_2$, COOH, C(=O)$NH_2$, or the group consisting of $C_{1-8}$ alkyl, $C_{1-8}$ heteroalkyl, $C_{3-6}$ cycloalkyl, 3-6 membered heterocycloalkyl and $C_{3-6}$ cycloalkyl-$C_{1-3}$ alkyl-, each of which is optionally substituted with 1, 2, or 3 R';
n is selected from 0, 1, 2, 3 and 4;
m is selected from 0, 1, 2, 3 and 4;
or, when m is 2, $R_3$ and $R_3$ are connected together to form a 5-6 membered ring;
R' is selected from the group consisting of F, Cl, Br, I, OH, CN, $NH_2$, COOH, Me, Et, $CF_3$, $CHF_2$, $CH_2F$, $NHCH_3$ and $N(CH_3)_2$;
"hetero" represents a heteroatom or a heteroatom group, which is selected from the group consisting of —C(=O)N(R)—, —N(R)—, —S(=O)$_2$N(R)—, —S(=O)N(R)—, —O—, —S—, =O, =S, —O—N=, —C(=O)O—, —C(=O)—, —C(=S)—, —S(=O)—, —S(=O)$_2$— and —N(R)C(=O)N(R)—;

in any of the above cases, the number of the heteroatom or the heteroatom group is independently selected from 1, 2 and 3.

3. The compound, the pharmaceutically acceptable salt or the hydrate thereof as defined in claim 2, wherein, R is selected from H, F, Cl, Br, I, OH, CN, $NH_2$, COOH, or the group consisting of $C_{1-5}$ alkyl, $C_{1-5}$ heteroalkyl, $C_{3-6}$ cycloalkyl-$C_{1-3}$ alkyl-, each of which is optionally substituted with 1, 2, or 3 R'.

4. The compound, the pharmaceutically acceptable salt or the hydrate thereof as defined in claim 3, wherein, R is selected from H, F, Cl, Br, I, OH, CN, $NH_2$, COOH, C(=O)$NH_2$, or the group consisting of $CH_3$, $CH_3CH_2$, S(=O)$CH_3$,

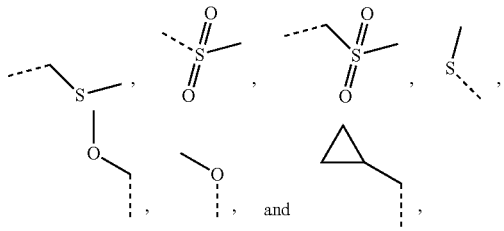

each of which is optionally substituted with 1, 2, or 3 R'.

5. The compound, the pharmaceutically acceptable salt or the hydrate thereof as defined in claim 4, wherein, R is selected from the group consisting of H, F, Cl, Br, I, OH, CN, $NH_2$, COOH, C(=O)$NH_2$, $CH_3$, $CH_2Cl$, $CH_2F$, $CHF_2$, $CF_3$, $OCF_3$, $CH_2OH$, Et, S(=O)$CH_3$,

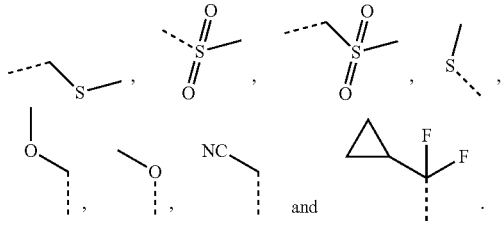

6. The compound, the pharmaceutically acceptable salt or the hydrate thereof as defined in claim 1, wherein, R is selected from H, F, Cl, Br, I, OH, CN, $NH_2$, COOH, or the group consisting of $C_{1-5}$ alkyl, $C_{1-5}$ heteroalkyl and $C_{3-6}$ cycloalkyl-$C_{1-3}$ alkyl-, each of which is optionally substituted with 1, 2, or 3 R'.

7. The compound, the pharmaceutically acceptable salt or the hydrate thereof as defined in claim 6, wherein, R is selected from H, F, Cl, Br, I, OH, CN, $NH_2$, COOH, C(=O)$NH_2$, or the group consisting of $CH_3$, $CH_3CH_2$, S(=O)$CH_3$,

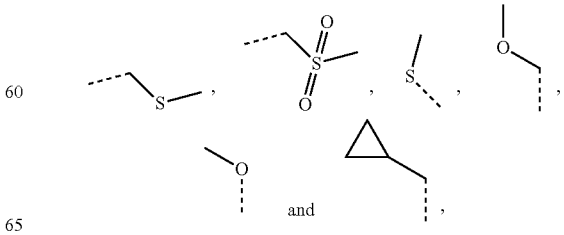

each of which is optionally substituted with 1, 2, or 3 R'.

8. The compound, the pharmaceutically acceptable salt or the hydrate thereof as defined in claim 7, wherein, R is selected from the group consisting of H, F, Cl, Br, I, OH, CN, NH$_2$, COOH, C(=O)NH$_2$, CH$_3$, CH$_2$Cl, CH$_2$F, CHF$_2$, CF$_3$, OCF$_3$, CH$_2$OH, Et, S(=O)CH$_3$,

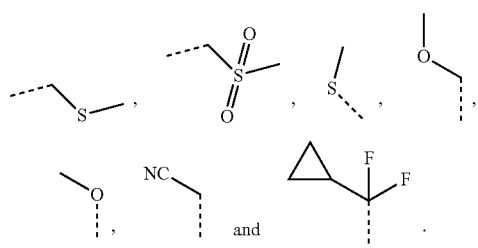

9. The compound, the pharmaceutically acceptable salt or the hydrate thereof as defined in claim 1, wherein, the structural unit

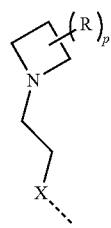

is selected from

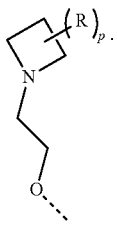

10. The compound, the pharmaceutically acceptable salt or the hydrate thereof as defined in claim 9, wherein, the structural unit

is selected from

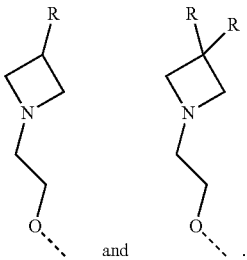

11. The compound, the pharmaceutically acceptable salt or the hydrate thereof as defined in claim 10, wherein, the structural unit

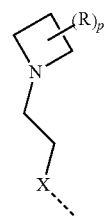

is selected from the group consisting of

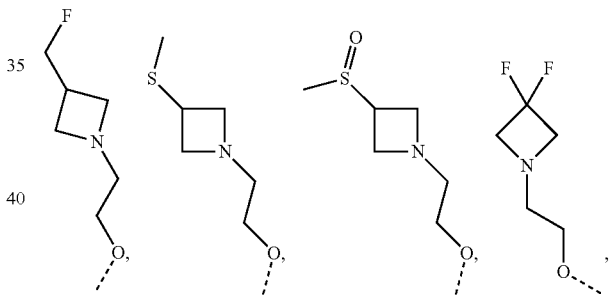

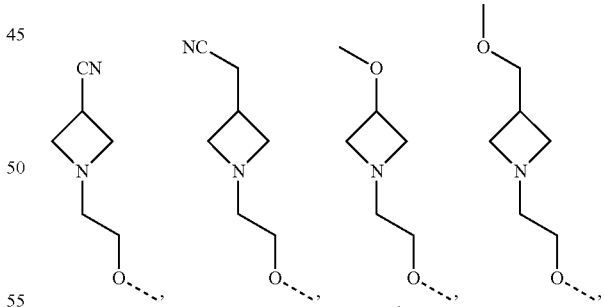

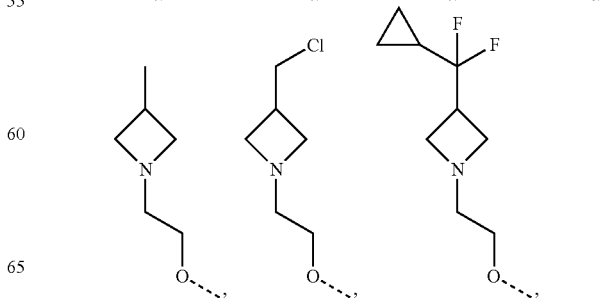

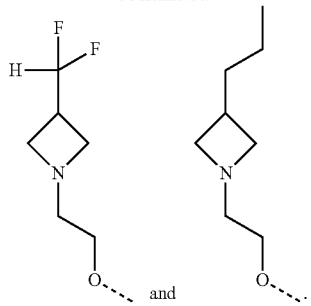
and

12. The compound, the pharmaceutically acceptable salt or the hydrate thereof as defined in claim 1, wherein, $R_2$ is selected from H, F, Cl, Br, I, CN, $NO_2$, OH, COOH, $NH_2$, or the group consisting of $C_{1-4}$ alkyl, $C_{1-4}$ alkoxy, $C_{1-4}$ alkylthio, NH($C_{1-4}$ alkyl), N,N-di($C_{1-3}$ alkyl)amino and $C_{3-6}$ cycloalkyl, each of which is optionally substituted with 1, 2, or 3 R, and/or, $R_3$ is selected from H, F, Cl, Br, I, CN, $NO_2$, OH, COOH, $NH_2$, or the group consisting of $C_{1-4}$ alkyl, $C_{1-4}$ alkoxy, $C_{1-4}$ alkylthio, NH($C_{1-4}$ alkyl), N,N-di($C_{1-3}$ alkyl) amino, $C_{3-6}$ cycloalkyl, 3-6 membered heterocycloalkyl, 5-6 membered aryl and 5-6 membered heteroaryl, each of which is optionally substituted with 1, 2, or 3 R, and/or, $R_4$ and $R_5$ are each independently selected from H, F, Cl, Br, I, CN, $NO_2$, OH, COOH, $NH_2$, or the group consisting of $C_{1-4}$ alkyl, $C_{1-4}$ alkoxy, $C_{1-4}$ alkylthio, NH($C_{1-4}$ alkyl), N,N-di($C_{1-3}$ alkyl)amino and $C_{3-6}$ cycloalkyl, each of which is optionally substituted with 1, 2, or 3 R, and/or, ring A is selected from the group consisting of phenyl, pyridyl, pyrazinyl, imidazolyl, pyrazolyl, oxazolyl, isoxazolyl, thiazolyl, isothiazolyl, thienyl, benzofuranyl, benzothienyl, indolyl, benzimidazolyl, benzothiazolyl, purinyl, quinolinyl and isoquinolinyl, and/or, $R_6$ is selected from

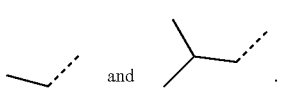
and

13. The compound, the pharmaceutically acceptable salt or the hydrate thereof as defined in claim 12, wherein, $R_3$ is selected from H, F, Cl, Br, I, CN, $NO_2$, OH, COOH, $NH_2$, or the group consisting of $CH_3$, $CH_3CH_2$, $CH_3O$, $CH_3CH_2O$ and

, each of which is optionally substituted with 1, 2, or 3 R.

14. The compound, the pharmaceutically acceptable salt or the hydrate thereof as defined in claim 13, wherein, $R_3$ is selected from the group consisting of H, F, Cl, CN, $CH_3$, $CF_3$ and

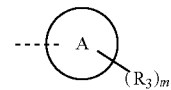

15. The compound, the pharmaceutically acceptable salt or the hydrate thereof as defined in claim 12, wherein, $R_4$ and $R_5$ are each independently selected from the group consisting of H, F, Cl, Br, CN and $CH_3$.

16. The compound, the pharmaceutically acceptable salt or the hydrate thereof as defined in claim 12, wherein, the structural unit

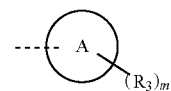

is selected from the group consisting of

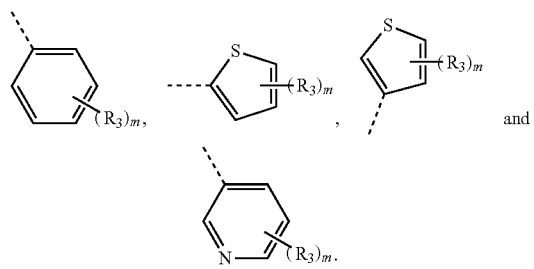

17. The compound, the pharmaceutically acceptable salt the hydrate thereof as defined in claim 16, wherein, the structural unit

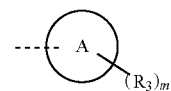

is selected from the group consisting of

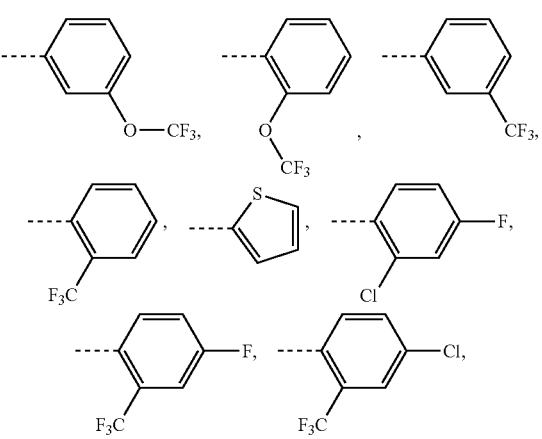

-continued

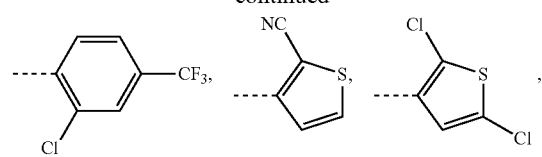

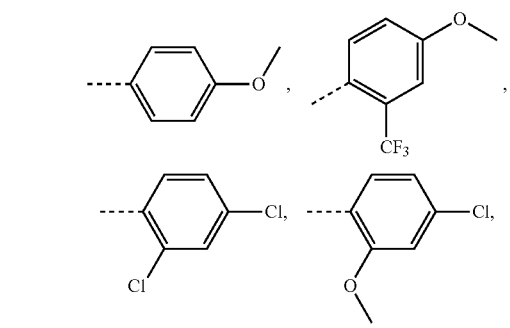

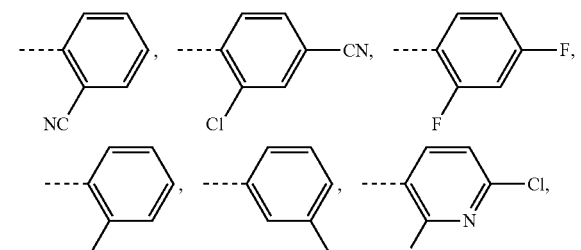

18. The compound, the pharmaceutically acceptable salt or the hydrate thereof as defined in claim 2, wherein, the structural unit

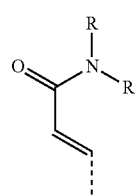

is selected from

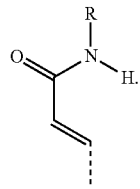

19. The compound, the pharmaceutically acceptable salt or the hydrate thereof as defined in claim 18, wherein, the structural unit

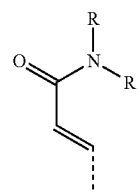

is selected from

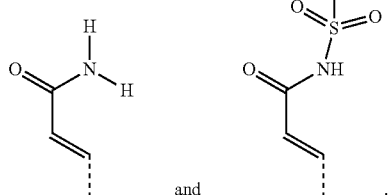

and

20. The compound, the pharmaceutically acceptable salt or the hydrate thereof as defined in claim 1, wherein, the compound is selected from the group consisting of

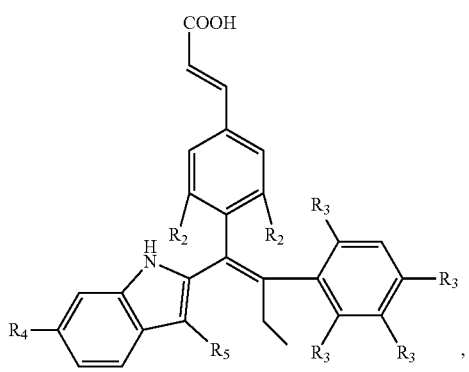

(II)

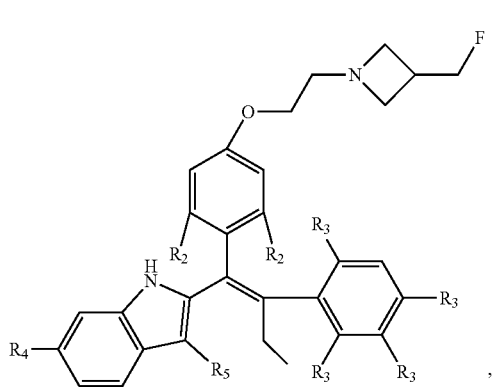
(III)

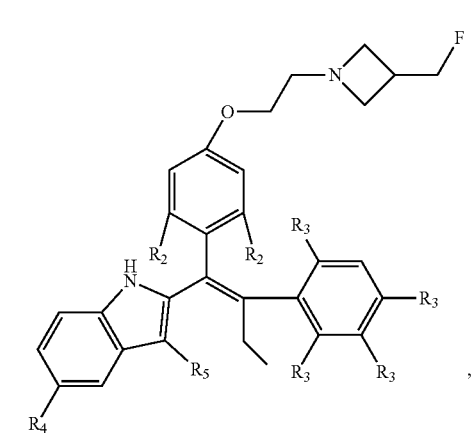
(IV)

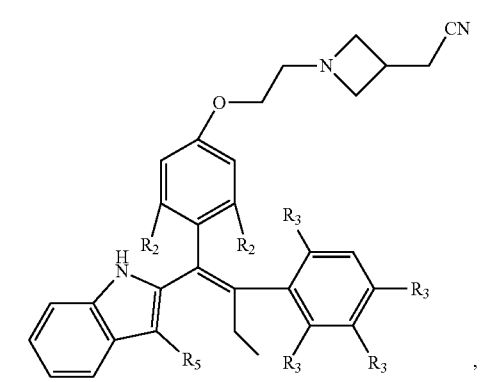
(V)

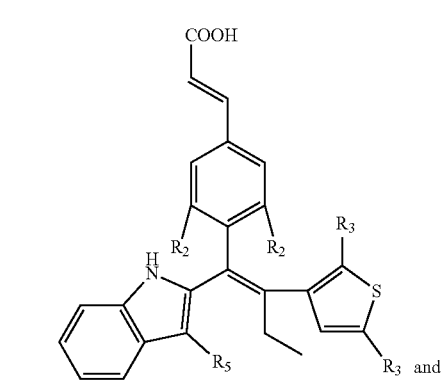
(VI)

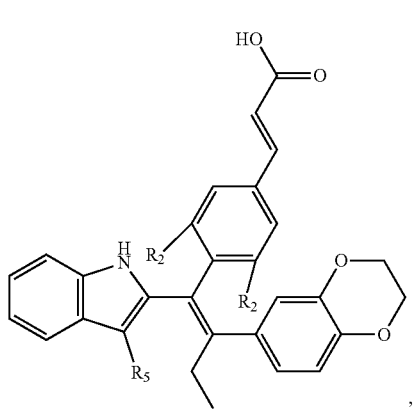
(VII)

wherein, $R_2$, $R_3$, $R_4$ and $R_5$ are defined as claim 1.

21. The compound, the pharmaceutically acceptable salt or the hydrate thereof as defined in claim 2, wherein, the compound is selected from

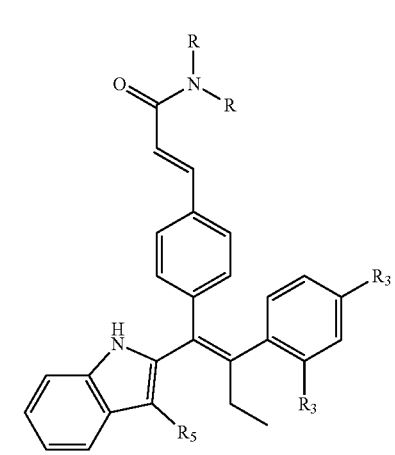
(VIII)

wherein, $R_3$, $R_5$ and R are defined as in claim 2.

22. The compound, pharmaceutically acceptable salt or hydrate thereof as defined in claim 1, wherein, the compound is selected from the group consisting of

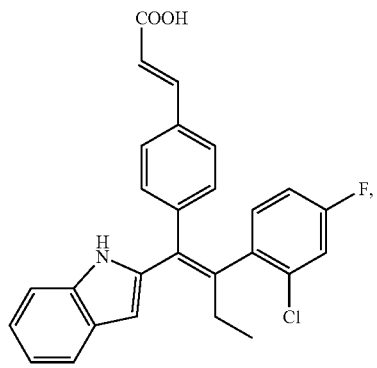
I-1

I-2
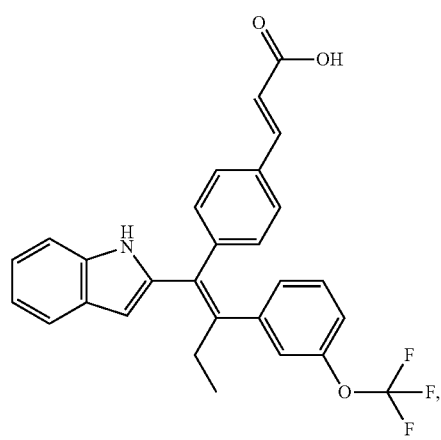
I-3
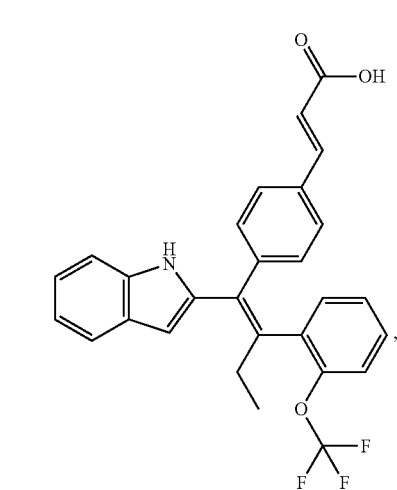
I-4
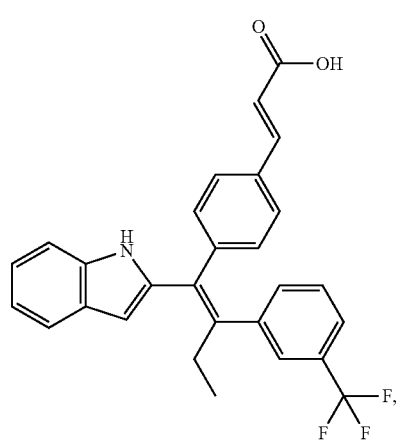
I-5
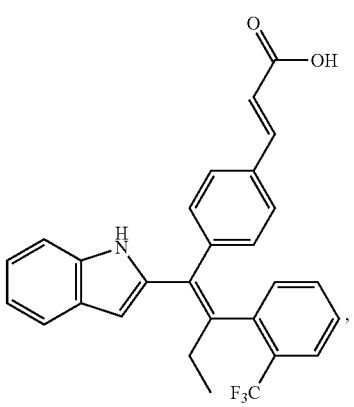
I-6
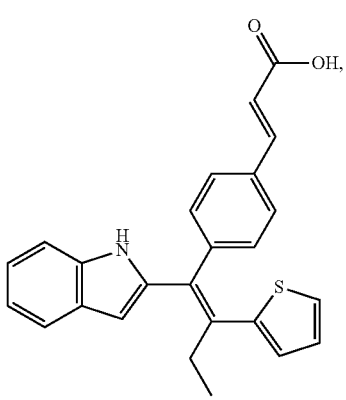
I-7
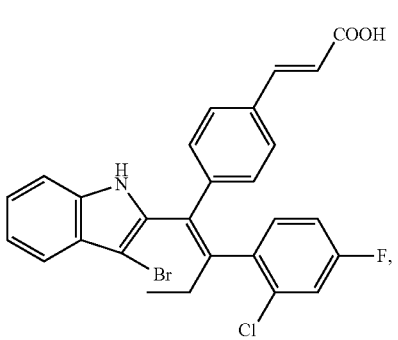
I-8
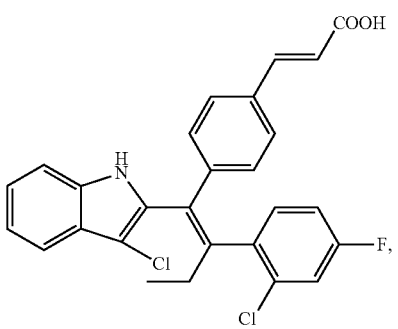

-continued
I-9
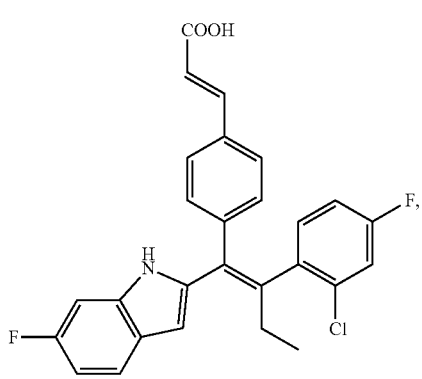
I-10
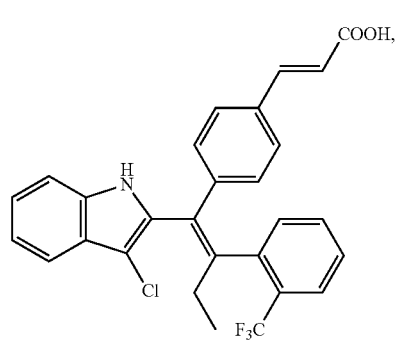
I-11
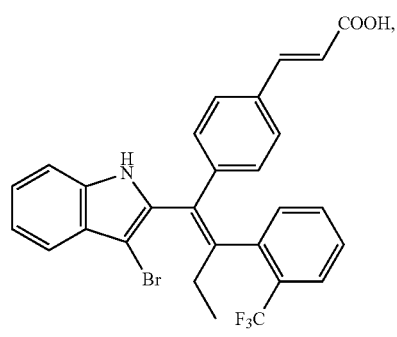
I-12
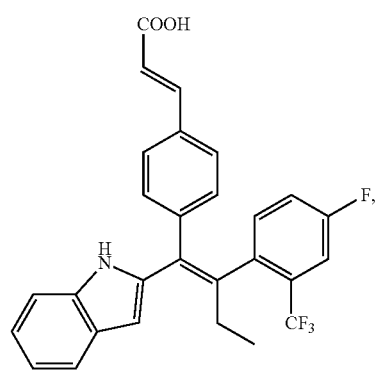
-continued
I-13
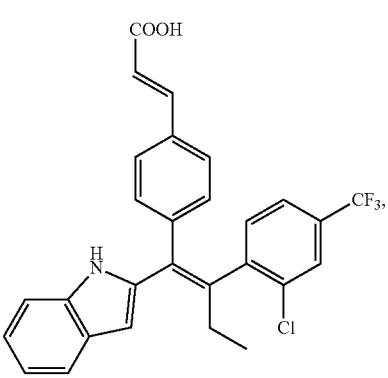
I-14
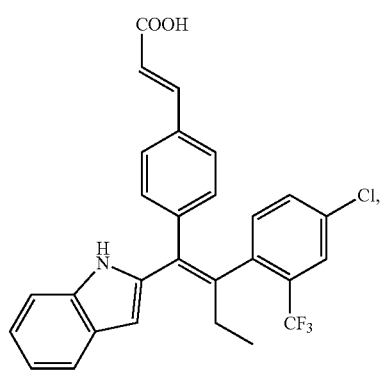
I-15
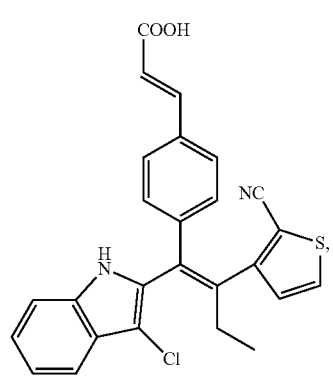
I-17
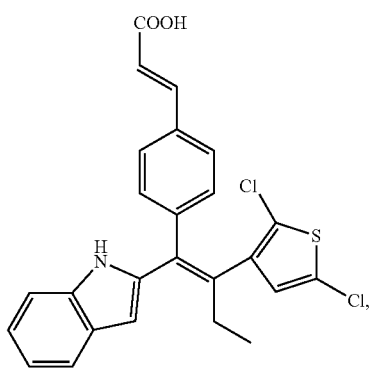

I-18
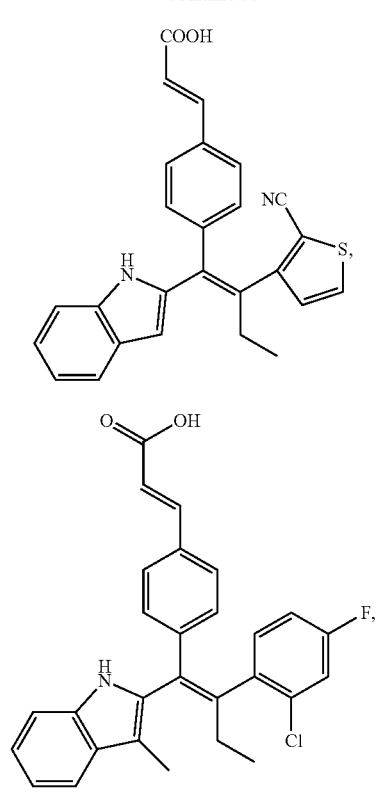
I-19
I-21
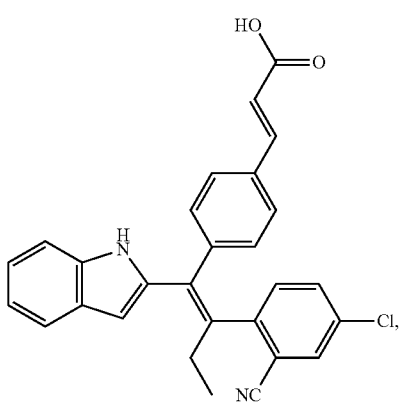
I-22
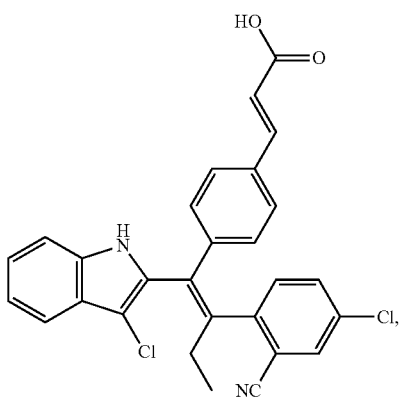
I-23
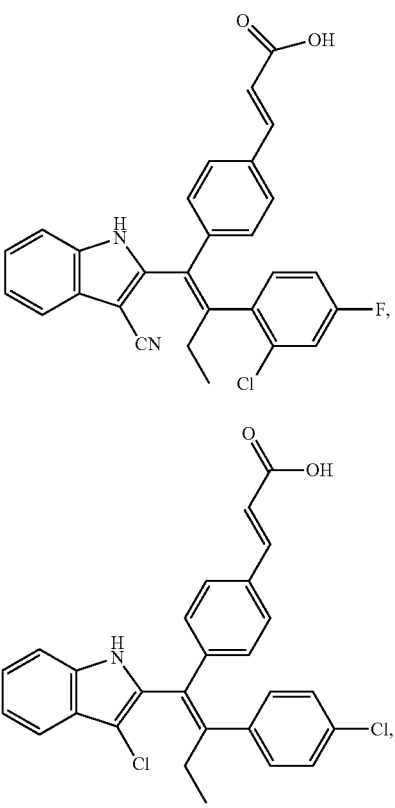
I-24
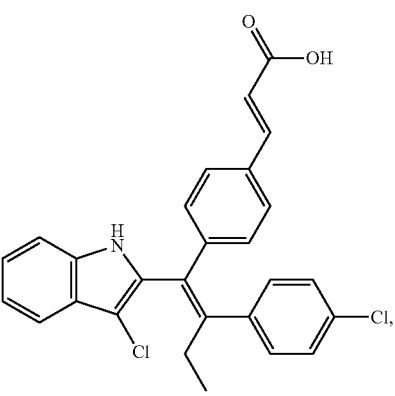
I-27
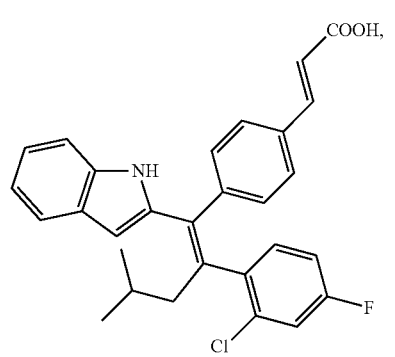
I-28
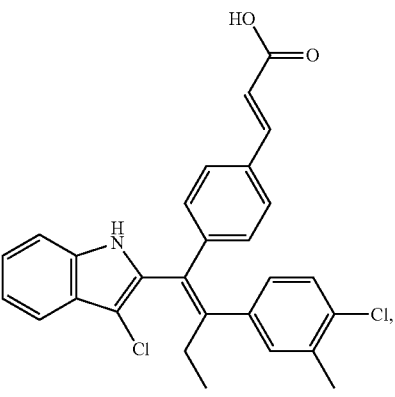

I-29
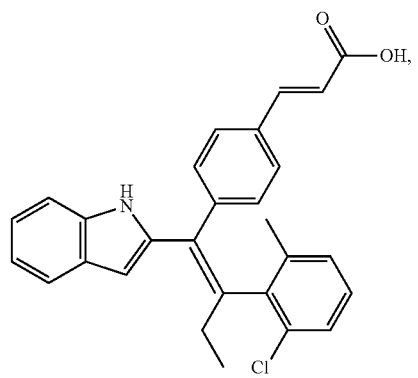
I-30
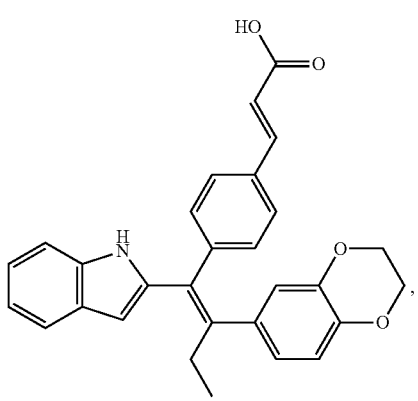
I-31
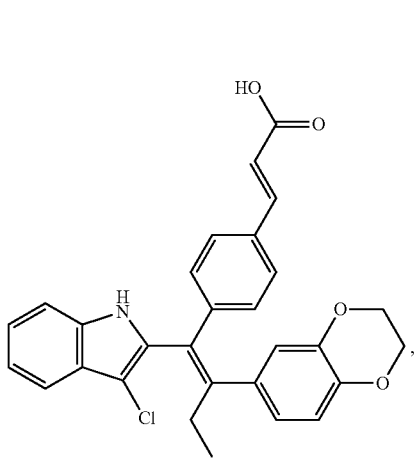
I-32
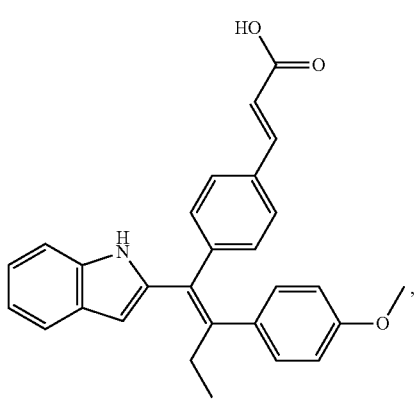
I-33
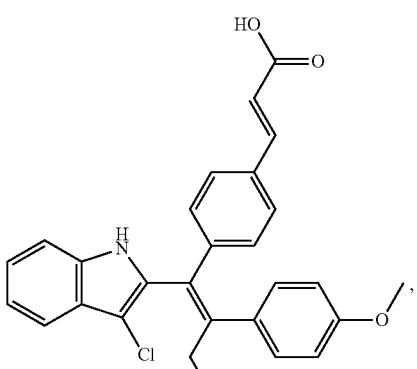
I-34
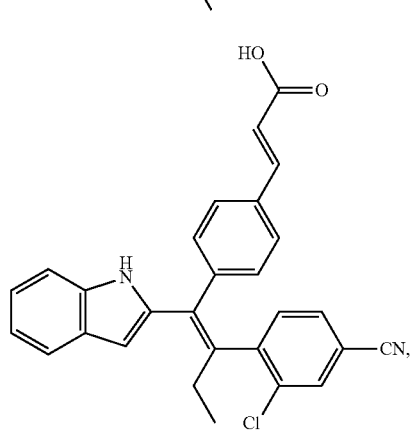
I-35
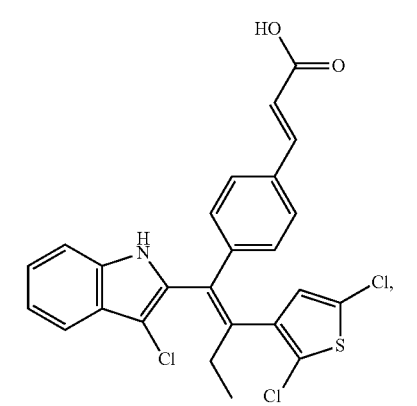
I-36
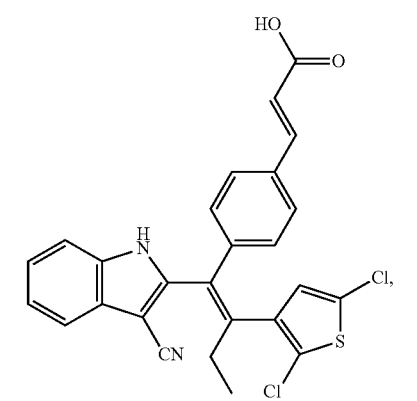

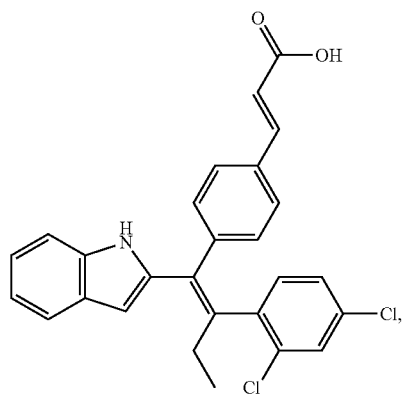
I-37
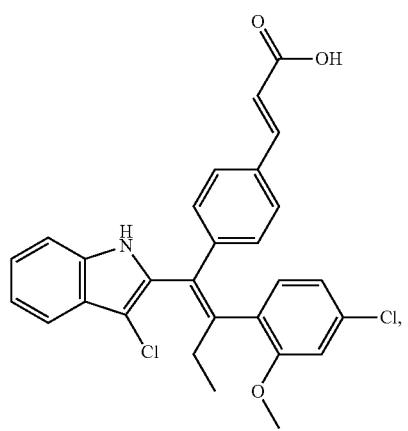
I-38
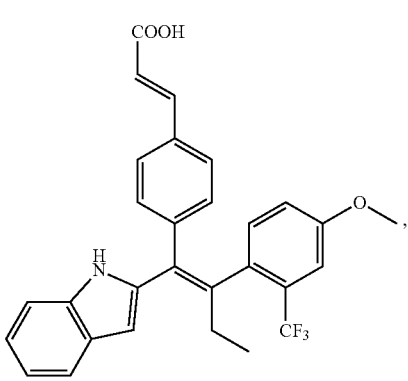
I-39
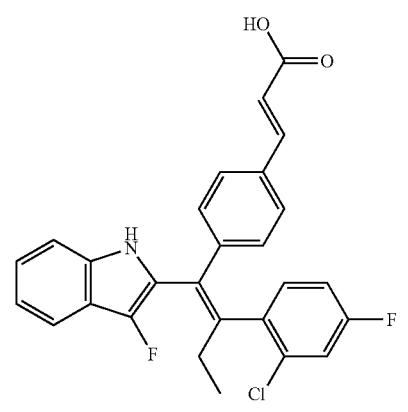
I-40
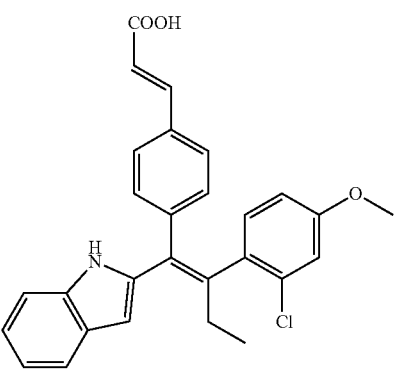
I-41
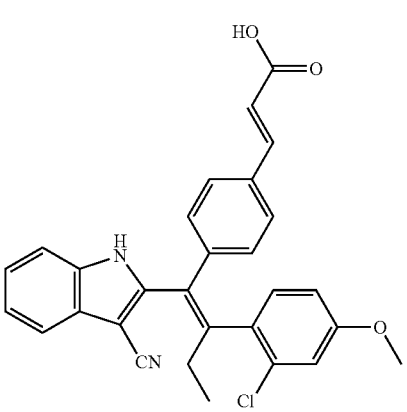
I-42
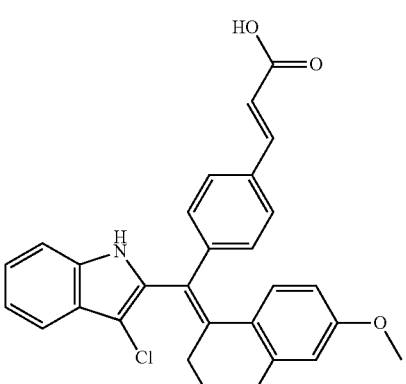
I-43
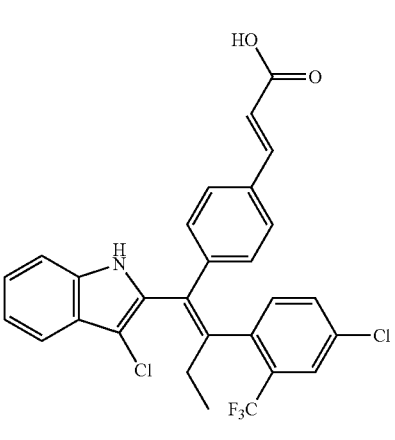
I-44

-continued
I-45
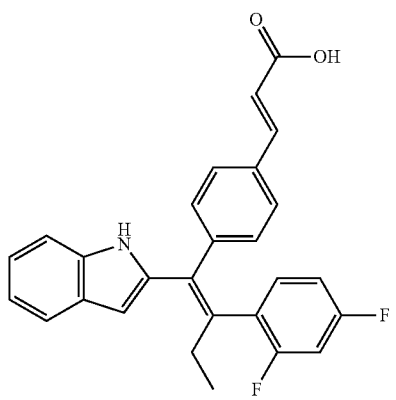
I-49
I-50
I-51
-continued
I-52
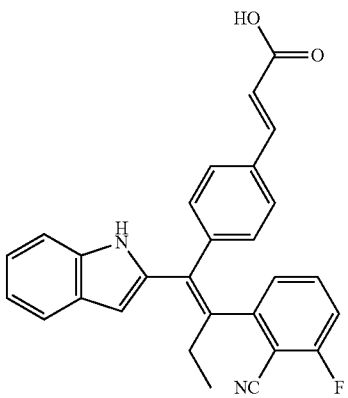
I-53
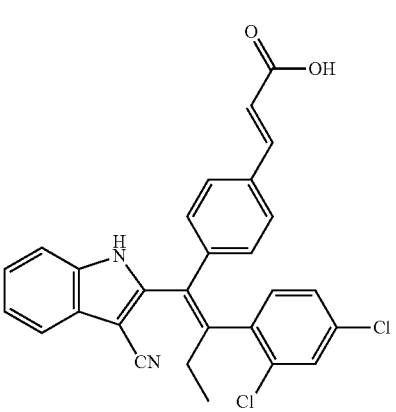
I-54
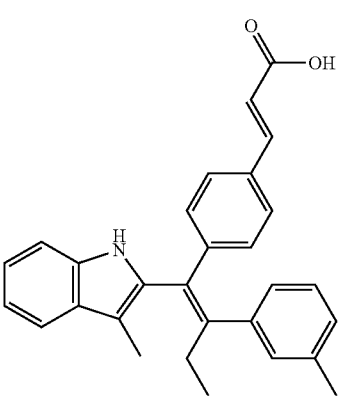
I-55
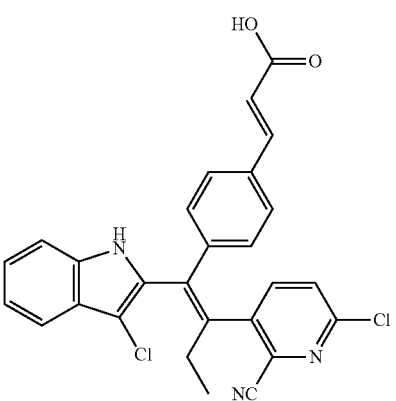

I-56
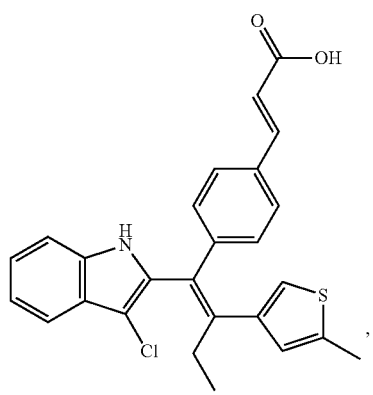
I-57
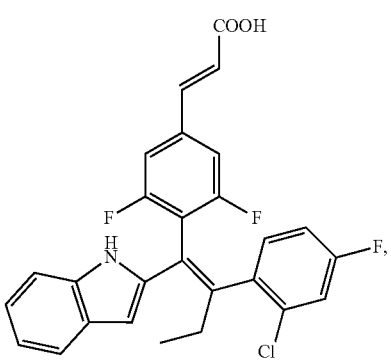
II-1
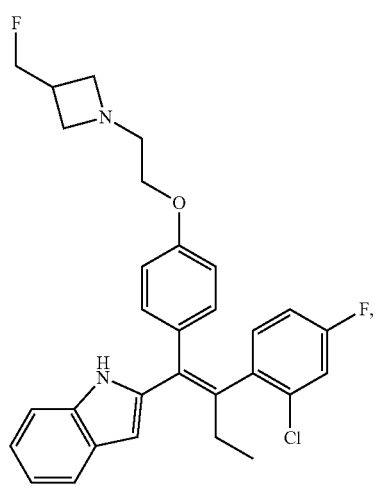
II-2
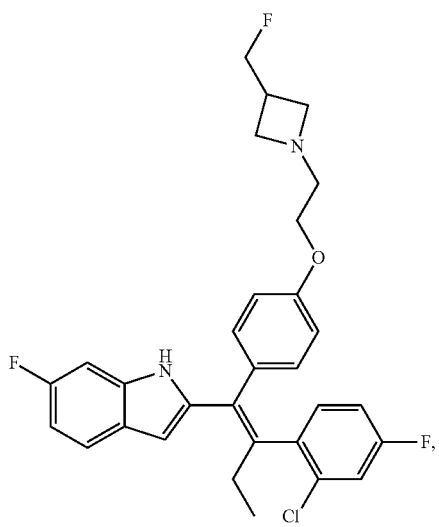
II-3
II-4
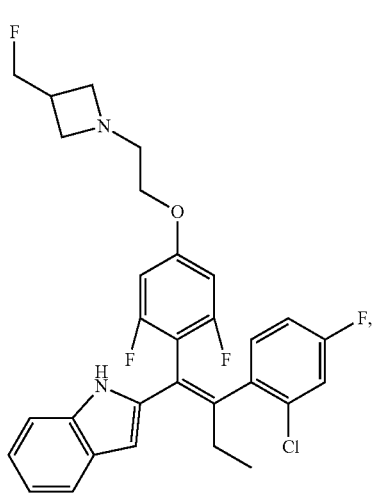

II-5
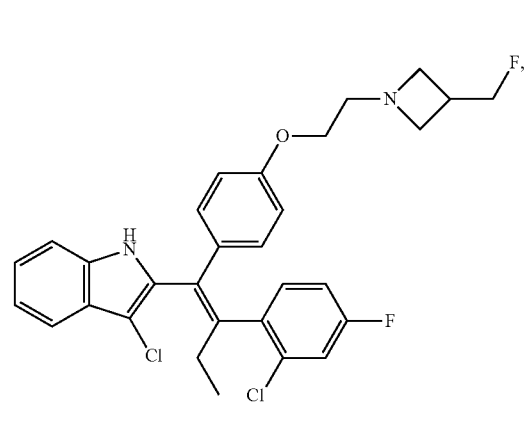
II-6
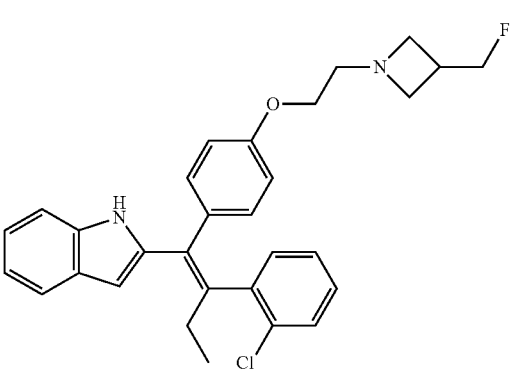
II-7
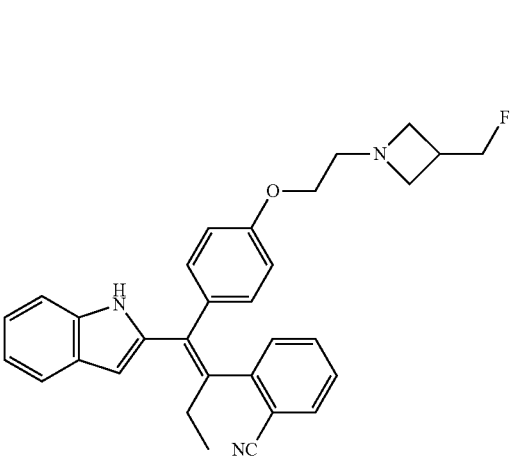
II-8
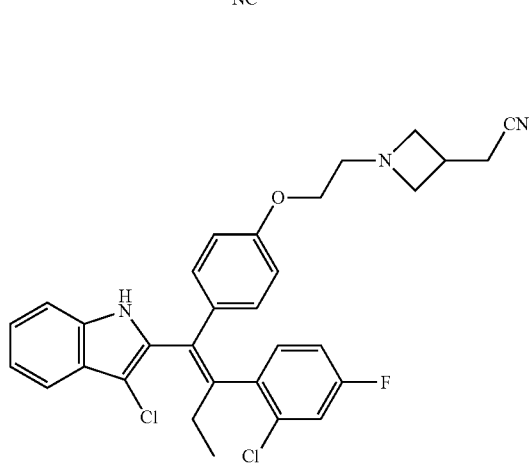
II-9
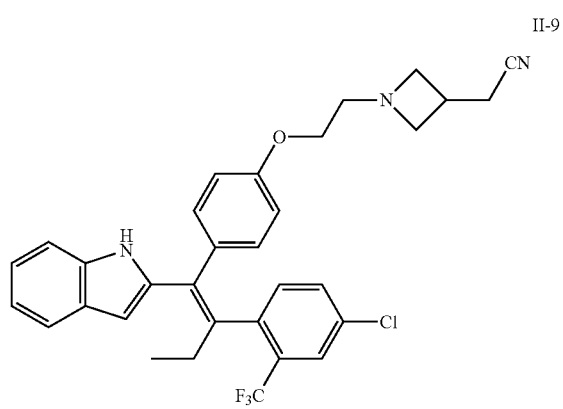
II-10
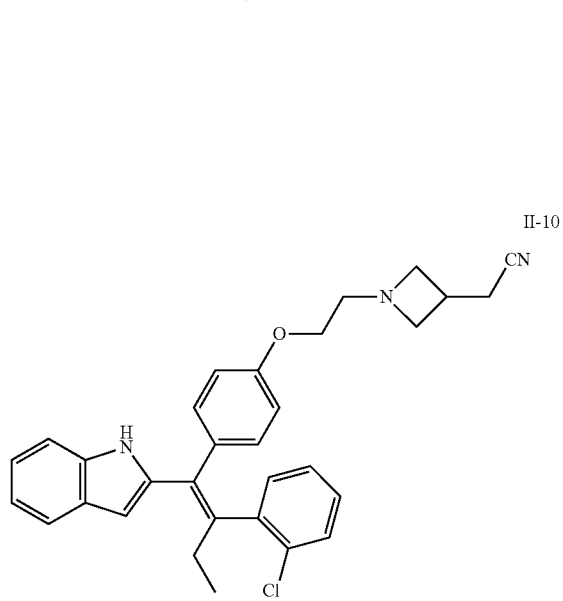
II-11
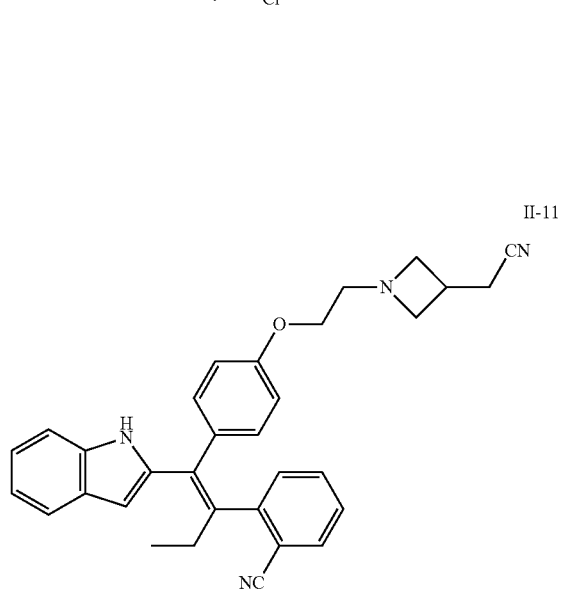

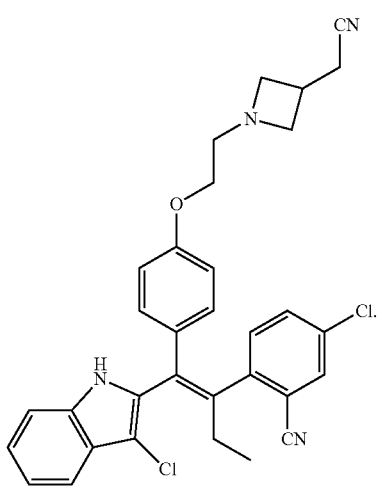

II-12

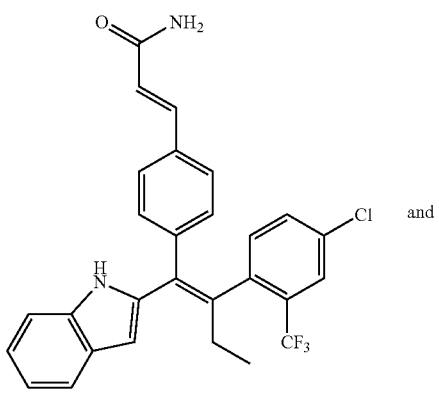

I-47

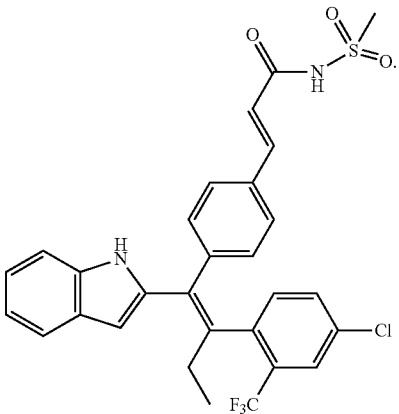

I-48

23. A pharmaceutical composition comprising a therapeutically effective amount of the compound, the pharmaceutically acceptable salt or the hydrate thereof as defined in claim 1 and a pharmaceutically acceptable carrier.

24. A method for treating a disorder associated with estrogen receptor in a subject in need thereof, comprising: administrating an effective amount of the compound, the pharmaceutically acceptable salt or the hydrate thereof as defined in claim 1, wherein, the disorder associated with estrogen receptor is estrogen receptor-positive breast cancer.

25. The compound, the pharmaceutically acceptable salt or the hydrate thereof as defined in claim 2, wherein, the compound is selected from the group consisting of

* * * * *

UNITED STATES PATENT AND TRADEMARK OFFICE
CERTIFICATE OF CORRECTION

PATENT NO. : 10,519,143 B2
APPLICATION NO. : 16/087861
DATED : December 31, 2019
INVENTOR(S) : Jianyu Lu et al.

Page 1 of 1

It is certified that error appears in the above-identified patent and that said Letters Patent is hereby corrected as shown below:

On the Title Page

At item (73), immediately following LUOXIN PHARMACEUTICAL (SHANGHAI) CO., LTD., insert -- SHANDONG LUOXIN PHARMACEUTICAL GROUP STOCK CO., LTD. --

Signed and Sealed this
Seventh Day of February, 2023

Katherine Kelly Vidal
*Director of the United States Patent and Trademark Office*